US008912200B2

(12) United States Patent
Brasca et al.

(10) Patent No.: US 8,912,200 B2
(45) Date of Patent: Dec. 16, 2014

(54) ALKYNYL SUBSTITUTED PYRIMIDINYL-PYRROLES ACTIVE AS KINASES INHIBITORS

(75) Inventors: Maria Gabriella Brasca, Nerviano (IT); Jay Aaron Bertrand, Didcot (GB); Paola Gnocchi, Stresa (IT); Ilaria Motto, Nerviano (IT); Marcella Nesi, Saronno (IT); Achille Panzeri, Merate (IT); Paola Vianello, Milan (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 14/235,477

(22) PCT Filed: Jul. 18, 2012

(86) PCT No.: PCT/EP2012/064056
§ 371 (c)(1),
(2), (4) Date: Feb. 25, 2014

(87) PCT Pub. No.: WO2013/014039
PCT Pub. Date: Jan. 31, 2013

(65) Prior Publication Data
US 2014/0194406 A1    Jul. 10, 2014

(30) Foreign Application Priority Data
Jul. 28, 2011 (EP) .................. 11175736

(51) Int. Cl.
*A01N 43/54* (2006.01)
*C07D 239/42* (2006.01)
*C07D 401/04* (2006.01)
*A61K 45/06* (2006.01)
*A61K 31/506* (2006.01)
*C07D 417/14* (2006.01)
*C07D 403/04* (2006.01)
*C07D 405/14* (2006.01)
*A61K 31/541* (2006.01)
*C07D 403/14* (2006.01)

(52) U.S. Cl.
CPC .............. *A61K 31/541* (2013.01); *A61K 45/06* (2013.01); *A61K 31/506* (2013.01); *C07D 417/14* (2013.01); *C07D 403/04* (2013.01); *C07D 405/14* (2013.01); *C07D 403/14* (2013.01)
USPC ............ 514/256; 514/275; 544/331; 544/333

(58) Field of Classification Search
USPC .............................. 514/256, 275; 544/331, 333
See application file for complete search history.

(56) References Cited

U.S. PATENT DOCUMENTS 5,472,933 A * 12/1995 Zimmerman et al. ........ 504/213
6,919,347 B2 * 7/2005 Ohlmeyer et al. ............ 514/269
7,799,796 B2 * 9/2010 Dillon et al. .................. 514/275
7,812,022 B2 * 10/2010 Uehling et al. ............ 514/235.8
2008/0182851 A1 * 7/2008 Thomas et al. .......... 514/252.02

FOREIGN PATENT DOCUMENTS

WO    WO 2007/110344 A1    10/2007
WO    WO 2009/133170 A1    11/2009
WO    WO 2011/057960 A1     5/2011
WO    WO 2011/061222 A1     5/2011

OTHER PUBLICATIONS

International Search Report dated Aug. 28, 2012 issued in PCT/EP2012/064056.
Almerico A.M. et al., "Preparation of Monohalopyrroles", J. Heterocyclic Chem. 19:977-979 (Jul.-Aug. 1982).
Alvarez J.V. et al., "Signal Transducer and Activator of Transcription 3 is Required for the Oncogenic Effects of Non-Small-Cell Lung Cancer-Associated Mutations of the Epidermal Growth Factor Receptor", Cancer Research 66 (6):3162-3168 (Mar. 15, 2006).
Ara T. et al., "Interleukin-6 in Bone Metastasis and Cancer Progression", Eur J. Cancer 46(7):1223-1231 (May 2010).
Araujo J. et al., "Dasatinib: A Potent SRC Inhibitor in Clinical Development for the Treatment of Solid Tumors", Cancer Treat Rev. 36(6):492-500 (2010).
Baker SJ et al., "Hematopoietic Cytokine Receptor Signaling", Oncogene 26:6724-6737 (2007).
Baxter E J et al., "Acquired Mutation of the Tyrosine Kinase JAK2 in Human Myeloproliferative Disorders", Lancet 365:1054-1061 (2005).
Benati D. et al., "Src Family Kinase as Potential Therapeutic Targets for Malignancies and Immunological Disorders", Current Medicinal Chemistry 15:1154-1165 (2008).
Boggon T J et al., "Structure and Regulation of Src Family Kinases", Oncogene 23:7918-7927 (2004).
Campbell P.J. et al., "Mechanisms of Disease—The Myeloproliferative Disorders", The New England Journal of Medicine 355:2452-2466 (Dec. 7, 2006).
Chinchilla R. et al., "The Sonogashira Reaction: A Booming Methodology in Synthetic Organic Chemistry", Chem. Rev. 107:874-922 (2007).
Clevenger C.V., "Roles and Regulation of Stat Family Transcription Factors in Human Breast Cancer", American Journal of Pathology 165(5):1449-1460 (Nov. 2004).
Cohen P., "Protein Kinases—The Major Drug Targets of the Twenty-First Century?", Nature Reviews—Drug Discovery 1:309-315 (Apr. 2002).
Cohen P., "The Development and Therapeutic Potential of Protein Kinase Inhibitors", Current Opinion in Chemical Biology 3:459-465 (1999).

(Continued)

Primary Examiner — James O. Wilson
Assistant Examiner — Alexander R Pagano
(74) Attorney, Agent, or Firm — Scully, Scott, Murphy & Presser, P.C.

(57) ABSTRACT

The present invention relates to alkynyl substituted pyrimidinyl-pyrrole compounds which modulate the activity of protein kinases and are therefore useful in treating diseases caused by dysregulated protein kinase activity, in particular Jak and/or Src family kinases. The present invention also provides methods for preparing these compounds, pharmaceutical compositions comprising these compounds, and methods of treating diseases utilizing such compounds or the pharmaceutical compositions containing them.

9 Claims, No Drawings

(56) References Cited

OTHER PUBLICATIONS

Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
Constantinescu S.N. et al., "Mining for JAK-STAT Mutations in Cancer", Trends in Biochemical Sciences 33 (3):122-131 (2008).
Ghoreschi K. et al., "Janus Kinases in Immune Cell Signaling", Immunol Rev. 228(1):273-287 (Mar. 2009).
Godeny M.D. et al., "Jak2 Tyrosine Kinase and Cancer: How Good Cells Get HiJAKed", Anti-Cancer Agents in Medicinal Chemistry 7:643-650 (2007).
Hercus T.R. et al., "The Granulocyte-Macrophage Colony-Stimulating Factor Receptor: Linking its Structure to Cell Signaling and its Role in Disease", Blood 114(7):1289-1298 (Aug. 13, 2009).
Ihle J.N., "Cytokine Receptor Signalling", Nature 377:591-594 (Oct. 19, 1995).
Ingley E. et al., "Cross-Regulation of JAK and Src Kinases", Growth Factors 24(1):89-95 (Mar. 2006).
James C. et al., "A Unique Clonal JAK2 Mutation Leading to Constitutive Signalling Causes Polycythaemia Vera", Nature 434:1144-1148 (Apr. 28, 2005).
Jeong E G et al., "Somatic Mutations of JAK1 and JAK3 in Acute Leukemias and Solid Cancers", Clin Cancer Res 14 (12):3716-3721 (Jun. 15, 2008).
Jolicoeur B. et al., "Pyrrole Protection", Tetrahedron 62:11531-11563 (2006).
Kopetz S. et al., "Src Continues Aging: Current and Future Clinical Directions", Clin Cancer Res 13(24):7232-7236 (Dec. 15, 2007).
Kralovics, Ph.D. R. et al., "A Gain-of-Function Mutation of JAK2 in Myeloproliferative Disorders", The New England Journal of Medicine 352(17):1779-1790 (Apr. 28, 2005).
Lacronique V. et al., "A TEL-JAK2 Fusion Protein With Constitutive Kinase Activity in Human Leukemia", Science 278:1309-1312 (Nov. 14, 1997).
Leonard W.J. et al., "JAKS and STATS: Biological Implications", Annu. Rev. Immunol. 16:293-322 (1998).
Levine R.L. et al., "Activating Mutation in the Tyrosine Kinase JAK2 in Polycythemia Vera, Essential Thrombocythemia, and Myeloid Metaplasia With Myelofibrosis", Cancer Cell 7:387-397 (Apr. 2005).
Mitchell R.H. et al., "N-Bromosuccinimide-Dimethylformamide: A Mild, Selective Nuclear Monobromination Reagent for Reactive Aromatic Compounds", J. Org. Chem. 44(25):4733-4735 (1979).
Miyaura N. et al., "Palladium-Catalyzed Cross-Coupling Reactions of Organoboron Compounds", Chem. Rev. 95:2457-2483 (1995).
Mullighan C.G. et al., "JAK Mutations in High-Risk Childhood Acute Lymphoblastic Leukemia", PNAS 106 (23):9414-9418 (Jun. 9, 2009).
Murray P.J., "The JAK-STAT Signaling Pathway: Input and Output Integration", The Journal of Immunology 178:2623-2629 (2007).
Onishi T. et al., "Future Directions of Bone-Targeted Therapy for Metastatic Breast Cancer", Nature Reviews—Clinical Oncology 7:641-651 (Nov. 2010).
Rane S G et al., "JAKs, STATs and Src Kinases in Hematopoiesis", Oncogene 21:3334-3358 (2002).
Roodman G.D., "New Potential Targets for Treating Myeloma Bone Disease", Clin Cancer Res 12(20 Suppl):6270s-6273s (Oct. 15, 2006).
Saito Y.D. et al., "Fyn—A Novel Molecular Target in Cancer", Cancer 116:1629-1637 (Apr. 1, 2010).
Sayyah J. et al., "Jak2 Inhibitors: Rationale and Role as Therapeutic Agents in Hematologic Malignancies", Curr Oncol Rep. 11(2):117-124 (Mar. 2009).
Sen B. et al., "Sustained Src Inhibition Results in Signal Transducer and Activator of Transcription 3 (STAT3) Activation and Cancer Cell Survival Via Altered Janus-Activated Kinase-STAT3 Binding", Cancer Res 69(5):1958-1965 (Mar. 1, 2009).
Snide K. et al., "Development of ET, Primary Myelofibrosis and PV in Mice Expressing JAK2 V617F", Leukemia 22:87-95 (2008).
Silver J.S. et al., "GP130 at the Nexus of Inflammation, Autoimmunity, and Cancer", Journal of Leukocyte Biology 88:1145-1156 (Dec. 2010).
Sonogashira K. et al., "A Convenient Synthesis of Acetylenes: Catalytic Substitutions of Acetylenic Hydrogen With Bromalkenes, Iodoarenes, and Bromopyridines", Tetrahedron Letters 50:4467-4470 (1975).
Soriano P. et al., "Targeted Disruption of the C-Src Proto-Oncogene Leads to Osteopetrosis in Mice", Cell 64:693-702 (Feb. 22, 1991).
Spivak J.L., "Animal Models of the MPD: Lack of the Clones", Blood 108(5):1427-1428 (Sep. 1, 2006).
Suzuki A., "Cross-Coupling Reactions of Organoboron Compounds with Organic Halides", Metal-Catalyzed Cross-Coupling Reactions, 1st edition, pp. 49-97 (1998).
Vanotti E. et al., "Regioselective Halogenation of Aminopyrimidinyl-Pyrrole Carboxylic Acid Derivatives", Tetrahedron 65:10418-10423 (2009).
Velculescu V.E., "Defining the Blueprint of the Cancer Genome", Carcinogensis 29(6):1087-1091 (2008).
Wallace T.A. et al., "Jak2 Tyrosine Kinase—A Mediator of Both Housekeeping and Ligand-Dependent Gene Expression", Cell Biochemistry and Biophysics 44:213-222 (2006).

* cited by examiner

SEQUENCE LISTING

```
<160> NUMBER OF SEQ ID NOS: 3

<210> SEQ ID NO 1
<211> LENGTH: 15
<212> TYPE: PRT
<213> ORGANISM: Artificial
<220> FEATURE:
<223> OTHER INFORMATION: Peptide substrate

<400> SEQUENCE: 1

Leu Pro Leu Asp Lys Asp Tyr Tyr Val Val Arg Glu Pro Gly Gln
1               5                   10                  15

<210> SEQ ID NO 2
<211> LENGTH: 16
<212> TYPE: PRT
<213> ORGANISM: Artificial
<220> FEATURE:
<223> OTHER INFORMATION: Peptide substrate

<400> SEQUENCE: 2

Lys Lys His Thr Asp Asp Gly Tyr Met Pro Met Ser Pro Gly Val Ala
1               5                   10                  15

<210> SEQ ID NO 3
<211> LENGTH: 12
<212> TYPE: PRT
<213> ORGANISM: Artificial
<220> FEATURE:
<223> OTHER INFORMATION: Peptide substrate

<400> SEQUENCE: 3

Glu Ala Ile Tyr Ala Ala Pro Phe Ala Lys Lys Lys
1               5                   10
```

ALKYNYL SUBSTITUTED PYRIMIDINYL-PYRROLES ACTIVE AS KINASES INHIBITORS

INCORPORATION BY REFERENCE OF SEQUENCE LISTING

The Sequence Listing in an ASCII text file, named as 30715_SequenceList.txt of 1 KB, created on Jan. 24, 2014, and submitted to the United States Patent and Trademark Office via EFS-Web, is incorporated herein by reference.

The present invention relates to certain alkynyl substituted pyrimidinyl-pyrrole compounds, which modulate the activity of protein kinases. The compounds of this invention are therefore useful in treating diseases related to dysregulated kinases activity, for example cancer, cell proliferative disorders, viral infections, immune disorders, neurodegenerative disorders, cardiovascular diseases and bone related diseases.

The present invention also provides methods for preparing these compounds, pharmaceutical compositions comprising these compounds, and methods of treating diseases utilizing pharmaceutical compositions comprising these compounds.

Protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein's biological function and are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-3 (IL-3), IL-2) and growth factors (e.g., granulocyte macrophage-colony-stimulating factor (GM-CSF), fibroblast growth factor (FGF) and Erythropoietin (EPO)). An extracellular stimulus may affect one or more cellular responses related to cell growth, migration, differentiation, secretion of hormones, activation of transcription factors, muscle contraction, glucose metabolism, control of protein synthesis and regulation of the cell cycle.

The malfunction of protein kinases (PKs) is the hallmark of numerous diseases. A large share of the oncogenes and proto-oncogenes involved in human cancers encode for PKs. The enhanced activities of PKs are also implicated in many non-malignant diseases that include, but are not limited to, autoimmune diseases, inflammatory diseases, psoriasis, bone diseases, metabolic diseases, neurological and neurodegenerative diseases, cardiovascular diseases, allergies and asthma, Alzheimer's disease, and hormone-related diseases. Accordingly, there has been a substantial effort in medicinal chemistry to find protein kinase inhibitors that are effective as therapeutic agents. For a general reference to PKs malfunctioning or deregulation see Current Opinions in Chemical Biology 1999, 3: 459-465; Nature Rev. Drug Discov. 2002, 1: 309-315 and Carcinogenesis 2008, 29: 1087-191.

The JAKs are a family of non-receptor tyrosine kinases consisting of JAK1, JAK2, JAK3 and TYK2. Whereas JAK1, JAK2 and TYK2 are expressed ubiquitously in mammals, JAK3 is primarily expressed in hematopoietic cells. The JAKs play a crucial role in hematopoietic cytokine and growth factors signaling (Nature 1995; 377: 591-594, Annu. Rev. Immunol. 1998; 16: 293-322) and are critically involved in cell growth, survival, development and differentiation of myeloid and immune cells. Effective innate and adaptive immune responses require functional JAK signaling to protect the organism from infections or tumors and mutations leading to loss of function make up some of the most common inherited severe immunodeficiencies. As a consequence JAK/STAT signaling has been implicated in the mediation of many abnormal immune responses such as allergies, asthma, autoimmune diseases, transplant rejection, rheumatoid arthritis, amyotrophic lateral sclerosis and multiple sclerosis as well as in solid and hematological malignancies like leukemias and lymphomas (Immunol Rev. 2009, 228: 273-287).

In particular JAK2 kinase is exclusively involved in the signal transduction mediated by Erythropoietin (EPO), Thrombopoietin (TPO), Growth Hormone (GH), Prolactin (PR) and by cytokines that signal through the common beta chain receptor IL-3, granulocyte-macrophage colony-stimulating factor (GM-CSF) and IL-5. In addition, JAK2 together with JAK1 and/or TYK2 are important for the cytokines that signal through gp130 receptors (e.g. IL-6, IL-11), Type II cytokine receptors like IL-10, IL-19, IL-20 and IL-22, p40-containing containing cytokine receptors IL-12 and IL-23 and for the signal of Type I and II IFNs receptors (Immunol Rev. 2009; 228: 273-287). JAK3 kinase is primarily expressed in hematopoietic cells and is selectively associated with the common γ chain (γc), which is a shared component of the receptors for IL-2, IL-4, IL-7, IL-9, IL-15, and IL-21 that are cytokines involved in lymphoid development and function, and homeostasis of the immune system. TYK2 is primarily associated with Interferons, IL-12 and IL-23, but also with IL-10 and IL-6 signalling. All these growth factors and cytokines are mainly involved in proliferation and differentiation of Myeloid cells, inflammatory response and cancer (Blood. 2009; 114: 1289-1298, Clin Cancer Res. 2006; 12: 6270s-6273s, J Leukoc Biol. 2010; 88:1145-1156, Eur J. Cancer. 2010; 46: 1223).

The binding of the ligand to the specific receptor seems to induce a conformational change in the receptor that allows trans- and/or autophosphorylation of the two bound JAK molecules. Activated JAK then phosphorylates specific tyrosine residues on the cytoplasmic tails of the receptors, creating docking sites for the SH2 domain of Signal Transducers and Activators of Transcription proteins (STAT). Once bound to the receptors, STATs are themselves phosphorylated by JAK on tyrosine residues. Phosphorylated STATs dimerize and translocate into the nucleus, where they regulate gene transcription. Thus, JAKs are responsible for transducing a signal from the cell surface to the nucleus through a tyrosine phosphorylation signalling mechanism (J. Immun. 2007, 178:2623-2629, Oncogene 2007, 26: 6724-6737 and Cell Biochem Biophys. 2006, 44: 213-222).

JAKs are characterized by 7 distinct JAK homology regions (JH1 to JH7), among these the JH1 regions form the kinase domain and is immediately adjacent to the pseudo-kinase domain (JH2) within the C-terminal half of the protein. The function of the pseudo-kinase domain is to negatively regulate the activity of the kinase domain (N. Engl. J. Med 2006, 355: 2452-2466). It should be point out that the majority of JAK activating mutations identified in tumors are in pseudo-kinase domain. For example an activating point mutation of JAK2 (Valine to Phenylalanine substitution, JAK2-V617F) in the pseudo-kinase domain together with other activating mutations, in the JAK2 exon12 and in the TPO Receptor (MPLW515L/K), have been identified in Hematopoietic cells of patients with myeloproliferative disorders or MPD (Nature 2005; 434: 1144-8, N Engl J Med 2005; 352: 1779-90, Lancet 2005; 365: 1054-61, Cancer Cell 2005; 7: 387-97, Blood 2006, 108: 1427-1428 and Leukemia 2008, 22: 87-95). All of this data suggests that JAK2 is a suitable target for the development of a MPD specific therapy (Curr. One. Reports 2009, 11: 117-124). In addition, the JAK/STAT pathway has been shown to be activated not only by mutation but also by amplification, translocation, silencing of JAK/STAT pathway inhibitors SOLS proteins and overexpression of cytokines in solid and hematological malignancies like, but not limited to, AML, ALL, Hodgkin's Lymphoma, Diffuse large B cell Lymphoma and Mediastinal large B-Cell Lymphoma, Lung, Prostate, Colon and Breast cancer. General observation about the role of JAK in cancer refer to Science 1997, 278:1309-1312; Oncogene 2007; 26: 6724-6737; Trends in Biochemical Sciences 2007; 33: 122-131, PNAS, 2009; 106: 9414-9418, Anti-Cancer Agents Med Chem, 2007, 7, 643-650.

Data from experimental mice and clinical observations have unraveled multiple signaling events mediated by JAKs in innate and adaptive immunity. Deficiency of JAK3 or TYK2 results in defined clinical disorders, which are also evident in mouse models. A striking phenotype associated with inactivating JAK3 mutations is severe combined immunodeficiency syndrome, whereas mutation of TYK2 results in another primary immunodeficiency termed autosomal recessive hyperimmunoglobulin E syndrome.

Combined this data supports the use of JAK inhibitors in several different diseases such as abnormal immune responses like allergies, asthma, autoimmune diseases, transplant rejection, rheumatoid arthritis, amyotrophic lateral sclerosis and multiple sclerosis as well as in solid and hematological malignancies like MPD, leukemias and lymphomas. General observations about the pharmaceutical intervention in the JAK/STAT pathway have been reviewed in J. Leukoc Biol. 2010; 88:1145-1156, Eur J. Cancer. 2010; 46: 1223-1231, Immunol Rev. 2009; 228: 273-287, Trends Blood. 2009; 114: 1289-1298, Clin Cancer Res. 2008; 14:3716-3721, Biochem. Sciences, 2007; 33: 122-131, Clin Cancer Res. 2006; 12: 6270s-6273s, Cancer Res 2006; 66: 3162-3168 and AJP 2004; 165: 1449-146. The Src family kinases (SFK) are non-receptor protein tyrosine kinases (PTKs) ubiquitously expressed and highly conserved throughout evolution. Based on their amino acidic sequences, SFK can be clustered into two subfamilies. The first group includes Src, Fyn, and Yes which are ubiquitously expressed, even though with quantitative differences. The second group includes Blk, Fgr, Hck, Lck, and Lyn which are found primarily in haematopoietic cells (Cancer 2010; 116: 1629-1637; Oncogene 2004; 23:7918-7927). All SFKs play pivotal roles in transducing signals triggered by a variety of surface receptors to downstream molecules to regulate cellular events, such as cell growth, adhesion and migration. Changes in SFK protein expression and/or activity have been causally linked to human carcinogenesis, as described for hematological and solid malignancies (Cancer Treat Rev., 2010; 36: 492-500). Another important role of SFK is regulation of osteoclast proliferation and function, as shown in Src Knockout mice (Cell, 1991; 64: 693-702). Since excessive osteoclast activity is detectable in bone metastasis, Src inhibition could have an effect in tumours that preferentially metastasize to bone (Nat. Rev. Clin. Oncol., 2010; 7: 641-651). In addition, cytokine receptors associate with members of the Src family kinase (SFK) and JAKs and SFK work in concert to activate many of the signalling molecules, with both kinase families required for optimal transmission of intracellular signals (Oncogene 2002; 21: 3334-3358; Growth Factors 2006; 24: 89-95). Moreover SFK have been found to induce activation of STAT protein in solid tumors, thus affecting cellular proliferation and survival and JAK are able to revert inhibition of STAT activation mediated by SFK inhibitors. These observations support the possibility to combine SFK and JAK inhibitors as therapeutical approach diseases like solid and haematological tumors (Cancer Res. 2009; 69: 1958-1965).

In addition SFK, have been shown to be involved in the signaling of T and B cell receptors respectively, support the potential use of specific inhibitors in immune disorders. All of this information supports the use of SFK in solid and hemathological tumors, to control bone metastasis and for the treatment of T-cell-mediated autoimmune and inflammatory disorders and/or organ transplant rejection. (Cancer Treat Rev., 2010; 36: 492-500; Curr. Med. Chem., 2008; 15: 1154-1165; Clin Cancer Res, 2007; 13: 7232-7236)

The present inventors have discovered that the alkynyl substituted pyrimidinyl-pyrrole of formula (I), described below, are potent JAK and Src family kinases inhibitors and are thus useful in therapy of cancer, cell proliferative disorders, viral infections, immune disorders, neurodegenerative disorders, cardiovascular diseases and bone related diseases. Accordingly, a first object of the present invention is to provide an alkynyl substituted pyrimidinyl-pyrrole compound represented by formula (I),

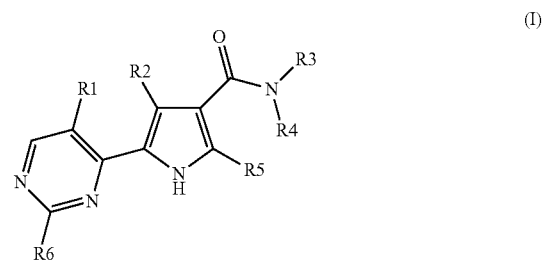

wherein:
one selected from R1 and R2 is hydrogen and the other is ethynyl-R7, wherein:
R7 is hydrogen, trialkylsylyl or an optionally substituted group selected from straight or branched $C_1$-$C_6$ alkyl, $C_3$-$C_7$ cycloalkyl, cycloalkyl-alkyl, aryl, aryl-alkyl, heterocyclyl and heterocyclyl-alkyl;
R3 and R4 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, aryl-alkyl, heterocyclyl and heterocyclyl-alkyl, or R3 and R4, taken together with the nitrogen atom to which they are bonded, may form an optionally substituted 5 to 7 membered heterocyclyl group optionally containing one additional heteroatom selected from N, O and S;
R5 is an optionally substituted aryl;
R6 is hydrogen, an optionally substituted straight or branched $C_1$-$C_6$ alkyl or NR8R9, wherein:
R8 and R9 are independently hydrogen or an optionally substituted group selected from straight or branched $C_1$-$C_6$ alkyl, $C_3$-$C_7$ cycloalkyl, cycloalkyl-alkyl, heterocyclyl and heterocyclyl-alkyl, or R8 and R9, taken together with the nitrogen atom to which they are bonded, may form an optionally substituted 5 to 7 membered heterocyclyl group optionally containing one additional heteroatom selected from N, O and S;
or a pharmaceutically acceptable salt thereof.

The present invention also provides methods of preparing the alkynyl substituted pyrimidinyl-pyrrole compounds, represented by formula (I), prepared through a process consisting of standard synthetic transformations.

The present invention also provides a method for treating diseases caused by and/or associated with a dysregulated protein kinase activity, particularly ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, Lck, Lyn, MAPKAPK2, MELK, MET, MNK2, MPS1, MST4, NEK6, NIM1, P38alpha, PAK-4, PDGFR, PDK1, PERK, PIM1, PIM2, PKAalpha, PKCbeta, PLK1, RET, ROS1, SULU1, Syk, TLK2, TRKA, TYK2, VEGFR2, VEGFR3, ZAP70, more particularly JAK and/or Src family kinases, which comprises administering to a mammal in need thereof, more particularly a human, an effective amount of an alkynyl substituted pyrimidinyl-pyrrole compound represented by formula (I) as defined above.

A preferred method of the present invention is to treat a disease caused by and/or associated with a dysregulated protein kinase activity selected from the group consisting of cancer, cell proliferative disorders, viral infections, immune-related disorders, neurodegenerative disorders, cardiovascular diseases and bone related diseases.

Another preferred method of the present invention is to treat specific types of cancer including but not limited to: carcinoma such as bladder, breast, brain, colon, kidney, liver, lung, including small cell lung cancer, head and neck, esophagus, gall-bladder, ovary, uterine, pancreas, stomach, cervix, thyroid, prostate, and skin, including squamous cell carcinoma; hematopoietic tumors of lymphoid lineage including leukaemia, T and B acute lymphoblastic leukemia (ALL), including DS-ALL, B-cell lymphoma, T-cell-lymphoma, Hodgkin's lymphoma, non-Hodgkin's lymphoma, Multiple Myeloma, hairy cell lymphoma, Burkett's lymphoma and mantle cell lymphoma; hematopoietic tumors of myeloid lineage, including acute and chronic myelogenous leukaemias, acute megakaryoblastic leukaemia, myelodysplastic syndrome and promyelocytic leukaemia, myeloproliferative disorders like Polycythemia Vera (PV), Essential Thrombocythemia (ET), Primary myelofibrosis and myelofibrosis secondary to PV and ET, chronic myelomonocytic leukaemia; tumors of mesenchymal origin, including sarcoma, fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer, Kaposi's sarcoma, mesothelioma.

Another preferred method of the present invention is to treat specific types of cell proliferative disorders including but not limited to: benign prostate hyperplasia, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections comprising the prevention of AIDS development in HIV-infected individuals.

A preferred method of the present invention is to treat immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis. Another preferred method of the present invention is to treat neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

Another preferred method of the present invention is to treat cardiovascular diseases including but not limited to: atherosclerosis primary or secondary to diabetes, heart attack and stroke.

Another preferred method of the present invention is to treat bone loss diseases including but not limited to osteoporosis and bone metastasis.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier and/or diluent.

In addition the present invention provides a pharmaceutical composition of a compound of the formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents like anti-HER agents, anti-EGFR agents, anti-Abl, anti-angiogenesis agents (e.g. angiogenesis inhibitors), farnesyl transferase inhibitors, ras-raf signal transduction pathway inhibitors, Akt pathway inhibitors, cell cycle inhibitors, other CDK inhibitors, tubulin binding agents, topoisomerase I inhibitors, topoisomerase II inhibitors, and the like.

The present invention further provides an in vitro method for inhibiting JAK and/or Src family kinase proteins activity which comprises contacting the said protein with an effective amount of a compound of formula (I) as defined above. Additionally, the invention provides a product or kit comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of the formula (I) per se as well as to any pharmaceutical composition thereof or to any therapeutic treatment comprising them, the present invention includes all of the hydrates, solvates, complexes, metabolites, pharmaceutically acceptable prodrugs, pharmaceutically acceptable bio-precursors, carriers, N-oxides and pharmaceutically acceptable salts of the compounds of this invention.

A metabolite of a compound of the formula (I) is any compound into which this same compound of the formula (I) is converted in vivo, for instance upon administration to a mammal in need thereof. Typically, without however representing a limiting example, upon administration of a compound of the formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of the formula (I).

"Pharmaceutically acceptable prodrug" and "pharmaceutically acceptable bio-precursors" are any covalently bonded compounds, which release in vivo the active parent drug according to the formula (I).

The terms "pharmaceutically acceptable prodrug" and "pharmaceutically acceptable bio-precursors" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the active parent drug, according to formula (I), in vivo, for example by hydrolysis in blood. A discussion is provided in T. Higuchi and V. Stella, Pro-drugs as Novel Delivery Systems, Vol. 14 of the A.C.S. Symposium Series, and in Edward B. Roche, Bioreversible Carriers in Drug Design, American Pharmaceutical Association and Pergamon Press, 1987.

N-oxides are compounds of the formula (I) wherein nitrogen and oxygen are tethered through a dative bond. Pharmaceutically acceptable salts of the compounds of the formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of the formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

In the present description, unless otherwise specified, the following terms have the following meanings.

The term "aryl" includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms selected from N, O and S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like.

With the term "heterocyclyl" (also known as "heterocycloalkyl") we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_3$-$C_7$ cycloalkyl", we intend, unless otherwise provided, 3- to 7-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene, cyclohexadiene, cycloeptane, cycloeptene, cycloeptadiene.

With the term "straight or branched $C_2$-$C_6$ alkenyl" we intend any of the groups such as, for instance, vinyl, allyl, 1-propenyl, isopropenyl, 1-butenyl, 2-butenyl, 3-butenyl, 2-pentenyl, 1-hexenyl, and the like.

With the term "straight or branched $C_2$-$C_6$ alkynyl" we intend any of the groups such as, for instance, ethynyl, 2-propynyl, 4-pentynyl, and the like.

According to the present invention and unless otherwise provided, any of the above R1, R2, R3, R4, R5, R6, R7 group may be optionally substituted, in any of their free positions, by one or more groups, for instance 1 to 6 groups, independently selected from: halogen atom, nitro, oxo groups (=O), cyano, $C_1$-$C_6$ alkyl, polyfluorinated alkyl, polyfluorinated alkoxy, alkenyl, alkynyl, hydroxyalkyl, hydroxyalkylamino, hydroxyheterocyclyl, aryl, arylalkyl, heterocyclyl, heterocyclyl-alkyl, $C_3$-$C_7$ cycloalkyl, cycloalkyl-alkyl, alkylaryl, alkyl-heterocyclyl, alkyl-cycloalkyl, alkylaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkyl-amino, hydroxy, alkoxy, aryloxy, heterocyclyloxy, alkyl-heterocyclyoxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclyloxycarbonyl, amino, ureido, alkylamino, aminoalkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, formylamino, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonylamino-alkylamino, alkoxycarbonyl heterocyclyl-alkylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate.

In their turn, whenever appropriate, each of the above substituent may be further substituted by one or more of the aforementioned groups.

In this respect, with the term "halogen atom" we intend a fluorine, chlorine, bromine or iodine atom.

With the term "cyano" we intend a —CN residue.

With the term "nitro" we intend a —NO$_2$ group.

With the term "polyfluorinated alkyl or alkoxy" we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "alkoxy", "cyclyloxy", "aryloxy", "heterocyclyloxy" and derivatives thereof we intend any of the above $C_1$-$C_6$ alkyl, $C_3$-$C_7$ cycloalkyl, aryl or heterocyclyl groups linked to the rest of the molecule through an oxygen atom (—O—). From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_7$ cycloalkyl and heterocyclyl moieties are as above defined.

Preferably, a compound of the formula (I) is characterized in that R1 is ethynyl-R7, R2 is hydrogen, and R3, R4, R5, R6 and R7 are as defined above.

Preferably, a compound of the formula (I) is characterized in that R1 is hydrogen, R2 is ethynyl-R7, and R3, R4, R5, R6 and R7 are as defined above.

More preferably, a compound of the formula (I) is characterized in that R1 is ethynyl-R7, R2 is hydrogen, R3 and R4 are independently hydrogen or an optionally substituted group selected from straight or branched $C_1$-$C_6$ alkyl, $C_3$-$C_7$ cycloalkyl, cycloalkyl-alkyl, aryl, aryl-alkyl, heterocyclyl and heterocyclyl-alkyl, and R5, R6 and R7 are as defined above.

More preferably, a compound of the formula (I) is characterized in that R1 is hydrogen, R2 is ethynyl-R7, R3 and R4 are independently hydrogen or an optionally substituted group selected from straight or branched $C_1$-$C_6$ alkyl, $C_3$-$C_7$ cycloalkyl, cycloalkyl-alkyl, aryl, aryl-alkyl, heterocyclyl and heterocyclyl-alkyl, and R5, R6, and R7 are as defined above.

Even more preferably, a compound of the formula (I) is characterized in that R1 is ethynyl-R7, wherein R7 is an optionally substituted aryl, R2 is hydrogen, and R3, R4, R5 and R6 are as defined above.

Even more preferably, a compound of the formula (I) is characterized in that R1 is hydrogen, R2 is ethynyl-R7, wherein R7 is an optionally substituted aryl, and R3, R4, R5 and R6 are as defined above.

Most preferably, a compound of the formula (I) is characterized in that R1 is ethynyl-R7, wherein R7 is an optionally substituted aryl, R2 is hydrogen, R5 is optionally substituted phenyl, and R3, R4 and R6 are as defined above.

Most preferably, a compound of the formula (I) is characterized in that R1 is hydrogen, R2 is ethynyl-R7, wherein R7 is an optionally substituted aryl, R5 is optionally substituted phenyl, R3, R4 and R6 are as defined above.

Specific, not limiting, preferred compounds (cmpds.) of the invention, whenever appropriate in the form of pharmaceutically acceptable salts, are the following:

5-[2-Amino-5-(phenylethynyl)pyrimidin-4-yl]-2-(5-chloro-2-methylphenyl)-1H-pyrrole-3-carboxamide (compd. 1), 5-{2-Amino-5-[(3-hydroxyphenyl)ethynyl]pyrimidin-4-yl}-2-(5-chloro-2-methylphenyl)-1H-pyrrole-3-carboxamide (compd. 2), 5-{2-Amino-5-[(4-methoxyphenyl)ethynyl]pyrimidin-4-yl}-2-(5-chloro-2-methylphenyl)-1H-pyrrole-3-carboxamide (compd. 3), 5-{2-amino-5-[(3-aminophenyl)ethynyl]pyrimidin-4-yl}-2-(5-chloro-2-methylphenyl)-1H-pyrrole-3-carboxamide (compd. 4), 5-{2-Amino-5-[(2-methoxyphenyl)ethynyl]pyrimidin-4-yl}-2-(5-chloro-2-methylphenyl)-1H-pyrrole-3-carboxamide (compd. 5), 5-{2-Amino-5-[(2-aminophenyl)ethynyl]pyrimidin-4-yl}-2-(5-chloro-2-methylphenyl)-1H-pyrrole-3-carboxamide (compd. 6), 5-{2-Amino-5-[(2,4-difluorophenyl)ethynyl]pyrimidin-4-yl}-2-(5-chloro-2-methylphenyl)-1H-pyrrole-3-carboxamide (compd. 7), 5-{2-Amino-5-[(4-aminophenyl)ethynyl]pyrimidin-4-yl}-2-(5-chloro-2-methylphenyl)-1H-pyrrole-3-carboxamide (compd. 8), 5-{2-Amino-5-[(5-amino-2-methoxyphenyl)ethynyl]pyrimidin-4-yl}-2-(5-chloro-2-methylphenyl)-1H-pyrrole-3-carboxamide (compd. 9), 5-{2-Amino-5-[(4-amino-2-methoxyphenyl)ethynyl]pyrimidin-4-yl}-2-(5-chloro-2-methylphenyl)-1H-pyrrole-3-carboxamide (compd. 10), 5-(2-Amino-5-{[4-(4-methylpiperazin-1-yl)phenyl]ethynyl}pyrimidin-4-yl)-2-(5-chloro-2-methylphenyl)-1H-pyrrole-3-carboxamide (compd. 11), 5-[2-Amino-5-({3-[(1-methylpiperidin-4-yl)amino]phenyl}ethynyl)pyrimidin-4-yl]-2-(5-chloro-2-methylphenyl)-1H-pyrrole-3-carboxamide (compd. 12), 5-(2-Amino-5-{[3-(tetrahydro-2H-pyran-4-ylamino)phenyl]ethynyl}pyrimidin-4-yl)-2-(5-chloro-2-methylphenyl)-1H-pyrrole-3-carboxamide (compd. 13), tert-Butyl (2-{[3-({2-amino-4-[4-carbamoyl-5-(5-chloro-2-methylphenyl)-1H-pyrrol-2-yl]pyrimidin-5-yl}ethynyl)phenyl]amino}ethyl)carbamate (compd. 14), 5-[2-Amino-5-({3-[(2-hydroxyethyl)amino]phenyl}ethynyl)pyrimidin-4-yl]-2-(5-chloro-2-methylphenyl)-1H-pyrrole-3-carboxamide (compd. 15), 5-[2-Amino-5-({4-[(1-methylpiperidin-4-yl)amino]phenyl}ethynyl)pyrimidin-4-yl]-2-(5-chloro-2-methylphenyl)-1H-pyrrole-3-carboxamide (compd. 16), tert-Butyl 3-({[3-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate (compd. 17), 5-(2-Amino-5-{[4-(tetrahydro-2H-pyran-4-ylamino)phenyl]ethynyl}pyrimidin-4-yl)-2-(5-chloro-2-methylphenyl)-1H-pyrrole-3-carboxamide (compd. 18), 5-[2-Amino-5-({4-[(2-hydroxyethyl)amino]phenyl}ethynyl)pyrimidin-4-yl]-2-(5-chloro-2-methylphenyl)-1H-pyrrole-3-carboxamide (compd. 19), tert-Butyl 3-({[4-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate (compd. 20), tert-Butyl (2-{[4-({2-amino-4-[4-carbamoyl-5-(5-chloro-2-methylphenyl)-1H-pyrrol-2-yl]pyrimidin-5-yl}ethynyl)phenyl]amino}ethyl)carbamate (compd. 21), 5-[2-Amino-5-({2-methoxy-5-[(1-methylpiperidin-4-yl)amino]phenyl}ethynyl)pyrimidin-4-yl]-2-(5-chloro-2-methylphenyl)-1H-pyrrole-3-carboxamide (compd. 22), 5-{2-Amino-5-[(4-formylphenyl)ethynyl]pyrimidin-4-yl}-2-(5-chloro-2-methylphenyl)-1H-pyrrole-3-carboxamide (compd. 23), 5-[2-Amino-5-({3-[(4-methylpiperazin-1-yl)methyl]phenyl}ethynyl)pyrimidin-4-yl]-2-(5-chloro-2-methylphenyl)-1H-pyrrole-3-carboxamide (compd. 24), 5-[2-Amino-5-({4-[4-(4-methylpiperazin-1-yl)piperidin-1-yl]phenyl}ethynyl)pyrimidin-4-yl]-2-(5-chloro-2-methylphenyl)-1H-pyrrole-3-carboxamide (compd. 25), 5-[2-Amino-5-({4-[4-(pyrrolidin-1-yl)piperidin-1-yl]phenyl}ethynyl)pyrimidin-4-yl]-2-(5-chloro-2-methylphenyl)-1H-pyrrole-3-carboxamide (compd. 26), 5-[2-Amino-5-({3-[(4-methylpiperazin-1-yl)carbonyl]phenyl}ethynyl)pyrimidin-4-yl]-2-(5-chloro-2-methylphenyl)-1H-pyrrole-3-carboxamide (compd. 27), 5-(2-Amino-5-{[4-(4-hydroxypiperidin-1-yl)phenyl]ethynyl}pyrimidin-4-yl)-2-(5-chloro-2-methylphenyl)-1H-pyrrole-3-carboxamide (compd. 28), 5-[2-Amino-5-({2-methoxy-4-[(1-methylpiperidin-4-yl)amino]phenyl}ethynyl)pyrimidin-4-yl]-2-(5-chloro-2-methylphenyl)-1H-pyrrole-3-carboxamide (compd. 29), 5-{2-Amino-5-[3-(1,1-dioxidothiomorpholin-4-yl)prop-1-yn-1-yl]pyrimidin-4-yl}-2-(5-chloro-2-methylphenyl)-1H-pyrrole-3-carboxamide (compd. 30), 5-[2-Amino-5-({4-[(2S)-2-(pyrrolidin-1-ylmethyl)pyrrolidin-1-yl]phenyl}ethynyl)pyrimidin-4-yl]-2-(5-chloro-2-methylphenyl)-1H-pyrrole-3-carboxamide (compd. 31), 5-[2-Amino-5-({3-[(1-methylpiperidin-4-yl)oxy]phenyl}ethynyl)pyrimidin-4-yl]-2-(5-chloro-2-methylphenyl)-1H-pyrrole-3-carboxamide (compd. 32), N-[3-({2-Amino-4-[4-carbamoyl-5-(5-chloro-2-methylphenyl)-1H-pyrrol-2-yl]pyrimidin-5-yl}ethynyl)-4-methoxyphenyl]-1-methyl piperidine-4-carboxamide (compd. 33), 5-(2-Amino-5-{[2-methoxy-5-(4-methylpiperazin-1-yl)phenyl]ethynyl}pyrimidin-4-yl)-2-(5-chloro-2-methylphenyl)-1H-pyrrole-3-carboxamide (compd. 34), 5-{2-Amino-5-[(5-bromo-2-methoxyphenyl)ethynyl]pyrimidin-4-yl}-2-(5-chloro-2-methylphenyl)-1H-pyrrole-3-carboxamide (compd. 35), 5-[2-Amino-5-(cyclohexylethynyl)pyrimidin-4-yl]-2-(5-chloro-2-methylphenyl)-1H-pyrrole-3-carboxamide (compd. 36), 5-[2-Amino-5-({2-methoxy-4-[(4-methylpiperazin-1-yl)carbonyl]phenyl}ethynyl)pyrimidin-4-yl]-2-(5-chloro-2-methylphenyl)-1H-pyrrole-3-carboxamide (compd. 37), 5-[2-Amino-5-(cyclopropylethynyl)pyrimidin-4-yl]-2-(5-chloro-2-methylphenyl)-1H-pyrrole-3-carboxamide (compd. 38), 5-[2-Amino-5-(3,3-dimethylbut-1-yn-1-yl)pyrimidin-4-yl]-2-(5-chloro-2-methylphenyl)-1H-pyrrole-3-carboxamide (compd. 39), 5-{2-Amino-5-[(4-bromophenyl)ethynyl]pyrimidin-4-yl}-2-(5-chloro-2-methylphenyl)-1H-pyrrole-3-carboxamide (compd. 40), 5-{2-Amino-5-[(4-bromo-2-fluorophenyl)ethynyl]pyrimidin-4-yl}-2-(5-chloro-2-methylphenyl)-1H-pyrrole-3-carboxamide (compd. 41), 5-(2-Amino-5-{[2-fluoro-4-(4-methylpiperazin-1-yl)phenyl]ethynyl}pyrimidin-4-yl)-2-(5-chloro-2-methylphenyl)-1H-pyrrole-3-carboxamide (compd. 42), 5-[2-Amino-5-({2-[(2-hydroxyethyl)amino]phenyl}ethynyl)pyrimidin-4-yl]-2-(5-chloro-2-methylphenyl)-1H-pyrrole-3-carboxamide (compd. 43), 5-{2-Amino-5-[3-(dimethylamino)prop-1-yn-1-yl]pyrimidin-4-yl}-2-(5-chloro-2-methylphenyl)-1H-pyrrole-3-carboxamide (compd. 44), 5-{2-Amino-5-[(2-{[2-(dimethylamino)ethyl]amino}phenyl)ethynyl]pyrimidin-4-yl}-2-(5-chloro-2-methylphenyl)-1H-pyrrole-3-carboxamide (compd. 45), 5-(2-Amino-5-{[2-methoxy-4-(4-methylpiperazin-1-yl)phenyl]ethynyl}pyrimidin-4-yl)-2-(5-chloro-2-methylphenyl)-1H-pyrrole-3-carboxamide (compd. 46), 5-(2-Amino-5-{[3-(4-methylpiperazin-1-yl)phenyl]ethynyl}pyrimidin-4-yl)-2-(5-chloro-2-methylphenyl)-1H-pyrrole-3-carboxamide (compd. 47), 5-[2-Amino-5-({4-[(1-methylpiperidin-4-yl)oxy]phenyl}ethynyl)pyrimidin-4-yl]-2-(5-chloro-2-methylphenyl)-1H-pyrrole-3-carboxamide (compd. 48), 5-(2-Amino-5-{[2-fluoro-5-(4-methylpiperazin-1-yl)phenyl]ethynyl}pyrimidin-4-yl)-2-(5-chloro-2-methylphenyl)-1H-pyrrole-3-carboxamide (compd. 49), 5-{2-Amino-5-[3-(4-methylpiperazin-1-yl)prop-1-yn-1-yl]pyrimidin-4-yl}-2-(5-chloro-2-methylphenyl)-1H-pyrrole-3-carboxamide (compd. 50), 5-(2-Amino-5-{3-[(1-methylpiperidin-4-yl)oxy]prop-1-yn-1-yl}pyrimidin-4-yl)-2-(5-chloro-2-methylphenyl)-1H-pyrrole-3-carboxamide (compd. 51), 5-[2-Amino-5-({2-[(1-methylpiperidin-4-yl)amino]phenyl}ethynyl)pyrimidin-4-yl]-2-(5-chloro-2-methylphenyl)-1H-pyrrole-3-carboxamide] (compd. 52), 5-[2-Amino-5-(pyridin-3-ylethynyl)pyrimidin-4-yl]-2-(5-chloro-2-methylphenyl)-1H-pyrrole-3-carboxamide (compd. 53), 5-[2-Amino-5-(3-hydroxy-3-methylbut-1-yn-1-yl)pyrimidin-4-yl]-2-(5-chloro-2-methylphenyl)-1H-pyrrole-3-carboxamide (compd. 54), 5-[2-Amino-5-(3-hydroxybut-1-yn-1-yl)pyrimidin-4-yl]-2-(5-chloro-2-methylphenyl)-1H-pyrrole-3-carboxamide (compd. 55), 5-(2-Amino-5-{3-[benzyl(methyl)amino]prop-1-yn-1-yl}pyrimidin-4-yl)-2-(5-chloro-2-methylphenyl)-1H-pyrrole-3-carboxamide (compd. 56), 5-[2-Amino-5-(phenylethynyl)pyrimidin-4-yl]-2-(5-chloro-2-methylphenyl)-N-methyl-1H-pyrrole-3-carboxamide (compd. 57), 5-(2-Amino-5-{[4-(4-methylpiperazin-1-yl)phenyl]ethynyl}pyrimidin-4-yl)-2-(5-chloro-2-methylphenyl)-N-methyl-1H-pyrrole-3-carboxamide (compd. 58), 5-[2-Amino-5-({4-[(4-methylpiperazin-1-yl)carbonyl]phenyl}ethynyl)pyrimidin-4-yl]-2-(5-chloro-2-methylphenyl)-1H-pyrrole-3-carboxamide (compd. 59), 5-[2-Amino-5-({4-[4-(dimethylamino)piperidin-1-yl]phenyl}ethynyl)pyrimidin-4-yl]-2-(5-chloro-2-methylphenyl)-1H-pyrrole-3-carboxamide (compd. 60), 5-[2-Amino-5-({3-[(azetidin-3-ylmethyl)amino]phenyl}ethynyl)pyrimidin-4-yl]-2-(5-chloro-2-methylphenyl)-1H-pyrrole-3-carboxamide (compd. 61), 5-[2-Amino-5-({4-[(azetidin-3-ylmethyl)amino]phenyl}ethynyl)pyrimidin-4-yl]-2-(5-chloro-2-methylphenyl)-1H-pyrrole-3-carboxamide (compd. 62), 5-[2-Amino-5-({3-[(2-aminoethyl)amino]phenyl}ethynyl)pyrimidin-4-yl]-2-(5-chloro-2-methylphenyl)-1H-pyrrole-3-carboxamide (compd. 63), 5-{2-Amino-5-[(3-{[(1-methylazetidin-3-yl)methyl]amino}phenyl)ethynyl]pyrimidin-4-yl}-2-(5-chloro-2-methylphenyl)-1H-pyrrole-3-carboxamide (compd. 64), 5-[2-Amino-5-({4-[(4-methylpiperazin-1-yl)methyl] phenyl}ethynyl)pyrimidin-4-yl]-2-(5-chloro-2-methylphenyl)-1H-pyrrole-3-carboxamide (compd. 65), 5-(2-Amino-5-{[4-(pyrrolidin-1-ylmethyl)phenyl] ethynyl}pyrimidin-4-yl)-2-(5-chloro-2-methylphenyl)-1H-pyrrole-3-carboxamide (compd. 66), 5-(2-Amino-5-{[4-(piperidin-1-ylmethyl)phenyl] ethynyl}pyrimidin-4-yl)-2-(5-chloro-2-methylphenyl)-1H-pyrrole-3-carboxamide (compd. 67), 5-(2-Amino-5-ethynylpyrimidin-4-yl)-2-(5-chloro-2-methylphenyl)-1H-pyrrole-3-carboxamide (compd. 68), 5-(2-Amino-pyrimidin-4-yl)-2-(5-chloro-2-methyl-phenyl)-4-phenylethynyl-1H-pyrrole-3-carboxamide (compd. 69), 5-(2-Aminopyrimidin-4-yl)-2-(5-chloro-2-methylphenyl)-4-[(3-hydroxyphenyl)ethynyl]-1H-pyrrole-3-carboxamide (compd. 70), 5-(2-Aminopyrimidin-4-yl)-2-(5-chloro-2-methylphenyl)-4-[(4-methoxyphenyl)ethynyl]-1H-pyrrole-3-carboxamide (compd. 71), 4-[(3-Aminophenyl)ethynyl]-5-(2-aminopyrimidin-4-yl)-2-(5-chloro-2-methylphenyl)-1H-pyrrole-3-carboxamide (compd. 72), 5-(2-Aminopyrimidin-4-yl)-2-(5-chloro-2-methylphenyl)-4-[(2-methoxyphenyl)ethynyl]-1H-pyrrole-3-carboxamide (compd. 73),

[(2-Aminophenyl)ethynyl]-4-(2-Amino-phenylethynyl)-5-(2-amino-pyrimidin-4-yl)-2-(5-chloro-2-methyl-phenyl)-1H-pyrrole-3-carboxamide (compd. 74), 4-[(4-amino-2-methoxyphenyl)ethynyl]-5-(2-aminopyrimidin-4-yl)-2-(5-chloro-2-methylphenyl)-1H-pyrrole-3-carboxamide (compd. 75), 4-[(4-Aminophenyl)ethynyl]-5-(2-amino-pyrimidin-4-yl)-2-(5-chloro-2-methyl-phenyl)-1H-pyrrole-3-carboxamide (compd. 76), 5-(2-Aminopyrimidin-4-yl)-2-(5-chloro-2-methylphenyl)-4-[(2-methylphenyl)ethynyl]-1H-pyrrole-3-carboxamide (compd. 77), 5-(2-Aminopyrimidin-4-yl)-2-(5-chloro-2-methylphenyl)-4-[(4-fluorophenyl)ethynyl]-1H-pyrrole-3-carboxamide (compd. 78), 4-[(5-Amino-2-methoxyphenyl)ethynyl]-5-(2-aminopyrimidin-4-yl)-2-(5-chloro-2-methylphenyl)-1H-pyrrole-3-carboxamide (compd. 79), 5-(2-Aminopyrimidin-4-yl)-2-(5-chloro-2-methylphenyl)-4-({3-[(1-methylpiperidin-4-yl)amino]phenyl}ethynyl)-1H-pyrrole-3-carboxamide (compd. 80), 5-(2-Aminopyrimidin-4-yl)-2-(5-chloro-2-methylphenyl)-4-({3-[(4-methylpiperazin-1-yl)methyl]phenyl}ethynyl)-1H-pyrrole-3-carboxamide (compd. 81), 4-({3-[(2-Aminoethyl)amino]phenyl}ethynyl)-5-(2-aminopyrimidin-4-yl)-2-(5-chloro-2-methylphenyl)-1H-pyrrole-3-carboxamide (compd. 82), 5-(2-Aminopyrimidin-4-yl)-2-(5-chloro-2-methylphenyl)-4-{[4-(4-methylpiperazin-1-yl)phenyl]ethynyl}-1H-pyrrole-3-carboxamide (compd. 83), 5-(2-Aminopyrimidin-4-yl)-2-(5-chloro-2-methylphenyl)-4-({2-[(2-hydroxyethyl)amino]phenyl}ethynyl)-1H-pyrrole-3-carboxamide (compd. 84), 5-(2-Aminopyrimidin-4-yl)-2-(5-chloro-2-methylphenyl)-4-{[2-fluoro-4-(4-methylpiperazin-1-yl)phenyl]ethynyl}-1H-pyrrole-3-carboxamide (compd. 85), 5-(2-Aminopyrimidin-4-yl)-2-(5-chloro-2-methylphenyl)-4-{[2-methoxy-5-(4-methylpiperazin-1-yl)phenyl]ethynyl}-1H-pyrrole-3-carboxamide (compd. 86), 5-(2-Aminopyrimidin-4-yl)-2-(5-chloro-2-methylphenyl)-4-[(2-{[2-(dimethylamino)ethyl]amino}phenyl)ethynyl]-1H-pyrrole-3-carboxamide (compd. 87), 5-(2-Aminopyrimidin-4-yl)-2-(5-chloro-2-methylphenyl)-4-[3-(dimethylamino)prop-1-yn-1-yl]-1H-pyrrole-3-carboxamide carboxamide (compd. 88), 5-(2-Aminopyrimidin-4-yl)-2-(5-chloro-2-methylphenyl)-4-{[2-methoxy-4-(4-methylpiperazin-1-yl)phenyl]ethynyl}-1H-pyrrole-3-carboxamide (compd. 89), 5-(2-Aminopyrimidin-4-yl)-2-(5-chloro-2-methylphenyl)-4-{[3-(4-methylpiperazin-1-yl)phenyl]ethynyl}-1H-pyrrole-3-carboxamide carboxamide (compd. 90), 5-(2-Aminopyrimidin-4-yl)-2-(5-chloro-2-methylphenyl)-4-({3-[(1-methylpiperidin-4-yl)oxy]phenyl}ethynyl)-1H-pyrrole-3-carboxamide (compd. 91), 5-(2-Aminopyrimidin-4-yl)-2-(5-chloro-2-methylphenyl)-4-({4-[(1-methylpiperidin-4-yl)oxy]phenyl}ethynyl)-1H-pyrrole-3-carboxamide (compd. 92), 5-(2-Aminopyrimidin-4-yl)-2-(5-chloro-2-methylphenyl)-4-{[2-fluoro-5-(4-methylpiperazin-1-yl)phenyl]ethynyl}-1H-pyrrole-3-carboxamide (compd. 93), 5-(2-Aminopyrimidin-4-yl)-2-(5-chloro-2-methylphenyl)-4-({2-[(1-methylpiperidin-4-yl)amino]phenyl}ethynyl)-1H-pyrrole-3-carboxamide (compd. 94), 5-(2-Aminopyrimidin-4-yl)-2-(5-chloro-2-methylphenyl)-4-({4-[4-(4-methylpiperazin-1-yl)piperidin-1-yl] phenyl}ethynyl)-1H-pyrrole-3-carboxamide (compd. 95), 5-(2-Aminopyrimidin-4-yl)-2-(5-chloro-2-methylphenyl)-4-({4-[4-(dimethylamino)piperidin-1-yl] phenyl}ethynyl)-1H-pyrrole-3-carboxamide (compd. 96), 5-(2-Aminopyrimidin-4-yl)-4-{[4-(1,4'-bipiperidin-1-yl) phenyl]ethynyl}-2-(5-chloro-2-methylphenyl)-1H-pyrrole-3-carboxamide (compd. 97), 5-(2-Aminopyrimidin-4-yl)-2-(5-chloro-2-methylphenyl)-4-({4-[4-(pyrrolidin-1-yl)piperidin-1-yl]phenyl}ethynyl)-1H-pyrrole-3-carboxamide (compd. 98), 5-(2-Aminopyrimidin-4-yl)-2-(5-chloro-2-methylphenyl)-4-{[4-(piperazin-1-yl)phenyl]ethynyl}-1H-pyrrole-3-carboxamide (compd. 99), 5-(2-Aminopyrimidin-4-yl)-2-(5-chloro-2-methylphenyl)-4-({4-[(4-methylpiperazin-1-yl)carbonyl] phenyl}ethynyl)-1H-pyrrole-3-carboxamide (compd. 100), 5-(2-Aminopyrimidin-4-yl)-2-(5-chloro-2-ethylphenyl)-4-[(2-{[2-(dimethylamino)ethyl]amino}phenyl)ethynyl]-1H-pyrrole-3-carboxamide (compd. 101), 5-(2-Aminopyrimidin-4-yl)-2-(5-chloro-2-ethylphenyl)-4-({3-[(1-methylpiperidin-4-yl)oxy]phenyl}ethynyl)-1H-pyrrole-3-carboxamide (compd. 102), 5-(2-Aminopyrimidin-4-yl)-2-(5-chloro-2-ethylphenyl)-4-{[4-(4-methylpiperazin-1-yl)phenyl]ethynyl}-1H-pyrrole-3-carboxamide (compd. 103), 2-(5-Chloro-2-methylphenyl)-5-[2-(methylamino)-5-{[4-(4-methylpiperazin-1-yl)phenyl]ethynyl}pyrimidin-4-yl]-1H-pyrrole-3-carboxamide (compd. 104), 2-(5-Chloro-2-methylphenyl)-5-(5-{[4-(4-methylpiperazin-1-yl)phenyl]ethynyl}pyrimidin-4-yl)-1H-pyrrole-3-carboxamide (compd. 105), 2-(5-Chloro-2-methylphenyl)-5-(2-methyl-5-{[4-(4-methylpiperazin-1-yl)phenyl]ethynyl}pyrimidin-4-yl)-1H-pyrrole-3-carboxamide (compd. 106), 2-(5-Chloro-2-methylphenyl)-5-[2-(methylamino)pyrimidin-4-yl]-4-{[4-(4-methylpiperazin-1-yl)phenyl]ethynyl}-1H-pyrrole-3-carboxamide (compd. 107), 2-(5-Chloro-2-methylphenyl)-4-{[4-(4-methyl piperazin-1-yl)phenyl]ethynyl}-5-(pyrimidin-4-yl)-1H-pyrrole-3-carboxamide (compd. 108), 2-(5-Chloro-2-methylphenyl)-4-{[4-(4-methyl piperazin-1-yl)phenyl]ethynyl}-5-(2-methylpyrimidin-4-yl)-1H-pyrrole-3-carboxamide (compd. 109), 5-(2-Amino-5-{[4-(4-methyl piperazin-1-yl)phenyl] ethynyl}pyrimidin-4-yl)-2-(5-chloro-2-ethylphenyl)-1H-pyrrole-3-carboxamide (compd. 110), 5-[2-Amino-5-(phenylethynyl)pyrimidin-4-yl]-2-(5-chloro-2-ethylphenyl)-N-methyl-1H-pyrrole-3-carboxamide (compd. 111) and 5-(2-Amino-5-{[4-(4-methyl piperazin-1-yl)phenyl] ethynyl}pyrimidin-4-yl)-2-(5-chloro-2-ethylphenyl)-N-methyl-1H-pyrrole-3-carboxamide (compd. 112).

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

A compound of formula (I) can be prepared according to the general synthetic processes described hereafter in schemes A, B, C, D, E and F.

The reported Scheme A shows the preparation of a compound of formula (I) wherein R1 is ethynyl-R7, R2 is hydrogen, R3, R4, R5, R6 and R7 are as defined above.

Scheme A

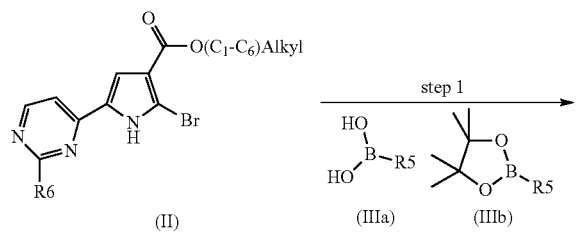

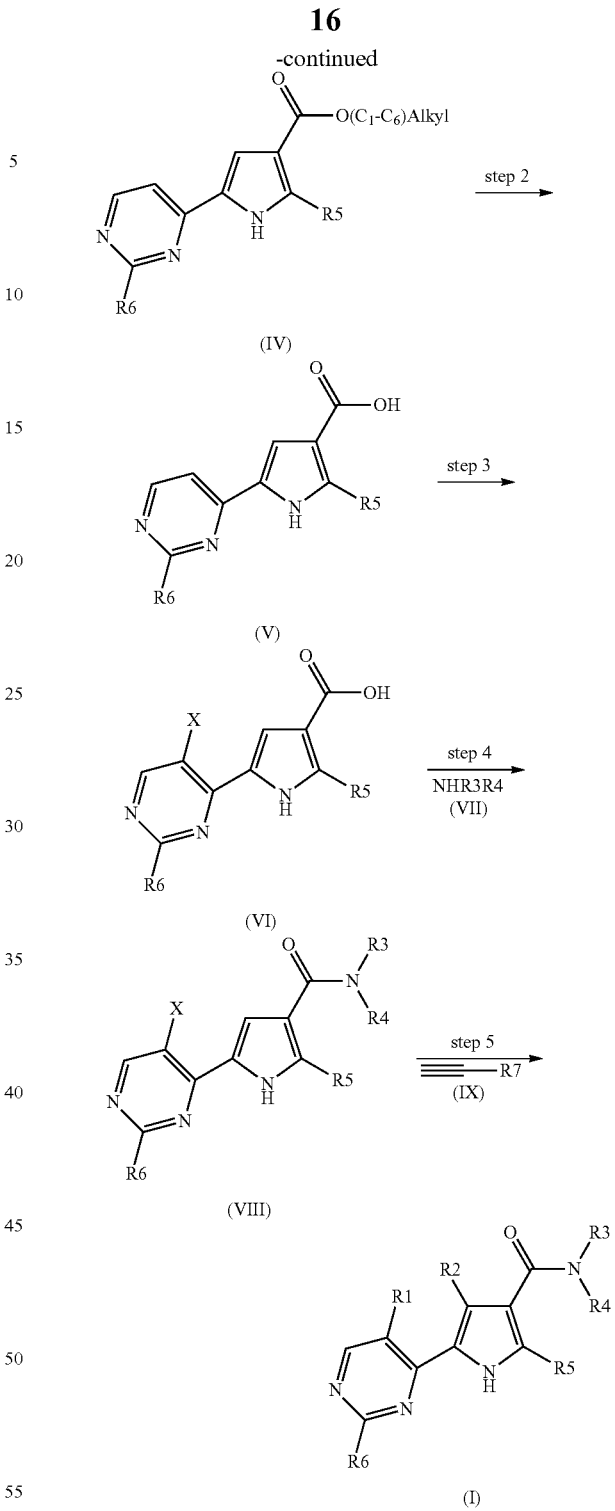

In the above Scheme R1 is ethynyl-R7, R2 is hydrogen, R3, R4, R5, R6 and R7 are as defined above, and X is halogen.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, a process of the present invention comprises the following steps:

Step 1: metal-catalyzed coupling reactions of a halo derivative of formula (II)

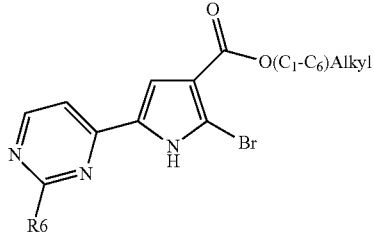
(II)

wherein R6 is as defined above, with an optionally substituted aryl boronic acid of formula (IIIa) or an optionally substituted aryl boronic-ester of formula (IIIb):

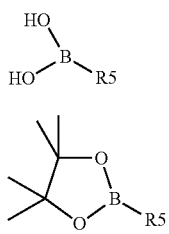
(IIIa)

(IIIb)

wherein R5 is as defined above;

Step 2: hydrolysis under basic conditions of the resultant compound of formula (IV)

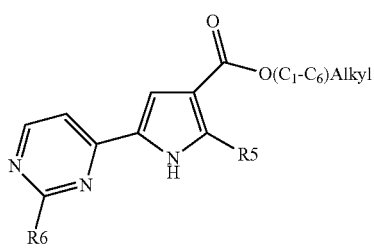
(IV)

wherein R5 and R6 are as defined above;

Step 3: regioselective mono-halogenation of the resultant carboxylic acid of formula (V)

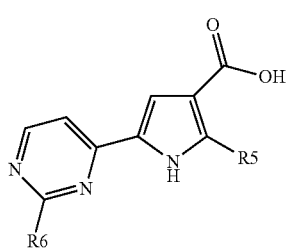
(V)

wherein R5 and R6 are as defined above;

Step 4: amidation of the resultant mono-halogenated carboxylic acid of formula (VI)

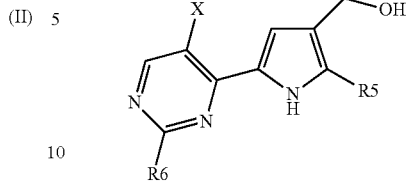
(VI)

wherein R5 and R6 are as defined above and X is an halogen, through reaction with a derivative of formula (VII)

NHR3R4 (VII)

wherein R3 and R4 are as defined above;

Step 5: metal-catalyzed coupling reactions of the resultant mono-halogenated carboxamide of formula (VIII)

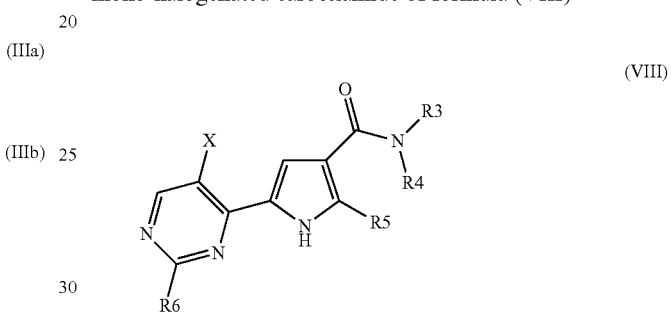
(VIII)

wherein R3, R4, R5 and R6 are as defined above and X is an halogen, through reaction with a derivative of formula (IX):

≡-R7 (IX)

wherein R7 is as defined above, to give a compound of formula (I)

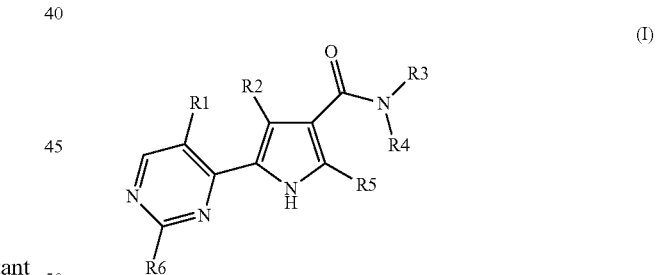
(I)

wherein R1 is ethynyl-R7, R2 is hydrogen, R3, R4, R5, R6 and R7 are as defined above;

optionally converting a compound of the formula (I) into another different compound of the formula (I), and, if desired, converting a compound of the formula (I) into a pharmaceutically acceptable salt thereof or converting a salt into the free compound (I).

According to the Step 1 of Scheme A, the conversion of a halo derivative of general formula (II) into a compound of formula (IV) can be accomplished in a variety of ways. For example a compound of formula (II) can be reacted by metal-catalyzed coupling reactions with an optionally substituted aryl boronic acid of formula (IIIa) or an optionally substituted aryl boronic-ester of formula (IIIb). Preferably, a compound of formula (IV) can be prepared from an intermediate of formula (II) by Pd-catalyzed Suzuki-Miyaura coupling with an optionally substituted aryl boronic acid of formula (IIIa) or an optionally substituted aryl boronic-ester of formula (IIIb). Transition metal-catalyzed couplings of (hetero)aryl halides with aryl boronic acids or boronic-esters are well known to the person skilled in the art, see references: a) Miyaura, Norio; Suzuki, Akira (1979). "Palladium-Catalyzed Cross-Coupling Reactions of Organoboron Compounds". *Chemical reviews* 95 (7): 2457-2483; b) Suzuki, A. In Metal-Catalyzed Cross-Coupling Reactions, Diederich, F., and Stang, P. J., Eds.; Wiley-VCH: New York, 1998, pp. 49-97. In the so called Suzuki-Miyaura reaction, coupling reaction of aryl boronic acids with (hetero)aryl halides is typically triggered by palladium complex. Phosphine-palladium complexes such as tetrakis(triphenylphosphine)palladium(0) are used for this reaction but also bis(triphenylphosphine)palladium(II) chloride, [1,1'-bis(diphenylphosphino) ferrocene] dichloro palladium(II) may be employed. A base such as potassium phosphate, sodium carbonate, cesium carbonate, potassium carbonate, potassium t-butoxide, tetraethyl ammonium hydroxide, triethylamine is added and tetrahydrofurane, dioxane, N,N-dimethylformamide, ethanol and toluene may be used as reaction media. Typically temperatures range from room temperature to 150° C. Conventional heating along with microwave irradiation may be employed. Reaction duration ranges from about 30 min to about 96 hours. Various Pd-catalyst/base/solvent combinations have been described in the literature, which allow the fine-tuning of the reaction conditions in order to allow for a broad set of additional functional groups on both coupling partners.

According to the Step 2 of Scheme A, the hydrolysis of a derivative of formula (IV) into a carboxylic acid of formula (V) can be accomplished in a variety of ways. Typically NaOH or KOH in alcoholic solution is used, at a temperature ranging from room temperature to 150° C., for a time ranging from about 30 min to about 96 hours.

According to the Step 3 of Scheme A, the introduction of halogens on a compound of formula (V) may be carried out in a variety of ways and experimental conditions, which are widely known in the art. The reagents that are commonly employed are: NCS, NBS or NIS in solvents such as DMF, THF, AcOH, TFA; $CF_3COOAg/Br_2$ or $I_2$ in TFA, DMF, acetonitrile; $PhI(OAc)_2$, $I_2$ in DCM; ICl in AcOH. Temperature ranging from about −40° C. to 100° C. and for a period of time varying from about 1 hour to about 24 hours. The most reactive positions towards sources of electrophylic $I^+$, $Br^+$ and $Cl^+$ in a compound of formula (V) are usually position 5' on the pyrimidine ring together with position 4 on the pyrrole ring but regioselective monohalogenation is often achieved by carefully choosing reaction conditions (see, for example: a) Mitchell, R. H.; Lai, Y-Y., Williams, R. V. N-Bromosuccinimide-Dimethylformamide: A Mild, Selective Nuclear Monobromination Reagent for Reactive Aromatic Compounds. *J. Org. Chem.* 1979, 44, 4733. b) Aiello, E.; Dattolo, G.; Cirrincione, G.; Almerico, A. M.; D'Asdia, I. Preparation of monohalopyrroles. *J. Het. Chem.* 1982, 19, 977-979. c) Vanotti E. et al. Regioselective monohalogenation of aminopyrimidinyl-pyrrole carboxylic acid derivatives. Tetr. 2009, 65, 10418-10423). In particular, a methodology was developed in order to introduce a iodine on position 5' of the pyrimidine moiety of a derivative of general formula (V) employing $CF_3COOAg/I_2$ in DMF at low temperature. According to the Step 4 of Scheme A, the conversion of a carboxylic acid of formula (VI) into an amide of formula (VIII) can be accomplished in a variety of ways and experimental conditions, which are widely known in the art for the preparation of carboxamides. As an example, a compound of formula (VI) can be converted into its corresponding acyl chloride in the presence of thionyl chloride or oxalyl chloride, in a suitable solvent, such as toluene, dichloromethane, chloroform, diethyl ether, tetrahydrofuran, dioxane, at a temperature ranging from about −10° C. to reflux and for a period of time varying from about 1 hour to about 96 hours. The acyl chloride can be isolated by evaporation of the solvent and further reacted with 33% ammonium hydroxide solution or with an amine NHR3R4 (VII) in a suitable solvent, such as toluene, dichloromethane, chloroform, diethyl ether, tetrahydrofuran, dioxane, at a temperature ranging from about −10° C. to reflux and for a period of time varying from about 1 hour to about 96 hours. Alternatively, a compound of formula (VI) can be reacted with the ammonium salt of 1-hydroxybenzotriazole or with an amine NHR3R4 (VII) in the presence of a carbodiimide such as dicyclohexyl carbodiimide, diisopropyl carbodiimide, 1-ethyl-3-(3'-dimethylamino)carbodiimide hydrochloric acid salt and hydroxybenzotriazole. Preferably, this reaction is carried out in a suitable solvent such as, for instance, tetrahydrofuran, dichloromethane, toluene, dioxane, N,N-dimethylformamide and in the presence of a proton scavenger such as, for example, triethylamine, N,N-diisopropylethylamine, at a temperature ranging from room temperature to reflux, for a time ranging from about 30 min to about 96 hours.

According to the Step 5 of Scheme A, the transformation of a compound of formula (VIII) into a compound of formula (I) can be accomplished in a variety of ways and experimental conditions, which are widely known in the art. For example compounds (VIII) can be reacted to give compounds of formula (I) by metal-catalyzed coupling reactions with respectively substituted alkynes of general formula (IX). More particularly, compounds of formula (I) can be prepared from intermediates of formula (VIII) by Pd-catalyzed Sonogashira-Hagihara coupling and Sonogashira-type coupling reactions (including Stephen-Castro couplings and Heck-Cassar alkynylations) with alkynes of general formula (IX). Transition metal-catalyzed couplings of (hetero)aryl halides with alkynes are well known to the person skilled in the art (see references: a) Sonogashira, Y. T.; Hagihara, N. *Tetrahedron Lett* 1975, 16, 4467; b) Chinchilla, R.; Najera, C. *Chem. Rev.* 2007, 107, 874). In the so called Sonogashira reaction, coupling reaction of terminal alkynes with (hetero)aryl halides is typically triggered by a zerovalent palladium complex and a halide salt of copper(I). Phosphine-palladium complexes such as tetrakis(triphenylphosphine)palladium(0) are used for this reaction but also bis(triphenylphosphine)palladium (II) chloride may be employed. An amine is added such as triethylamine or diisopropylethylamine and DMF, acetonitrile or even ether may be used as reaction media. Typically temperatures range from room temperature to 150° C. Conventional heating along with microwave irradiation may be employed. Reaction duration ranges from about 30 min to about 96 hours. Various Pd-catalyst/co-catalyst/ligand/base/solvent combinations have been described in the literature, which allow the fine-tuning of the reaction conditions in order to allow for a broad set of additional functional groups on both coupling partners. In addition, recently developed procedures employing for example zinc acetylides, alkynyl magnesium salts or alkynyl trifluoroborate salts further broaden the scope of the reaction.

The present invention further provides an alternative process for the preparation of a compound of formula (I), wherein R1 is ethynyl-R7, R2 is hydrogen, R3, R4, R5, R6 and R7 are as defined above, which is shown in Scheme B below.

Scheme B

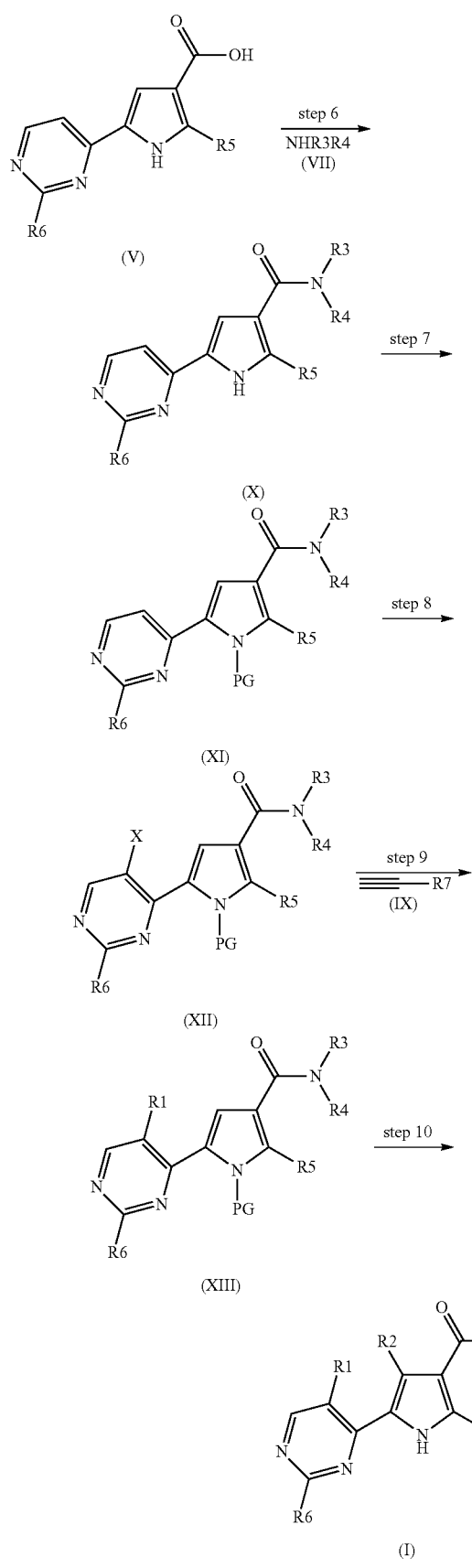

In the above Scheme R1 is ethynyl-R7, R2 is hydrogen, R3, R4, R5, R6 and R7 are as defined above, X is halogen, and PG is a protecting group such as SEM, Boc.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, another process of the present invention comprises the following steps:

Step 6: amidation of the carboxylic acid of formula (V) as defined above, through reaction with an amine of formula (VII) as defined above;

Step 7: regioselective introduction of a protecting group on the pyrrole nitrogen of the resultant carboxamide of formula (X)

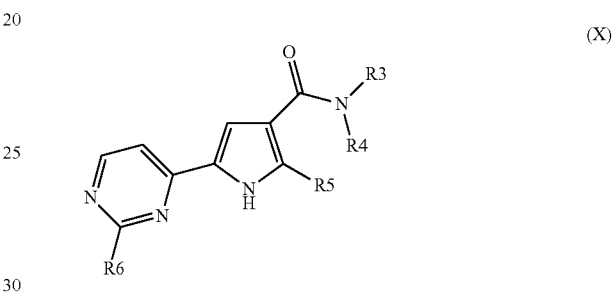

wherein R3, R4, R5 and R6 are as defined above.

Step 8: regioselective mono-halogenation of the resultant protected compound of formula (XI)

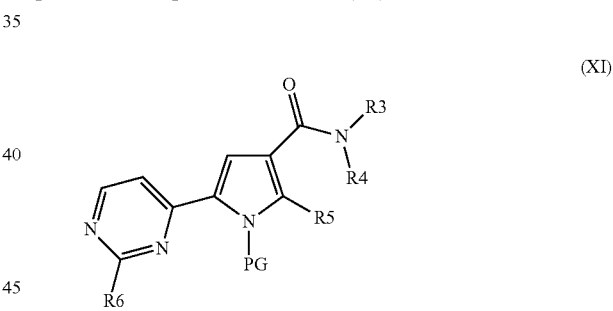

wherein R3, R4, R5 and R6 are as defined above, and PG is a protecting group such as SEM, Boc.

Step 9: metal-catalyzed coupling reaction of the resultant mono-halogenated carboxamide of formula (XII)

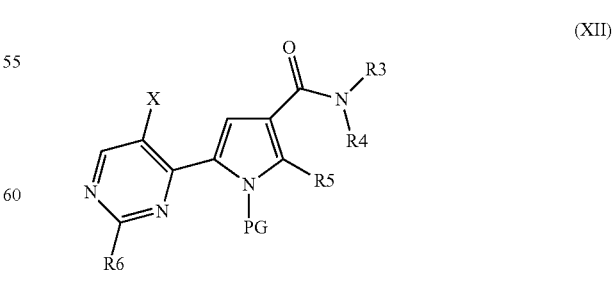

wherein R3, R4, R5, R6 and PG are as defined above, and X is a halogen, through reaction with a derivative of formula (IX) as defined above;

Step 10: deprotection of the resultant compound of formula (XIII)

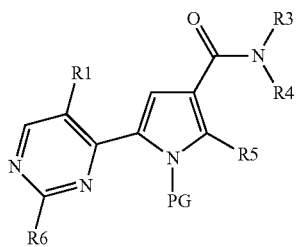

(XIII)

wherein R1 is ethynyl-R7, R3, R4, R5, R6, R7 and PG are as defined above, to give a compound of formula (I)

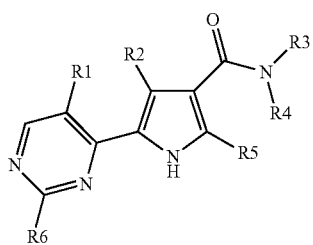

(I)

wherein R1 is ethynyl-R7, R2 is hydrogen, R3, R4, R5, R6 and R7 are as defined above;
optionally converting a compound of the formula (I) into another different compound of the formula (I), and, if desired, converting a compound of the formula (I) into a pharmaceutically acceptable salt thereof or converting a salt into the free compound (1).

According to the Step 6 of Scheme B, the conversion of a carboxylic acid of formula (V) into an amide of formula (X) can be accomplished in a variety of ways and experimental conditions, already described in Step 4 of Scheme A.

According to the Step 7 of Scheme B, the regioselective introduction of the protecting group PG on the pyrrole nitrogen of a compound of general formula (X) is possible by carefully controlling the reaction conditions. A wide set of protecting groups is available, which are well known to the person skilled in the art (see for example Green, Theodora W. and Wuts, Peter G. M.—*Protective Groups in Organic Synthesis*, Third Edition, John Wiley & Sons Inc., New York (NY), 1999; Jolicoeur, B.; Chapman, E. E.; Thommpson, A.; Lubell, W. D. *Tetrahedron* 2006, 62, 11531). Strong bases such as NaH or KH in solvents such as THF, DCM or DMF as well as trialkylamines in DCM or MeCN, sometimes in the presence of DMAP or phase transfer catalysts, are usually employed at temperatures ranging from −40° C. to 50° C. The pyrrole nitrogen reacts then with an activated source of the protecting group such as benzenesulfonyl chloride (BsCl), toluensulfonyl chloride (TsCl), trimethylsilylethylsulfonyl chloride (SESCl), di-tert-butyldicarbonate (Boc)$_2$O, benzyl bromide (BnBr), 2-(trimethylsilyl)ethoxymethyl chloride (SEMCl), triisopropylsilyltrifluoromethane sulfonate (TIPSOTf), 4-methoxy-benzyl chloride and 2,4-dimethoxybenzyl chloride. According to the Step 8 of Scheme B, the monohalogenation of the compound of formula (XI) to give a halo derivative of formula (XII) may be carried out under the variety of conditions already described in Step 3 of Scheme A.

According to the Step 9 of Scheme B, the conversion of the halo derivative of formula (XII) into a compound of formula (XIII) may be carried out under the variety of conditions already described in Step 5 of Scheme A.

According to the Step 10 of Scheme B, the removal of the protecting group PG on the pyrrole ring of a compound of formula (XIII) may be carried out following procedures which are well known in the art (Jolicoeur, B.; Chapman, E. E.; Thommpson, A.; Lubell, W. D. *Tetrahedron* 2006, 62, 11531). Depending on the protecting group of choice, the following conditions may be employed: benzenesulfonyl (Bs) and toluensulfonyl (Ts) groups may be removed with KOH, NaOH, K$_2$CO$_3$, Triton B, magnesium also in the presence of ammonium chloride in solvents such as MeOH, dioxane at temperatures ranging from room temperature to reflux; trimethylsilylethylsulfonyl (SES) group may be removed using TBAF in THF at room temperature; tert-butoxycarbonyl (Boc) may be removed in the presence of TFA in DCM or by Na$_2$CO$_3$ in DME, DMF at a temperature ranging from room temperature to 130° C.; 4-methoxy-benzyl (MB) and 2,4-dimethoxybenzyl (DMB) groups may be removed by exposure to acid in the presence of anisole to trap the benzyl carbonium ion (e.g. 5% H$_2$SO$_4$ TFA, anisole); 2-(trimethylsilyl)ethoxymethyl (SEM) and triisopropylsilyl (TIPS) may be removed with TBAF, HF, Py or TFA in solvents such as THF, DCM at room temperature or below.

The present invention further provides an alternative process for the preparation of a compound of formula (I), wherein R1 is ethynyl or optionally substituted aryl-ethynyl, R2 is hydrogen, R3, R4, R5 and R6 are as defined above, which is shown in Scheme C below.

Scheme C

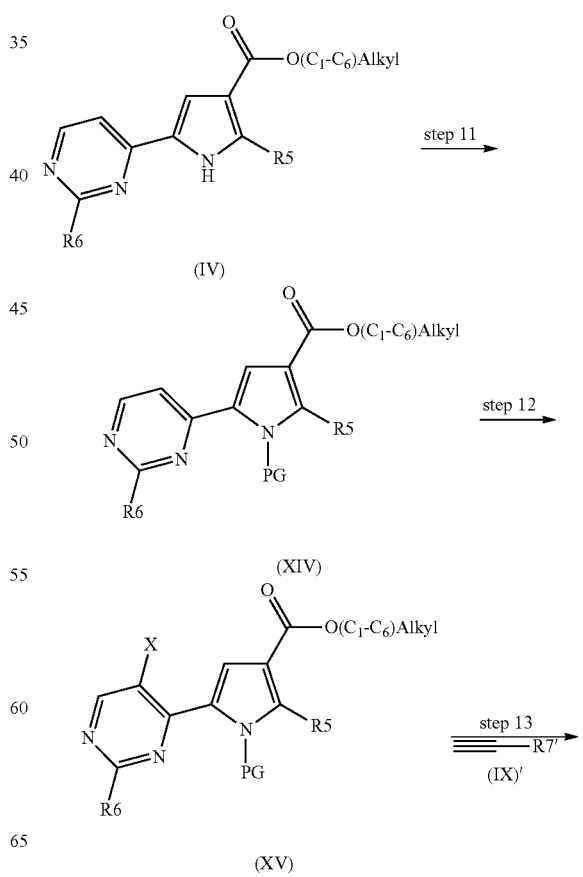

-continued

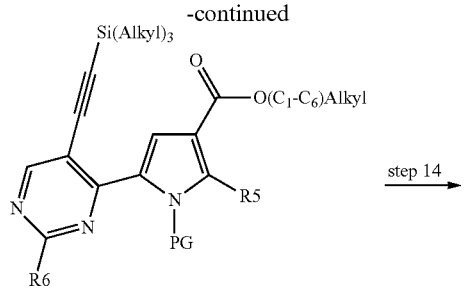

(XVI)

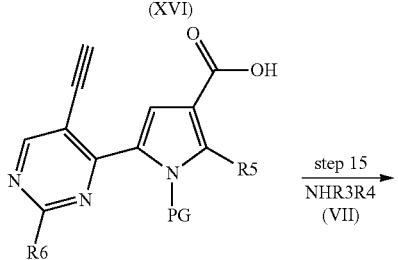

(XVII)

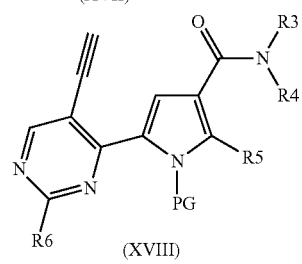

(XVIII)

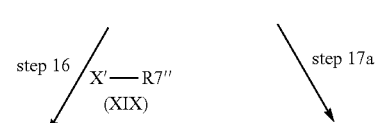

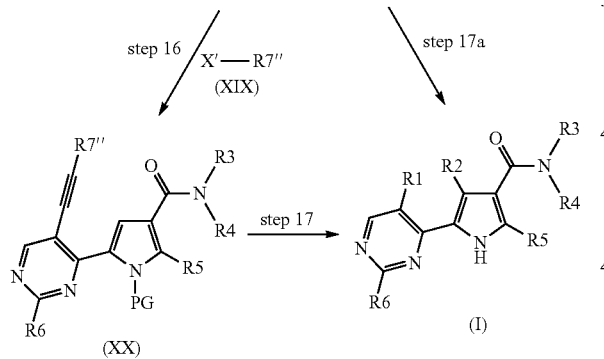

In the above Scheme R1 is ethynyl or optionally substituted aryl-ethynyl, R2 is hydrogen, R3, R4, R5, R6, X and PG are as defined above, R7' is trialkylsylyl, R7" is optionally substituted aryl, and X' is bromine or iodine.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, another process of the present invention comprises the following steps:

Step 11: regioselective introduction of a protecting group on the pyrrole nitrogen of the carboxylic ester of formula (IV) as defined above;

Step 12: regioselective mono-halogenation of the resultant protected carboxylic ester of formula (XIV)

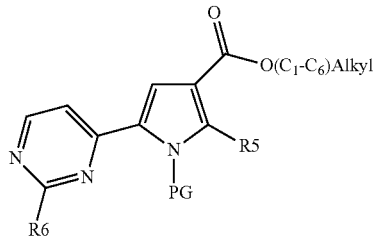

wherein R5, R6 and PG are as defined above;
Step 13: metal-catalyzed coupling reaction of the resultant mono-halogenated carboxylic ester of formula (XV)

(XV)

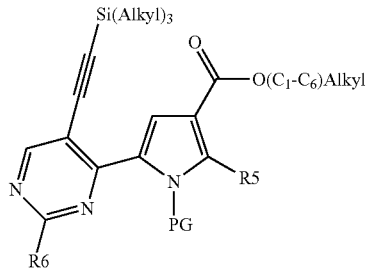

wherein R5, R6, X and PG are as defined above, through reaction with a derivative of formula (IX)

$$\equiv\text{-R7'} \quad \text{(IX)'}$$

wherein R7' is trialkylsylyl;
Step 14: hydrolysis under basic conditions of the resultant trialkylsilyl-protected alkyne of formula (XVI)

(XVI)

wherein R5, R6 and PG are as defined above;
Step 15: amidation of the resultant carboxylic acid of formula (XVII)

(XVII)

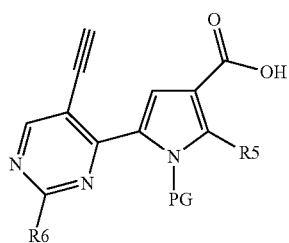

wherein R5, R6 and PG are as defined above, through reaction with an amine derivative of formula (VII) as defined above; either Step 16: metal-catalyzed coupling reaction of the terminal alkyne of the resultant carboxamide of formula (XVIII)

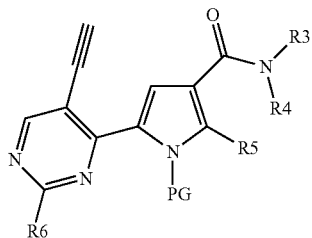
(XVIII)

wherein R3, R4, R5, R6 and PG are as defined above, through reaction with a halo derivative of formula (XIX):

X'—R7"  (XIX)

wherein R7" is an optionally substituted aryl group and X' is bromine or iodine;

Step 17: then deprotection of the resultant compound of formula (XX)

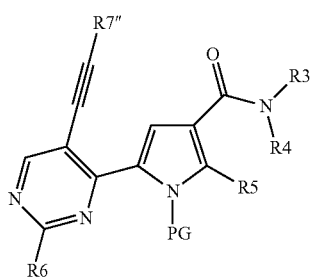
(XX)

wherein R7", R3, R4, R5, R6 and PG are as defined above, to give a compound of general formula (I)

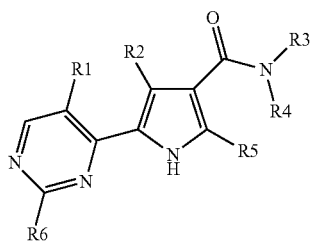
(I)

wherein R1 is optionally substituted arylethynyl, R2 is hydrogen, R3, R4, R5 and R6 are as defined above;
or Step 17a: direct deprotection of the terminal alkyne compound of formula (XVIII) as defined above, to give a compound of general formula (I)

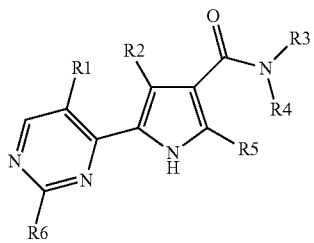
(I)

wherein R1 is ethynyl, R2 is hydrogen, R3, R4, R5 and R6 are as defined above;

optionally converting a compound of the formula (I) into another different compound of the formula (I), and, if desired, converting a compound of the formula (I) into a pharmaceutically acceptable salt thereof or converting a salt into the free compound (I).

According to Step 11 of Scheme C, the regioselective introduction of protecting group PG on the pyrrole nitrogen of a compound of formula (IV) can be accomplished in a variety of ways and experimental conditions, already described in the Step 7 of Scheme B.

According to the Step 12 of Scheme C, the mono-halogenation of a compound of formula (XIV) to give a halo derivative of formula (XV) may be carried out under the variety of conditions already described in Step 3 of Scheme A.

According to the Step 13 of Scheme C, the conversion of a halo derivative of formula (XV) into a compound of formula (XVI) may be carried out under the variety of conditions already described in Step 5 of Scheme A.

According to the Step 14 of Scheme C, the hydrolysis of a derivative of formula (XVI) into a carboxylic acid of formula (XVII) can be accomplished in a variety of ways, already described in Step 2 of Scheme A. In the mean time removal of trialkylsilyl-protecting group occurs.

According to the Step 15 of Scheme C, the conversion of a carboxylic acid of formula (XVII) into an amide of formula (XVIII) can be accomplished in a variety of ways and experimental conditions, already described in Step 4 of Scheme A.

According to the Step 16 of the Scheme C, metal-catalyzed coupling reactions of terminal alkynes of general formula (XVIII) with optionally substituted aryl halides of formula (XIX) may be carried out under the variety of conditions already described in Step 5 of Scheme A.

According to the Step 17 of Scheme C, the removal of the protecting group PG on the pyrrole ring of a compound of general formula (XX) may be carried out following procedures already described in Step 10 of Scheme B.

According to the Step 17a of Scheme C, the removal of the protecting group PG on the pyrrole ring of a compound of general formula (XVIII) may be carried out following procedures already described in Step 10 of Scheme B.

The present invention further provides an alternative process for the preparation of a compound of formula (I) wherein R1 is amino-aryl-ethynyl, R2 is hydrogen, R3, R4, R5 and R6 are as defined above, which is shown in Scheme D below.

Scheme D

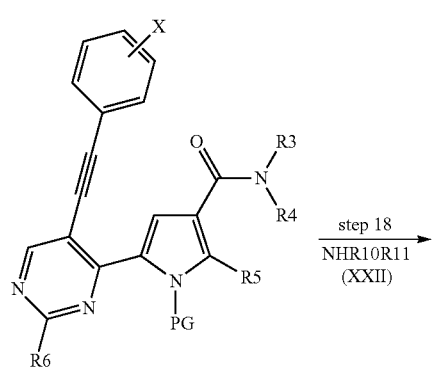

(XXI)

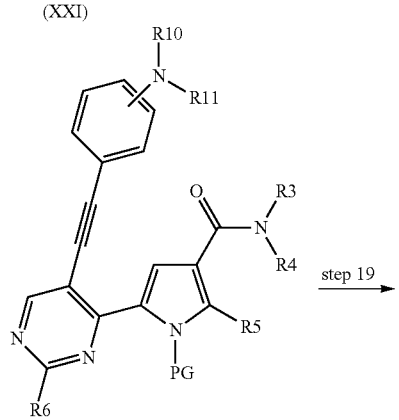

(XXIII)

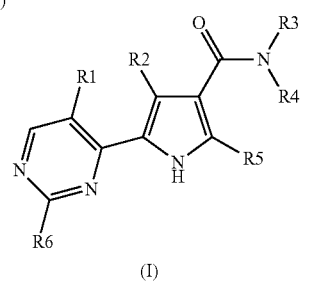

(I)

In the above Scheme R1 is amino-aryl-ethynyl, R2 is hydrogen, R3, R4, R5, R6, X and PG are as defined above, and R10 and R11 are independently hydrogen or an optionally substituted group selected from straight or branched $C_1$-$C_6$ alkyl, $C_3$-$C_7$ cycloalkyl, cycloalkyl-alkyl, heterocyclyl and heterocyclyl-alkyl, or R10 and R11, taken together with the nitrogen atom to which they are bonded, may form an optionally substituted 5 to 7 membered heterocyclyl group optionally containing one additional heteroatom selected from N, O and S.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, another process of the present invention comprises the following steps:

Step 18: metal-catalyzed coupling reaction of a halo derivative of formula (XXI)

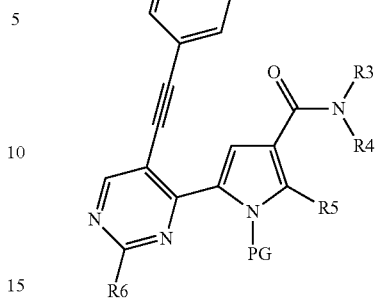

wherein R3, R4, R5, R6, X and PG are as defined above, through reaction with a derivative of formula (XXII)

NHR10R11 (XXII)

wherein R10 and R11 are independently hydrogen or an optionally substituted group selected from straight or branched $C_1$-$C_6$ alkyl, $C_3$-$C_7$ cycloalkyl, cycloalkyl-alkyl, heterocyclyl and heterocyclyl-alkyl, or R10 and R11, taken together with the nitrogen atom to which they are bonded, may form an optionally substituted 5 to 7 membered heterocyclyl group optionally containing one additional heteroatom selected from N, O and S;

Step 19: deprotection of the resultant compound of formula (XXIII)

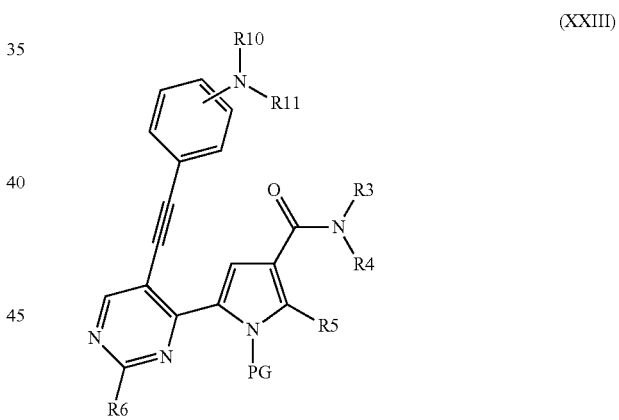

wherein R3, R4, R5, R6, R10, R11 and PG are as defined above, to give a compound of general formula (I)

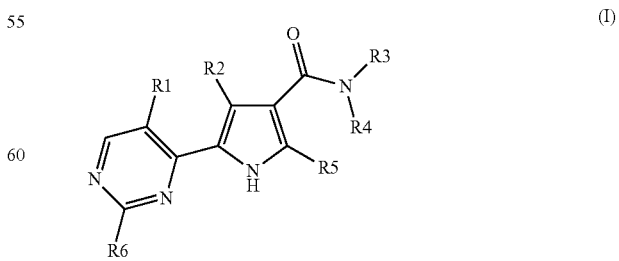

wherein R1 is amino-aryl-ethynyl, R2 is hydrogen, R3, R4, R5 and R6 are as defined above;

optionally converting a compound of the formula (I) into another different compound of the formula (I), and, if desired, converting a compound of the formula (I) into a pharmaceutically acceptable salt thereof or converting a salt into the free compound (I).

According to the Step 18 of Scheme D, metal-catalyzed coupling reactions of a halo derivative of formula (XXI) with an amine of formula NHR10R11 (XXII) may be carried out in a suitable solvent such as THF or dioxane, and in the presence of catalytic amounts of Pd₂(dba)₃, 2-dicyclohexylphosphino-2'-(N,N-dimethylamino)-biphenyl and a base such as LiN(TMS)₂ at a temperature ranging from room temperature to reflux and for a time ranging from 1 to about 24 hours.

According to the Step 19 of Scheme D, the removal of the protecting group PG on the pyrrole ring of a compound of formula (XXIII) may be carried out following procedures already described in Step 10 of Scheme B.

The present invention further provides an alternative process for the preparation of a compound of formula (I) wherein R1 is hydrogen, R2 is ethynyl-R7, R3, R4, R5 and R6 are as defined above, which is shown in Scheme E below.

Step 20: regioselective mono-halogenation of a compound of formula (X) as defined above;

Step 21: metal-catalyzed coupling reaction of the resultant halo derivative of formula (XXIV)

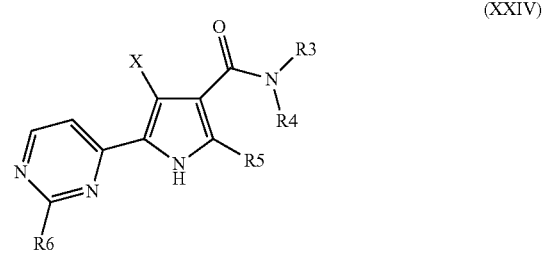

wherein R3, R4, R5, R6 and X are as defined above, through reaction with a derivative of formula (IX) as defined above, to give a compound of formula (I)

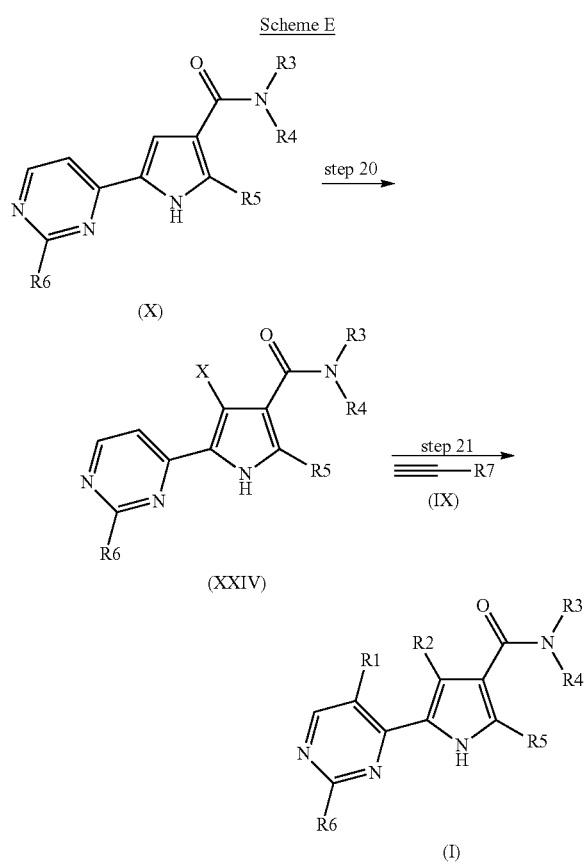

wherein R1 is hydrogen, R2 is ethynyl-R7, R3, R4, R5, R6 and R7 are as defined above;

optionally converting a compound of formula (I) into another different compound of formula (I), and, if desired, converting a compound of formula (I) into a pharmaceutically acceptable salt thereof or converting a salt into the free compound of formula (I).

According to the Step 20 of Scheme E, the introduction of halogens on a compound of formula (X) may be carried out in a variety of ways and experimental conditions, already described in the Step 3 of Scheme A.

According to the Step 21 of Scheme E, the conversion of a halo derivative of general formula (XXIV) into a compound of formula (I) may be carried out under the variety of conditions already described in Step 5 of Scheme A.

The present invention further provides an alternative process for the preparation of a compound of formula (I) wherein R1 is ethynyl-R7, R2 is hydrogen, R3, R4, R5, R6 and R7 are as defined above, which is shown in Scheme F below.

In the above scheme R1 is hydrogen, R2 ethynyl-R7, and R3, R4, R5, R6, R7 and X are as defined above.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, another process of the present invention comprises the following steps:

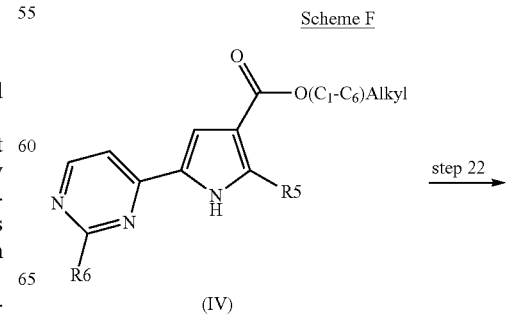

-continued

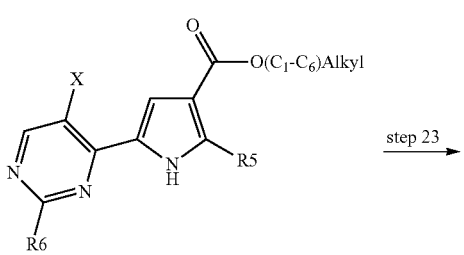

(XXV)

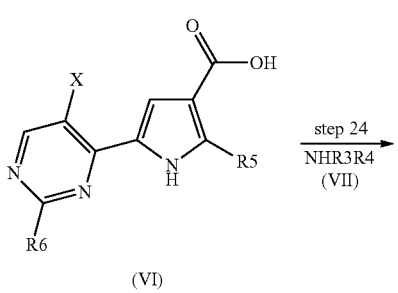

(VI)

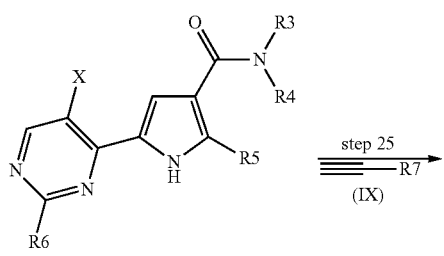

(VIII)

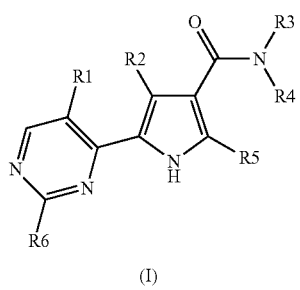

(I)

In the above Scheme R1 is ethynyl-R7, R2 is hydrogen, R3, R4, R5, R6 and R7 are as defined above, and X is halogen.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, another process of the present invention comprises the following steps:

Step 22: regioselective mono-halogenation of the carboxylic ester of formula (IV) as defined above;

Step 23: hydrolysis under basic conditions of the resultant compound of formula (XXV)

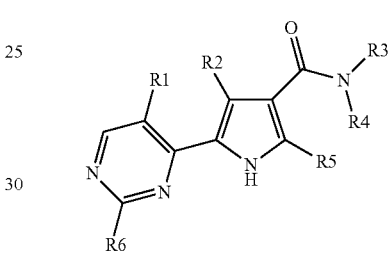

wherein R5 and R6 are as defined above and X is a halogen;

Step 24: amidation of the resultant mono-halogenated carboxylic acid of formula (VI) as defined above through reaction with a derivative of formula (VII) as defined above;

Step 25: metal-catalyzed coupling reactions of the resultant mono-halogenated carboxamide of formula (VIII) as defined above through reaction with a derivative of formula (IX) as defined above to give a compound of formula (I)

(I)

wherein R1 is ethynyl-R7, R2 is hydrogen, R3, R4, R5, R6 and R7 are as defined above;

optionally converting a compound of formula (I) into another different compound of formula (I), and, if desired, converting a compound of formula (I) into a pharmaceutically acceptable salt thereof or converting a salt into the free compound of formula (I).

According to the Step 22 of Scheme F, the mono-halogenation of a compound of formula (IV) to give a halo derivative of formula (XXV) may be carried out under the variety of conditions already described in Step 3 of Scheme A.

According to the Step 23 of Scheme F, the hydrolysis of a derivative of formula (XXV) into a carboxylic acid of formula (VI) can be accomplished in a variety of ways, already described in Step 2 of Scheme A.

According to the Step 24 of Scheme F, the conversion of a carboxylic acid of formula (VI) into an amide of formula (VIII) can be accomplished in a variety of ways and experimental conditions, already described in Step 4 of Scheme A.

According to the Step 25 of the Scheme F, metal-catalyzed coupling reactions of terminal alkynes of general formula (IX) with optionally substituted aryl halides of formula (VIII) may be carried out under the variety of conditions already described in Step 5 of Scheme A.

As indicated above, a compound of formula (I) which is prepared according to the processes object of the invention, can be conveniently converted into another compound of formula (I) by operating according to well-known synthetic conditions, the following being examples of possible conversions:

Conv. a) converting a compound of formula (I) wherein an amino group is protected as a Boc derivative into the corresponding compound of formula (I) wherein the amino group is free, by hydrolysis of the Boc group;

Conv. b) converting a compound of formula (I), wherein a primary or secondary amino substituent is present, into the corresponding compound of formula (I), by reaction with a suitable aldehyde or ketone in the presence of a reducing agent;

Conv. c) converting a compound of formula (I), wherein a substituent like CH=O is present, into the corresponding compound of formula (I) wherein such substituent is CH$_2$NR10R11 group, wherein R10 and R11 are defined above, by reaction with a suitable primary or secondary amine in the presence of a reducing agent:

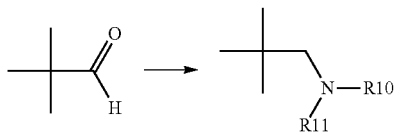

From all of the above it is clear to the skilled person that any compound of the formula (I) bearing a functional group which can be further derivatized to another functional group, by working according to methods well known in the art thus leading to other compounds of the formula (I), is intended to be comprised within the scope of the present invention.

Needless to say, also any of the intermediates of the above described processes could be converted into a different intermediate, if wanted and necessary, by operating in an analogous way as in any one of the conversion reaction here above described.

From all of the above, it is clear to the skilled person that when preparing the compounds of the formula (I) according to any one of the aforementioned process variants, optional functional groups within the starting materials or the intermediates thereof that could give rise to unwanted side reactions, need to be properly protected according to conventional techniques. Likewise, the conversion of these latter into the free deprotected compounds may be carried out according to known procedures.

As it will be readily appreciated, if the compounds of the formula (I) prepared according to the process described above are obtained as mixture of isomers, their separation using conventional techniques into the single isomers of the formula (I), is within the scope of the present invention.

The final compounds may be isolated and purified using conventional procedures, for example chromatography and/or crystallization and salt formation.

The carboxamides of the formula (I) as defined above can be converted into pharmaceutically acceptable salts. The carboxamides of the formula (I) as defined above, or the pharmaceutically acceptable salts thereof, can be subsequently formulated with a pharmaceutically acceptable carrier or diluent to provide a pharmaceutical composition.

The synthesis of a compound of formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resultant from the two or more steps is isolated and purified.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—*Enantiomers, Racemates, and Resolutions*, John Wiley & Sons Inc., New York (NY), 1981.

According to any variant of the process for preparing the compounds of the formula (I), the starting materials and any other reactants are known or easily prepared according to known methods.

The starting materials of the formula (II) can be prepared as described in WO2007/110344.

The compounds of the formula (IIIa), (IIIb), (VII), (IX), (IX)', (X), (XIX) and (XXII) are either commercially available or can be prepared with known methods; the compounds of the formula (IIIa) can also be prepared as described in the experimental part below (Preparation A); the compounds of the formula (IX) can also be prepared as described in the experimental part below (Preparations B to P); the compounds of the formula (X) can also be prepared as described in the experimental part below (Preparations Q).

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of the formula (I) may be used sequentially with known anticancer agents when a combination formulation is inappropriate.

The compounds of the formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of the formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of the formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

Experimental Section

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

General Purification and Analytical Methods

The synthetic preparation of some compounds of the formula (I) of the invention is described in the following examples. The compounds of the present invention, as prepared according to the following examples, were also characterized by $^1$H NMR and/or by Exact mass data ESI(+).

$^1$H-NMR spectrometry was performed on a Mercury VX 400 operating at 400.45 MHz equipped with a 5 mm double resonance probe [$^1$H (15N-31P) ID_PFG Varian]. ESI(+) high resolution mass spectra (HRMS) were obtained on a Waters Q-T of Ultima directly connected with micro HPLC 1100 Agilent as previously described (M. Colombo, F. Riccardi-Sirtori, V. Rizzo, *Rapid Commun. Mass Spectrom.* 2004, 18, 511-517). Column chromatography was conducted either under medium pressure on silica (Merck silica gel 40-63 μm) or on prepacked silica gel cartridges (Biotage). Components were visualized by UV light (λ: 254 nm) and by iodine vapor. HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was water/acetonitrile (5:95). Gradient from 10 to 90% B in 8 minutes, hold 90% B 2 minutes. UV detection at 220 nm and 254 nm. Flow rate 1 mL/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 μm) column or on a Waters X Terra RP 18 (30×150 mm, 5 μm) column using a Waters preparative HPLC 600 equipped with a 996 Waters PDA detector and a Micromass mod. ZQ single quadrupole mass spectrometer, electron spray ionization, positive mode.

Method 1: Phase A: 0.1% TFA/ACN 95/5; phase B: ACN/H$_2$O 95/5. Gradient from 10 to 90% B in 8 min, hold 90% B 2 min; flow rate 20 mL/min.

Method 2: Phase A: 0.05% NH$_4$OH/ACN 95/5; Phase B: ACN/H$_2$O 95/5. Gradient from 10 to 100% B in 8 min, hold 100% B 2 min. Flow rate 20 mL/min.

In the examples below as well as throughout the application, the following abbreviations have the following meanings. If not defined, the terms have their generally accepted meanings.

ABBREVIATIONS

ACN acetonitrile
AcOH acetic acid
CuI copper(I) iodide
DCM dichloromethane
DIAD di-iso-propyl azadicarboxylate
DIPEA N,N-diisopropyethylamine
DMF N,N-dimethylformamide
DMSO dimethyl sulfoxide
eq equivalents
ESI electrospray ionization
EtOAc ethyl acetate
EDCl N-ethyl-N,N-diisopropyl carbodiimide hydrochloride
Et$_2$O diethyl ether
EtOH ethanol
g gram(s)
h hour(s)
HCl hydrochloric acid
HOBT 1-hydroxybenzotriazole
HOBT.NH$_3$ 1H-benzotriazol-1-ol ammonium salt
HPLC high performance liquid chromatography
K$_2$CO$_3$ potassium carbonate
K$_3$PO$_4$ potassium phosphate
KOH potassium hydroxide
$^t$BuOK potassium tert-butoxide
LiCl lithium chloride
LiHMDS lithium hexamethyldisilazide
M molar
MeOH methanol
MeNH$_2$ methylamine
mg milligram(s)
min minutes
mL milliliter(s)
mmol millimole(s)
mol mol(s)
N normal NaCl sodium chloride
Na$_2$CO$_3$ sodium carbonate
Na$_2$S$_2$O$_3$ sodium thiosulfate
Na$_2$SO$_4$ sodium sulfate
NaH sodium hydride
NaHCO$_3$ sodium hydrogen carbonate
NaOH sodium hydroxide
NH$_4$Cl ammonium chloride
NH$_4$OH ammonium hydroxide
Pd$_2$(dba)$_3$ tris(dibenzylideneacetone)dipalladium(0)
Pd(PPh$_3$)$_2$Cl$_2$ bis(triphenylphosphine)-palladium(II)chloride
Pd(dppf)Cl$_2$ [1,1'-bis(diphenylphosphino)ferrocene]palladium(11)chloride
Ph$_3$P triphenylphosphine
rt room temperature
SnCl$_2$ tin(II) chloride
TBAF tetrabutyl ammonium fluoride
TEA triethylamine
TFA trifluoroacetic acid
THF tetrahydrofurane
μL microliter(s)

EXAMPLES

Preparation of a Compound of Formula (IIIa)

Preparation A (5-Chloro-2-ethylphenyl)boronic acid

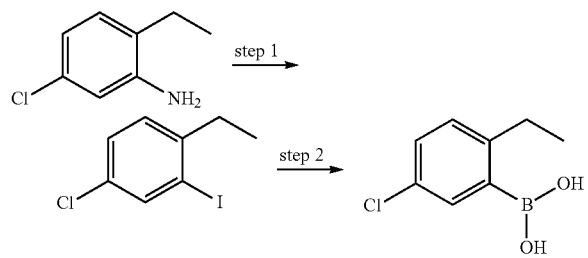

Step 1: 4-Chloro-1-ethyl-2-iodobenzene

A mixture of 5-chloro-2-ethylaniline (3.35 g, 21.5 mmol), p-toluensulfonic acid (12.29 g, 64.6 mmol) and water (2.15 mL) were ground in a mortar for few minutes, to obtain a homogeneous paste to which solid sodium nitrite (3.71 g, 53.8 mmol) was added and the paste ground for 10 min. Solid potassium iodide (8.94 g, 53.8 mmol) was added and the paste ground for 20 min. The paste was then dissolved in water (50 mL) and treated with sodium sulfite (10% aq. sol.), before being extracted with EtOAc (3×100 mL). The combined organic layers were dried over sodium sulfate and the crude was purified by flash chromatography (hexane) to obtain the title compound as a light-yellow oil (4.35 g, 76%).

$^1$H NMR (400 MHz, DMSO-d$_6$) δ ppm 1.12 (t, J=7.51 Hz, 3H), 2.66 (q, J=7.53 Hz, 2H), 7.29-7.35 (m, 1H), 7.42 (dd, J=8.30, 2.20 Hz, 1H), 7.87 (d, J=2.20 Hz, 1H).

Step 2: (5-Chloro-2-ethylphenyl)boronic acid i-Propylmagnesium chloride (2M in THF, 8.98 mL, 17.95 mmol) was added drop wise to a solution of 4-chloro-1-ethyl-2-iodobenzene (4.35 g, 16.3 mmol) in dry THF (40 mL) at −30° C. and the reaction mixture was stirred at the same temperature for 30 min, under argon. After this time, trimethylborate (3.63 mL, 32.6 mmol) was added drop wise and the reaction mixture was stirred at the same temperature for 1.5 h. HCl (1 M, 16 mL) was added and the reaction mixture extracted with EtOAc (3×50 mL). The combined organic layers were dried over sodium sulfate and, after removal of the solvent, a solid was obtained, which was triturated with hexane to obtain the title compound as a white solid (2.15 g, 72%).

$^1$H NMR (400 MHz, DMSO-d$_6$) δ 1.12 ppm (t, J=7.51 Hz, 3H), 2.72 (q, J=7.69 Hz, 2H), 7.17 (d, J=8.18 Hz, 1H), 7.25-7.32 (m, 1H), 7.36 (d, J=2.32 Hz, 1H), 8.19 (s, 2H).

Preparation of a Compound of Formula (IX)

Preparation B

N-(3-Ethynylphenyl)-1-methylpiperidin-4-amine

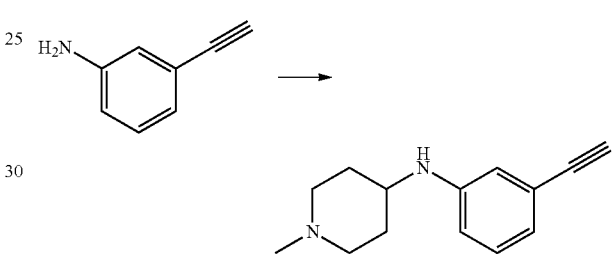

3-Ethynyl-phenylamine (0.1 mL, 1 mmol) and 1-methylpiperidin-4-one (0.15 mL, 1.2 mmol) in 1,4-dioxane (4 mL) was treated first with TFA (0.2 mL, 2.6 mmol) and then with sodium triacetoxyborohydride (318 mg, 1.5 mmol). After stirring for 2 h, 10% NH$_4$OH was added to the reaction mixture (15 mL). Extraction with DCM (3×25 mL), drying over sodium sulfate, evaporation, purification by flash chromatography over silica gel (DCM/7N NH$_3$ in MeOH 9/1) afforded the title compound (200 mg, 93%).

$^1$H NMR (400 MHz, DMSO-d$_6$) δ ppm 1.28-1.45 (m, 2H) 1.85 (d, J=12.57 Hz, 2H) 2.02 (t, J=10.50 Hz, 2H) 2.17 (s, 3H) 2.72 (d, J=11.72 Hz, 2H) 3.07-3.21 (m, 1H) 3.98 (s, 1H) 5.59 (d, J=8.06 Hz, 1H) 6.59 (t, J=8.18 Hz, 2H) 6.62-6.65 (m, 2H) 7.04 (t, J=7.81 Hz, 1H).

The above procedure using suitable aldehydes or ketones and amines was employed to synthesize the following compounds:

N-(3-Ethynylphenyl)tetrahydro-2H-pyran-4-amine $^1$H NMR (400 MHz, DMSO-d$_6$) δ ppm 1.24-1.39 (m, 2H) 1.74-1.88 (m, 2H) 3.38 (td, J=10.99, 1.83 Hz, 2H) 3.54 (s, 1H) 3.76-3.87 (m, 2H) 5.64 (d, J=8.06 Hz, 1H) 6.57 (dt, J=7.51, 1.07 Hz, 1H) 6.59-6.62 (m, 1H) 6.62-6.66 (m, 1H) 7.02 (t, J=7.81 Hz, 1H).

tert-Butyl {2-[(3-ethynylphenyl)amino]ethyl}carbamate $^1$H NMR (400 MHz, DMSO-d$_6$) δ ppm 1.38 (s, 9H) 3.06 (bs, 4H) 3.98 (s, 1H) 5.77 (bs, 1H) 6.55-6.65 (m, 3H) 6.84 (bs, 1H) 7.06 (t, J=8.00 Hz, 1H).

N-(2-{[tert-butyl(dimethyl)silyl]oxy}ethyl)-3-ethynylaniline

¹H NMR (400 MHz, DMSO-d$_6$) δ ppm 0.02 (s, 6H) 0.86 (s, 9H) 3.13 (q, J=5.82 Hz, 2H) 3.69 (t, J=6.04 Hz, 2H) 3.97 (s, 1H) 5.69 (t, J=6.04 Hz, 1H) 6.58-6.64 (m, 2H) 6.64-6.67 (m, 1H) 7.05 (t, J=7.81 Hz, 1H).

N-(4-Ethynylphenyl)-1-methylpiperidin-4-amine

¹H NMR (400 MHz, DMSO-d$_6$) δ ppm 1.29-1.47 (m, 2H) 1.85 (d, J=11.84 Hz, 2H) 2.01 (t, J=11.35 Hz, 2H) 2.17 (s, 3H) 2.72 (d, J=11.72 Hz, 2H) 3.08-3.24 (m, 1H) 3.76 (s, 1H) 5.89 (d, J=7.93 Hz, 1H) 6.52 (d, J=8.67 Hz, 2H) 7.15 (d, J=8.67 Hz, 2H).

tert-Butyl 3-{[(3-ethynylphenyl)amino]methyl}azetidine-1-carboxylate

¹H NMR (400 MHz, DMSO-d$_6$) δ ppm 1.37 (s, 9H) 2.65-2.78 (m, 1H) 3.19 (d, J=7.20 Hz, 2H) 3.53 (m, 2H) 3.89 (m, 2H) 3.99 (s, 1H) 5.88 (bs, 1H) 6.56-6.68 (m, 3H) 7.01-7.11 (m, 1H).

N-(4-Ethynylphenyl)tetrahydro-2H-pyran-4-amine

¹H NMR (400 MHz, DMSO-d$_6$) δ ppm 1.36 (dddd, J=12.82, 11.20, 10.89, 4.39 Hz, 2H) 1.80-1.90 (m, 2H) 3.40 (td, J=11.47, 2.20 Hz, 2H) 3.41-3.51 (m, 2H) 3.77 (s, 1H) 3.85 (dt, J=11.38, 3.52 Hz, 2H) 5.96 (d, J=7.81 Hz, 1H) 6.56 (d, J=8.79 Hz, 2H) 7.16 (d, J=8.67 Hz, 2H).

N-(2-{[tert-Butyl(dimethyl)silyl]oxy}ethyl)-4-ethynylaniline

¹H NMR (400 MHz, DMSO-d$_6$) δ ppm 0.02 (s, 6H) 0.85 (s, 9H) 3.16 (q, J=6.10 Hz, 2H) 3.69 (t, J=6.04 Hz, 2H) 3.78 (s, 1H) 5.97 (t, J=5.98 Hz, 1H) 6.54 (d, J=8.67 Hz, 2H) 7.16 (d, J=8.67 Hz, 2H).

tert-Butyl 3-{[(4-ethynylphenyl)amino]methyl}azetidine-1-carboxylate

¹H NMR (400 MHz, DMSO-d$_6$) δ ppm 1.37 (s, 9H) 2.68-2.80 (m, 1H) 3.22 (m, J=12.94 Hz, 2H) 3.53 (br. s., 2H) 3.78 (s, 1H) 3.89 (t, J=7.75 Hz, 2H) 6.15 (t, J=5.92 Hz, 1H) 6.53 (d, J=8.79 Hz, 2H) 7.17 (d, J=8.67 Hz, 2H).

N-(2-Ethynylphenyl)-1-methylpiperidin-4-amine

¹H NMR (400 MHz, DMSO-d$_6$) δ ppm 1.40-1.49 (m, 2H) 1.87-1.91 (m, 2H) 2.04-2.11 (m, 2H) 2.17 (s, 3H) 2.65-2.88 (m, 2H) 4.44 (s, 1H) 4.68-4.70 (m, 1H) 6.53-6.57 (m, 1H) 6.68 (d, J=8.30 Hz, 1H) 7.16-7.20 (m, 1H) 7.23 (dd, J=7.57 Hz, 1.59 Hz, 1H).

N-(2-Chloroethyl)-2-ethynylaniline

¹H NMR (400 MHz, DMSO-d$_6$) δ ppm 3.53 (q, J=6.43 Hz, 2H) 3.76 (t, J=6.29 Hz, 2H) 4.44 (s, 1H) 5.39-5.48 (m, 1H) 6.59 (td, J=7.45, 0.98 Hz, 1H) 6.71 (d, J=8.18 Hz, 1H) 7.16-7.23 (m, 1H) 7.25 (dd, J=7.57, 1.59 Hz, 1H).

Preparation C

2-[(3-Ethynylphenyl)amino]ethanol

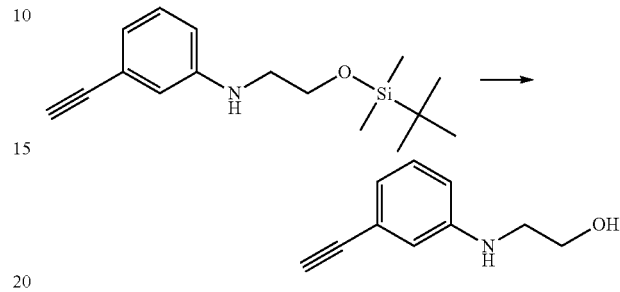

N-(2-{[tert-Butyl(dimethyl)silyl]oxy}ethyl)-3-ethynylaniline (335 mg, 1.22 mmol) was treated with 1M TBAF in THF (1.5 mL, 1.5 mmol) at room temperature for 5 min. The volatiles were removed and the crude was dissolved in EtOAc (30 mL). The organic phase was washed with water (20 mL) and finally with brine, dried over sodium sulfate and evaporated to give the corresponding alcohol as brownish oil.

¹H NMR (600 MHz, DMSO-d$_6$) δ ppm 3.07 (q, J=5.86 Hz, 2H) 3.53 (q, J=5.92 Hz, 2H) 3.97 (s, 1H) 4.68 (t, J=5.49 Hz, 1H) 5.68 (t, J=5.49 Hz, 1H) 6.49-6.71 (m, 3H) 7.05 (t, J=7.78 Hz, 1H).

The above procedure was employed to synthesize the following compound:

2-[(4-Ethynylphenyl)amino]ethanol

¹H NMR (600 MHz, DMSO-d$_6$) δ ppm 3.03-3.11 (m, 2H) 3.53 (q, J=5.80 Hz, 2H) 3.77 (s, 1H) 4.70 (t, J=5.40 Hz, 1H) 5.96 (t, J=5.59 Hz, 1H) 6.51-6.57 (m, 2H) 7.13-7.18 (m, 2H).

Preparation D

N'-(2-Ethynylphenyl)-N,N-dimethylethane-1,2-diamine

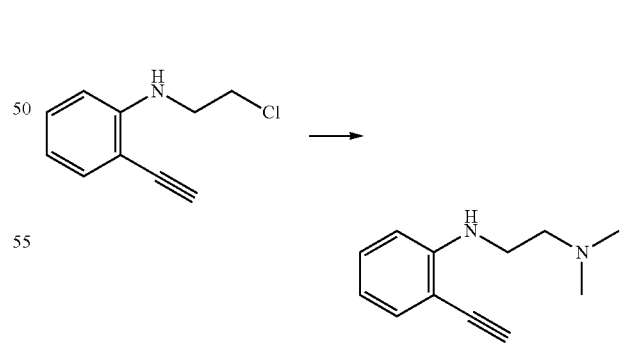

N-(2-Chloroethyl)-2-ethynylaniline (0.5 g, 2.79 mmol) in ACN (16 mL) was treated with 2M dimethylamine in THF (4.2 mL, 8.37 mmol), sodium iodide (1.25 g, 8.37 mmol), sodium carbonate (887 mg, 8.37 mmol) and heated in a sealed tube at 80° C. (oil bath temperature) for 15 h, with stirring. EtOAc was added (100 mL) and the organic phase was washed first with water (100 mL) and then with brine.

Removal of the volatiles by evaporation, after drying over sodium sulfate and purification of the crude over silica gel (DCM/7N NH$_3$ in MeOH 9/1) afforded the title compound (265 mg, 50%).

$^1$H NMR (400 MHz, DMSO-d$_6$) δ ppm 2.19 (s, 6H) 2.46-2.50 (m, 2H) 3.16 (q, J=5.98 Hz, 2H) 4.41 (s, 1H) 5.26 (t, J=5.43 Hz, 1H) 6.55 (td, J=7.45, 1.10 Hz, 1H) 6.62 (d, J=8.30 Hz, 1H) 7.16-7.24 (m, 2H).

Preparation E 1-(3-Ethynylbenzyl)-4-methylpiperazine

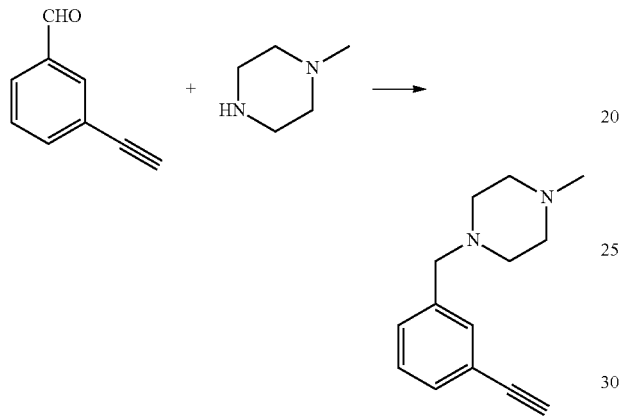

3-Ethynylbenzaldehyde (90 mg, 0.69 mmol) and 1-methylpiperazine (92 μL, 0.828 mmol) in 1,4-dioxane (2.6 mL), under a nitrogen atmosphere, at room temperature were treated first with TFA (128 μL, 1.66 mmol), then with sodium triacetoxyborohydride (210 mg, 1.035 mmol) and stirred for 5 h. EtOAc was added to the reaction mixture (20 mL) and 10% NH$_4$OH (15 mL) was added drop wise. The organic layer was separated, dried over sodium sulfate and evaporated. Purification of the crude by flash chromatography over silica gel (DCM/7N NH$_3$ in MeOH 9/1) afforded the title compound (56 mg, 38%).

$^1$H NMR (400 MHz, DMSO-d$_6$) δ ppm 2.15 (s, 3H) 2.33 (bs, 8H) 3.44 (s, 2H) 4.15 (s, 1H) 7.31-7.40 (m, 4H).

Preparation F 4-(3-Ethynylphenoxy)-1-methylpiperidine

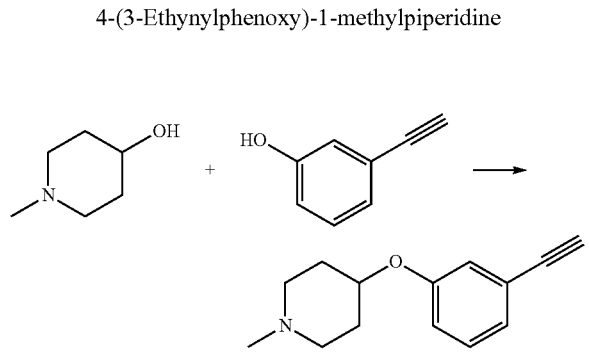

Ph$_3$P (1.32 g, 5.04 mmol) in DCM (4 mL), under a nitrogen atmosphere, was cooled with an ice bath and treated with neat DIAD (397 μL, 4.6 mmol). After 25 min the solution was added drop wise to 1-methylpiperidin-4-ol hydrochloride (547 g, 4.6 mmol) and 3-ethynylphenol (277 μL, 4.2 mmol) in DCM (8 mL), cooled with an ice bath, under a nitrogen atmosphere, with stirring. The reaction was then stirred at room temperature 4 h. The volatiles were partially removed by evaporation and the residue was purified by flash chromatography (DCM/MeOH 95/5) affording the title compound as a colorless oil (360 mg, 39%).

$^1$H NMR (400 MHz, DMSO-d$_6$) δ ppm 1.53-1.71 (m, 2H) 1.90 (m, J=5.86 Hz, 2H) 2.11-2.24 (m, 5H) 2.60 (m, J=10.62 Hz, 2H) 4.14 (s, 1H) 4.31-4.44 (m, 1H) 6.92-7.10 (m, 2H) 7.21-7.33 (m, 1H).

The above procedure was employed to synthesize the following compound:

4-(4-Ethynylphenoxy)-1-methylpiperidine $^1$H NMR (400 MHz, DMSO-d$_6$) δ ppm 1.61 (m, 2H) 1.88 (m, 2H) 2.17 (m, 5H) 2.64 (m, 2H) 3.96 (s, 1H) 4.38 (m, 1H) 6.91 (d, J=8.91 Hz, 2H) 7.35 (d, J=8.79 Hz, 2H).

Preparation G (4-Ethynylphenyl)(4-methylpiperazin-1-yl)methanone

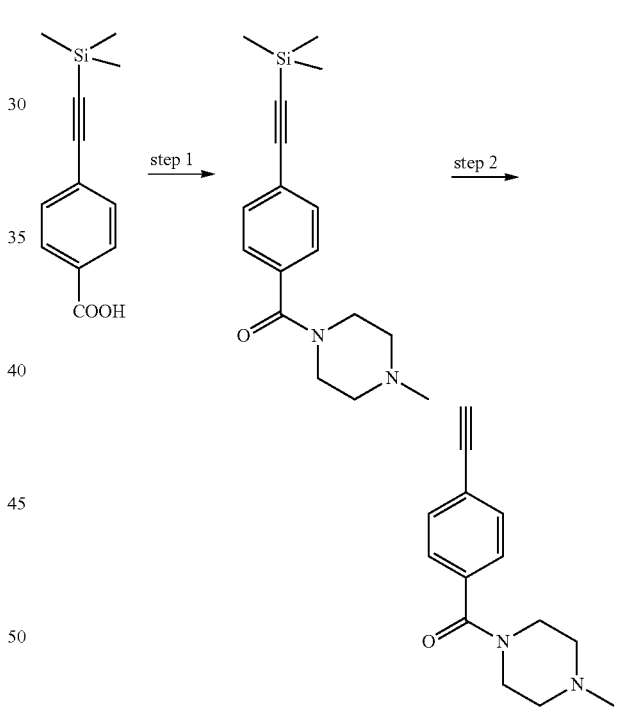

Step 1: (4-Methylpiperazin-1-yl){4-[(trimethylsilyl)ethynyl]phenyl}methanone

1-Methylpiperazine (0.66 mL, 6.0 mmol), HOBt (0.84 g, 6.2 mmol) and EDCl (1.15 g, 6.0 mmol) were added to a solution of 4-[(trimethylsilyl)ethynyl]benzoic acid (1.0 g, 4.6 mmol) in dry DCM (45 mL). The mixture was stirred at room temperature for 4 h, washed with saturated aqueous sodium bicarbonate (30 mL), brine, dried over sodium sulphate, and evaporated. The crude was purified by flash chromatography on silica gel (DCM/MeOH 96/4) to afford the title compound (1.29 g, 93%).

$^1$H NMR (400 MHz, DMSO-d$_6$) δ ppm 0.24 (s, 9H) 2.19 (s, 3H) 2.25-2.40 (m, 4H) 3.18-3.73 (m, 4H) 7.30-7.42 (m, 2H) 7.47-7.55 (m, 2H).

HRMS (ESI) m/z calcd for C$_{17}$H$_{24}$N$_2$OSi+H$^+$ 301.1732. found 301.1731.

Step 2:
(4-Ethynylphenyl)(4-methylpiperazin-1-yl)methanone (4-Methylpiperazin-1-yl){4-[(trimethylsilyl)ethynyl]phenyl}methanone (1.29 g, 4.26 mmol) in MeOH (20 mL) was treated with solid K$_2$CO$_3$ (0.118 g, 0.85 mmol). After stirring at room temperature for 3 h the volatiles were removed by evaporation, the residue was taken up with DCM (40 mL), washed with water (30 mL), brine, dried over sodium sulfate and evaporated. The crude was purified by flash chromatography on silica gel (DCM/MeOH 95/5) to afford the title compound as white solid (0.690 g, 71%).

$^1$H NMR (400 MHz, DMSO-d$_6$) δ ppm 2.19 (s, 3H) 2.22-2.41 (m, 4H) 3.18-3.69 (m, 4H) 4.29 (s, 1H) 7.36-7.41 (m, 2H) 7.47-7.56 (m, 2H).

HRMS (ESI) m/z calcd for C$_{14}$H$_{16}$N$_2$O+H$^+$ 229.1336. found 229.1339.

Preparation H (3-Ethynylphenyl)(4-methylpiperazin-1-yl)methanone

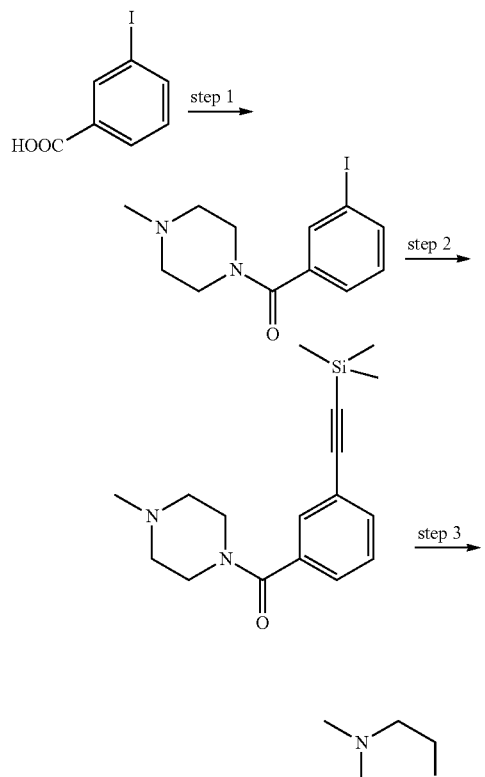

Step 1:
(3-Iodophenyl)(4-methylpiperazin-1-yl)methanone

1-Methylpiperazine (0.58 mL, 5.2 mmol), HOBt (0.70 g, 5.2 mmol) and EDCl (1.0 g, 5.2 mmol) were added to a solution of 3-iodobenzoic acid (1.0 g, 4.0 mmol) in dry DCM (40 mL). The mixture was stirred at room temperature for 16 h, washed with saturated aqueous sodium bicarbonate (30 mL), water (15 mL), brine, dried over sodium sulphate, and evaporated to afford the title compound (1.27 g, 96%).

$^1$H NMR (400 MHz, DMSO-d$_6$) δ ppm 2.19 (s, 3H) 2.22-2.42 (m, 4H) 3.19-3.29 (m, 2H) 3.50-3.68 (m, 2H) 7.19-7.28 (m, 1H) 7.35-7.41 (m, 1H) 7.70-7.72 (m, 1H) 7.80-7.82 (m, 1H).

HRMS (ESI) m/z calcd for C$_{12}$H$_{15}$IN$_2$O+H$^+$ 331.0302. found 331.0301.

Step 2: (4-Methylpiperazin-1-yl){3-[(trimethylsilyl)ethynyl]phenyl}methanone (3-Iodophenyl)(4-methylpiperazin-1-yl)methanone (1.15 g, 3.5 mmol) and ethynyl-trimethyl-silane (0.58 mL, 4.2 mmol) in dry acetonitrile (30 mL) were purged with nitrogen and treated with TEA (0.97 mL, 7.0 mmol, 2 eq.), CuI (0.033 g, 0.17 mmol) and Pd (Ph$_3$P)$_2$Cl$_2$ (0.120 g, 0.17 mmol). The reaction was stirred at room temperature for 2 h, then was diluted with EtOAc (30 mL), washed with water (2×20 mL), brine, dried over sodium sulphate, and evaporated. The crude was purified by flash chromatography on silica gel (DCM/MeOH 95/5) to afford the title compound (0.95 g, 91%).

$^1$H NMR (400 MHz, DMSO-d$_6$) δ ppm 0.24 (s, 9H), 2.20 (s, 3H), 2.25-2.45 (m, 4H), 3.50-3.70 (m, 4H), 7.36-7.42 (m, 2H) 7.42-7.47 (m, 1H) 7.50-7.54 (m, 1H).

HRMS (ESI) m/z calcd for C$_{17}$H$_{24}$N$_2$OSi+H$^+$ 301.1731. found 301.1732.

Step 3:
(3-Ethynylphenyl)(4-methylpiperazin-1-yl)methanone

1M TBAF in THF (0.30 mL, 0.30 mmol) was added to a solution of (4-methylpiperazin-1-yl){3-[(trimethylsilyl)ethynyl]phenyl}methanone (90 mg, 0.30 mmol) in dry THF (1.5 mL) and the mixture was stirred at room temperature for 2 h. The solvent was evaporated and the residue taken up with EtOAc (3 mL), washed with brine, dried over sodium sulfate and evaporated to afford the title compound (53 mg, 78%).

HRMS (ESI) m/z calcd for C$_{14}$H$_{16}$N$_2$O+H$^+$ 229.2989. found 229.2995.

Preparation I

1-[1-(4-Ethynylphenyl)piperidin-4-yl]-4-methylpiperazine

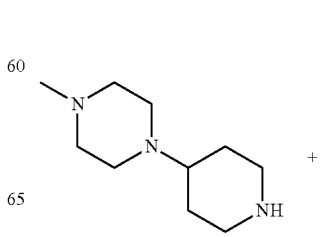

-continued

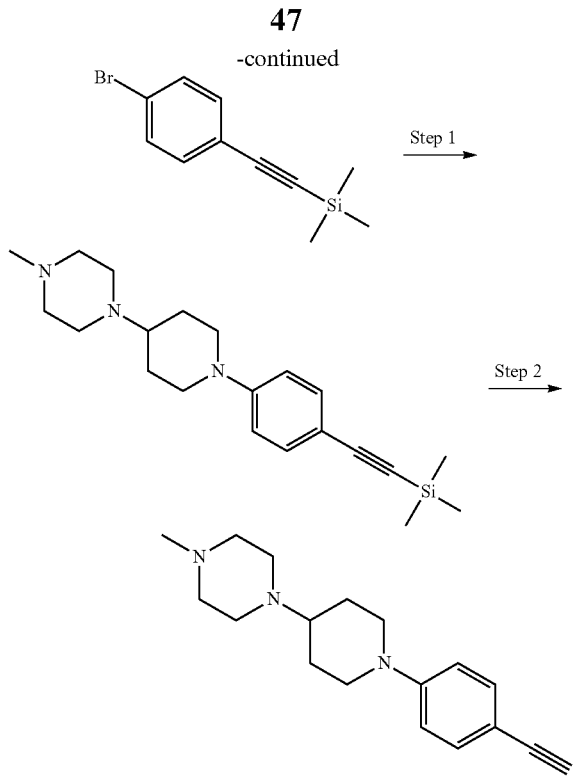

Step 1: 1-Methyl-4-(1-{4-[(trimethylsilyl)ethynyl]phenyl}piperidin-4-yl)piperazine A suspension of [(4-bromophenyl)ethynyl](trimethyl)silane (2.210 g, 8.73 mmol), Pd$_2$(dba)$_3$ (0.400 g, 0.436 mmol), 2-dicyclohexylphosphino-2'-(N,N'-dimethylamino)biphenyl (0.172 g, 0.436 mmol) in anhydrous THF (60 mL) was degassed and backfilled with Argon for three times. 1-Methyl-4-(piperidin-4-yl)piperazine (4.00 g, 21.82 mmol) was added and the mixture was degassed and backfilled with Argon for three times again. Finally LiHMDS 1 M in THF (17.46 mL) was added by a syringe and the mixture was heated to reflux for 2 h. After cooling to room temperature the reaction mixture was filtered on a pad of celite washing with THF (300 mL). The filtrate was evaporated under vacuum and the black oil so obtained was purified by flash chromatography on silica gel (DCM/MeOH/NH$_4$OH 90/10/0.2) to afford the title compound as a yellow solid (2.55 g, 82%).

$^1$H NMR (400 MHz, DMSO-d$_6$) δ ppm 0.19 (s, 9H) 1.35-1.49 (m, 2H) 1.81 (m, J=11.72 Hz, 2H) 2.13 (s, 3H) 2.20-2.55 (m, 9H) 2.68-2.78 (m, 2H) 3.72-3.83 (m, 2H) 6.87 (d, J=9.03 Hz, 2H) 7.18-7.28 (m, 2H).

HRMS m/z calcd for [M+H] 356.2517. found 356.2511.

The above procedure using suitable amines was employed to synthesize the following compounds:

1'-{-(4-[(Trimethylsilyl)ethynyl]phenyl}-1,4'-bipiperidine 4-(Pyrrolidin-1-yl)-1-{4-[(trimethylsilyl)ethynyl]phenyl}piperidine $^1$H NMR (400 MHz, DMSO-d$_6$) δ ppm 0.16-0.21 (m, 9H) 1.46 (d, J=10.50 Hz, 2H) 1.69 (br. s., 4H) 1.90 (d, J=11.84 Hz, 2H) 2.11-2.30 (m, 1H) 2.72-2.86 (m, 2H) 3.71 (d, J=12.82 Hz, 2H) 6.88 (d, J=8.91 Hz, 2H) 7.25 (d, J=8.91 Hz, 2H).

HRMS m/z calcd for [M+H] 327.2251. found 327.2259.

N,N-Dimethyl-1-{4-[(trimethylsilyl)ethynyl]phenyl}piperidin-4-amine $^1$H NMR (400 MHz, DMSO-d$_6$) δ ppm 0.19 (s, 9H) 1.41 (qd, J=11.92, 3.78 Hz, 2H) 1.81 (d, J=12.33 Hz, 2H) 2.18 (s, 6H) 2.25 (br. s., 1H) 2.72 (td, J=12.36, 2.38 Hz, 2H) 3.78 (d, J=12.82 Hz, 2H) 3.88 (s, 1H) 6.85-6.92 (m, 2H) 7.23-7.30 (m, 2H).

HRMS m/z calcd for [M+H] 301.2095. found 301.2093.

1-{4-[(Trimethylsilyl)ethynyl]phenyl}piperazine

1-{4-[(Trimethylsilyl)ethynyl]phenyl}-4-methylpiperazine

1-{4-[(Trimethylsilyl)ethynyl]phenyl}piperidin-4-ol (2S)-2-(Pyrrolidin-1-ylmethyl)-1-{4-[(trimethylsilyl)ethynyl]phenyl}pyrrolidine Step 2: 1-[1-(4-Ethynylphenyl)piperidin-4-yl]-4-methylpiperazine A solution of 1-methyl-4-(1-{4-[(trimethylsilyl)ethynyl]phenyl}piperidin-4-yl)piperazine (2.55 g, 7.179 mmol) in anhydrous methanol (25 mL) was treated with powdered anhydrous potassium carbonate (99.2 mg, 0.718 mmol) under stirring at room temperature for 3 h. After removing the solvent under vacuum the residue was taken up with DCM (50 mL) and water (5 mL). The phases were separated, the organic phase was washed with a saturated solution of sodium hydrogencarbonate (3×10 mL), brine (3×10 mL), water (10 mL), dried over sodium sulfate and the solvent removed under vacuum. The yellowish solid obtained was purified by chromatography on silica gel (DCM/MeOH/TEA 90/10/0.2) to give the title compound as yellow solid (1.534 g, 76%).

$^1$H NMR (400 MHz, DMSO-d$_6$) δ ppm 1.43 (qd, J=11.98, 3.97 Hz, 2H) 1.81 (m, J=12.21 Hz, 2H) 2.14 (s, 3H) 2.20-2.55 (m, 9H) 2.66-2.80 (m, 2H) 3.67-3.84 (m, 4H) 3.88 (s, 1H) 6.82-6.93 (m, 2H) 7.20-7.32 (m, 2H).

HRMS m/z calcd for [M+H] 284.2121. found 284.2133.

The above procedure was employed to synthesize the following compounds:

1'-(4-Ethynylphenyl)-1,4'-bipiperidine $^1$H NMR (400 MHz, DMSO-d$_6$) δ ppm 1.25-2.04 (m, 10H) 2.50 (m, 5H) 2.73 (t, J=12.21 Hz, 2H) 3.90 (s, 1H) 3.81-3.95 (m, 2H) 6.91 (d, J=8.54 Hz, 2H) 7.29 (d, J=8.79 Hz, 2H).

HRMS m/z calcd for [M+H] 269.2012. found 269.2002.

1-(4-Ethynylphenyl)-4-(pyrrolidin-1-yl)piperidine $^1$H NMR (400 MHz, DMSO-d$_6$) δ ppm 1.38-1.51 (m, 2H) 1.67 (dt, J=6.65, 3.14 Hz, 4H) 1.88 (dd, J=12.94, 2.93 Hz, 2H) 2.09-2.20 (m, 1H) 2.73-2.84 (m, 2H) 3.68 (dt, J=13.03, 3.49 Hz, 2H) 3.88 (s, 1H) 6.85-6.92 (m, 2H) 7.24-7.29 (m, 2H).

HRMS m/z calcd for [M+H] 255.1856. found 255.1857.

1-(4-Ethynylphenyl)-N,N-dimethylpiperidin-4-amine $^1$H NMR (400 MHz, DMSO-d$_6$) ppm 1.41 (qd, J=11.92, 3.78 Hz, 2H) 1.81 (d, J=12.33 Hz, 2H) 2.19 (s, 6H) 2.25 (br. s., 1H) 2.72 (td, J=12.36, 2.38 Hz, 2H) 3.78 (d, J=12.82 Hz, 2H) 3.88 (s, 1H) 6.85-6.92 (m, 2H) 7.23-7.30 (m, 2H).

HRMS m/z calcd for [M+H] 229.1699. found 229.1702.

1-(4-Ethynylphenyl)piperazine $^1$H NMR (400 MHz, DMSO-$d_6$) δ ppm 2.77-2.90 (m, 4H) 3.01-3.15 (m, 4H) 3.89 (s, 1H) 6.88 (d, J=8.91 Hz, 2H) 7.23-7.38 (m, 2H).
HRMS m/z calcd for [M+H] 187.123. found 187.1225.

1-(4-Ethynylphenyl)-4-methylpiperazine $^1$H NMR (400 MHz, DMSO-$d_6$) δ ppm 2.23 (s, 3H) 2.35-2.55 (m, 4H) 3.15-3.23 (m, 4H) 3.90 (s, 1H) 6.90 (d, J=9.03 Hz, 2H) 7.29 (d, J=8.91 Hz, 2H).
HRMS m/z calcd for [M+H] 201.1386. found 201.1379.

1-(3-Ethynylphenyl)-4-methylpiperazine $^1$H NMR (400 MHz, DMSO-$d_6$) δ ppm 2.26 (bs, 3H) 3.16 (bs, 4H) 4.07 (s, 1H) 6.82-6.90 (m, 1H) 6.97-7.02 (m, 2H) 7.18-7.24 (m, 1H).

1-(4-Ethynylphenyl)piperidin-4-ol $^1$H NMR (400 MHz, DMSO-$d_6$) δ ppm 1.41 (m, J=12.98, 9.35, 9.35, 3.84 Hz, 2H) 1.78 (dd, J=9.15, 3.91 Hz, 2H) 2.91 (ddd, J=13.00, 10.01, 3.11 Hz, 2H) 3.53-3.71 (m, 3H) 3.88 (s, 1H) 4.65 (br. s., 1H) 6.84-6.92 (m, 2H) 7.24-7.29 (m, 2H).
HRMS m/z calcd for [M+H] 202.1227. found 202.1227.

(2S)-1-(4-Ethynylphenyl)-2-(pyrrolidin-1-ylmethyl)pyrrolidine $^1$H NMR (400 MHz, DMSO-$d_6$) δ ppm 3.01-3.12 (m, 1H) 3.33-3.41 (m, 1H) 3.82-3.83 (m, 1H) 3.82-3.88 (m, 1H) 6.49-6.56 (m, 2H) 7.23-7.29 (m, 2H).
HRMS m/z calcd for [M+H] 255.1856. found 255.185.

Preparation J

4-Ethynyl-3-methoxy-phenylamine

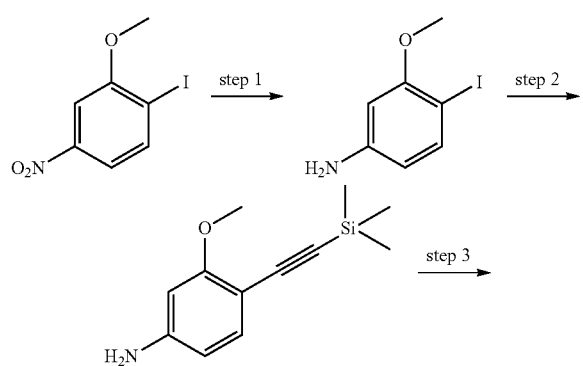

Step 1: 4-Iodo-3-methoxy-phenylamine

1-Iodo-2-methoxy-4-nitro-benzene (6.01 g, 21.54 mmol) in absolute ethanol (127 mL) was cooled with an ice bath and treated with SnCl$_2$ (18.83 g, 99.31 mmol). The bath was removed and the mixture was stirred at room temperature for 4 h then poured into ice (300 mL), stirred and treated carefully with saturated aqueous sodium bicarbonate (250 mL) (pH 7-8). The solid was filtered with suction and the panel washed thoroughly with EtOAc (500 mL and 4×200 mL). The aqueous layer was separated, dried over sodium sulphate and evaporated. Purification of the crude by flash chromatography on silica gel (hexane/EtOAc 1/1) furnished the title compound (3.17 g, 59%).

Step 2: 3-Methoxy-4-trimethylsilanylethynyl-phenylamine

4-Iodo-3-methoxy-phenylamine (3.17 g, 12.7 mmol) and ethynyl-trimethyl-silane (3.5 mL, 25 mmol) in dry acetonitrile were purged with nitrogen and treated with TEA (17.6 mL, 127 mmol), CuI (123 mg, 0.635 mmol) and Pd(Ph$_3$P)$_2$Cl$_2$ (447 mg, 0.635 mmol). The reaction was stirred at room temperature for 2 h. The volatiles were evaporated, the residue was taken up with EtOAc (200 mL), washed with water (50 mL), dried over sodium sulfate and purified by flash chromatography on silica gel (hexane/EtOAc 55/45) to afford the title compound (1.86 g, 66%).

Step 3: 4-Ethynyl-3-methoxy-phenylamine

3-Methoxy-4-trimethylsilanylethynyl-phenylamine (1.86 g, 8.45 mmol) in MeOH (17 mL) was treated with solid K$_2$CO$_3$ (1.17 g, 8.45 mmol). After stirring at room temperature the volatiles were removed by evaporation, the residue was taken up with EtOAc (50 mL), washed with water (50 mL), brine, dried over sodium sulfate and evaporated. The crude was purified by flash chromatography on silica gel (heptane/EtOAc 65/35) to afford 520 mg of title compound (42% yield).

$^1$H NMR (400 MHz, DMSO-$d_6$) δ ppm 3.67 (s, 3H) 4.15 (s, 1H) 5.32 (s, 2H) 6.11 (dd, J=8.48, 2.50 Hz, 1H) 6.26 (d, J=2.44 Hz, 1H) 7.07 (d, J=8.54 Hz, 1H).

The above procedure was employed to synthesize the following compound:

3-Ethynyl-4-methoxy-phenylamine $^1$H NMR (400 MHz, DMSO-$d_6$) δ ppm 3.67 (s, 3H) 4.04 (s, 1H) 4.77 (br. s., 2H) 6.58 (dd, J=8.67, 2.81 Hz, 1H) 6.63 (d, J=2.81 Hz, 1H) 6.75 (d, J=8.67 Hz, 1H).

Preparation K

N-(3-Ethynyl-4-methoxyphenyl)-1-methylpiperidine-4-carboxamide

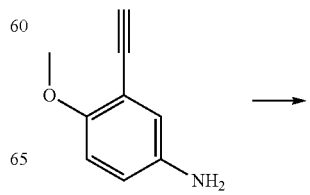

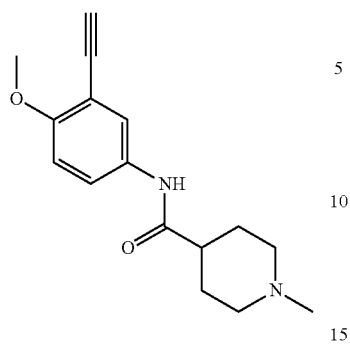

3-Ethynyl-4-methoxyaniline (300 mg, 2 mmol) in DCM (20 mL) was treated in a subsequent manner with HOBt (351 mg, 2.6 mmol), isonipecotic acid hydrochloride (467 mg, 2.6 mmol), DIPEA (906 µL, 5.2 mmol) and finally EDCl (498 mg, 2.6 mmol). The reaction was stirred at room temperature for 1.5 h. The organic phase was washed with saturated sodium hydrogen carbonate solution and dried over sodium sulfate. Evaporation of the solvent left a brownish solid which was employed in the following reaction without further purification.

$^1$H NMR (400 MHz, DMSO-d$_6$) δ ppm 1.65 (m, J=12.05, 12.05, 3.23 Hz, 2H) 1.74 (m, J=3.30 Hz, 2H) 1.88-2.02 (m, 2H) 2.14-2.29 (m, 4H) 2.86 (dt, J=11.35, 3.91 Hz, 2H) 3.77 (s, 3H) 4.19 (s, 1H) 6.98 (d, J=9.03 Hz, 1H) 7.52 (dd, J=9.03, 2.69 Hz, 1H) 7.68 (d, J=2.56 Hz, 1H) 9.76 (s, 1H).

Preparation L (4-Ethynyl-3-methoxyphenyl)(4-methylpiperazin-1-yl)methanone

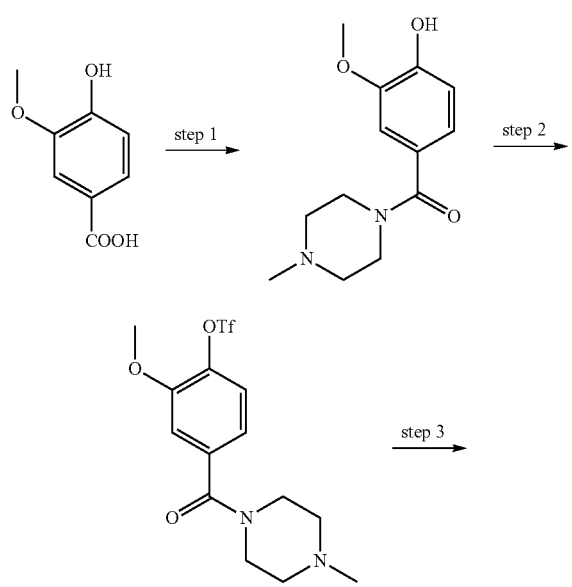

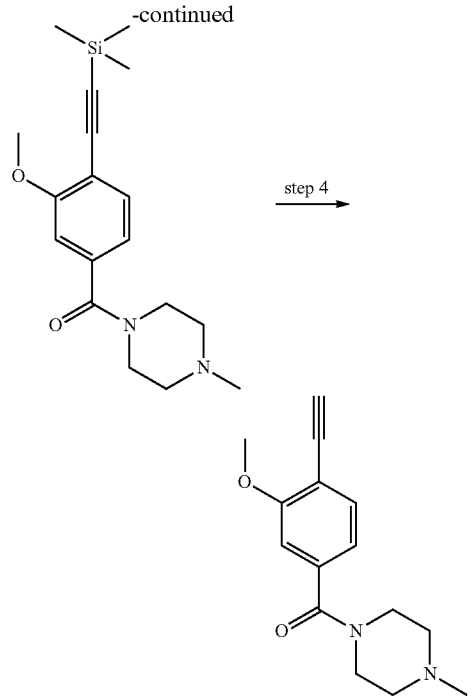

Step 1: (4-Hydroxy-3-methoxyphenyl)(4-methylpiperazin-1-yl)methanone

1-Methylpiperazine (0.58 mL, 5.2 mmol), HOBt (0.70 g, 5.2 mmol.) and EDCl (1.0 g, 5.2 mmol) were added to a solution of 4-hydroxy-3-methoxybenzoic acid (0.69 g, 4.0 mmol.) in dry DCM (40 mL). The mixture was stirred at room temperature for 16 h, washed with saturated aqueous sodium bicarbonate (20 mL), brine, dried over sodium sulphate and evaporated to give the title compound (0.96 g, 96%).
$^1$H NMR (400 MHz, DMSO-d$_6$) δ ppm 2.19 (s, 3H) 2.25-2.32 (m, 4H) 3.42-3.55 (m, 4H) 3.77 (s, 3H) 6.77-6.81 (m, 1H) 6.81-6.84 (m, 1H) 6.91-6.94 (m, 1H) 9.38 (bs, 1H).
HRMS (ESI) m/z calcd for $C_{13}H_{18}N_2O_3+H^+$ 251.1390. found 251.1386.

Step 2: 2-Methoxy-4-[(4-methylpiperazin-1-yl)carbonyl]phenyl trifluoromethanesulfonate Pyridine (1.60 mL, 19.2 mmol) was added to a solution of (4-hydroxy-3-methoxyphenyl)(4-methylpiperazin-1-yl)methanone (0.96 g, 3.84 mmol) in dry DCM (38 mL) at 10° C. Then triflic anhydride (3.2 mL, 19.2 mmol) was added drop wise and the reaction stirred at the same temperature for 7 h. The mixture was diluted with DCM (50 mL) and the organic layer washed with water (30 mL), brine, dried over sodium sulphate, and evaporated. The crude was purified by flash chromatography on silica gel (DCM/MeOH/7N NH$_3$ in MeOH 95/5/0.5) to afford the title compound as brown oil (0.68 g, 46%).
$^1$H NMR (400 MHz, DMSO-d$_6$) ppm 2.20 (s, 3H) 2.23-2.45 (m, 4H) 3.52-3.74 (m, 4H) 3.92 (s, 3H) 7.06 (dd, J=8.30, 1.95 Hz, 1H) 7.32 (d, J=1.95 Hz, 1H) 7.47-7.51 (m, 1H).
HRMS (ESI) m/z calcd for $C_{14}H_{17}F_3N_2O_5S+H^+$ 383.0883. found 383.0884.

Step 3: {3-Methoxy-4-[(trimethylsilyl)ethynyl]phenyl}(4-methylpiperazin-1-yl)methanone To a degassed solution of 2-methoxy-4-[(4-methylpiperazin-1-yl)carbonyl]phenyl trifluoromethanesulfonate (0.570 g, 1.49 mmol) in dry acetonitrile (11 mL) ethynyl(trimethyl)silane (0.312 mL, 2.25 mmol), TEA (0.414 mL, 2.98 mmol.), CuI (0.021 g, 0.11 mmol) and Pd(PPh$_3$)$_2$Cl$_2$ (0.082 g, 0.11 mmol) were added. The mixture was stirred at room temperature for 7 h, then diluted with EtOAc (40 mL), washed with water (20 mL), 10% NH$_4$OH (15 mL), brine, dried over sodium sulphate, and evaporated. The crude was purified by flash chromatography on silica gel (DCM/MeOH/7N NH$_3$ in MeOH 90/10/1) to afford the title compound (0.480 g, 98%).

$^1$H NMR (400 MHz, DMSO-d$_6$) δ ppm 0.22 (s, 9H) 2.18-2.20 (m, 3H) 2.25-2.40 (m, 4H) 3.50-3.70 (m, 4H) 3.83 (s, 3H) 6.89 (dd, J=7.75, 1.40 Hz, 1H) 7.00 (d, J=1.40 Hz, 1H) 7.42 (d, J=7.75 Hz, 1H).

HRMS (ESI) m/z calcd for C$_{18}$H$_{26}$N$_2$O$_2$Si+H$^+$ 331.1837. found 331.1835.

Step 4: (4-Ethynyl-3-methoxyphenyl)(4-methylpiperazin-1-yl)methanone

1M TBAF in THF (1.43 mL, 1.05 mmol) was added to a solution of {3-methoxy-4-[(trimethylsilyl)ethynyl]phenyl} (4-methylpiperazin-1-yl)methanone (0.450 g, 1.36 mmol) in dry THF (7 mL) and the mixture was stirred at room temperature for 2 h. The solvent was evaporated and the residue taken up with EtOAc (30 mL), washed with brine, dried over sodium sulfate and evaporated to afford the title compound (0.263 g, 75%).

Preparation M 1-(4-Ethynyl-3-methoxyphenyl)-4-methylpiperazine

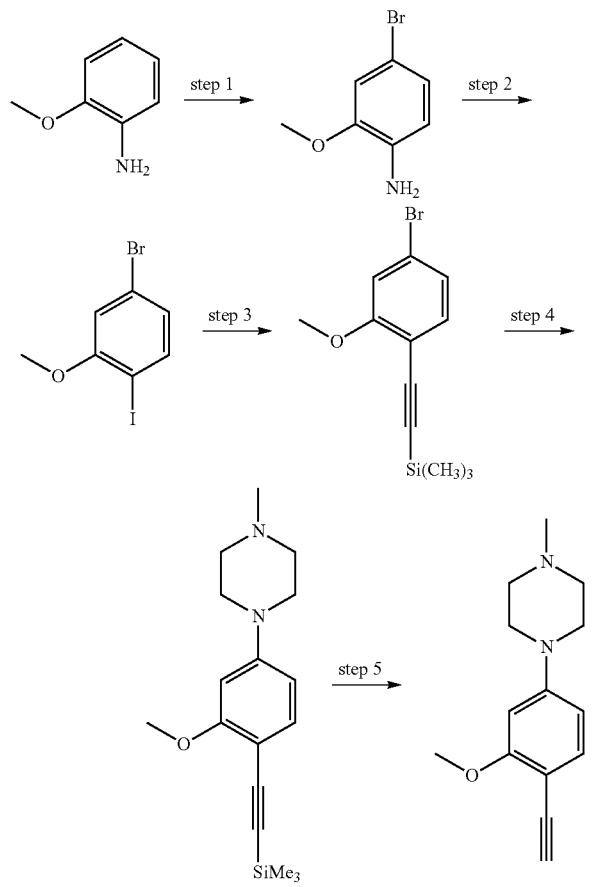

Step 1: 4-Bromo-2-methoxy-phenylamine

To a solution of 2-methoxy-phenylamine (11.27 mL, 12.31 g, 0.1 mol) in glacial acetic acid (250 mL) maintained at about 10° C. a solution of bromine (5.65 mL, 17.58 g, 0.11 mol) in glacial acetic acid (7 mL) was added over 2 h. A purple precipitate was formed, that was filtered on a Buchner funnel and rinsed with glacial acetic acid and petroleum ether (3×100 mL) to afford a whitish solid mixture of 4-bromo-2-methoxy-phenylamine and 4,5-dibromo-2-methoxy-phenylamine (26.9 g). The mixture was separated by flash chromatography on silica gel (hexane/EtOAc 40/60) and the desired compound was crystallized from tert-butylmethyl ether (18.73 g, 82.9%).

$^1$H NMR (400 MHz, DMSO-d$_6$) δ ppm 3.83 (s, 3H) 6.83 (d, J=8.42 Hz, 1H) 6.98 (dd, J=8.30, 2.08 Hz, 1H) 7.11 (d, J=1.95 Hz, 1H).

HRMS m/z calcd for [M+H] 201.9862. found 201.9866.

Step 2: 4-Bromo-1-iodo-2-methoxybenzene

4-Bromo-2-methoxy-phenylamine (2.02 g, 10 mmol) was added to a solution of p-toluensulphonic acid monohydrate (3.80 g, 20 mmol) in acetonitrile (30 mL). The mixture was cooled in an ice bath and treated with an solution of sodium nitrite (0.69 g, 10 mmol) and potassium iodide (4.15 g, 25 mmol) in water (7 mL) over 15 min maintaining the internal temperature below 10° C. After stirring at that temperature for 15 min and then for 0.5 h at room temperature, the reaction mixture was diluted with water and extracted with EtOAc (5×50 mL). The combined organic extracts were washed with 2M sodium thiosulfate (10 mL), brine (4×20 mL), water (20 mL), anhydrified over sodium sulphate, and evaporated to dryness affording a black oil that was purified by flash chromatography (petroleum ether/tert-butylmethyl ether 5/1) to yield the title compound (1.63 g, 52.2%).

$^1$H NMR (400 MHz, DMSO-d$_6$) δ ppm 3.85 (s, 3H) 6.95 (dd, J=8.24, 2.14 Hz, 1H) 7.19 (d, J=2.08 Hz, 1H) 7.69 (d, J=8.18 Hz, 1H).

Step 3: [(4-Bromo-2-methoxyphenyl)ethynyl](trimethyl)silane

To a solution of 4-bromo-1-iodo-2-methoxybenzene (1.634 g, 5.221 mmol) in dry acetonitrile (20 mL) CuI (49.7 mg, 0.261 mmol) and Pd(Ph$_3$P)$_2$Cl$_2$ (183.2 mg, 0.261 mmol) were added under Argon atmosphere and the mixture was degassed and backfilled with Argon for three times. TEA (0.728 mL, 5.221 mmol) and (ethynyl)trimethylsilane (1.48 mL, 1.03 g, 10.442 mmol) were added with a syringe and the reaction mixture, that darkened within 10 min, was stirred at room temperature for 1 h. The solvent was removed under vacuum and the residue was taken up with EtOAc (100 mL), washed with brine (3×20 mL), water (20 mL), dried over sodium sulphate and evaporated to dryness. The crude was purified by chromatography on silica gel (petroleum ether/ diethyl ether 9/1) to yield the title compound as an orange solid (1.426 g, 96.5%).

$^1$H NMR (400 MHz, DMSO-d$_6$) δ ppm 0.21 (s, 9H) 3.83 (s, 3H) 7.11 (dd, J=8.18, 1.83 Hz, 1H) 7.26 (d, J=1.83 Hz, 1H) 7.31 (d, J=8.06 Hz, 1H).

The above procedure was employed to synthesize the following compounds:

[(4-Bromo-2-fluorophenyl)ethynyl](trimethyl)silane

[(5-Bromo-2-methoxyphenyl)ethynyl](trimethyl)silane $^1$H NMR (400 MHz, DMSO-$d_6$) δ ppm 0.22 (s, 9H) 3.81 (s, 3H) 6.97-7.06 (m, 1H) 7.42-7.58 (m, 2H).

[(5-Bromo-2-fluorophenyl)ethynyl](trimethyl)silane

Step 4: 1-{3-methoxy-4-[(trimethylsilyl)ethynyl]phenyl-4-methylpiperazine

A solution of [(4-bromo-2-methoxyphenyl)ethynyl](trimethyl)silane (1.426 g, 5.035 mmol) in dry THF (25 mL) was degassed and backfilled with argon for three times. Pd$_2$(dba)$_3$ (230.5 mg, 0.252 mmol) and 2-dicyclohexylphosphino-2-(N,N'-dimethylamino)biphenyl (79.3 mg, 0.201 mmol) were added under argon atmosphere and the mixture was degassed and backfilled with argon for three times. Then 1 M LiHMDS in THF (12.1 mL, 12.084 mmol) and N-methylpiperazine (1.34 mL, 1.21 g, 12.083 mmol) were added by a syringe and the mixture was degassed and backfilled with Argon for three times. The reaction mixture was heated to reflux for 1 h. After cooling to room temperature the reaction mixture was filtered on a pad of celite washing with THF (200 mL). The filtrate was evaporated under vacuum and the black oil so obtained was purified by chromatography on silica gel (DCM/MeOH 9/1) to afford the title compound as a brownish solid (1.042 g, 68.4%).

$^1$H NMR (400 MHz, DMSO-$d_6$) δ ppm 0.18 (s, 9H) 2.22 (s, 3H) 2.43 (m, 4H) 3.18-3.24 (m, 4H) 3.78 (s, 3H) 6.44 (dd, 1H) 6.48 (d, J=2.20 Hz, 1H) 7.15 (d, J=8.54 Hz, 1H).

HRMS m/z calcd for [M+H] 303.1887. found 303.1892.

The above procedure was employed to synthesize the following compounds:

1-{3-Fluoro-4-[(trimethylsilyl)ethynyl]phenyl}-4-methylpiperazine $^1$H NMR (400 MHz, DMSO-$d_6$) δ ppm 0.21 (m, 9H) 2.21 (s, 3H) 2.37-2.43 (m, 2H) 3.21-3.26 (m, 2H) 6.71 (dd, J=8.79, 2.44 Hz, 1H) 6.77 (dd, J=13.79, 2.44 Hz, 1H) 7.27 (t, J=8.73 Hz, 1H).

1-{4-Methoxy-3-[(trimethylsilyl)ethynyl]phenyl-4-methylpiperazine

1-{4-Fluoro-3-[(trimethylsilyl)ethynyl]phenyl}-4-methylpiperazine $^1$H NMR (400 MHz, DMSO-$d_6$) δ ppm 0.23 (s, 9H) 2.22 (s, 3H) 2.43 (m, J=5.00 Hz, 4H) 2.95-3.14 (m, 4H) 6.95 (dd, J=5.86, 3.17 Hz, 1H) 6.97-7.04 (m, 1H) 7.07-7.14 (m, 1H).

1-Methyl-4-{4-[(trimethylsilyl)ethynyl]phenyl}piperazine $^1$H NMR (400 MHz, DMSO-$d_6$) δ ppm 0.20 (s, 9H) 2.22 (s, 3H) 2.39-2.47 (m, 4H) 3.16-3.22 (m, 4H) 6.88 (d, J=8.91 Hz, 2H) 7.27 (d, J=8.91 Hz, 2H).

HRMS m/z calcd for [M+H] 273.1782. found 273.1776.

Step 5:
1-(4-Ethynyl-3-methoxyphenyl)-4-methylpiperazine

A solution of 1-{3-methoxy-4-[(trimethylsilyl)ethynyl]phenyl-4-methylpiperazine (583 mg, 1.927 mmol) in anhydrous methanol (12 mL) is treated with powdered anhydrous potassium carbonate under stirring at room temperature for 1.5 h. After removing the solvent under vacuum the residue was taken up with EtOAc (80 mL) and water (5 mL). The phases were separated, the organic phase was washed with brine (3×10 mL), water (10 mL), dried over sodium sulfate and the solvent removed under vacuum. The dark oil obtained was purified by chromatography on silica gel (DCM/MeOH/TEA 90/10/0.1) to give the title compound as brownish solid (374 mg, 84.2%).

$^1$H NMR (400 MHz, DMSO-$d_6$) δ ppm 2.22 (s, 3H) 2.39-2.46 (m, 4H) 3.16-3.25 (m, 4H) 3.79 (s, 3H) 3.92 (s, 1H) 6.45 (dd, 1H) 6.46 (d, 1H) 7.18 (d, J=8.42 Hz, 1H).

HRMS m/z calcd for [M+H] 231.1492. found 231.1496.

The above procedure was employed to synthesize the following compounds:

1-(4-Ethynyl-3-fluorophenyl)-4-methylpiperazine $^1$H NMR (400 MHz, DMSO-$d_6$) δ ppm 2.20 (s, 3H) 2.35-2.43 (m, 4H) 3.17-3.24 (m, 4H) 4.16 (s, 1H) 6.72 (dd, J=8.73, 2.50 Hz, 1H) 6.78 (dd, J=13.79, 2.44 Hz, 1H) 7.29 (t, J=8.67 Hz, 1H).

HRMS m/z calcd for [M+H] 219.1292. found 219.1292.

4-Bromo-1-ethynyl-2-fluorobenzene 1-(3-Ethynyl-4-methoxyphenyl)-4-methylpiperazine HRMS m/z calcd for [M+H] 231.1492. found 231.1501.

4-Bromo-2-ethynyl-1-methoxybenzene $^1$H NMR (400 MHz, DMSO-$d_6$) δ ppm 3.82 (s, 3H) 4.35 (s, 1H) 6.72-7.11 (m, 1H) 7.51-7.58 (m, 2H).

4-Bromo-1-ethynyl-2-methoxybenzene

4-Bromo-2-ethynyl-1-fluorobenzene 1-(3-Ethynyl-4-fluorophenyl)-4-methylpiperazine $^1$H NMR (400 MHz, DMSO-$d_6$) δ ppm 2.21 (s, 3H) 2.40-2.46 (m, 4H) 3.03-3.11 (m, 4H) 4.39 (s, 1H) 6.96-7.05 (m, 2H) 7.09-7.16 (m, 1H).

Preparation N

N-(3-Ethynyl-4-methoxyphenyl)-1-methylpiperidin-4-amine

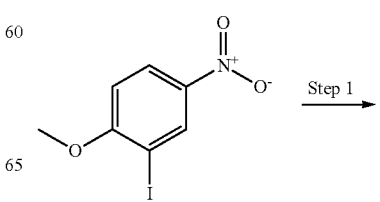

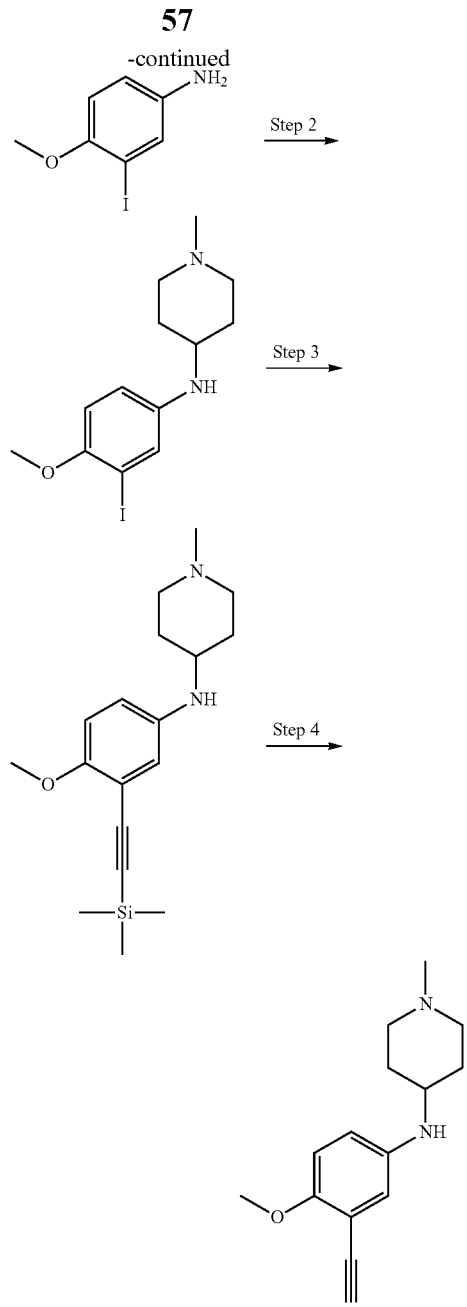

Step 1: 3-Iodo-4-methoxyaniline

To 2-iodo-1-methoxy-4-nitrobenzene (485 mg, 1.74 mmol) suspended in methanol (6 mL) a solution of NH₄Cl (465 mg, 8.69 mmol) in water (4.9 mL) and powdered Fe (290 mg, 5.192 mmol) were added and the mixture was heated to reflux for 3 h. The precipitate formed was filtered off and the filtrate was evaporated until the methanol was eliminated. After diluting with water and alkalinization with sodium carbonate the mixture was extracted with EtOAc (4×20 mL). The combined organic extracts were washed with brine (3×10 mL), water (10 mL), dried over sodium sulfate and the solvent was removed under vacuum. The crude dark oil was purified by flash chromatography on silica gel (hexane/EtOAc 1/1) to afford 400 mg of solid that was crystallized from n-pentane and diethyl ether to yield the title compound (363 mg, 83%).

$^1$H NMR (400 MHz, DMSO-d$_6$) δ ppm 3.66 (s, 3H) 4.79 (s, 2H) 6.56 (dd, J=8.61, 2.62 Hz, 1H) 6.73 (d, J=8.67 Hz, 1H) 7.02 (d, J=2.69 Hz, 1H)

Step 2: N-(3-Iodo-4-methoxyphenyl)-1-methylpiperidin-4-amine

To a solution of 3-iodo-4-methoxyaniline (180 mg, 0723 mmol) in DCM (5 mL) 1-methyl-4-piperidone (0.116 mL, 106 mg, 0.940 mmol), TFA (0.290 mL, 429 mg, 3.760 mmol) and tetramethylammonium triacetoxyborohydride (285 mg, 1.084 mmol) were added in sequence. The reaction is completed in 30 min. The reaction mixture was diluted with DCM, washed with saturated solution of sodium hydrogen carbonate (3×5 mL), brine (3×5 mL), dried over sodium sulfate and the solvent was removed under vacuum. The solid crude so obtained was purified by flash chromatography (EtOAc/TEA 99/1) to afford a beige solid that was crystallized from diethylether to afford the title compound as a whitish solid (197 mg, 79%).

$^1$H NMR (400 MHz, DMSO-d$_6$) δ ppm 1.32 (qd, J=11.50, 3.60 Hz, 2H) 1.82 (d, J=11.96 Hz, 2H) 1.99 (t, J=11.17 Hz, 2H) 2.15 (s, 3H) 2.70 (d, J=11.96 Hz, 2H) 2.99-3.13 (m, 1H) 3.67 (s, 3H) 5.14 (d, J=8.54 Hz, 1H) 6.57 (dd, J=8.79, 2.69 Hz, 1H) 6.77 (d, J=8.79 Hz, 1H) 7.01 (d, J=2.81 Hz, 1H).

HRMS m/z calcd for [M+H] 347.0615. found 347.0627.

The above procedure was employed to synthesize the following compound:

N-(4-Iodo-3-methoxyphenyl)-1-methylpiperidin-4-amine

Step 3: N-{4-Methoxy-3-[(trimethylsilyl)ethynyl]phenyl}-1-methylpiperidin-4-amine Into a flask maintained under argon atmosphere N-(3-iodo-4-methoxyphenyl)-1-methylpiperidin-4-amine (180 mg, 0.52 mmol), CuI (9.9 mg, 0.052 mmol) and Pd(Ph₃P)Cl₂ (36.5 mg, 0.052 mmol) were added and dissolved in acetonitrile (5 mL) and dioxane (5 mL). The solution was degassed and backfilled with argon for three times. TEA (0.725 mL, 526 mg, 5.2 mmol) and (ethynyl)trimethylsilane (0.147 mL, 0.102 mg, 1.04 mmol) were added with a syringe and the solution was stirred at room temperature for 75 min. The volatiles were evaporated and the residue was taken up with EtOAc (30 mL), washed with water (3×5 mL), dried over sodium sulfate and the solvent was removed under vacuum.

The black oil obtained was purified by flash chromatography on silica gel (EtOAc/MeOH/33% NH₄OH) to afford the title compound as brown solid (155 mg, 94%).

$^1$H NMR (400 MHz, DMSO-d$_6$) δ ppm 0.20 (s, 9H) 1.51 (bs, 2H) 1.99 (d, J=11.35 Hz, 2H) 2.64 (bs, 3H) 2.88 (bs, 2H) 3.69 (s, 3H) 5.24 (d, J=7.57 Hz, 1H) 6.57-6.67 (m, 2H) 6.82 (d, J=9.76 Hz, 1H) 9.25 (bs, 1H).

HRMS m/z calcd for [M+H] 317.2044. found 317.2053.

The above procedure was employed to synthesize the following compound:

N-{3-Methoxy-4-[(trimethylsilyl)ethynyl]phenyl}-1-methylpiperidin-4-amine

Step 4: N-(3-Ethynyl-4-methoxyphenyl)-1-methylpiperidin-4-amine

To a solution of N-{4-methoxy-3-[(trimethylsilyl)ethynyl]phenyl}-1-methylpiperidin-4-amine (128 mg, 0.404 mmol) in methanol (2 mL) powdered anhydrous potassium carbonate (56 mg, 0.404 mmol) was added and the mixture was stirred at room temperature for 1 h. The solvent was removed under vacuum and the residue was taken up with EtOAc (30 mL). The solution obtained was washed with brine, (3×5 mL), water (5 m), dried over sodium sulfate and the solvent was removed under vacuum. The dark brown oil was purified by flash chromatography (EtOAc/MeOH/33% NH₄OH 90/10/0.1) to yield the title compound as a yellow solid (85 mg, 86%).

$^1$H NMR (400 MHz, DMSO-d$_6$) δ ppm 1.27-1.42 (m, 2H) 1.83 (m, J=2.93 Hz, 2H) 1.94-2.09 (m, 2H) 2.17 (s, 3H) 2.67-2.79 (m, 2H) 3.08 (m, J=2.81 Hz, 1H) 3.68 (s, 3H) 4.06 (s, 1H) 5.08 (d, J=8.30 Hz, 1H) 6.54-6.67 (m, 2H) 6.73-6.85 (m, 1H).

HRMS m/z calcd for [M+H] 245.1649. found 245.1652.

The above procedure was employed to synthesize the following compound:

N-(4-Ethynyl-3-methoxyphenyl)-1-methylpiperidin-4-amine

Preparation O

1-Methyl-4-(prop-2-yn-1-yloxy)piperidine

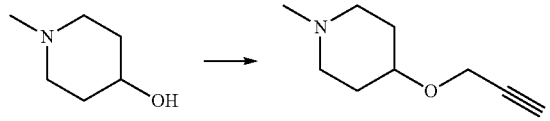

A solution of 1-methylpiperidin-4-ol (1.15 g, 10.0 mmol) in dry THF (5 mL) was added drop wise to a suspension of NaH (60% dispersion in mineral oil, 0.400 g, 10.0 mmol) in dry THF (5 mL) at 0° C. The reaction was kept at the same temperature for 15 min then stirred at room temperature for 1 h. 3-Bromoprop-1-yne (0.75 mL, 10.0 mmol), was slowly added and the mixture was stirred at room temperature for 16 h. After solvent removal, the residue was taken up with DCM (50 mL), washed with water (50 mL), dried over sodium sulfate and purified by flash chromatography on silica gel (DCM/MeOH/TEA 90/10/0.1) to afford the title compound (0.140 g, 9%).

$^1$H NMR (400 MHz, DMSO-d$_6$) δ ppm 1.35-1.50 (m, 2H) 1.75-1.85 (m, 2H) 1.95-2.05 (m, 2H) 2.13 (s, 3H) 2.54-2.62 (m, 2H) 3.35 (t, J=2.44 Hz, 1H) 3.39-3.47 (m, 1H) 4.13 (d, J=2.44 Hz, 2H).

HRMS (ESI) m/z calcd for C$_9$H$_{15}$NO+H$^+$ 154.1227. found 154.1230.

Preparation P

1-Methyl-4-(prop-2-yn-1-yl)piperazine

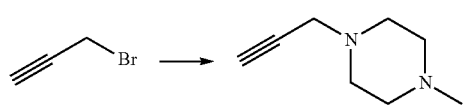

A solution of 3-bromoprop-1-yne (1.70 mL, 22.5 mmol in acetone (7 mL) was added to a suspension of 1-methylpiperazine (3.77 mL, 33.7 mmol) and K$_2$CO$_3$ (4.66 g, 33.7 mmol) in acetone (40 mL) at 0° C. The mixture was stirred at room temperature for 4 h and then filtered. The filtrate was evaporated to dryness and the residue was taken up with water (80 mL) and extracted with DCM (2×20 mL). The separated organic phase was washed with brine (3×5 mL), dried over sodium sulfate and evaporated to afford the title compound as brown oil (1.60 g, 51%).

$^1$H NMR (400 MHz, DMSO-d$_6$) δ ppm 2.14 (s, 3H) 2.24-2.37 (m, 4H) 2.38-2.48 (m, 4H) 3.11 (t, J=2.44 Hz, 1H) 3.23 (d, J=2.44 Hz, 2H).

HRMS (ESI) m/z calcd for C$_8$H$_{14}$N$_2$+H$^+$ 139.1230. found 139.1227.

Preparation of a Compound of Formula (X)

Preparation Q 2-(5-Chloro-2-methyl-phenyl)-5-(2-methylamino-pyrimidin-4-yl)-1H-pyrrole-3-carbonitrile

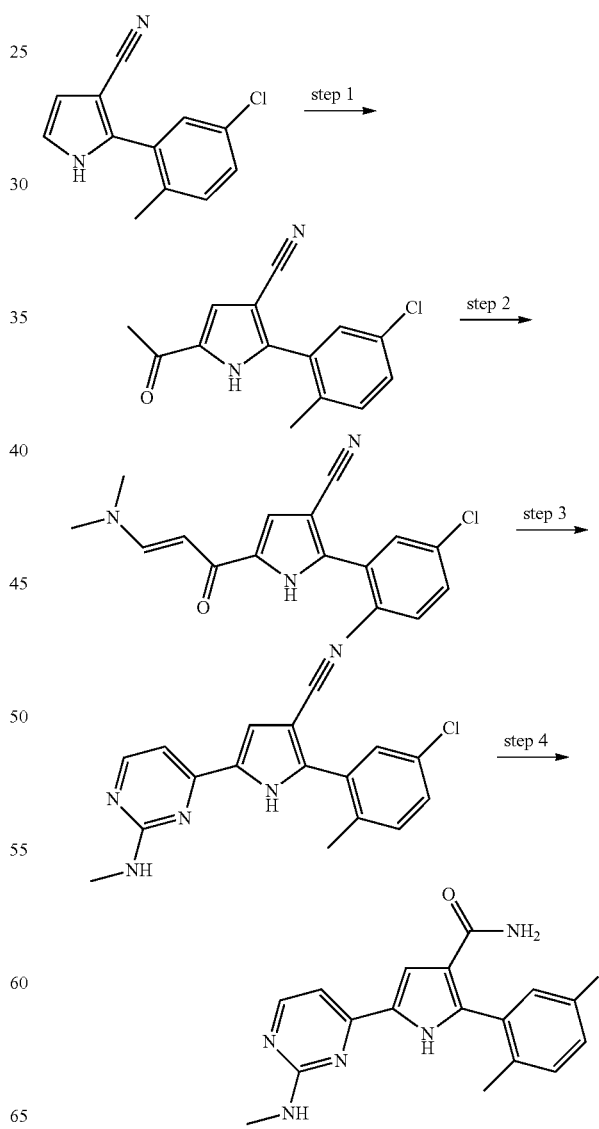

Step 1: 5-Acetyl-2-(5-chloro-2-methyl-phenyl)-1H-pyrrole-3-carbonitrile

To a mixture of 2-(5-chloro-2-methyl-phenyl)-1H-pyrrole-3-carbonitrile (1.80 g, 8.28 mmol) in DCM (40 mL) was added acetyl chloride (0.936 mL, 13.14 mmol) at room temperature, under nitrogen. The resultant mixture was cooled to 0° C. and anhydrous aluminum trichloride (2.62 g, 19.8 mmol) was added in small portions during a period of 10 min, keeping the internal temperature below 5° C. Upon complete addition, the mixture was brought to room temperature and allowed to stir for 30 min. Then, the mixture was slowly poured in a solution of ice-cooled 1 M HCl (18 mL). The aqueous layer was separated and extracted twice with DCM (40 mL). The combined organic extracts were washed with brine, dried over $Na_2SO_4$ and concentrated under reduced pressure. The crude material was chromatographed on silica gel (10 to 20% EtOAc/hexane) to afford the title compound (2.0 g, 86%).

$^1$H NMR (400 MHz, DMSO-$d_6$) δ ppm 2.24 (s, 3H) 2.43 (s, 3H) 7.38-7.42 (m, 1H) 7.43 (d, J=2.32 Hz, 1H) 7.46-7.50 (m, 1H) 7.60 (s, 1H) 12.89 (bs, 1H).

HRMS (ESI) calcd for $C_{14}H_{11}ClN_2O+H^+$ 259.0633. found 259.0638.

Step 2: 2-(5-Chloro-2-methyl-phenyl)-5-(E)-3-dimethylamino-acryloyl)-1H-pyrrole-3-carbonitrile To a suspension of 5-acetyl-2-(5-chloro-2-methyl-phenyl)-1H-pyrrole-3-carbonitrile (1.98 g, 7.66 mmol) in DMF (10 mL) was added N,N-dimethylformamide diisopropyl acetal (4.8 mL, 23.0 mmol). The mixture was allowed to stir overnight at 90° C. The mixture was evaporated in vacuo and used in the next step without further purification.

Step 3: 2-(5-Chloro-2-methyl-phenyl)-5-(2-methylamino-pyrimidin-4-yl)-1H-pyrrole-3-carbonitrile To a suspension of the crude 2-(5-chloro-2-methyl-phenyl)-5-(E)-3-dimethylamino-acryloyl)-1H-pyrrole-3-carbonitrile coming from the previous step in DMF (10 mL) was added methylguanidine hydrochloride (920 mg, 8.4 mmol) and $K_2CO_3$ (1.27 g, 9.16 mmol). The mixture was heated to 110° C. overnight under efficient stirring. The resultant mixture was concentrated and chromatographed on silica gel (10 to 30% EtOAc/hexane) to afford the title compound (1.19 g, 48%, 2 steps).

$^1$H NMR (400 MHz, DMSO-$d_6$) δ ppm 2.28 (s, 3H) 2.88 (d, J=4.52 Hz, 3H) 6.83-6.95 (m, 1H) 6.95-7.03 (m, 1H) 7.36-7.41 (m, 1H) 7.41-7.46 (m, 1H) 7.46-7.53 (m, 3H) 8.27 (d, J=4.64 Hz, 1H) 12.53 (bs, 1H).

HRMS (ESI) calcd for $C_{17}H_{14}ClN_5+H^+$ 324.1011. found 324.1013.

According to this step, but using guanidine carbonate, the following compound was prepared:

5-(2-Aminopyrimidin-4-yl)-2-(5-chloro-2-methylphenyl)-1H-pyrrole-3-carbonitrile $^1$H NMR (400 MHz, DMSO-$d_6$) δ ppm 2.28 (s, 3H) 7.05 (bs, 1H) 7.14 (d, J=5.74 Hz, 1H) 7.41-7.46 (m, 1H) 7.46-7.54 (m, 3H) 8.30 (d, J=5.74 Hz, 1H) 12.79 (bs, 1H).

HRMS (ESI) calcd for $C_{16}H_{12}ClN_5+H^+$ 310.0854. found 310.0853.

According to this step, but using formamidine acetate, the following compound was prepared:

2-(5-Chloro-2-methyl-phenyl)-5-(pyrimidin-4-yl)-1H-pyrrole-3-carbonitrile $^1$H NMR (400 MHz, DMSO-$d_6$) δ ppm 2.30 (s, 3H) 7.40-7.45 (m, 1H) 7.46-7.53 (m, 2H) 7.61 (s, 1H) 7.90 (dd, J=5.43, 1.28 Hz, 1H) 8.79 (d, J=5.37 Hz, 1H) 9.13 (d, J=1.22 Hz, 1H) 12.98 (bs, 1H).

HRMS (ESI) calcd for $C_{17}H_{14}N_5O+H^+$ 295.0745. found 295.0750.

According to this step, but using acetamidine acetate, the following compound was prepared:

2-(5-Chloro-2-methylphenyl)-5-(2-methylpyrimidin-4-yl)-1H-pyrrole-3-carbonitrile $^1$H NMR (600 MHz, DMSO-$d_6$) δ ppm 2.28 (s, 3H), 2.61-2.64 (m, 3H), 7.39-7.45 (m, 1H), 7.46-7.52 (m, 2H), 7.55 (s, 1H), 7.68 (d, J=5.31 Hz, 1H), 8.67 (d, J=5.31 Hz, 1H), 12.84 (bs, 1H).

ESI (+) MS: m/z 309 (MH$^+$).

Step 4: 2-(5-Chloro-2-methyl-phenyl)-5-(2-methylamino-pyrimidin-4-yl)-1H-pyrrole-3-carboxamide To a solution of 2-(5-chloro-2-methyl-phenyl)-5-(2-methylamino-pyrimidin-4-yl)-1H-pyrrole-3-carbonitrile (1.15 g, 3.55 mmol) in TFA (15.0 mL) were sequentially added water (2.25 mL) and 98% sulfuric acid (4.5 mL) under efficient stirring. The mixture was allowed to stir for 8 h at 70° C. and then was diluted by drop wise addition of water (45 mL). The reaction mixture was made basic (pH 10-12) by adding 30% aqueous ammonia (15 mL) under stirring. The precipitated solid was collected by filtration, washed with water and finally dried in a vacuum oven at 50° C. affording the title compound as an off-white solid (1.07 g, 88%).

$^1$H NMR (400 MHz, DMSO-$d_6$) δ ppm 2.12 (s, 3H) 2.88 (d, J=4.15 Hz, 3H) 6.67-6.83 (m, 1H) 6.88 (d, J=5.13 Hz, 1H) 7.19 (bs, 1H) 7.26-7.32 (m, 2H) 7.34-7.38 (m, 1H) 7.39 (s, 1H) 8.20 (d, J=5.37 Hz, 1H) 11.87 (bs, 1H).

HRMS (ESI) calcd for $C_{17}H_{16}ClN_5O+H^+$ 342.1116. found 342.1118.

The above procedure was employed to synthesize the following compounds:

2-(5-Chloro-2-methyl-phenyl)-5-(pyrimidin-4-yl)-1H-pyrrole-3-carboxamide $^1$H NMR (400 MHz, DMSO-$d_6$) δ ppm 2.13 (s, 3H) 6.81 (bs, 1H) 7.19-7.33 (m, 3H) 7.33-7.40 (m, 1H) 7.57 (d, J=2.69 Hz, 1H) 7.74 (dd, J=5.43, 1.40 Hz, 1H) 8.70 (d, J=5.49 Hz, 1H) 9.04 (d, J=1.10 Hz, 1H) 12.22 (bs, 1H).

HRMS (ESI) calcd for $C_{16}H_{13}N_4O+H^+$ 313.0851. found 313.0853.

2-(5-Chloro-2-methylphenyl)-5-(2-methylpyrimidin-4-yl)-1H-pyrrole-3-carboxamide $^1$H NMR (400 MHz, DMSO-$d_6$) δ ppm 2.12 (s, 3H) 2.59 (s, 3H) 6.80 (bs, 1H) 7.24-7.31 (m, 2H) 7.33 (bs, 1H) 7.34-7.38 (m, 1H) 7.50-7.58 (m, 2H) 8.59 (d, J=5.34 Hz, 1H) 12.13 (bs, 1H).

HRMS (ESI) calcd for $C_{16}H_{13}N_4O+H^+$ 327.1007. found 327.1011.

5-(2-Aminopyrimidin-4-yl)-2-(5-chloro-2-methylphenyl)-1H-pyrrole-3-carboxamide $^1$H NMR (400 MHz, DMSO-$d_6$) δ ppm 2.12 (s, 3H), 6.35 (bs, 2H), 6.73 (bs, 1H), 6.93 (d, J=5.24 Hz, 1H), 7.22 (bs, 1H), 7.25-7.30 (m, 2H), 7.32-7.36 (m, 2H), 8.20 (d, J=5.24 Hz, 1H), 11.85 (bs, 1H).

HRMS (ESI) m/z calcd for $C_{16}H_{14}ClN_5O+H^+$ 328.0960. found 328.0959.

Example 1

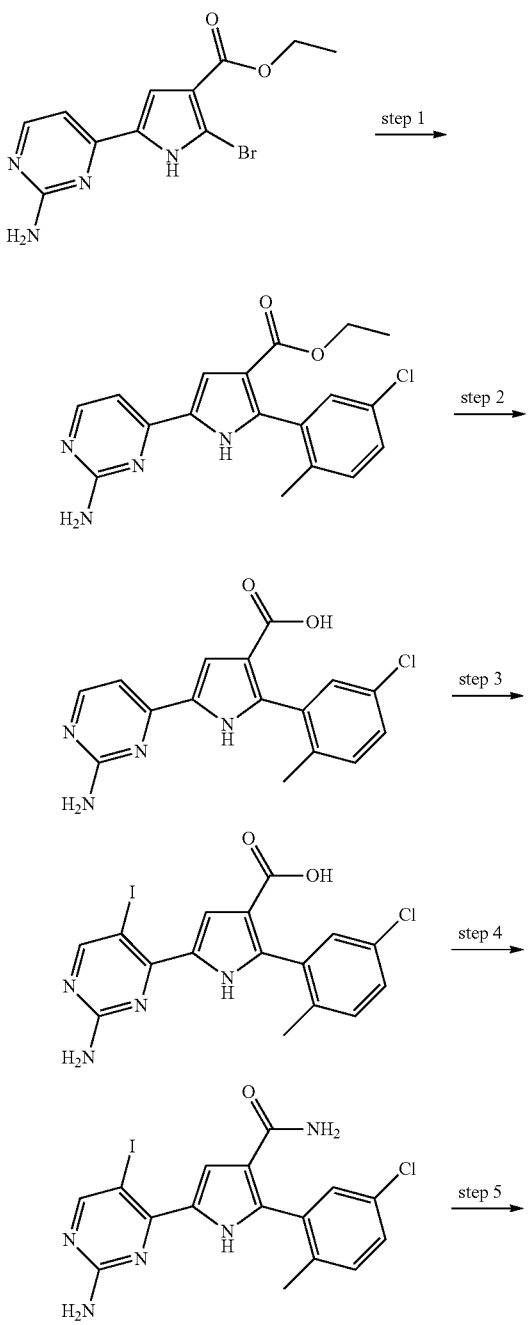

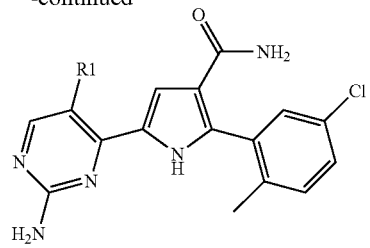

Scheme A, Steps 1, 2, 3, 4, 5

Step 1: Ethyl 5-(2-aminopyrimidin-4-yl)-2-(5-chloro-2-methyl-phenyl)-1H-pyrrole-3-carboxylate (IV)

To a solution of ethyl 5-(2-aminopyrimidin-4-yl)-2-bromo-1H-pyrrole-3-carboxylate (prepared according to WO2007/110344, 2.0 g, 6.43 mmol) dissolved in EtOH (20 mL) and toluene (20 mL), LiCl (408 mg, 9.64 mmol), 1 M aq $Na_2CO_3$ (17 mmol), 5-chloro-2-methylphenylboronic acid (1.423 g, 8.35 mmol) and $Pd(Ph_3P)_2Cl_2$ (470 mg, 0.67 mmol) were added and the reaction mixture was heated at 100° C. for 5 h. After cooling to room temperature, the precipitate was filtered and the filtrate was evaporated under reduced pressure, dissolved in DCM and washed with water. The organic layer was then dried over sodium sulfate and concentrated. The crude material was chromatographed on silica gel (DCM/EtOAc 50/50) to afford the title compound (1.99 g, 87%).

$^1$H NMR (400 MHz, DMSO-$d_6$) δ ppm 1.09 (t, J=7.14 Hz, 3H) 2.11 (s, 3H) 4.04 (q, J=7.12 Hz, 2H) 6.41 (s, 2H) 7.01 (d, J=5.25 Hz, 1H) 7.25-7.36 (m, 3H) 7.37-7.43 (m, 1H) 8.21 (d, J=5.13 Hz, 1H) 12.17 (bs, 1H).

According to the above procedure, but starting from the suitable aryl boronic acid, the following compounds were prepared:

Ethyl 5-(2-aminopyrimidin-4-yl)-2-[2-methyl-5-(trifluoromethyl)phenyl]-1H-pyrrole-3-carboxylate (IV)

$^1$H NMR (400 MHz, DMSO-$d_6$) δ ppm 1.04 (t, J=7.14 Hz, 3H) 2.21 (s, 3H) 4.02 (q, J=7.04 Hz, 2H) 6.41 (s, 2H) 7.01 (d, J=5.25 Hz, 1H) 7.32 (d, J=2.44 Hz, 1H) 7.54 (d, J=8.06 Hz, 1H) 7.59 (d, J=1.46 Hz, 1H) 7.70 (dd, J=8.06, 1.46 Hz, 1H) 8.21 (d, J=5.25 Hz, 1H) 12.24 (bs, 1H).

Ethyl 5-(2-aminopyrimidin-4-yl)-2-(5-chloro-2-ethylphenyl)-1H-pyrrole-3-carboxylate (IV)

$^1$H NMR (400 MHz, DMSO-$d_6$) δ ppm 0.97 (t, J=7.57 Hz, 3H) 1.06 (t, J=7.08 Hz, 3H) 2.44 (q, J=7.57 Hz, 2H) 4.03 (q, J=7.08 Hz, 2H) 7.21 (d, J=6.10 Hz, 1H) 7.32 (d, J=2.32 Hz, 1H) 7.38 (d, J=8.42 Hz, 1H) 7.47 (dd, J=8.30, 2.32 Hz, 1H) 7.50 (d, J=2.56 Hz, 1H) 8.25 (d, J=5.98 Hz, 1H) 12.52 (bs, 1H).

Ethyl 5-(2-aminopyrimidin-4-yl)-2-[2-ethyl-5-(trifluoromethyl)phenyl]-1H-pyrrole-3-carboxylate (IV)

$^1$H NMR (400 MHz, DMSO-$d_6$) δ ppm 1.01 (t, J=7.15 Hz, 6H) 2.54 (q, J=7.60 Hz, 2H) 4.00 (q, J=7.08 Hz, 2H) 6.41 (bs, 2H) 7.01 (d, J=5.25 Hz, 1H) 7.31 (d, J=2.56 Hz, 1H) 7.56 (d, J=1.60 Hz, 1H) 7.58 (d, J=8.20 Hz, 1H) 7.74 (dd, J=8.12, 1.53 Hz, 1H) 8.21 (d, J=5.13 Hz, 1H) 12.27 (bs, 1H).

Step 2: 5-(2-Aminopyrimidin-4-yl)-2-(5-chloro-2-methyl-phenyl]-1H-pyrrole-3-carboxylic acid (V)

Ethyl 5-(2-aminopyrimidin-4-yl)-2-(5-chloro-2-methylphenyl)-1H-pyrrole-3-carboxylate (1.0 g, 2.80 mmol) was treated with a 1.5 M solution of potassium hydroxide in 95% EtOH (32.4 mL, 20 eq) under reflux for 20 h. After cooling, the residue was concentrated, dissolved in water and washed with DCM. To the aqueous phase cooled to 5° C., a solution of 2 N HCl was added, under agitation. The resultant precipitate was collected by filtration to give the title compound (0.92 g, 95%).
$^1$H NMR (400 MHz, DMSO-$d_6$) δ ppm 2.12 (s, 3H) 7.28-7.37 (m, 3H) 7.40-7.45 (m, 1H) 7.59 (d, J=2.56 Hz, 1H) 7.77 (bs, 1H) 8.28 (d, J=6.44 Hz, 1H) 12.06 (s, 1H) 12.54 (bs, 1H).

Step 3: 5-(2-Amino-5-iodo-pyrimidin-4-yl)-2-(5-chloro-2-methyl-phenyl)-1H-pyrrole-3-carboxylic acid (VI)

5-(2-Amino-pyrimidin-4-yl)-2-(5-chloro-2-methyl-phenyl)-1H-pyrrole-3-carboxylic acid (0.70 g, 2.13 mmol) and Iodine (1.134 g, 4.47 mmol) in dry DMF (5 mL), under a nitrogen atmosphere, were stirred at −40° C. (internal temperature) and treated drop wise with silver trifluoroacetate (0.987 g, 4.47 mmol) in DMF (5 mL). The mixture was stirred at −40° C. for 7 h and then filtered over a short plug of celite. The panel was washed with DMF (5 mL) and the filtrate was collected in a flask containing 10% $Na_2S_2O_3$ (50 mL). Precipitation of a pale yellow solid occurred. Dilution with water (50 mL) and filtration of the solid afforded 0.79 g of crude product, which was reacted in the next step with no further purification.

According to the above procedure the following compound was prepared:

5-(2-Amino-5-iodo-pyrimidin-4-yl)-2-phenyl-1H-pyrrole-3-carboxylic acid (VI)

Step 4: 5-(2-Amino-5-iodo-pyrimidin-4-yl)-2-(5-chloro-2-methyl-phenyl)-1H-pyrrole-3-carboxamide (VIII)

Crude 5-(2-amino-5-iodo-pyrimidin-4-yl)-2-(5-chloro-2-methyl-phenyl)-1H-pyrrole-3-carboxylic acid (691 mg, 1.52 mmol) in DMF (5 mL) and DIPEA (1.06 mL, 6.08 mmol) was stirred at 0° C. EDCl (582 mg, 3.04 mmol) and HOBT.NH$_3$ (469 mg, 3.04 mmol) were added and the reaction mixture was stirred for 2 h at room temperature. The reaction mixture was poured into saturated solution of sodium hydrogen carbonate. The solid was filtered with suction and the panel washed thoroughly with water and dried under vacuum in an oven at 50° C. The crude compound may be purified by flash chromatography (DCM/MeOH 95/5) to give the title compound (518 mg, 75%).
$^1$H NMR (400 MHz, DMSO-$d_6$) δ ppm 2.13 (s, 3H) 6.53 (bs, 2H) 6.78 (bs, 1H) 7.11 (bs, 1H) 7.28 (d, J=2.32 Hz, 1H) 7.29 (d, J=8.30 Hz, 1H) 7.36 (dd, J=8.30, 2.32 Hz, 1H) 7.77 (d, J=2.69 Hz, 1H) 8.50 (s, 1H) 11.53 (bs, 1H).

According to this step, but starting from 5-(2-amino-5-iodo-pyrimidin-4-yl)-2-phenyl-1H-pyrrole-3-carboxylic acid, the following compound was prepared:

5-(2-Amino-5-iodo-pyrimidin-4-yl)-2-phenyl-1H-pyrrole-3-carboxamide (VIII)

$^1$H NMR (400 MHz, DMSO-$d_6$) δ ppm 6.63 (bs, 2H), 6.90 (bs, 1H), 7.28 (bs, 1H), 7.33-7.39 (m, 1H), 7.39-7.45 (m, 2H), 7.64-7.69 (m, 3H), 8.50-8.52 (m, 1H), 11.27 (bs, 1H).

According to the above procedure, but starting from ethyl 5-(2-aminopyrimidin-4-yl)-2-(5-chloro-2-ethylphenyl)-1H-pyrrole-3-carboxylate, the following compound was prepared:

5-(2-Amino-5-iodo-pyrimidin-4-yl)-2-(5-chloro-2-ethyl-phenyl)-1H-pyrrole-3-carboxamide (VIII)

ESI (+) MS: m/z 468 (MH$^+$).

According to the above procedure, but starting from ethyl 5-(2-aminopyrimidin-4-yl)-2-[2-methyl-5-(trifluoromethyl)phenyl]-1H-pyrrole-3-carboxylate, the following compound was prepared:

5-(2-Amino-5-iodo-pyrimidin-4-yl)-2-[2-methyl-5-(trifluoromethyl)phenyl]-1H-pyrrole-3-carboxamide (VIII)

ESI (+) MS: m/z 488 (MH$^+$).

According to the above procedure, but starting from ethyl 5-(2-aminopyrimidin-4-yl)-2-[2-ethyl-5-(trifluoromethyl)phenyl]-1H-pyrrole-3-carboxylate, the following compound was prepared:

5-(2-Amino-5-iodo-pyrimidin-4-yl)-2-[2-ethyl-5-(trifluoromethyl)phenyl]-1H-pyrrole-3-carboxamide (VIII)

ESI (+) MS: m/z 502 (MH$^+$).

According to the above procedure, but employing the suitable amine, the following compound was prepared:

5-(2-Amino-5-iodopyrimidin-4-yl)-2-(5-chloro-2-methylphenyl)-N-methyl-1H-pyrrole-3-carboxamide (VIII)

HRMS (ESI) calcd for $C_{17}H_{16}ClIN_5O+H^+$ 468.7012. found 468.7018.

According to the above procedure, but starting from ethyl 5-(2-aminopyrimidin-4-yl)-2-(5-chloro-2-ethylphenyl)-1H-pyrrole-3-carboxylate and employing the suitable amine, the following compound was prepared:

5-(2-Amino-5-iodo-pyrimidin-4-yl)-2-(5-chloro-2-ethyl-phenyl)-N-methyl-1H-pyrrole-3-carboxamide (VIII)

ESI (+) MS: m/z 482 (MH$^+$).

According to the above procedure, but starting from ethyl 5-(2-aminopyrimidin-4-yl)-2-[2-methyl-5-(trifluoromethyl)phenyl]-1H-pyrrole-3-carboxylate and employing the suitable amine, the following compound was prepared:

5-(2-Amino-5-iodo-pyrimidin-4-yl)-2-[2-methyl-5-(trifluoromethyl)phenyl]-N-methyl-1H-pyrrole-3-carboxamide (VIII)

ESI (+) MS: m/z 502 (MH$^+$).

According to the above procedure, but starting from ethyl 5-(2-aminopyrimidin-4-yl)-2-[2-ethyl-5-(trifluoromethyl)

phenyl]-1H-pyrrole-3-carboxylate and employing the suitable amine, the following compound was prepared:

5-(2-Amino-5-iodo-pyrimidin-4-yl)-2-[2-ethyl-5-(trifluoromethyl)phenyl]-N-methyl-1H-pyrrole-3-carboxamide (VIII)

ESI (+) MS: m/z 516 (MH$^+$).

Step 5: General Procedure 5-(2-Amino-5-iodo-pyrimidin-4-yl)-2-(5-chloro-2-methylphenyl)-1H-pyrrole-3-carboxamide (100 mg, 0.22 mmol, 1 eq) in dry ACN (4 mL) was treated with the alkyne (0.44 mmol, 2 eq) and TEA (0.31 mL, 2.2 mmol, 10 eq). The flask was stirred and purged with nitrogen and then solid CuI (0.011 mmol, 0.05 eq) and Pd(Ph$_3$P)$_2$Cl$_2$ (0.011 mmol, 0.05 eq) were added. The reaction was then either refluxed or heated under microwave irradiation at 80° C. until full conversion of the starting material was observed (typically from 1 to several h were required). If precipitation of the product occurred upon cooling, the solid was filtered, washed in sequence with ACN (3×1 mL), H$_2$O/MeOH 9/1 (2×1 mL) and finally dried under vacuum at 50° C. Conversely, the reaction was diluted with DCM (20 mL), washed with water (5 mL), dried over sodium sulfate and evaporated. The residue was then purified by flash chromatography, typically, DCM/MeOH 95/5 under gradient conditions or reverse phase purification (Phase A: 0.05 NH$_4$OH/ACN 95/5; Phase B: ACN/H$_2$O 95/5 Gradient: 10-70 in 10 CV).

The above procedure was employed to synthesize the following compounds:

5-[2-Amino-5-(phenylethynyl)pyrimidin-4-yl]-2-(5-chloro-2-methylphenyl)-1H-pyrrole-3-carboxamide [(I), R1=phenylethynyl, R2=R3=R4=H, R5=5-chloro-2-methylphenyl, R6=NH$_2$] (compd. 1)

$^1$H NMR (400 MHz, DMSO-d$_6$) δ ppm 2.14 (s, 3H) 6.79 (bs, 3H) 6.99 (bs, 1H) 7.30 (d, J=8.30 Hz, 1H) 7.31 (d, J=2.44 Hz, 1H) 7.37 (dd, J=8.30, 2.32 Hz, 1H) 7.83 (d, J=2.69 Hz, 1H) 8.45 (s, 1H) 11.66 (bs, 1H).
HRMS (ESI) calcd for C$_{24}$H$_{18}$ClN$_5$O+H$^+$ 428.1273. found 428.1278.

5-{2-Amino-5-[(3-hydroxyphenyl)ethynyl]pyrimidin-4-yl}-2-(5-chloro-2-methylphenyl)-1H-pyrrole-3-carboxamide [(I), R1=(3-hydroxyphenyl)ethynyl, R2=R3=R4=H, R5=5-chloro-2-methylphenyl, R6=NH$_2$] (compd. 2)

$^1$H NMR (400 MHz, DMSO-d$_6$) δ ppm 2.14 (s, 3H) 6.78 (bs, 1H) 6.81 (ddd, J=8.21, 2.47, 0.92 Hz, 1H) 6.85 (bs, 1H) 6.93 (bs, 1H) 6.94 (dd, J=2.14, 1.65 Hz, 1H) 7.04 (dt, J=7.69, 1.10 Hz, 1H) 7.18-7.25 (m, 1H) 7.31 (d, J=2.30 Hz, 1H) 7.30 (d, J=8.10 Hz, 1H) 7.36 (dd, J=8.06, 2.20 Hz, 1H) 7.79 (d, J=2.56 Hz, 1H) 8.44 (s, 1H) 9.66 (s, 1H) 11.64 (bs, 1H).
HRMS (ESI) calcd for C$_{24}$H$_{18}$ClN$_5$O$_2$+H$^+$ 444.1222. found 444.1220.

5-{2-Amino-5-[(4-methoxyphenyl)ethynyl]pyrimidin-4-yl}-2-(5-chloro-2-methylphenyl)-1H-pyrrole-3-carboxamide [(I), R1=(4-methoxyphenyl)ethynyl, R2=R3=R4=H, R5=5-chloro-2-methylphenyl, R6=NH$_2$] (compd. 3)

$^1$H NMR (400 MHz, DMSO-d$_6$) δ ppm 2.14 (s, 3H) 3.80 (s, 3H) 6.99 (d, J=8.91 Hz, 2H) 7.31 (d, J=2.30 Hz, 1H) 7.30 (d, J=8.10 Hz, 1H) 7.37 (dd, J=8.10, 2.30 Hz, 1H) 7.55 (d, J=8.91 Hz, 2H) 7.81 (d, J=2.56 Hz, 1H) 8.42 (s, 1H) 11.63 (d, J=1.46 Hz, 1H).
HRMS (ESI) calcd for C$_{25}$H$_{20}$ClN$_5$O$_2$+H$^+$ 458.1379. found 458.1371.

5-{2-amino-5-[(3-aminophenyl)ethynyl]pyrimidin-4-yl}-2-(5-chloro-2-methylphenyl)-1H-pyrrole-3-carboxamide [(I), R1=(3-aminophenyl)ethynyl, R2=R3=R4=H, R5=5-chloro-2-methylphenyl, R6=NH$_2$] (compd. 4)

$^1$H NMR (400 MHz, DMSO-d$_6$) δ ppm 2.14 (s, 3H) 5.18 (bs, 2H) 6.60 (ddd, J=8.12, 2.26, 0.98 Hz, 1H) 6.73-6.79 (m, 2H) 6.78-6.94 (bs, 3H) 7.05 (t, J=7.75 Hz, 1H) 7.30 (d, J=8.10 Hz, 1H) 7.32 (d, J=2.20 Hz, 1H) 7.37 (dd, J=8.10, 2.30 Hz, 1H) 7.79 (d, J=2.69 Hz, 1H) 8.40 (s, 1H) 11.63 (bs, 1H).
HRMS (ESI) calcd for C$_{24}$H$_{19}$ClN$_6$O+H$^+$ 443.1382. found 443.1384.

5-{2-Amino-5-[(2-methoxyphenyl)ethynyl]pyrimidin-4-yl}-2-(5-chloro-2-methylphenyl)-1H-pyrrole-3-carboxamide [(I), R1=(2-methoxyphenyl)ethynyl, R2=R3=R4=H, R5=5-chloro-2-methylphenyl, R6=NH$_2$] (compd. 5)

$^1$H NMR (400 MHz, DMSO-d$_6$) δ ppm 2.14 (s, 3H) 3.82 (s, 3H) 6.75 (bs, 2H) 6.82 (bs, 2H) 6.99 (td, J=7.48, 0.92 Hz, 1H) 7.09 (dd, J=8.48, 0.67 Hz, 1H) 7.30 (d, J=8.20 Hz, 1H) 7.32 (d, J=2.20 Hz, 1H) 7.37 (dd, J=8.20, 2.20 Hz, 2H) 7.38 (ddd, J=8.42, 7.32, 1.71 Hz, 2H) 7.53 (dd, J=7.57, 1.59 Hz, 1H) 7.95 (d, J=2.69 Hz, 1H) 8.41 (s, 1H) 11.55 (bs, 1H).
HRMS (ESI) calcd for C$_{25}$H$_{20}$ClN$_5$O$_2$+H$^+$ 458.1379. found 458.1375.

5-{2-Amino-5-[(2-aminophenyl)ethynyl]pyrimidin-4-yl}-2-(5-chloro-2-methylphenyl)-1H-pyrrole-3-carboxamide [(I), R1=(2-aminophenyl)ethynyl, R2=R3=R4=H, R5=5-chloro-2-methylphenyl, R6=NH$_2$] (compd. 6)

$^1$H NMR (400 MHz, DMSO-d$_6$) δ ppm 2.14 (s, 3H) 5.47 (s, 2H) 6.55 (td, J=7.45, 0.98 Hz, 1H) 6.74 (dd, J=8.24, 0.67 Hz, 1H) 7.07 (ddd, J=8.24, 7.14, 1.59 Hz, 1H) 7.29 (d, J=8.20 Hz, 1H) 7.31 (d, J=2.20 Hz, 1H) 7.32 (dd, J=7.60, 1.40 Hz, 1H) 7.36 (dd, J=8.20, 2.20 Hz, 1H) 7.84 (d, J=2.56 Hz, 1H) 8.57 (s, 1H) 11.62 (s, 1H).
HRMS (ESI) calcd for C$_{24}$H$_{19}$ClN$_6$O+H$^+$ 443.1382. found 443.1376.

5-{2-Amino-5-[(2,4-difluorophenyl)ethynyl]pyrimidin-4-yl}-2-(5-chloro-2-methylphenyl)-1H-pyrrole-3-carboxamide [(I), R1=(2,4-difluorophenyl)ethynyl, R2=R3=R4=H, R5=5-chloro-2-methylphenyl, R6=NH$_2$] (compd. 7)

$^1$H NMR (400 MHz, DMSO-d$_6$) δ ppm 2.13 (s, 3H) 6.79 (bs, 2H) 6.83 (bs, 1H) 6.95 (bs, 1H) 7.19 (m, J=8.54, 8.54, 2.56, 0.85 Hz, 1H) 7.28 (d, J=8.20 Hz, 1H) 7.29 (d, J=2.20 Hz, 1H) 7.36 (dd, J=8.20, 2.20 Hz, 1H) 7.42 (td, J=9.64, 2.69 Hz, 1H) 7.75 (td, J=8.54, 6.59 Hz, 1H) 7.80 (d, J=2.56 Hz, 1H) 8.45 (s, 1H) 11.65 (bs, 1H).
HRMS (ESI) calcd for C$_{24}$H$_{16}$ClF$_2$N$_5$O+H$^+$ 464.1084. found 464.1081.

5-{2-Amino-5-[(4-aminophenyl)ethynyl]pyrimidin-4-yl}-2-(5-chloro-2-methylphenyl)-1H-pyrrole-3-carboxamide [(I), R1=(4-aminophenyl)ethynyl, R2=R3=R4=H, R5=5-chloro-2-methylphenyl, R6=NH$_2$] (compd. 8)

$^1$H NMR (400 MHz, DMSO-d$_6$) δ ppm 2.14 (s, 3H) 5.53 (bs, 2H) 6.57 (d, J=8.67 Hz, 2H) 6.63 (bs, 2H) 6.79 (bs, 1H) 6.90 (bs, 1H) 7.26 (d, J=8.67 Hz, 2H) 7.30 (d, J=8.20 Hz, 1H) 7.32 (d, J=2.32 Hz, 1H) 7.36 (dd, J=8.20, 2.20 Hz, 1H) 7.80 (d, J=2.56 Hz, 1H) 8.36 (s, 1H) 11.57 (bs, 1H).
HRMS (ESI) calcd for C$_{24}$H$_{19}$ClN$_6$O+H$^+$ 443.1382. found 443.1378.

5-{2-Amino-5-[(5-amino-2-methoxyphenyl)ethynyl]pyrimidin-4-yl}-2-(5-chloro-2-methylphenyl)-1H-pyrrole-3-carboxamide [(I), R1=(5-amino-2-methoxyphenyl)ethynyl, R2=R3=R4=H, R5=5-chloro-2-methylphenyl, R6=NH$_2$] (compd. 9)

$^1$H NMR (400 MHz, DMSO-d$_6$) δ ppm 2.14 (s, 3H) 3.67 (s, 3H) 4.76 (bs, 2H) 6.61 (dd, J=8.67, 2.81 Hz, 1H) 6.73 (bs, 3H) 6.76 (d, J=2.81 Hz, 1H) 6.80 (d, J=8.79 Hz, 1H) 6.85 (bs, 1H) 7.29 (d, J=8.42 Hz, 1H) 7.32 (d, J=2.20 Hz, 1H) 7.36 (dd, J=8.18, 2.32 Hz, 1H) 7.95 (d, J=2.56 Hz, 1H) 8.38 (s, 1H) 11.52 (bs, 1H).
HRMS (ESI) calcd for C$_{25}$H$_{21}$ClN$_6$O$_2$+H$^+$ 473.1488. found 473.1483.

5-{2-Amino-5-[(4-amino-2-methoxyphenyl)ethynyl]pyrimidin-4-yl}-2-(5-chloro-2-methylphenyl)-1H-pyrrole-3-carboxamide [(I), R1=(4-amino-2-methoxyphenyl)ethynyl, R2=R3=R4=H, R5=5-chloro-2-methylphenyl, R6=NH$_2$] (compd. 10)

$^1$H NMR (400 MHz, DMSO-d$_6$) δ ppm 2.14 (s, 3H) 3.70 (s, 3H) 5.49 (bs, 2H) 6.17 (dd, J=8.61, 2.50 Hz, 1H) 6.32 (d, J=2.44 Hz, 1H) 6.65 (bs, 2H) 6.80 (bs, 1H) 6.88 (bs, 1H) 7.25 (d, J=8.54 Hz, 1H) 7.29 (d, J=8.69 Hz, 1H) 7.31 (d, J=2.32 Hz, 1H) 7.36 (dd, J=8.06, 2.32 Hz, 1H) 7.82 (d, J=2.69 Hz, 1H) 8.53 (s, 1H) 11.59 (bs, 1H).
HRMS (ESI) calcd for C$_{25}$H$_{21}$ClN$_6$O$_2$+H$^+$ 473.1488. found 473.1481.

5-(2-Amino-5-{[4-(4-methylpiperazin-1-yl)phenyl]ethynyl}pyrimidin-4-yl)-2-(5-chloro-2-methylphenyl)-1H-pyrrole-3-carboxamide [(I), R1=[4-(4-methylpiperazin-1-yl)phenyl]ethynyl, R2=R3=R4=H, R5=5-chloro-2-methylphenyl, R6=NH$_2$] (compd. 11)

$^1$H NMR (400 MHz, DMSO-d$_6$) δ ppm 2.14 (s, 3H) 2.22 (s, 3H) 2.42-2.47 (m, 4H) 3.19-3.25 (m, 4H) 6.68 (bs, 2H) 6.78 (bs, 1H) 6.91-6.99 (m, 3H) 7.26-7.35 (m, 2H) 7.35-7.38 (m, 1H) 7.40-7.48 (m, 2H) 7.81 (d, J=2.56 Hz, 1H) 8.40 (s, 1H) 11.60 (s, 1H).
HRMS (ESI) calcd for C$_{29}$H$_{28}$ClN$_7$O+H$^+$ 526.2117. found 526.2121.

5-[2-Amino-5-({3-[(1-methylpiperidin-4-yl)amino]phenyl}ethynyl)pyrimidin-4-yl]-2-(5-chloro-2-methylphenyl)-1H-pyrrole-3-carboxamide [(I), R1={3-[(1-methylpiperidin-4-yl)amino]phenyl}ethynyl, R2=R3=R4=H, R5=5-chloro-2-methylphenyl, R6=NH$_2$] (compd. 12)

$^1$H NMR (400 MHz, DMSO-d$_6$) δ ppm 1.30-1.45 (m, 2H) 1.86 (bs, 2H) 1.96-2.06 (m, 2H) 2.11-2.17 (m, 6H) 2.64-2.76 (m, 2H) 3.14-3.23 (m, 1H) 5.56 (d, J=8.06 Hz, 1H) 6.58-6.64 (m, 2H) 6.72-6.76 (m, 2H) 7.08 (t, J=8.06 Hz, 1H) 7.27-7.33 (m, 2H) 7.34-7.39 (m, 1H) 7.79 (d, J=2.44 Hz, 1H) 8.42 (s, 1H) 11.62 (bs, 1H).
HRMS (ESI) calcd for C$_{30}$H$_{30}$ClN$_7$O+H$^+$ 540.2273. found 540.2279.

5-(2-Amino-5-{[3-(tetrahydro-2H-pyran-4-ylamino)phenyl]ethynyl}pyrimidin-4-yl)-2-(5-chloro-2-methylphenyl)-1H-pyrrole-3-carboxamide [(I), R1=[3-(tetrahydro-2H-pyran-4-ylamino)phenyl]ethynyl, R2=R3=R4=H, R5=5-chloro-2-methylphenyl, R6=NH$_2$] (compd. 13)

$^1$H NMR (400 MHz, DMSO-d$_6$) δ ppm 1.29-1.44 (m, 2H) 1.85-1.92 (m, 2H) 2.15 (s, 3H) 3.39-3.46 (m, 2H) 3.47-3.54 (m, 1H) 3.77-3.90 (m, 2H) 5.64 (d, J=7.66 Hz, 1H) 6.65 (dd, J=8.24, 2.14 Hz, 1H) 6.74-6.80 (m, 2H) 6.84 (bs, 3H) 7.09 (t, J=7.81 Hz, 1H) 7.27-7.35 (m, 2H) 7.35-7.40 (m, 1H) 7.81 (d, J=2.56 Hz, 1H) 8.42 (s, 1H) 11.63 (s, 1H).
HRMS (ESI) calcd for C$_{26}$H$_{27}$ClN$_6$O$_2$+H$^+$ 527.1957. found 527.1961.

tert-Butyl (2-{[3-({2-amino-4-[4-carbamoyl-5-(5-chloro-2-methylphenyl)-1H-pyrrol-2-yl]pyrimidin-5-yl}ethynyl)phenyl]amino}ethyl)carbamate [(I), R1=tert-butyl {2-[(3-ethynylphenyl)amino]ethyl}carbamate, R2=R3=R4=H, R5=5-chloro-2-methylphenyl, R6=NH$_2$] (compd. 14)

ESI (+) MS: m/z 586 (MH$^+$).

5-[2-Amino-5-({3-[(2-hydroxyethyl)amino]phenyl}ethynyl)pyrimidin-4-yl]-2-(5-chloro-2-methylphenyl)-1H-pyrrole-3-carboxamide [(I), R1={3-[(2-hydroxyethyl)amino]phenyl}ethynyl, R2=R3=R4=H, R5=5-chloro-2-methylphenyl, R6=NH$_2$] (compd. 15)

$^1$H NMR (400 MHz, DMSO-d$_6$) δ ppm 2.14 (s, 3H) 3.12 (q, J=5.94 Hz, 2H) 3.56 (q, J=5.90 Hz, 2H) 4.68 (t, J=5.49 Hz, 1H) 5.65 (t, J=5.68 Hz, 1H) 6.64 (ddd, J=8.30, 2.32, 0.85 Hz, 1H) 6.74-6.80 (m, 2H) 7.06-7.12 (m, 1H) 7.28-7.33 (m, 2H) 7.35-7.39 (m, 1H) 7.83 (d, J=2.69 Hz, 1H) 8.42 (s, 1H) 11.63 (s, 1H).
HRMS (ESI) calcd for C$_{26}$H$_{23}$ClN$_6$O$_2$+H$^+$ 487.1644. found 487.1644.

5-[2-Amino-5-({4-[(1-methylpiperidin-4-yl)amino]phenyl}ethynyl)pyrimidin-4-yl]-2-(5-chloro-2-methylphenyl)-1H-pyrrole-3-carboxamide [(I), R1={4-[(1-methylpiperidin-4-yl)amino]phenyl}ethynyl, R2=R3=R4=H, R5=5-chloro-2-methylphenyl, R6=NH$_2$] (compd. 16)

$^1$H NMR (400 MHz, DMSO-d$_6$) δ ppm 1.33-1.48 (m, 2H) 1.88 (d, J=11.96 Hz, 2H) 2.02 (t, J=10.86 Hz, 2H) 2.14 (s, 3H) 2.17 (s, 3H) 2.73 (d, J=11.11 Hz, 2H) 3.13-3.27 (m, 1H) 5.94 (d, J=7.81 Hz, 1H) 6.58 (d, J=8.79 Hz, 2H) 6.63 (bs, 2H) 6.79 (bs, 1H) 6.89 (bs, 1H) 7.27-7.31 (m, 3H) 7.32 (d, J=2.32 Hz, 1H) 7.34-7.39 (m, 1H) 7.80 (d, J=2.69 Hz, 1H) 8.36 (s, 1H) 11.57 (s, 1H).
HRMS (ESI) calcd for C$_{30}$H$_{30}$ClN$_7$O+H$^+$ 540.2273. found 540.2278.

tert-Butyl 3-({[3-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate [(I), R1=tert-butyl 3-{[(3-ethynylphenyl)amino]methyl}azetidine-1-carboxylate, R2=R3=R4=H, R5=5-chloro-2-methylphenyl, R6=NH$_2$] (compd. 17)

$^1$H NMR (400 MHz, DMSO-d$_6$) δ ppm 1.37 (s, 9H) 2.14 (s, 3H) 2.70-2.80 (m, 1H) 3.21-3.27 (m, 2H) 3.52-3.60 (m, 2H) 3.90 (t, J=8.85 Hz, 2H) 5.88 (t, J=5.60 Hz, 1H) 6.62 (ddd, J=8.24, 2.26, 0.85 Hz, 1H) 6.74 (bs, 3H) 6.75-6.80 (m, 2H) 6.90 (bs, 1H) 7.06-7.14 (m, 1H) 7.28-7.31 (m, 1H) 7.32 (d, J=2.32 Hz, 1H) 7.34-7.40 (m, 1H) 7.82 (d, J=2.69 Hz, 1H) 8.42 (s, 1H) 11.63 (d, J=2.20 Hz, 1H).

HRMS (ESI) calcd for C$_{30}$H$_{30}$ClN$_7$O+H$^+$ 612.2485. found 612.2492.

5-(2-Amino-5-{[4-(tetrahydro-2H-pyran-4-ylamino)phenyl]ethynyl}pyrimidin-4-yl)-2-(5-chloro-2-methylphenyl)-1H-pyrrole-3-carboxamide [(I), R1=[4-(tetrahydro-2H-pyran-4-ylamino)phenyl]ethynyl, R2=R3=R4=H, R5=5-chloro-2-methylphenyl, R6=NH$_2$] (compd. 18)

$^1$H NMR (400 MHz, DMSO-d$_6$) δ ppm 1.33-1.44 (m, 2H) 1.84-1.91 (m, 2H) 2.14 (s, 3H) 3.42 (td, J=11.53, 2.20 Hz, 2H) 3.45-3.54 (m, 1H) 3.87 (ddd, J=11.47, 3.78, 3.42 Hz, 2H) 6.01 (d, J=7.93 Hz, 1H) 6.63 (bs, 2H) 6.62 (d, J=8.79 Hz, 2H) 6.80 (bs, 1H) 6.89 (bs, 1H) 7.27-7.34 (m, 4H) 7.34-7.39 (m, 1H) 7.80 (d, J=2.56 Hz, 1H) 8.36 (s, 1H) 11.58 (d, J=1.95 Hz, 1H).

HRMS (ESI) calcd for C$_{29}$H$_{27}$ClN$_6$O$_2$+H$^+$ 527.1957. found 527.1961.

5-[2-Amino-5-({4-[(2-hydroxyethyl)amino]phenyl}ethynyl)pyrimidin-4-yl]-2-(5-chloro-2-methylphenyl)-1H-pyrrole-3-carboxamide [(I), R1={4-[(2-hydroxyethyl)amino]phenyl}ethynyl, R2=R3=R4=H, R5=5-chloro-2-methylphenyl, R6=NH$_2$] (compd. 19)

$^1$H NMR (400 MHz, DMSO-d$_6$) δ ppm 2.14 (s, 3H) 3.13 (q, J=5.90 Hz, 2H) 3.56 (q, J=5.90 Hz, 2H) 4.70 (t, J=5.49 Hz, 1H) 6.03 (t, J=5.80 Hz, 1H) 6.60 (d, J=8.91 Hz, 2H) 6.63 (bs, 2H) 6.79 (bs, 1H) 6.90 (bs, 1H) 7.28-7.34 (m, 4H) 7.34-7.38 (m, 1H) 7.81 (d, J=2.69 Hz, 1H) 8.36 (s, 1H) 11.57 (s, 1H).

HRMS (ESI) calcd for C$_{26}$H$_{23}$ClN$_6$O$_2$+H$^+$ 487.1644. found 487.1651.

tert-Butyl 3-({[4-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate [(I), R1=tert-butyl 3-{[(4-ethynylphenyl)amino]methyl}azetidine-1-carboxylate, R2=R3=R4=H, R5=5-chloro-2-methylphenyl, R6=NH$_2$] (compd. 20)

$^1$H NMR (400 MHz, DMSO-d$_6$) δ ppm 1.37 (s, 9H) 2.14 (s, 3H) 2.70-2.80 (m, 1H) 3.22-3.28 (m, 2H) 3.55 (t, J=5.90 Hz, 2H) 3.91 (t, J=8.12 Hz, 2H) 6.21 (t, J=5.90 Hz, 1H) 6.59 (d, J=8.79 Hz, 2H) 6.64 (bs, 2H) 6.79 (bs, 1H) 6.90 (bs, 1H) 7.27-7.34 (m, 4H) 7.35-7.39 (m, 1H) 7.80 (d, J=2.69 Hz, 1H) 8.36 (s, 1H) 11.58 (d, J=1.95 Hz, 1H).

HRMS (ESI) calcd for C$_{33}$H$_{34}$ClN$_7$O$_3$+H$^+$ 612.2485. found 612.2485.

tert-Butyl (2-{[4-({2-amino-4-[4-carbamoyl-5-(5-chloro-2-methylphenyl)-1H-pyrrol-2-yl]pyrimidin-5-yl}ethynyl)phenyl]amino}ethyl)carbamate [(I), R1=tert-butyl {2-[(4-ethynylphenyl)amino]ethyl}carbamate, R2=R3=R4=H, R5=5-chloro-2-methylphenyl, R6=NH$_2$] (compd. 21)

$^1$H NMR (400 MHz, DMSO-d$_6$) δ ppm 1.39 (s, 9H) 2.14 (s, 3H) 3.10 (bs, 4H) 6.09 (t, J=5.25 Hz, 1H) 6.58 (d, J=8.67 Hz, 2H) 6.63 (bs, 2H) 6.79 (bs, 1H) 6.84-6.90 (m, 1H) 6.91 (bs, 1H) 7.28-7.34 (m, 4H) 7.34-7.39 (m, 1H) 7.80 (d, J=2.56 Hz, 1H) 8.37 (s, 1H) 11.57 (bs, 1H).

HRMS (ESI) calcd for C$_{31}$H$_{32}$ClN$_7$O$_3$+H$^+$ 586.2328. found 586.2322.

5-[2-Amino-5-({2-methoxy-5-[(1-methylpiperidin-4-yl)amino]phenyl}ethynyl)pyrimidin-4-yl]-2-(5-chloro-2-methylphenyl)-1H-pyrrole-3-carboxamide [(I), R1={2-methoxy-5-[(1-methylpiperidin-4-yl)amino]phenyl}ethynyl, R2=R3=R4=H, R5=5-chloro-2-methylphenyl, R6=NH$_2$] (compd. 22)

$^1$H NMR (400 MHz, DMSO-d$_6$) δ ppm 1.29-1.42 (m, 2H) 1.82-1.90 (m, 2H) 1.95-2.05 (m, 2H) 2.14 (s, 3H) 2.16 (s, 3H) 2.67-2.74 (m, 2H) 3.08-3.17 (m, 1H) 3.68 (s, 3H) 5.06 (d, J=8.42 Hz, 1H) 6.63 (dd, J=8.91, 2.93 Hz, 1H) 6.73 (d, J=2.81 Hz, 2H) 6.84 (d, J=9.03 Hz, 2H) 7.26-7.34 (m, 2H) 7.34-7.40 (m, 1H) 7.95 (d, J=2.69 Hz, 1H) 8.40 (s, 1H) 11.53 (s, 1H).

HRMS (ESI) calcd for C$_{31}$H$_{32}$ClN$_7$O$_2$+H$^+$ 570.2379. found 570.2375.

5-{2-Amino-5-[(4-formylphenyl)ethynyl]pyrimidin-4-yl}-2-(5-chloro-2-methylphenyl)-1H-pyrrole-3-carboxamide [(I), R1=(4-formylphenyl)ethynyl, R2=R3=R4=H, R5=5-chloro-2-methylphenyl, R6=NH$_2$] (compd. 23)

$^1$H NMR (400 MHz, DMSO-d$_6$) δ ppm 2.13-2.15 (m, 3H) 6.81-7.07 (m, 4H) 7.26-7.33 (m, 2H) 7.35-7.40 (m, 1H) 7.77-7.85 (m, 3H) 7.92-7.98 (m, 2H) 8.50 (s, 1H) 10.03 (s, 1H) 11.73 (d, J=2.07 Hz, 1H).

HRMS (ESI) calcd for C$_{25}$H$_{18}$ClN$_6$O$_2$+H$^+$ 456.1222. found 456.1219.

5-[2-Amino-5-({3-[(4-methylpiperazin-1-yl)methyl]phenyl}ethynyl)pyrimidin-4-yl]-2-(5-chloro-2-methylphenyl)-1H-pyrrole-3-carboxamide [(I), R1={3-[(4-methylpiperazin-1-yl)methyl]phenyl}ethynyl, R2=R3=R4=H, R5=5-chloro-2-methylphenyl, R6=NH$_2$] (compd. 24)

$^1$H NMR (400 MHz, DMSO-d$_6$) δ ppm 2.15 (s, 3H) 2.17 (s, 3H) 2.27-2.45 (m, 8H) 3.48 (s, 2H) 7.28-7.41 (m, 5H) 7.47-7.52 (m, 2H) 7.83 (d, J=2.56 Hz, 1H) 8.46 (s, 1H) 11.67 (s, 1H).

HRMS (ESI) calcd for C$_{30}$H$_{30}$ClN$_7$O+H$^+$ 540.2273. found 540.2278.

5-[2-Amino-5-({4-[4-(4-methylpiperazin-1-yl)piperidin-1-yl]phenyl}ethynyl)pyrimidin-4-yl]-2-(5-chloro-2-methylphenyl)-1H-pyrrole-3-carboxamide [(I), R1={4-[4-(4-methylpiperazin-1-yl)piperidin-1-yl]phenyl}ethynyl, R2=R3=R4=H, R5=5-chloro-2-methylphenyl, R6=NH$_2$] (compd. 25)

$^1$H NMR (400 MHz, DMSO-d$_6$) δ ppm 1.38-1.53 (m, 2H) 1.82 (m, J=11.47 Hz, 2H) 2.14 (s, 3H) 3.78-3.91 (m, 2H) 6.96

(d, J=9.15 Hz, 2H) 7.28-7.33 (m, 2H) 7.34-7.40 (m, 1H) 7.43 (d, J=8.54 Hz, 2H) 7.81 (d, J=2.69 Hz, 1H) 8.39 (s, 1H) 9.32 (bs, 1H) 11.61 (bs, 1H).

HRMS (ESI) calcd for $C_{34}H_{37}ClN_8O+H^+$ 609.2852. found 609.2850.

5-[2-Amino-5-({4-[4-(pyrrolidin-1-yl)piperidin-1-yl]phenyl}ethynyl)pyrimidin-4-yl]-2-(5-chloro-2-methylphenyl)-1H-pyrrole-3-carboxamide [(I), R1={4-[4-(pyrrolidin-1-yl)piperidin-1-yl]phenyl}ethynyl, R2=R3=R4=H, R5=5-chloro-2-methylphenyl, R6=NH₂] (compd. 26)

¹H NMR (400 MHz, DMSO-d₆) δ ppm 1.35-1.58 (m, 2H) 1.73 (bs, 4H) 1.95 (m, J=10.99 Hz, 2H) 2.14 (s, 3H) 2.56-2.74 (m, 2H) 2.82 (t, J=11.11 Hz, 2H) 3.77 (m, J=7.32 Hz, 2H) 6.68 (bs., 2H) 6.78 (bs, 1H) 6.92 (bs, 1H) 6.96 (d, J=8.91 Hz, 2H) 7.21-7.34 (m, 2H) 7.34-7.39 (m, 1H) 7.43 (d, J=8.91 Hz, 2H) 7.81 (d, J=2.56 Hz, 1H) 8.39 (s, 1H) 11.61 (bs, 1H).

HRMS (ESI) calcd for $C_{33}H_{34}ClN_7O+H^+$ 580.2586. found 580.2579.

5-[2-Amino-5-({3-[(4-methylpiperazin-1-yl)carbonyl]phenyl}ethynyl)pyrimidin-4-yl]-2-(5-chloro-2-methylphenyl)-1H-pyrrole-3-carboxamide [(I), R1={3-[(4-methylpiperazin-1-yl)carbonyl]phenyl}ethynyl, R2=R3=R4=H, R5=5-chloro-2-methylphenyl, R6=NH₂] (compd. 27)

¹H NMR (400 MHz, DMSO-d₆) δ ppm 2.14 (s, 3H) 2.19 (s, 3H) 2.25-2.41 (m, 4H) 3.62 (bs, 2H) 6.79 (bs, 2H) 7.28-7.32 (m, 2H) 7.34-7.41 (m, 2H) 7.47-7.53 (m, 1H) 7.56 (t, J=1.34 Hz, 1H) 7.67 (dt, J=7.81, 1.34 Hz, 1H) 7.82 (d, J=2.69 Hz, 1H) 8.47 (s, 1H) 11.67 (s, 1H).

HRMS (ESI) calcd for $C_{30}H_{28}ClN_7O_2+H^+$ 554.2066. found 554.2071.

5-(2-Amino-5-{[4-(4-hydroxypiperidin-1-yl)phenyl]ethynyl}pyrimidin-4-yl)-2-(5-chloro-2-methylphenyl)-1H-pyrrole-3-carboxamide [(I), R1=[4-(4-hydroxypiperidin-1-yl)phenyl]ethynyl, R2=R3=R4=H, R5=5-chloro-2-methylphenyl, R6=NH₂] (compd. 28)

¹H NMR (400 MHz, DMSO-d₆) δ ppm 1.34-1.53 (m, 2H) 1.80 (m, J=8.54 Hz, 2H) 2.14 (s, 3H) 2.95 (ddd, J=12.91, 10.10, 2.99 Hz, 2H) 3.54-3.73 (m, 3H) 4.66 (bs, 1H) 6.67 (bs, 2H) 6.78 (bs, 1H) 6.88-6.98 (m, 3H) 7.27-7.33 (m, 2H) 7.34-7.39 (m, 1H) 7.39-7.45 (m, 2H) 7.81 (d, J=2.56 Hz, 1H) 8.39 (s, 1H) 11.60 (s, 1H).

HRMS (ESI) calcd for $C_{26}H_{27}ClN_6O_2+H^+$ 527.1957. found 527.1954.

5-[2-Amino-5-({2-methoxy-4-[(1-methylpiperidin-4-yl)amino]phenyl}ethynyl)pyrimidin-4-yl]-2-(5-chloro-2-methylphenyl)-1H-pyrrole-3-carboxamide [(I), R1={2-methoxy-4-[(1-methylpiperidin-4-yl)amino]phenyl}ethynyl, R2=R3=R4=H, R5=5-chloro-2-methylphenyl, R6=NH₂] (compd. 29)

¹H NMR (400 MHz, DMSO-d₆) δ ppm 2.13 (s, 3H) 3.76 (s, 3H) 5.02 (d, J=8.06 Hz, 1H) 6.20-6.32 (m, 3H) 6.70 (bs, 2H) 6.85 (bs, 2H) 7.23-7.32 (m, 2H) 7.34-7.40 (m, 1H) 7.76 (d, J=2.44 Hz, 1H) 8.47 (s, 1H) 11.63 (s, 1H).

HRMS (ESI) calcd for $C_{31}H_{32}ClN_7O_2+H^+$ 570.2379. found 570.2372.

5-{2-Amino-5-[3-(1,1-dioxidothiomorpholin-4-yl)prop-1-yn-1-yl]pyrimidin-4-yl}-2-(5-chloro-2-methylphenyl)-1H-pyrrole-3-carboxamide [(I), R1=3-(1,1-dioxidothiomorpholin-4-yl)prop-1-yn-1-yl, R2=R3=R4=H, R5=5-chloro-2-methylphenyl, R6=NH₂] (compd. 30)

¹H NMR (400 MHz, DMSO-d₆) δ ppm 2.13 (s, 3H) 3.05 (m, J=5.37 Hz, 4H) 3.16 (m, J=5.61 Hz, 4H) 3.81 (s, 2H) 6.69 (bs, 2H) 6.93 (br, 3H) 7.23-7.32 (m, 2H) 7.32-7.39 (m, 1H) 7.70 (d, J=2.69 Hz, 1H) 8.32 (s, 1H) 11.59 (d, J=1.83 Hz, 1H).

HRMS (ESI) calcd for $C_{23}H_{23}ClN_6O_3S+H^+$ 499.1314. found 499.1309.

5-[2-Amino-5-({4-[(2S)-2-(pyrrolidin-1-ylmethyl)pyrrolidin-1-yl]phenyl}ethynyl)pyrimidin-4-yl]-2-(5-chloro-2-methylphenyl)-1H-pyrrole-3-carboxamide [(I), R1={4-[(2S)-2-(pyrrolidin-1-ylmethyl)pyrrolidin-1-yl]phenyl}ethynyl, R2=R3=R4=H, R5=5-chloro-2-methylphenyl, R6=NH₂] (compd. 31)

¹H NMR (400 MHz, DMSO-d₆) δ ppm 1.80-2.10 (m, 8H) 2.14 (s, 3H) 2.45 (bs, 2H) 2.61 (bs, 2H) 3.11 (m, J=6.59 Hz, 2H) 3.37-3.47 (m, 2H) 3.76-4.05 (m, 1H) 6.62 (bs, 4H) 6.81 (bs, 3H) 7.26-7.34 (m, 3H) 7.35-7.39 (m, 1H) 7.41 (m, J=2.69 Hz, 1H) 7.81 (d, J=2.56 Hz, 1H) 8.38 (s, 1H) 11.59 (bs, 1H).

HRMS (ESI) calcd for $C_{33}H_{34}ClN_7O+H^+$ 580.2586. found 580.2579.

5-[2-Amino-5-({3-[(1-methylpiperidin-4-yl)oxy]phenyl}ethynyl)pyrimidin-4-yl]-2-(5-chloro-2-methylphenyl)-1H-pyrrole-3-carboxamide [(I), R1={3-[(1-methylpiperidin-4-yl)oxy]phenyl}ethynyl, R2=R3=R4=H, R5=5-chloro-2-methylphenyl, R6=NH₂] (compd. 32)

¹H NMR (400 MHz, DMSO-d₆) δ ppm 1.54-1.71 (m, 2H) 1.93 (dd, J=10.86, 6.84 Hz, 2H) 2.09-2.26 (m, 8H) 2.55-2.64 (m, 2H) 4.37-4.47 (m, 1H) 6.79 (bs, 2H) 6.98 (ddd, J=8.33, 2.53, 0.98 Hz, 1H) 7.12-7.19 (m, 1H) 7.26-7.33 (m, 2H) 7.34-7.40 (m, 1H) 7.81 (d, J=2.69 Hz, 1H) 8.45 (s, 1H) 11.65 (bs, 1H).

HRMS (ESI) calcd for $C_{30}H_{29}ClN_6O_2+H^+$ 541.2114. found 541.2108.

N-[3-({2-Amino-4-[4-carbamoyl-5-(5-chloro-2-methylphenyl)-1H-pyrrol-2-yl]pyrimidin-5-yl}ethynyl)-4-methoxyphenyl]-1-methylpiperidine-4-carboxamide [(I), R1={5-methoxy-3-[(4-methylpiperidin-1-yl)carbonylamino]phenyl}ethynyl, R2=R3=R4=H, R5=5-chloro-2-methylphenyl, R6=NH₂] (compd. 33)

¹H NMR (400 MHz, DMSO-d₆) δ ppm 1.54-1.71 (m, 2H) 1.93 (dd, J=10.86, 6.84 Hz, 2H) 2.09-2.26 (m, 8H) 2.55-2.64 (m, 2H) 4.37-4.47 (m, 1H) 6.79 (bs, 2H) 6.98 (ddd, J=8.33, 2.53, 0.98 Hz, 1H) 7.12-7.19 (m, 1H) 7.26-7.33 (m, 2H) 7.34-7.40 (m, 1H) 7.81 (d, J=2.69 Hz, 1H) 8.45 (s, 1H) 11.65 (bs, 1H).

HRMS (ESI) calcd for $C_{32}H_{32}ClN_7O_3+H^+$ 598.2328. found 598.2322.

5-(2-Amino-5-{[2-methoxy-5-(4-methylpiperazin-1-yl)phenyl]ethynyl}pyrimidin-4-yl)-2-(5-chloro-2-methylphenyl)-1H-pyrrole-3-carboxamide [(I), R1=[2-methoxy-5-(4-methylpiperazin-1-yl)phenyl]ethynyl, R2=R3=R4=H, R5=5-chloro-2-methylphenyl, R6=NH₂] R2=H, R3=NH₂, R4=CH₃, R5=Cl] (compd. 34)

¹H NMR (400 MHz, DMSO-d₆) δ ppm 2.14 (s, 3H) 2.23 (s, 3H) 2.47 (m, J=3.91 Hz, 4H) 3.02-3.10 (m, 4H) 3.75 (s, 3H)

6.74 (bs, 1H) 6.83 (bs, 2H) 6.92-7.01 (m, 2H) 7.10 (d, J=1.71 Hz, 1H) 7.26-7.34 (m, 2H) 7.34-7.40 (m, 1H) 7.91-7.98 (m, 1H) 8.41 (s, 1H) 11.55 (s, 1H).

HRMS (ESI) calcd for $C_{30}H_{30}ClN_7O_2+H^+$ 556.2223. found 556.2228.

5-{2-Amino-5-[(5-bromo-2-methoxyphenyl)ethynyl] pyrimidin-4-yl}-2-(5-chloro-2-methylphenyl)-1H-pyrrole-3-carboxamide [(I), R1=(5-bromo-2-methoxyphenyl)ethynyl, R2=R3=R4=H, R5=5-chloro-2-methylphenyl, R6=NH$_2$] (compd. 35)

$^1$H NMR (400 MHz, DMSO-d$_6$) δ ppm 2.14 (s, 3H) 3.84 (s, 3H) 6.65-6.91 (m, 4H) 7.07 (d, J=9.03 Hz, 1H) 7.26-7.33 (m, 2H) 7.34-7.39 (m, 1H) 7.53 (dd, J=8.91, 2.56 Hz, 1H) 7.70 (d, J=2.56 Hz, 1H) 7.93 (d, J=2.69 Hz, 1H) 8.44 (bs, 1H) 11.57 (bs, 1H).

HRMS (ESI) calcd for $C_{25}H_{19}BrClN_5O_2+H^+$ 536.0484. found 536.0490.

5-[2-Amino-5-(cyclohexylethynyl)pyrimidin-4-yl]-2-(5-chloro-2-methylphenyl)-1H-pyrrole-3-carboxamide [(I), R1=cyclohexylethynyl, R2=R3=R4=H, R5=5-chloro-2-methylphenyl, R6=NH$_2$] (compd. 36)

$^1$H NMR (400 MHz, DMSO-d$_6$) δ ppm 1.23-1.40 (m, 3H) 1.52 (m, J=9.52 Hz, 3H) 1.70 (m, J=6.10 Hz, 2H) 1.84-1.96 (m, 2H) 2.14 (s, 3H) 2.69-2.78 (m, 1H) 6.58 (bs, 2H) 6.80 (bs, 1H) 6.87 (bs, 1H) 7.26-7.32 (m, 2H) 7.34-7.39 (m, 1H) 7.73 (d, J=2.56 Hz, 1H) 8.25 (s, 1H) 11.48 (bs, 1H).

HRMS (ESI) calcd for $C_{24}H_{24}ClN_5O+H^+$ 434.1742. found 434.1744.

5-[2-Amino-5-({2-methoxy-4-[(4-methylpiperazin-1-yl)carbonyl]phenyl}ethynyl)pyrimidin-4-yl]-2-(5-chloro-2-methylphenyl)-1H-pyrrole-3-carboxamide [(I), R1={2-methoxy-4-[(4-methylpiperazin-1-yl)carbonyl]phenyl}ethynyl, R2=R3=R4=H, R5=5-chloro-2-methylphenyl, R6=NH$_2$] (compd. 37)

$^1$H NMR (400 MHz, DMSO-d$_6$) δ ppm 2.17 (s, 3H) 2.20 (s, 3H) 3.86 (s, 3H) 6.78 (bs, 2H) 6.84 (bs, 2H) 6.97 (dd, J=7.75, 1.40 Hz, 1H) 7.05 (d, J=1.34 Hz, 1H) 7.12-7.18 (m, 1H) 7.27-7.40 (m, 2H) 7.57 (d, J=7.81 Hz, 1H) 7.94 (s, 1H) 8.43 (s, 1H) 11.57 (bs, 1H).

HRMS (ESI) calcd for $C_{31}H_{30}ClN_7O_3+H^+$ 584.2172. found 584.2166.

5-[2-Amino-5-(cyclopropylethynyl)pyrimidin-4-yl]-2-(5-chloro-2-methylphenyl)-1H-pyrrole-3-carboxamide [(I), R1=cyclopropylethynyl, R2=R3=R4=H, R5=5-chloro-2-methylphenyl, R6=NH$_2$] (compd. 38)

$^1$H NMR (400 MHz, DMSO-d$_6$) δ ppm 0.75-0.94 (m, 4H) 1.59-1.70 (m, 1H) 2.14 (s, 3H) 6.56 (bs, 2H) 6.80 (bs, 1H) 6.92 (bs, 1H) 7.24-7.32 (m, 2H) 7.33-7.38 (m, 1H) 7.61-7.66 (m, 1H) 8.14-8.30 (m, 1H) 11.50 (bs, 1H).

HRMS (ESI) calcd for $C_{21}H_{18}ClN_5O+H^+$ 392.1273. found 392.1266.

5-[2-Amino-5-(3,3-dimethylbut-1-yn-1-yl)pyrimidin-4-yl]-2-(5-chloro-2-methylphenyl)-1H-pyrrole-3-carboxamide [(I), R1=3,3-dimethylbut-1-yn-1-yl, R2=R3=R4=H, R5=5-chloro-2-methylphenyl, R6=NH$_2$] (compd. 39)

$^1$H NMR (400 MHz, DMSO-d$_6$) δ ppm 1.35 (s, 9H) 2.14 (s, 3H) 6.56 (bs, 2H) 6.80 (bs, 2H) 7.24-7.34 (m, 2H) 7.34-7.39 (m, 1H) 7.76 (d, J=2.56 Hz, 1H) 8.23 (bs, 1H) 11.50 (bs, 1H).

HRMS (ESI) calcd for $C_{22}H_{22}ClN_5O+H^+$ 408.1586. found 408.1578.

5-{2-Amino-5-[(4-bromophenyl)ethynyl]pyrimidin-4-yl}-2-(5-chloro-2-methylphenyl)-1H-pyrrole-3-carboxamide [(I), R1=(4-bromophenyl)ethynyl, R2=R3=R4=H, R5=5-chloro-2-methylphenyl, R6=NH$_2$] (compd. 40)

$^1$H NMR (400 MHz, DMSO-d$_6$) δ ppm 2.14 (s, 3H) 6.79 (bs, 3H) 7.04 (bs, 1H) 7.26-7.33 (m, 2H) 7.34-7.39 (m, 1H) 7.51-7.58 (m, 2H) 7.60-7.68 (m, 2H) 7.78 (d, J=2.56 Hz, 1H) 8.46 (s, 1H) 11.66 (bs, 1H).

HRMS (ESI) calcd for $C_{24}H_{17}BrClN_5O+H^+$ 506.0378. found 506.0373.

5-{2-Amino-5-[(4-bromo-2-fluorophenyl)ethynyl]pyrimidin-4-yl}-2-(5-chloro-2-methylphenyl)-1H-pyrrole-3-carboxamide [(I), R1=(4-bromo-2-fluorophenyl)ethynyl, R2=R3=R4=H, R5=5-chloro-2-methylphenyl, R6=NH$_2$] (compd. 41)

$^1$H NMR (400 MHz, DMSO-d$_6$) δ ppm 2.13 (s, 3H) 6.59-7.15 (m, 4H) 7.26-7.33 (m, 2H) 7.33-7.40 (m, 1H) 7.71 (dd, J=9.28, 1.83 Hz, 1H) 7.80 (d, J=2.56 Hz, 1H) 8.46 (s, 1H) 11.66 (bs, 1H).

HRMS (ESI) calcd for $C_{24}H_{16}BrClFN_5O+H^+$ 524.0284. found 524.0277.

5-(2-Amino-5-{[2-fluoro-4-(4-methylpiperazin-1-yl)phenyl]ethynyl}pyrimidin-4-yl)-2-(5-chloro-2-methylphenyl)-1H-pyrrole-3-carboxamide [(I), R1=[2-fluoro-4-(4-methylpiperazin-1-yl)phenyl]ethynyl, R2=R3=R4=H, R5=5-chloro-2-methylphenyl, R6=NH$_2$] (compd. 42)

$^1$H NMR (400 MHz, DMSO-d$_6$) δ ppm 2.14 (s, 3H) 2.23 (s, 3H) 2.44 (bs, 4H) 6.46-6.96 (m, 6H) 7.25-7.32 (m, 2H) 7.32-7.39 (m, 1H) 7.45 (t, J=8.73 Hz, 1H) 7.81 (d, J=2.56 Hz, 1H) 8.39 (s, 1H) 11.59 (s, 1H).

HRMS (ESI) calcd for $C_{29}H_{27}ClFN_7O+H^+$ 544.2023. found 544.2018.

5-[2-Amino-5-({2-[(2-hydroxyethyl)amino]phenyl}ethynyl)pyrimidin-4-yl]-2-(5-chloro-2-methylphenyl)-1H-pyrrole-3-carboxamide [(I), R1={2-[(2-hydroxyethyl)amino]phenyl}ethynyl, R2=R3=R4=H, R5=5-chloro-2-methylphenyl, R6=NH$_2$] (compd. 43)

$^1$H NMR (400 MHz, DMSO-d$_6$) δ ppm 2.14 (s, 3H) 3.20-3.26 (m, 2H) 3.60 (q, J=5.74 Hz, 2H) 4.84 (t, J=5.25 Hz, 1H) 5.41 (t, J=5.61 Hz, 1H) 6.60 (td, J=7.45, 0.98 Hz, 1H) 6.70 (d, J=7.93 Hz, 1H) 6.92 (bs, 4H) 7.15-7.23 (m, 1H) 7.27-7.32 (m, 2H) 7.34-7.41 (m, 2H) 7.80 (d, J=2.69 Hz, 1H) 8.51 (s, 1H) 11.63 (s, 1H).

HRMS (ESI) calcd for $C_{26}H_{23}ClN_6O_2+H^+$ 487.1644. found 487.1634.

5-{2-Amino-5-[3-(dimethylamino)prop-1-yn-1-yl]pyrimidin-4-yl}-2-(5-chloro-2-methylphenyl)-1H-pyrrole-3-carboxamide [(I), R1=3-(dimethylamino)prop-1-yn-1-yl, R2=R3=R4=H, R5=5-chloro-2-methylphenyl, R6=NH$_2$] (compd. 44)

$^1$H NMR (400 MHz, DMSO-d$_6$) δ ppm 2.13 (s, 3H) 2.26 (s, 6H) 3.57 (s, 2H) 6.64 (bs, 2H) 6.79 (bs, 1H) 7.01 (bs, 1H) 7.25-7.30 (m, 2H) 7.33-7.38 (m, 1H) 7.76 (d, J=2.69 Hz, 1H) 8.32 (s, 1H) 11.54 (bs, 1H).

5-{2-Amino-5-[(2-{[2-(dimethylamino)ethyl]amino}phenyl)ethynyl]pyrimidin-4-yl}-2-(5-chloro-2-methylphenyl)-1H-pyrrole-3-carboxamide [(I), R1=(2-{[2-(dimethylamino)ethyl]amino}phenyl)ethynyl, R2=R3=R4=H, R5=5-chloro-2-methylphenyl, R6=NH$_2$] (compd. 45)

$^1$H NMR (400 MHz, DMSO-d$_6$) δ ppm 2.14 (s, 3H) 2.18 (s, 6H) 3.18 (q, J=5.86 Hz, 2H) 5.55 (t, J=5.00 Hz, 1H) 6.51-6.64 (m, 1H) 6.66 (d, J=8.18 Hz, 1H) 6.79 (bs, 2H) 6.95 (bs, 1H) 7.16-7.25 (m, 1H) 7.25-7.33 (m, 2H) 7.34-7.43 (m, 2H) 7.84 (d, J=2.56 Hz, 1H) 8.46 (s, 1H) 11.64 (s, 1H).

HRMS (ESI) calcd for C$_{28}$H$_{28}$ClN$_7$O+H$^+$ 514.2117. found 514.2111.

5-(2-Amino-5-{[2-methoxy-4-(4-methylpiperazin-1-yl)phenyl]ethynyl}pyrimidin-4-yl)-2-(5-chloro-2-methylphenyl)-1H-pyrrole-3-carboxamide [(I), R1=[2-methoxy-4-(4-methylpiperazin-1-yl)phenyl]ethynyl, R2=R3=R4=H, R5=5-chloro-2-methylphenyl, R6=NH$_2$] (compd. 46)

$^1$H NMR (400 MHz, DMSO-d$_6$) δ ppm 2.14 (s, 3H) 2.24 (s, 3H) 2.46 (bs, 4H) 3.22-3.28 (m, 4H) 3.78 (s, 3H) 6.49-6.56 (m, 2H) 7.27-7.34 (m, 3H) 7.35-7.38 (m, 1H) 7.92 (d, J=2.56 Hz, 1H) 8.36 (s, 1H) 11.49 (d, J=1.95 Hz, 1H).

HRMS (ESI) calcd for C$_{30}$H$_{30}$ClN$_7$O$_2$+H$^+$ 556.2223. found 556.2215.

5-(2-Amino-5-{[3-(4-methylpiperazin-1-yl)phenyl]ethynyl}pyrimidin-4-yl)-2-(5-chloro-2-methylphenyl)-1H-pyrrole-3-carboxamide [(I), R1=[3-(4-methylpiperazin-1-yl)phenyl]ethynyl, R2=R3=R4=H, R5=5-chloro-2-methylphenyl, R6=NH$_2$] (compd. 47)

$^1$H NMR (400 MHz, DMSO-d$_6$) δ ppm 2.14 (s, 3H) 2.26 (bs, 3H) 3.19 (bs, 4H) 6.81 (bs, 4H) 6.93-7.04 (m, 2H) 7.11-7.16 (m, 1H) 7.22-7.27 (m, 1H) 7.28-7.33 (m, 1H) 7.34-7.40 (m, 1H) 7.85 (d, J=2.69 Hz, 1H) 8.43 (s, 1H) 11.64 (s, 1H).

HRMS (ESI) calcd for C$_{29}$H$_{28}$ClN$_7$O+H$^+$ 526.2117. found 526.2122.

5-[2-Amino-5-({4-[(1-methylpiperidin-4-yl)oxy]phenyl}ethynyl)pyrimidin-4-yl]-2-(5-chloro-2-methylphenyl)-1H-pyrrole-3-carboxamide [(I), R1={4-[(1-methylpiperidin-4-yl)oxy]phenyl}ethynyl, R2=R3=R4=H, R5=5-chloro-2-methylphenyl, R6=NH$_2$] (compd. 48)

$^1$H NMR (400 MHz, DMSO-d$_6$) δ ppm 1.64 (m, 2H) 1.94 (m, 2H) 2.18 (m, 8H) 2.62 (m, 2H) 4.24-4.54 (m, 1H) 6.72 (bs, 2H) 6.94-7.03 (m, 2H) 7.26-7.33 (m, 2H) 7.33-7.39 (m, 1H) 7.45-7.60 (m, 2H) 7.80 (d, J=2.56 Hz, 1H) 8.41 (s, 1H) 11.62 (s, 1H).

HRMS (ESI) calcd for C$_{30}$H$_{29}$ClN$_6$O$_2$+H$^+$ 541.2114. found 541.2121.

5-(2-Amino-5-{[2-fluoro-5-(4-methylpiperazin-1-yl)phenyl]ethynyl}pyrimidin-4-yl)-2-(5-chloro-2-methylphenyl)-1H-pyrrole-3-carboxamide [(I), R1=[2-fluoro-5-(4-methylpiperazin-1-yl)phenyl]ethynyl, R2=R3=R4=H, R5=5-chloro-2-methylphenyl, R6=NH$_2$-] (compd. 49)

$^1$H NMR (400 MHz, DMSO-d$_6$) δ ppm 2.14 (s, 3H) 2.22 (s, 3H) 2.46 (m, J=4.88 Hz, 4H) 3.06-3.17 (m, 4H) 6.84 (bs, 4H) 7.01 (dt, J=7.75, 4.42 Hz, 1H) 7.11-7.19 (m, 2H) 7.27-7.32 (m, 2H) 7.34-7.39 (m, 1H) 7.85 (d, J=2.56 Hz, 1H) 8.44 (s, 1H) 11.65 (s, 1H)

HRMS (ESI) calcd for C$_{29}$H$_{27}$ClFN$_7$O+H$^+$ 544.2023. found 544.2022.

5-{2-Amino-5-[3-(4-methylpiperazin-1-yl)prop-1-yn-1-yl]pyrimidin-4-yl}-2-(5-chloro-2-methylphenyl)-1H-pyrrole-3-carboxamide [(I), R1=(4-methylpiperazin-1-yl)prop-1-yn-1-yl, R2=R3=R4=H, R5=5-chloro-2-methylphenyl, R6=NH$_2$] (compd. 50)

$^1$H NMR (400 MHz, DMSO-d$_6$) δ ppm 2.13 (s, 3H) 3.63-3.80 (m, 2H) 6.68 (bs, 2H) 6.85 (bs, 1H) 6.97 (bs, 1H) 7.28 (d, J=1.95 Hz, 2H) 7.34-7.40 (m, 1H) 7.73 (d, J=2.56 Hz, 1H) 8.34 (s, 1H) 11.60 (bs, 1H).

HRMS (ESI) calcd for C$_{24}$H$_{26}$ClN$_7$O+H$^+$ 464.1960. found 464.1965.

5-(2-Amino-5-{3-[(1-methylpiperidin-4-yl)oxy]prop-1-yn-1-yl}pyrimidin-4-yl)-2-(5-chloro-2-methylphenyl)-1H-pyrrole-3-carboxamide [(I), R1=3-[(1-methylpiperidin-4-yl)oxy]prop-1-yn-1-yl, R2=R3=R4=H, R5=5-chloro-2-methylphenyl, R6=NH$_2$] (compd. 51)

$^1$H NMR (400 MHz, DMSO-d$_6$) δ ppm 1.41-1.56 (m, 2H) 1.82-1.91 (m, 2H) 1.98-2.07 (m, 2H) 2.10-2.18 (m, 6H) 2.56-2.65 (m, 2H) 3.53-3.62 (m, 1H) 4.51-4.56 (m, 2H) 7.25-7.31 (m, 2H) 7.33-7.38 (m, 1H) 7.68-7.72 (m, 1H) 8.32 (s, 1H) 11.58 (bs, 1H).

HRMS (ESI) calcd for C$_{25}$H$_{27}$ClN$_6$O$_2$+H$^+$ 479.1957. found 479.1942.

5-[2-Amino-5-({2-[(1-methylpiperidin-4-yl)amino]phenyl}ethynyl)pyrimidin-4-yl]-2-(5-chloro-2-methylphenyl)-1H-pyrrole-3-carboxamide [(I), R1={2-[(1-methylpiperidin-4-yl)amino]phenyl}ethynyl, R2=R3=R4=H, R5=5-chloro-2-methylphenyl, R6=NH$_2$] (compd. 52)

$^1$H NMR (400 MHz, DMSO-d$_6$) δ ppm 1.49 (q, J=9.64 Hz, 2H) 1.90 (d, J=10.74 Hz, 2H) 2.13 (s, 3H) 4.89 (d, J=8.30 Hz, 1H) 6.61 (t, J=7.57 Hz, 1H) 6.72 (d, J=8.42 Hz, 1H) 6.78 (bs, 2H) 6.89 (bs, 2H) 7.14-7.22 (m, 1H) 7.27-7.31 (m, 2H) 7.34-7.38 (m, 1H) 7.38-7.41 (m, 1H) 7.78 (d, J=2.56 Hz, 1H) 8.49 (s, 1H) 11.65 (d, J=1.95 Hz, 1H).

HRMS (ESI) calcd for C$_{30}$H$_{30}$ClN$_7$O+H$^+$ 540.2273. found 540.2269.

5-[2-Amino-5-(pyridin-3-ylethynyl)pyrimidin-4-yl]-2-(5-chloro-2-methylphenyl)-1H-pyrrole-3-carboxamide [(I), R1=pyridin-3-ylethynyl, R2=R3=R4=H, R5=5-chloro-2-methylphenyl, R6=NH$_2$] (compd. 53)

$^1$H NMR (400 MHz, DMSO-d$_6$) δ ppm 2.14 (s, 3H) 6.81 (bs, 3H) 7.12 (bs, 1H) 7.26-7.32 (m, 2H) 7.34-7.38 (m, 1H) 7.47-7.55 (m, 1H) 7.83 (d, J=2.69 Hz, 1H) 8.03 (d, J=8.18 Hz, 1H) 8.50 (s, 1H) 8.63 (bs, 1H) 8.87 (bs, 1H) 11.71 (bs, 1H).

HRMS (ESI) calcd for C$_{23}$H$_{17}$ClN$_6$O+H$^+$ 429.1225. found 429.1218.

5-[2-Amino-5-(3-hydroxy-3-methylbut-1-yn-1-yl)pyrimidin-4-yl]-2-(5-chloro-2-methylphenyl)-1H-pyrrole-3-carboxamide [(I), R1=3-hydroxy-3-methylbut-1-yn-1-yl, R2=R3=R4=H, R5=5-chloro-2-methylphenyl, R6=NH$_2$] (compd. 54)

$^1$H NMR (400 MHz, DMSO-d$_6$) δ ppm 1.53 (s, 6H) 2.13 (s, 3H) 5.54 (s, 1H) 6.63 (bs, 1H) 6.84 (s, 2H) 7.25-7.31 (m, 2H) 7.33-7.38 (m, 1H) 7.83 (d, J=2.56 Hz, 1H) 8.26 (bs, 1H) 11.55 (bs, 1H).

HRMS (ESI) calcd for C$_{21}$H$_{20}$ClN$_5$O$_2$+H$^+$ 410.1379. found 410.1377.

5-[2-Amino-5-(3-hydroxybut-1-yn-1-yl)pyrimidin-4-yl]-2-(5-chloro-2-methylphenyl)-1H-pyrrole-3-carboxamide [(I), R1=3-hydroxybut-1-yn-1-yl, R2=R3=R4=H, R5=5-chloro-2-methylphenyl, R6=NH₂] (compd. 55)

$^1$H NMR (400 MHz, DMSO-d$_6$) δ ppm 1.45 (d, J=6.59 Hz, 3H) 2.13 (s, 3H) 4.67-4.76 (m, 1H) 5.52 (d, J=5.49 Hz, 1H) 6.63 (bs, 2H) 6.88 (bs, 2H) 7.25-7.32 (m, 2H) 7.32-7.37 (m, 1H) 7.80 (d, J=2.56 Hz, 1H) 8.28 (bs, 1H) 11.56 (bs, 1H).

HRMS (ESI) calcd for C$_{20}$H$_{18}$ClN$_5$O$_2$+H$^+$ 396.1222. found 396.1225.

5-(2-Amino-5-{3-[benzyl(methyl)amino]prop-1-yn-1-yl}pyrimidin-4-yl)-2-(5-chloro-2-methylphenyl)-1H-pyrrole-3-carboxamide [(I), R1=3-[benzyl(methyl)amino]prop-1-yn-1-yl, R2=R3=R4=H, R5=5-chloro-2-methylphenyl, R6=NH₂] (compd. 56)

$^1$H NMR (400 MHz, DMSO-d$_6$) δ ppm 2.13 (s, 3H) 2.29 (s, 3H) 3.61 (bs, 2H) 3.65 (bs, 2H) 6.67 (bs, 2H) 6.79 (bs, 1H) 6.99 (bs, 1H) 7.20-7.39 (m, 9H) 7.76 (d, J=2.56 Hz, 1H) 8.36 (bs, 1H) 11.56 (bs, 1H).

HRMS (ESI) calcd for C$_{27}$H$_{26}$ClN$_6$O+H$^+$ 485.1851. found 485.1844.

According to this step, but starting from 5-(2-amino-5-iodo-pyrimidin-4-yl)-2-(5-chloro-2-methyl-phenyl)-N-methyl-1H-pyrrole-3-carboxamide, the following compounds were prepared:

5-[2-Amino-5-(phenylethynyl)pyrimidin-4-yl]-2-(5-chloro-2-methylphenyl)-N-methyl-1H-pyrrole-3-carboxamide [(I), R1=phenylethynyl, R2=H, R3=CH$_3$, R4=H, R5=5-chloro-2-methylphenyl, R6=NH₂] (compd. 57)

ESI (+) MS: m/z 442 (MH$^+$).

5-(2-Amino-5-{[4-(4-methylpiperazin-1-yl)phenyl]ethynyl}pyrimidin-4-yl)-2-(5-chloro-2-methylphenyl)-N-methyl-1H-pyrrole-3-carboxamide [(I), R1=[4-(4-methylpiperazin-1-yl)phenyl]ethynyl, R2=H, R3=CH$_3$, R4=H, R5=5-chloro-2-methylphenyl, R6=NH₂] (compd. 58)

ESI (+) MS: m/z 540 (MH$^+$).

According to this step, but starting from 5-(2-amino-5-iodo-pyrimidin-4-yl)-2-(5-chloro-2-ethyl-phenyl)-N-methyl-1H-pyrrole-3-carboxamide, the following compounds were prepared:

5-[2-Amino-5-(phenylethynyl)pyrimidin-4-yl]-2-(5-chloro-2-ethylphenyl)-N-methyl-1H-pyrrole-3-carboxamide [(I), R1=phenylethynyl, R2=H, R3=CH$_3$, R4=H, R5=5-chloro-2-ethylphenyl, R6=NH₂] (compd. 111)

ESI (+) MS: m/z 456 (MH$^+$).

5-(2-Amino-5-{[4-(4-methylpiperazin-1-yl)phenyl]ethynyl}pyrimidin-4-yl)-2-(5-chloro-2-ethylphenyl)-N-methyl-1H-pyrrole-3-carboxamide [(I), R1=[4-(4-methylpiperazin-1-yl)phenyl]ethynyl, R2=H, R3=CH$_3$, R4=H, R5=5-chloro-2-ethylphenyl, R6=NH₂] (compd. 112)

ESI (+) MS: m/z 564 (MH$^+$).

Example 2

5-[2-Amino-5-({4-[(4-methylpiperazin-1-yl)carbonyl]phenyl}ethynyl)pyrimidin-4-yl]-2-(5-chloro-2-methylphenyl)-1H-pyrrole-3-carboxamide [(I), R1={4-[(4-methylpiperazin-1-yl)carbonyl]phenyl}ethynyl, R2=R3=R4=H, R5=5-chloro-2-methylphenyl, R6=NH₂] (compd. 59)

Scheme B, Steps 6, 7, 8, 9, 10

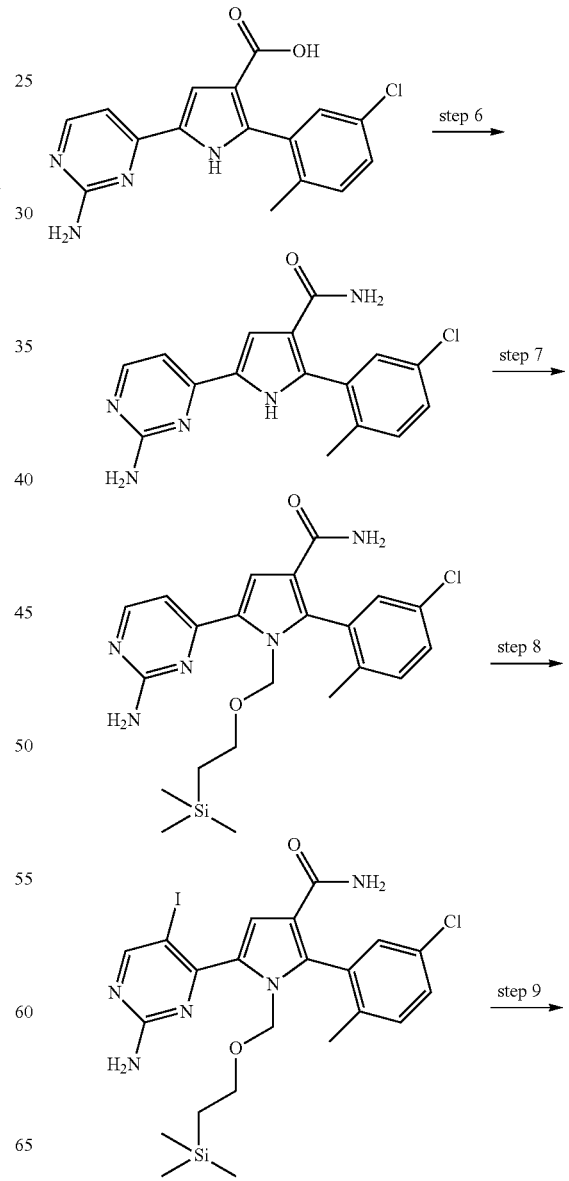

-continued

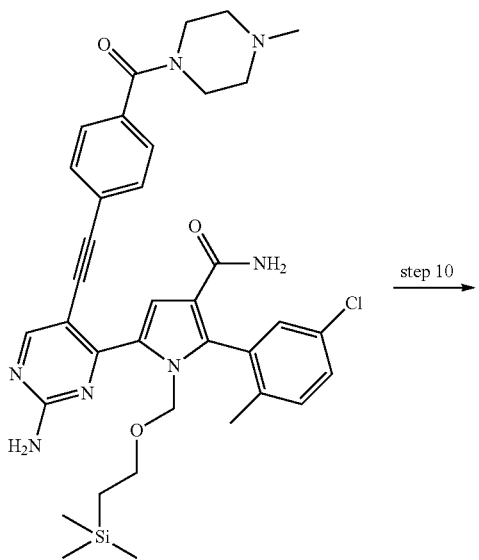

step 10

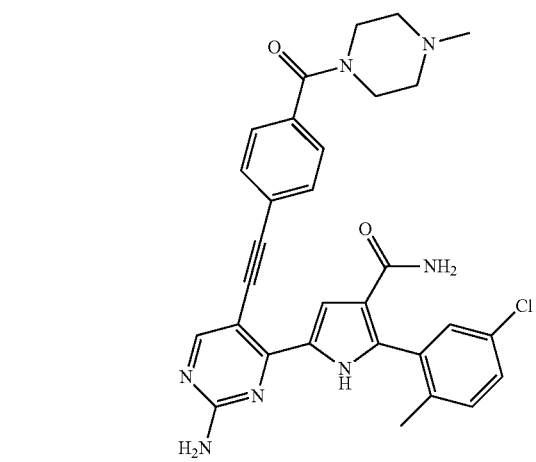 [SMILES: Cc1ccc(Cl)cc1-c1[nH]c(-c2nc(N)ncc2C#Cc2ccc(C(=O)N3CCN(C)CC3)cc2)cc1C(N)=O]

Step 6: 5-(2-Aminopyrimidin-4-yl)-2-(5-chloro-2-methylphenyl)-1H-pyrrole-3-carboxamide (X)

A solution of 5-(2-amino-pyrimidin-4-yl)-2-(5-chloro-2-methyl-phenyl)-1H-pyrrole-3-carboxylic acid (11.62 g, 30.4 mmol) in DMF (100 mL) and DIPEA (21.2 mL, 121.6 mmol) was stirred at 0° C. EDCl (11.64 g, 60.8 mmol) and HOBT.NH$_3$ (9.38 g, 60.8 mmol) were added and the reaction mixture was stirred for 3 h at room temperature. The mixture was diluted with water and the resultant precipitate was collected by filtration to afford the title compound (8.17 g, 82%).

$^1$H NMR (400 MHz, DMSO-d$_6$) δ ppm 2.12 (s, 3H), 6.35 (bs, 2H), 6.73 (bs, 1H), 6.93 (d, J=5.24 Hz, 1H), 7.22 (bs, 1H), 7.25-7.30 (m, 2H), 7.32-7.36 (m, 2H), 8.20 (d, J=5.24 Hz, 1H), 11.85 (bs, 1H).

HRMS (ESI) m/z calcd for C$_{16}$H$_{14}$ClN$_6$O+H$^+$ 328.0960. found 328.0959.

Step 7: 5-(2-Aminopyrimidin-4-yl)-2-(5-chloro-2-methylphenyl)-1-{[2-trimethylsilyl)ethoxy]methyl}-1H-pyrrole-3-carboxamide (XI)

NaH (60% dispersion in mineral oil, 0.452 g, 11.3 mmol) was added to a suspension of 5-(2-aminopyrimidin-4-yl)-2-(5-chloro-2-methylphenyl)-1H-pyrrole-3-carboxamide (2.62 g, 8.0 mmol) in dry THF (25 mL) at 0° C. The reaction was kept at the same temperature for 20 min then 2-(chloromethoxy)ethyl](trimethyl)silane (2.0 mL, 11.3 mmol) was added and the mixture was stirred at room temperature for 2 h. Saturated aqueous NaCl (30 mL) was added at 0° C. and the mixture was extracted with EtOAc (2×35 mL). The separated organic phase was dried over sodium sulfate and the solvent evaporated. The crude was purified by flash chromatography on silica gel (DCM/EtOH 94/6) to afford the title compound (1.39 g, 38%).

$^1$H NMR (400 MHz, DMSO-d$_6$) δ ppm 0.17 (s, 9H) 0.54-0.72 (m, 2H) 2.02 (s, 3H) 3.16-3.23 (m, 2H) 5.47 (d, J=10.13 Hz, 1H) 5.77 (d, J=10.13 Hz, 1H) 6.60 (s, 2H) 6.80 (bs, 1H) 6.83 (d, J=5.25 Hz, 1H) 7.13 (bs, 1H) 7.20-7.23 (m, 1H) 7.29-7.36 (m, 2H) 7.37-7.43 (m, 1H) 8.23 (d, J=5.25 Hz, 1H).

HRMS (ESI) m/z calcd for C$_{22}$H$_{28}$ClN$_6$O$_2$Si+H$^+$ 458.1774. found 458.1774.

Step 8: 5-(2-Amino-5-iodopyrimidin-4-yl)-2-(5-chloro-2-methylphenyl)-1-{[2-(trimethylsilyl)ethoxy]methyl}-1H-pyrrole-3-carboxamide (XII)

N-iodosuccinimide (720 mg, 3.2 mmol) was added to a solution of 5-(2-aminopyrimidin-4-yl)-2-(5-chloro-2-methylphenyl)-1-{[2-(trimethylsilyl)ethoxy]methyl}-1H-pyrrole-3-carboxamide (1.39 g, 3.0 mmol) in dry DMF (6 mL). The reaction mixture was heated at 65° C. for 7 h, allowed to cool to room temperature and then diluted with EtOAc (30 mL), washed with water (2×20 mL) brine, dried over sodium sulphate, and evaporated. The crude was purified by flash chromatography on silica gel (DCM/MeOH 97/3) to afford the title compound as yellow solid (1.07 g, 60%).

$^1$H NMR (400 MHz, DMSO-d$_6$) δ ppm 0.13 (s, 9H) 0.51-0.66 (m, 2H) 2.04 (s, 3H) 3.03 (m, 2H) 5.07 (d, J=10.74 Hz, 1H) 5.26 (d, J=10.74 Hz, 1H) 6.78 (bs, 1H) 6.89 (s, 2H) 7.11 (bs, 1H) 7.17-7.19 (m, 1H) 7.20 (s, 1H) 7.31-7.35 (m, 1H) 7.38-7.42 (m, 1H) 8.58 (s, 1H).

HRMS (ESI) m/z calcd for C$_{22}$H$_{27}$ClIN$_6$O$_2$Si+H$^+$ 584.0740. found 584.0744.

Step 9: 5-[2-Amino-5-({4-[(4-methylpiperazin-1-yl)carbonyl]phenyl}ethynyl)pyrimidin-4-yl]-2-(5-chloro-2-methylphenyl)-1-{[2-(trimethylsilyl)ethoxy]methyl}-1H-pyrrole-3-carboxamide (XIII)

To a degassed solution of 5-(2-amino-5-iodopyrimidin-4-yl)-2-(5-chloro-2-methylphenyl)-1-{[2-(trimethylsilyl)ethoxy]methyl}-1H-pyrrole-3-carboxamide (140 mg, 0.24 mmol), (4-ethynylphenyl)(4-methylpiperazin-1-yl)methanone (98 mg, 0.43 mmol) and TEA (0.335 mL, 2.4 mmol) in dry ACN (2.5 mL) were added copper iodide (2.5 mg, 0.012 mmol) and Pd(PPh$_3$)$_2$Cl$_2$ (8.4 mg, 0.012 mmol). The mixture was heated at 80° C. for 2 h, then the solvent was evaporated. The crude was purified by flash chromatography on silica gel (DCM/MeOH/7N NH$_3$ in MeOH 95/4/1) to afford the title compound (131 mg, 80%).

83

¹H NMR (400 MHz, DMSO-d₆) δ ppm 0.20 (s, 9H) 0.48-0.65 (m, 2H) 2.04 (s, 3H) 2.83 (s, 3H) 3.11 (t, J=8.24 Hz, 2H) 3.15-3.52 (m, 8H) 5.30 (d, J=10.38 Hz, 1H) 5.62 (d, J=10.38 Hz, 1H) 6.80 (bs, 1H) 7.03 (bs, 1H) 7.13-7.30 (m, 3H) 7.31-7.37 (m, 1H) 7.39-7.45 (m, 1H) 7.46-7.52 (m, 2H) 7.55-7.61 (m, 2H) 7.68 (s, 1H) 8.41-8.54 (s, 1H).

HRMS (ESI) m/z calcd for $C_{36}H_{42}ClN_7O_3Si+H^+$ 684.2880. found 684.2884.

The above procedure was employed to synthesize the following compound:

5-{2-Amino-5-[(4-bromophenyl)ethynyl]pyrimidin-4-yl}-2-(5-chloro-2-methylphenyl)-1-{[2-(trimethylsilyl) ethoxy]methyl}-1H-pyrrole-3-carboxamide (XIII)

ESI (+) MS: m/z 637 (MH⁺).

Step 10: 5-[2-Amino-5-({4-[(4-methylpiperazin-1-yl)carbonyl]phenyl}ethynyl)pyrimidin-4-yl]-2-(5-chloro-2-methylphenyl)-1H-pyrrole-3-carboxamide Trifluoroacetic acid (1.4 mL) was added to a solution of 5-[2-amino-5-({4-[(4-methylpiperazin-1-yl)carbonyl]phenyl}ethynyl)pyrimidin-4-yl]-2-(5-chloro-2-methylphenyl)-1-{[2-(trimethylsilyl)ethoxy]methyl}-1H-pyrrole-3-carboxamide (0.110 g, 0.14 mmol) in dry DCM (2.8 mL) and stirred for 4 h at room temperature. After solvent removal, the residue was treated with EtOH (3 mL), 33% NH₄OH (0.4 mL) and stirred for 0.5 h. The solvent was evaporated to dryness and the residue was purified by flash-chromatography on silica gel (DCM/MeOH/7N NH₃ in MeOH 94/5/1) to afford the title compound as white solid (0.055 g, 71%).

¹H NMR (400 MHz, DMSO-d₆) δ ppm 2.14 (s, 3H) 2.20 (s, 3H) 2.27-2.41 (m, 4H) 3.44-3.69 (m, 4H) 6.81 (bs, 3H) 7.02 (bs, 1H) 7.22-7.33 (m, 2H) 7.33-7.39 (m, 1H) 7.40-7.46 (m, 2H) 7.63-7.69 (m, 2H) 7.80-7.83 (m, 1H) 8.47 (s, 1H) 11.68 (s, 1H).

HRMS (ESI) m/z calcd for $C_{30}H_{28}ClN_7O_2+H^+$ 554.2066. found 554.2068.

The above procedure was employed to synthesize the following compound:

5-[2-Amino-5-({4-[4-(dimethylamino)piperidin-1-yl]phenyl}ethynyl)pyrimidin-4-yl]-2-(5-chloro-2-methylphenyl)-1H-pyrrole-3-carboxamide [(I), R1={4-[4-(dimethylamino)piperidin-1-yl] phenyl}ethynyl, R2=R3=R4=H, R5=5-chloro-2-methylphenyl, R6=NH₂] (compd. 60)

¹H NMR (400 MHz, DMSO-d₆) δ ppm 1.37-1.53 (m, 2H) 1.79-1.88 (m, 2H) 2.14 (s, 3H) 2.22 (bs, 6H) 2.27-2.35 (m, 1H) 2.71-2.81 (m, 2H) 3.78-3.88 (m, 2H) 6.67 (bs, 3H) 6.79 (bs, 1H) 6.91-6.99 (m, 2H) 7.27-7.33 (m, 2H) 7.34-7.39 (m, 1H) 7.40-7.46 (m, 2H) 7.81 (d, J=2.56 Hz, 1H) 8.39 (bs, 1H) 11.55-11.65 (m, 1H).

HRMS (ESI) m/z calcd for $C_{31}H_{32}ClN_7O+H^+$ 554.2430. found 554.2428.

84

Example 3

5-[2-Amino-5-({3-[(azetidin-3-ylmethyl)amino]phenyl}ethynyl)pyrimidin-4-yl]-2-(5-chloro-2-methylphenyl)-1H-pyrrole-3-carboxamide [(I), R1={3-[(azetidin-3-ylmethyl)amino]phenyl}ethynyl, R2=R3=R4=H, R5=5-chloro-2-methylphenyl, R6=NH₂] (compd. 61)

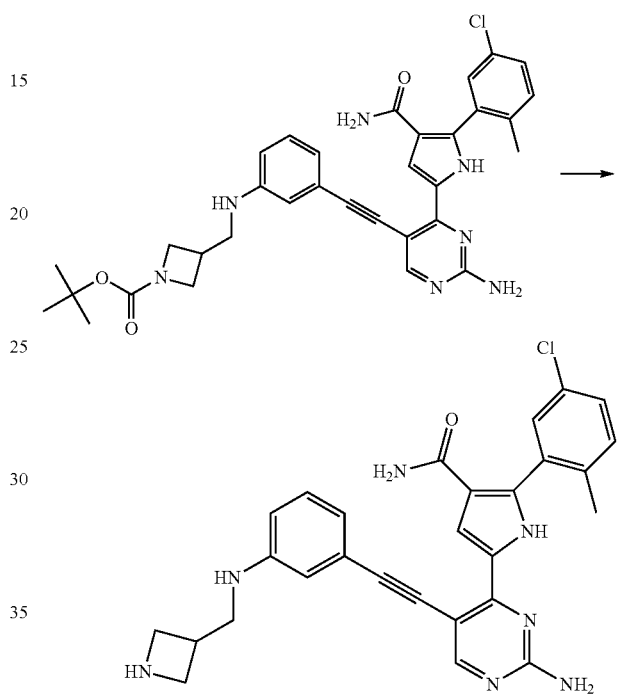

Conv. a tert-Butyl 3-({[3-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate (190 mg, 0.311 mmol) in DCM (2.2 mL) and TFA (240 μL, 3.1 mmol) was stirred at room temperature for 48 h, then DCM (25 mL), water (25 mL) and 2 mL of 10% NH₄OH were added. The organic layer was separated and the aqueous phase was further extracted employing DCM/MeOH. After drying over sodium sulfate, evaporation of the solvent, purification by flash chromatography over silica gel (DCM/7N NH₃ in MeOH 8/2) and crystallization from Et₂O/MeOH, the title compound was obtained as a light yellow solid (113 mg, 71%).

¹H NMR (400 MHz, DMSO-d₆) δ ppm 2.15 (s, 3H) 2.83-2.97 (m, 1H) 3.43 (dd, J=9.52, 6.96 Hz, 2H) 3.74 (t, J=8.48 Hz, 2H) 5.85 (t, J=5.68 Hz, 1H) 6.62 (ddd, J=8.24, 2.20, 0.79 Hz, 1H) 6.75 (bs, 2H) 6.75-6.80 (m, 2H) 6.90 (bs, 2H) 7.07-7.14 (m, 1H) 7.28-7.34 (m, 2H) 7.35-7.40 (m, 1H) 7.84 (s, 1H) 8.42 (s, 1H) 11.59 (bs, 1H).

HRMS (ESI) m/z calcd for $C_{28}H_{26}ClN_7O+H^+$ 512.1960. found 512.1962.

The above procedure was employed to synthesize the following compounds:

5-[2-Amino-5-({4-[(azetidin-3-ylmethyl)amino]
phenyl}ethynyl)pyrimidin-4-yl]-2-(5-chloro-2-methylphenyl)-1H-pyrrole-3-carboxamide [(I), R1={4-
[(azetidin-3-ylmethyl)amino]phenyl}ethynyl,
R2=R3=R4=H, R5=5-chloro-2-methylphenyl,
R6=NH$_2$] (compd. 62)

HRMS (ESI) m/z calcd for C$_{28}$H$_{26}$ClN$_7$O+H$^+$ 512.1960. found 512.1968.

5-[2-Amino-5-({3-[(2-aminoethyl)amino]
phenyl}ethynyl)pyrimidin-4-yl]-2-(5-chloro-2-methylphenyl)-1H-pyrrole-3-carboxamide [(I), R1={3-
[(2-aminoethyl)amino]phenyl}ethynyl,
R2=R3=R4=H, R5=5-chloro-2-methylphenyl,
R6=NH$_2$] (compd. 63)

$^1$H NMR (400 MHz, DMSO-d$_6$) δ ppm 2.15 (s, 3H) 2.73 (t, J=6.29 Hz, 2H) 3.04 (q, J=6.10 Hz, 2H) 5.72 (t, J=5.74 Hz, 1H) 6.63 (dt, J=8.94, 1.27 Hz, 1H) 6.75-6.79 (m, 2H) 6.74-6.79 (m, 2H) 7.10 (t, J=8.12 Hz, 1H) 7.28-7.33 (m, 2H) 7.34-7.39 (m, 1H) 7.83 (s, 1H) 8.42 (s, 1H).
HRMS (ESI) calcd for C$_{26}$H$_{24}$ClN$_7$O+H$^+$ 486.1804. found 486.1809.

Example 4

5-{2-Amino-5-[(3-{[(1-methylazetidin-3-yl)methyl]
amino}phenyl)ethynyl]pyrimidin-4-yl}-2-(5-chloro-
2-methylphenyl)-1H-pyrrole-3-carboxamide [(I),
R1=(3-{[(1-methylazetidin-3-yl)methyl]
amino}phenyl)ethynyl, R2=R3=R4=H, R5=5-
chloro-2-methylphenyl, R6=NH$_2$] (compd. 64)

Conv. b
5-[2-Amino-5-({3-[(azetidin-3-ylmethyl)amino]
phenyl}ethynyl)pyrimidin-4-yl]-2-(5-chloro-2-methylphenyl)-1H-pyrrole-3-carboxamide (55 mg, 0.11 mmol) in DMF (1 mL), under a nitrogen atmosphere, was treated with formaldehyde 37 wt % in water (9 μL, 0.13 mmol) and sodium triacetoxyborohydride (35 mg, 0.165 mmol). After 45 minutes the reaction mixture was added drop wise to 10% NH$_4$OH (25 mL) and left at 4° C. for 2 h. The solid was filtered, washed with water and dried at 40° C., under vacuum. Purification by reverse phase chromatography (Phase A: 0.05 NH$_4$OH %/ACN 95/5; Phase B: ACN/H$_2$O 95/5. Gradient: 10-100% of phase B) afforded the title compound (20 mg, 35%).
$^1$H NMR (400 MHz, DMSO-d$_6$) δ ppm 2.15 (s, 3H) 2.19 (s, 3H) 2.53-2.59 (m, 1H) 2.88 (t, J=6.23 Hz, 2H) 3.16-3.25 (m, 4H) 5.76 (t, J=5.55 Hz, 1H) 6.58-6.63 (m, 1H) 6.72-6.78 (m, 2H) 6.80-6.97 (m, 4H) 7.09 (t, J=7.81 Hz, 1H) 7.25-7.34 (m, 2H) 7.33-7.40 (m, 1H) 7.82 (d, J=2.56 Hz, 1H) 8.42 (s, 1H) 11.63 (bs, 1H).
HRMS (ESI) calcd for C$_{29}$H$_{28}$ClN$_7$O+H$^+$ 526.2117. found 526.2110.

Example 5

5-[2-Amino-5-({4-[(4-methylpiperazin-1-yl)methyl]
phenyl}ethynyl)pyrimidin-4-yl]-2-(5-chloro-2-methylphenyl)-1H-pyrrole-3-carboxamide [(I), R1={4-
[(4-methylpiperazin-1-yl)methyl]phenyl}ethynyl,
R2=R3=R4=H, R5=5-chloro-2-methylphenyl,
R6=NH$_2$] (compd. 65)

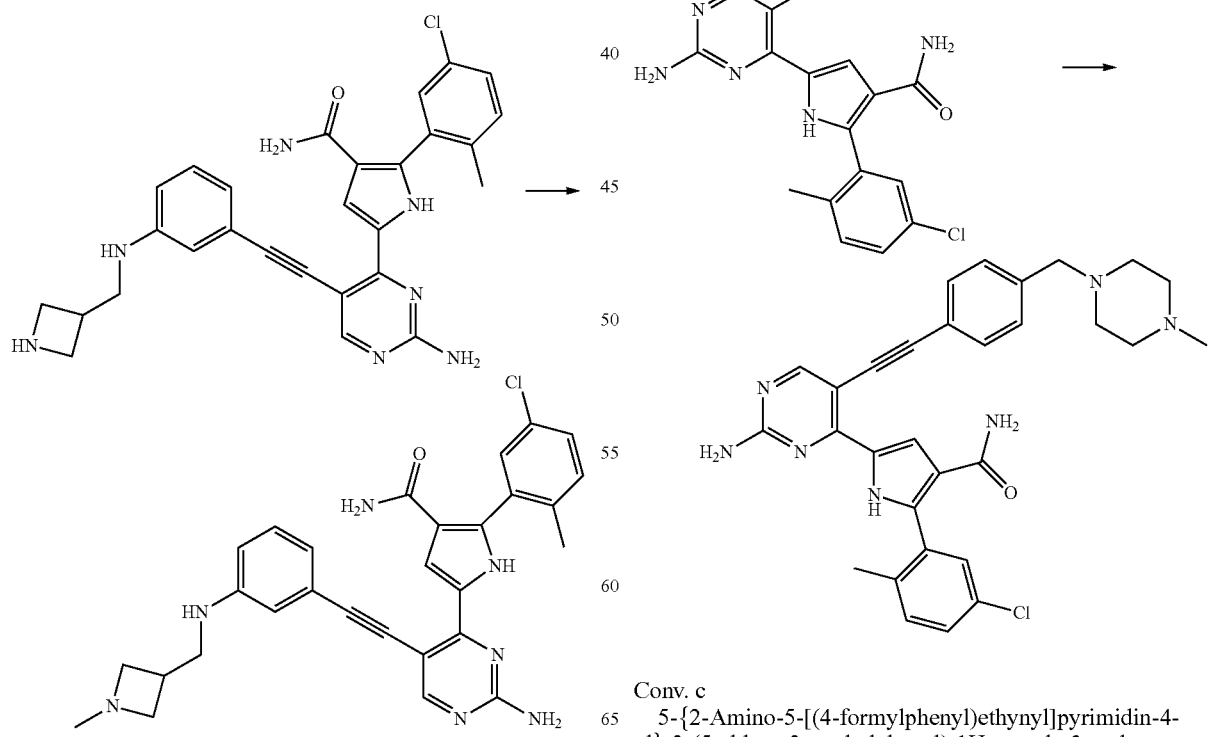

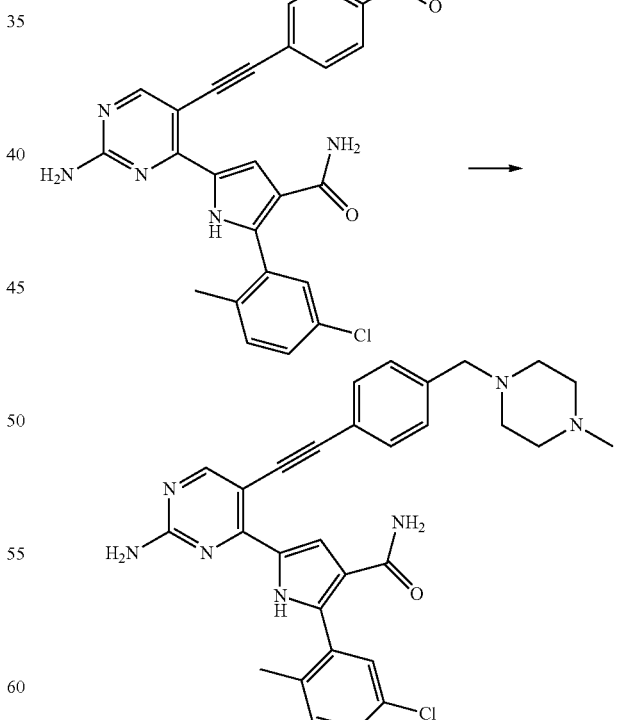

Conv. c
5-{2-Amino-5-[(4-formylphenyl)ethynyl]pyrimidin-4-yl}-2-(5-chloro-2-methylphenyl)-1H-pyrrole-3-carboxamide (53 mg, 0.1176 mmol) and 1-methylpiperazine (16 μL, 0.1411 mmol) in 1,4-dioxane (2 mL) and DMF (0.5 mL), under a nitrogen atmosphere, were treated first with AcOH (24 μL, 0.4234 mmol) and then with sodium triacetoxyborohydride (37 mg, 0.1764 mmol, 1.5 eq.). After stirring for 1 h, DCM (20 mL) was added and the organic phase was washed subsequently with 10% NH$_4$OH (15 mL) and brine, dried over sodium sulfate and evaporated. The crude was purified by flash chromatography over silica gel (DCM/MeOH/7N NH$_3$ in MeOH 9/1/0.1) to afford the title compound as a white solid (28 mg, 44%).

$^1$H NMR (400 MHz, DMSO-d$_6$) δ ppm 2.14 (s, 3H) 2.17 (s, 3H) 2.27-2.46 (m, 8H) 3.49 (s, 2H) 7.27-7.40 (m, 5H) 7.53-7.58 (m, 2H) 7.82 (d, J=2.69 Hz, 1H) 8.44 (s, 1H) 11.61-11.68 (m, 1H).

HRMS (ESI) calcd for C$_{30}$H$_{30}$ClN$_7$O+H$^+$ 540.2273. found 540.2271.

According to this procedure, but using the suitable amine, the following compounds were prepared:

5-(2-Amino-5-{[4-(pyrrolidin-1-ylmethyl)phenyl]ethynyl}pyrimidin-4-yl)-2-(5-chloro-2-methylphenyl)-1H-pyrrole-3-carboxamide [(I), R1=[4-(pyrrolidin-1-ylmethyl)phenyl]ethynyl, R2=R3=R4=H, R5=5-chloro-2-methylphenyl, R6=NH$_2$] (compd. 66)

$^1$H NMR (400 MHz, DMSO-d$_6$) δ ppm 1.54-1.80 (m, 4H) 2.14 (s, 3H) 2.45 (bs, 4H) 3.61 (bs, 1H) 6.78 (bs, 2H) 6.99 (bs, 1H) 7.25-7.33 (m, 2H) 7.33-7.40 (m, 3H) 7.52-7.58 (m, 2H) 7.82 (d, J=2.69 Hz, 1H) 8.44 (s, 1H) 11.64 (s, 1H).

HRMS (ESI) calcd for C$_{26}$H$_{27}$ClN$_6$O+H$^+$ 511.2008. found 511.2010.

5-(2-Amino-5-{[4-(piperidin-1-ylmethyl)phenyl]ethynyl}pyrimidin-4-yl)-2-(5-chloro-2-methylphenyl)-1H-pyrrole-3-carboxamide [(I), R1=[4-(piperidin-1-ylmethyl)phenyl]ethynyl, R2=R3=R4=H, R5=5-chloro-2-methylphenyl, R6=NH$_2$] (compd. 67)

$^1$H NMR (400 MHz, DMSO-d$_6$) δ ppm 1.34-1.44 (m, 2H) 1.50 (quin, J=5.52 Hz, 4H) 2.14 (s, 3H) 2.27-2.38 (m, 4H) 3.45 (s, 2H) 6.78 (bs, 3H) 6.98 (bs, 1H) 7.26-7.39 (m, 5H) 7.52-7.59 (m, 2H) 7.82 (d, J=2.69 Hz, 1H) 8.44 (s, 1H) 11.64 (s, 1H).

HRMS (ESI) calcd for C$_{30}$H$_{26}$ClN$_6$O+H$^+$ 525.2164. found 525.2159.

Example 6

5-[2-Amino-5-(phenylethynyl)pyrimidin-4-yl]-2-(5-chloro-2-methylphenyl)-1H-pyrrole-3-carboxamide [(I), R1=phenylethynyl, R2=R3=R4=H, R5=5-chloro-2-methylphenyl, R6=NH$_2$] (compd. 1)

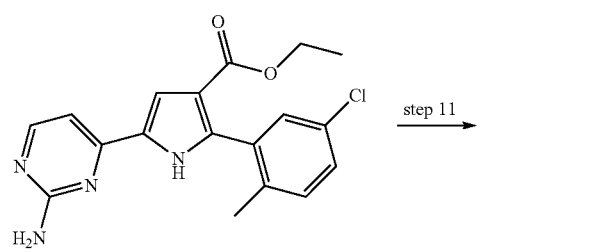

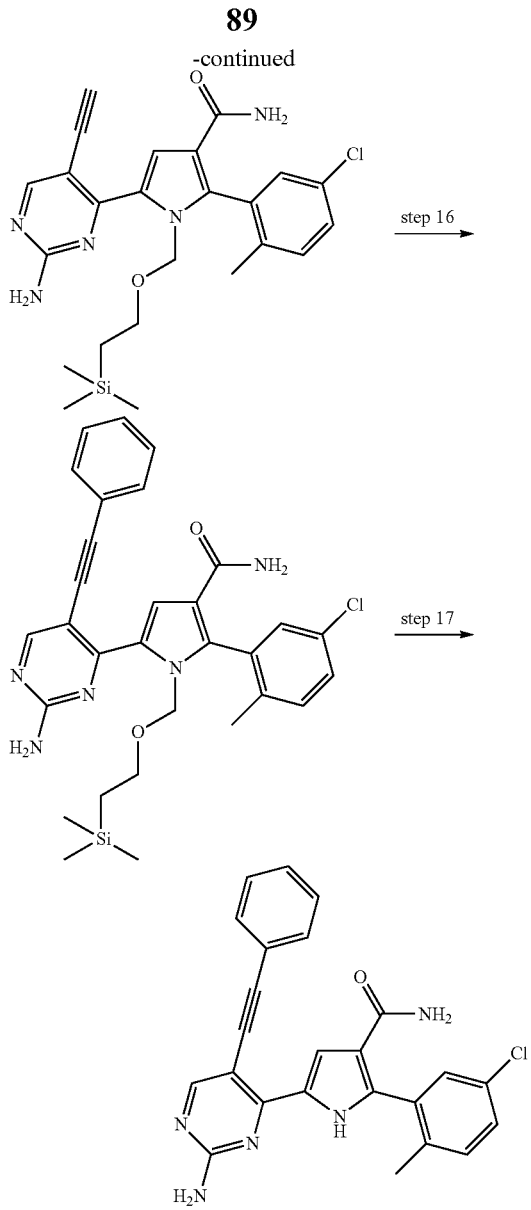

Scheme C, Steps 11, 12, 13, 14, 15, 16, 17

Step 11: Ethyl 5-(2-aminopyrimidin-4-yl)-2-(5-chloro-2-methylphenyl)-1-{[2-(trimethylsilyl)ethoxy]methyl}-1H-pyrrole-3-carboxylate (XIV)

To a solution of ethyl 5-(2-aminopyrimidin-4-yl)-2-(5-chloro-2-methylphenyl)-1H-pyrrole-3-carboxylate (1.0 g, 2.8 mmol) in dry THF (40 mL) cooled to 0° C. NaH 60% (1.342 g, 3.36 mmol) was added portion wise and the reaction mixture stirred for 30 min. (2-Chloromethoxy-ethyl)-trimethyl-silane (0.417 mL, 3.36 mmol) was added drop wise. The reaction mixture was allowed to warm up slowly to room temperature and stirred for 2 h. Saturated aqueous NaCl (30 mL) was added at 0° C. and the mixture was extracted with EtOAc (2×35 mL). The separated organic phase was dried over sodium sulfate and the solvent evaporated. The crude was purified by flash chromatography on silica gel (DCM/MeOH 98/2) to afford the title compound as an orange oil (0.80 g, 57%).

$^1$H NMR (400 MHz, DMSO-d$_6$) δ ppm −0.17 (s, 9H) 0.59-0.69 (m, 2H) 1.01 (t, J=7.08 Hz, 3H) 2.02 (s, 3H) 3.23 (t, J=8.30 Hz, 2H) 4.00 (q, J=7.16 Hz, 2H) 5.54 (d, J=10.01 Hz, 1H) 5.82 (d, J=10.01 Hz, 1H) 6.63 (s, 2H) 6.98 (d, J=5.25 Hz, 1H) 7.25 (s, 1H) 7.27 (d, J=2.32 Hz, 1H) 7.36 (d, J=8.18 Hz, 1H) 7.44 (dd, J=8.18, 2.20 Hz, 1H) 8.22 (d, J=5.25 Hz, 1H).

Step 12: Ethyl 5-(2-amino-5-iodopyrimidin-4-yl)-2-(5-chloro-2-methylphenyl)-1-{[2-(trimethylsilyl)ethoxy]methyl}-1H-pyrrole-3-carboxylate (XV)

N-iodosuccinimide (356 mg, 1.58 mmol) was added to a solution of ethyl 5-(2-aminopyrimidin-4-yl)-2-(5-chloro-2-methylphenyl)-1-{[2-(trimethylsilyl)ethoxy]methyl}-1H-pyrrole-3-carboxylate (700 mg, 1.44 mmol) in DMF (15 mL). The reaction mixture was heated at 60° C. for 4 h, allowed to cool to room temperature, concentrated and then diluted with EtOAc (30 mL). The organic phase was washed with sodium sulfite, water, brine, dried over sodium sulphate, and evaporated to afford the title compound as yellow solid (0.70 g, 79%).

$^1$H NMR (400 MHz, DMSO-d$_6$) δ ppm −0.14 (s, 9H) 0.59 (ddd, J=10.41, 6.26, 2.87 Hz, 2H) 1.01 (t, J=7.08 Hz, 3H) 2.04 (s, 3H) 3.06 (qd, J=8.56, 2.62 Hz, 2H) 4.01 (q, J=7.08 Hz, 2H) 5.15 (d, J=10.74 Hz, 1H) 5.36 (d, J=10.74 Hz, 1H) 6.92 (bs, 2H) 7.11 (s, 1H) 7.22 (d, J=2.32 Hz, 1H) 7.37 (d, J=8.30 Hz, 1H) 7.45 (dd, J=8.30, 2.32 Hz, 1H) 8.60 (s, 1H).

Step 13: Ethyl 5-{2-amino-5-[(trimethylsilyl)ethynyl]pyrimidin-4-yl}-2-(5-chloro-2-methylphenyl)-1-{[2-(trimethylsilyl)ethoxy]methyl}-1H-pyrrole-3-carboxylate (XVI)

In a sealed tube filled with argon, a mixture of ethyl 5-(2-amino-5-iodopyrimidin-4-yl)-2-(5-chloro-2-methylphenyl)-1-{[2-(trimethylsilyl)ethoxy]methyl}-1H-pyrrole-3-carboxylate (612 mg, 1.0 mmol), Pd(PPh$_3$)$_2$Cl$_2$ (70 mg, 0.1 mmol), CuI (19 mg, 0.1 mmol), ethynyl(trimethyl)silane (0.415 mL, 3 mmol) and triethylamine (10 mmol) in degassed ACN (10 mL) was stirred at room temperature overnight. To the reaction mixture was added N,N,N',N'-tetramethylethylenediamine (0.3 mL, 2 mmol) and the reaction mixture stirred at the same temperature for 15 min. The solvent was evaporated under vacuum and the residue purified by flash chromatography (hexane/EtOAc 8/2) to obtain the title compound (495 mg, 85%).

$^1$H NMR (400 MHz, DMSO-d$_6$) δ ppm −0.18 (s, 9H) 0.22 (s, 2H) 0.51-0.66 (m, 2H) 1.06 (t, J=7.08 Hz, 3H) 2.03 (s, 3H) 3.06-3.17 (m, 2H) 4.02 (q, J=7.08 Hz, 2H) 5.43 (d, J=10.25 Hz, 1H) 5.70 (d, J=10.25 Hz, 1H) 7.16 (s, 2H) 7.25 (d, J=2.32 Hz, 1H) 7.37 (d, J=8.18 Hz, 1H) 7.45 (dd, J=8.18, 2.32 Hz, 1H) 7.64 (s, 1H) 8.40 (s, 1H).

Step 14: 5-(2-Amino-5-ethynylpyrimidin-4-yl)-2-(5-chloro-2-methylphenyl)-1-{[2-(trimethylsilyl)ethoxy]methyl}-1H-pyrrole-3-carboxylic acid (XVII)

Ethyl 5-{2-amino-5-[(trimethylsilyl)ethynyl]pyrimidin-4-yl}-2-(5-chloro-2-methylphenyl)-1-{[2-(trimethylsilyl)ethoxy]methyl}-1H-pyrrole-3-carboxylate (466 mg, 0.8 mmol) was treated with a 1.5 M solution of potassium hydroxide in 95% EtOH (5.33 mL, 8 mmol) and stirred at 50° C. overnight. After cooling, the residue was concentrated, dissolved in water and washed with DCM. The aqueous layer was acidified until pH<1 with the addition of 2 N HCl and extracted with EtOAc (3×). The combined organic layers were dried over Na$_2$SO$_4$ and the solvent evaporated under vacuum to obtain the title compound as an orange oil (367 mg, 95%).

$^1$H NMR (400 MHz, DMSO-d$_6$) δ ppm −0.17 (s, 9H) 0.54-0.63 (m, 2H) 2.04 (s, 3H) 3.11 (td, J=8.24, 1.95 Hz, 2H) 4.41 (s, 1H) 5.37 (d, J=10.25 Hz, 1H) 5.64 (d, J=10.25 Hz, 1H) 7.13 (s, 2H) 7.25 (d, J=2.32 Hz, 1H) 7.36 (d, J=8.30 Hz, 1H) 7.43 (dd, J=8.30, 2.32 Hz, 1H) 7.51 (s, 1H) 8.43 (s, 1H) 11.94 (bs, 1H).

Step 15: 5-(2-Amino-5-ethynylpyrimidin-4-yl)-2-(5-chloro-2-methylphenyl)-1-{[2-(trimethylsilyl)ethoxy]methyl}-1H-pyrrole-3-carboxamide (XVIII)

A solution of 5-(2-amino-5-ethynylpyrimidin-4-yl)-2-(5-chloro-2-methylphenyl)-1-{[2-(trimethylsilyl)ethoxy]methyl}-1H-pyrrole-3-carboxylic acid (338 mg, 0.7 mmol) in dry THF (5 mL) and DIPEA (0.48 mL, 2.8 mmol) was stirred at 0° C. EDCl (268 mg, 1.4 mmol), HOBT.NH$_3$ (213 mg, 1.4 mmol) were added and the reaction mixture was stirred at room temperature overnight. The solvent was evaporated, the residue taken-up in saturated solution of NaHCO$_3$ and extracted with EtOAc. The combined organic layers were dried over sodium sulfate to obtain the title compound as a light-orange oil (334 mg, 99%).

$^1$H NMR (400 MHz, DMSO-d$_6$) δ ppm −0.17 (s, 9H) 0.53-0.63 (m, 2H) 2.04 (s, 3H) 3.08 (td, J=8.24, 1.45 Hz, 2H) 4.32 (s, 1H) 5.28 (d, J=10.50 Hz, 1H) 5.55 (d, J=10.38 Hz, 1H) 6.79 (bs, 1H) 7.01 (bs, 1H) 7.11 (s, 2H) 7.22 (d, J=2.20 Hz, 1H) 7.34 (d, J=8.20 Hz, 1H) 7.41 (dd, J=8.20, 2.30 Hz, 1H) 7.50 (s, 1H) 8.42 (s, 1H).

Step 16: 5-[2-Amino-5-(phenylethynyl)pyrimidin-4-yl]-2-(5-chloro-2-methylphenyl)-1-{[2-(trimethylsilyl)ethoxy]methyl}-1H-pyrrole-3-carboxamide (XX)

In a sealed tube filled with argon, a mixture of 5-(2-amino-5-ethynylpyrimidin-4-yl)-2-(5-chloro-2-methylphenyl)-1-{[2-(trimethylsilyl)ethoxy]methyl}-1H-pyrrole-3-carboxamide (120 mg, 0.25 mmol), Pd(PPh$_3$)$_2$Cl$_2$ (21 mg, 0.03 mmol), CuI (6 mg, 0.03 mmol), iodobenzene (153 mg, 0.75 mmol) and TEA (0.348 mL, 2.5 mmol) in degassed ACN (2.5 mL) was stirred at room temperature overnight. To the reaction mixture was added N,N,N',N'-tetramethylethylenediamine (0.075 mL, 0.5 mmol) and the reaction mixture stirred at the same temperature for 15 min. The solvent was evaporated under vacuum and the residue purified by flash chromatography (hexane/EtOAc 1/1+1% TEA), to obtain the title compounds (91 mg, 65%).

$^1$H NMR (400 MHz, DMSO-d$_6$) δ ppm −0.20 (s, 9H) 0.50-0.65 (m, 2H) 2.04 (s, 3H) 3.10 (td, J=8.27, 1.40 Hz, 2H) 5.29 (d, J=10.50 Hz, 1H) 5.61 (d, J=10.50 Hz, 1H) 6.79 (bs, 1H) 7.06 (bs, 1H) 7.15 (s, 2H) 7.23 (d, J=2.20 Hz, 1H) 7.34 (d, J=8.20 Hz, 1H) 7.37-7.45 (m, 4H) 7.59-7.63 (m, 2H) 7.67 (s, 1H) 8.52 (s, 1H).

Step 17: 5-[2-Amino-5-(phenylethynyl)pyrimidin-4-yl]-2-(5-chloro-2-methylphenyl)-1H-pyrrole-3-carboxamide [(I), R1=phenylethynyl, R2=R3=R4=H, R5=5-chloro-2-methylphenyl, R6=NH$_2$] (compd. 1)

Trifluoroacetic acid (1.4 mL) was added to a solution of 5-[2-amino-5-(phenylethynyl)pyrimidin-4-yl]-2-(5-chloro-2-methylphenyl)-1-{[2-(trimethylsilyl)ethoxy]methyl}-1H-pyrrole-3-carboxamide (78 mg, 0.14 mmol) in dry DCM (2.8 mL) and stirred for 4 h at room temperature. After solvent removal, the residue was treated with EtOH (3 mL), 33% NH$_4$OH (0.4 mL) and stirred for 0.5 h. The solvent was evaporated to dryness and the residue was purified by flash-chromatography on silica gel (DCM/MeOH/7N NH$_3$ in MeOH 94/5/1) to afford the title compound as white solid (45 mg, 75%).

$^1$H NMR (400 MHz, DMSO-d$_6$) δ ppm 2.14 (s, 3H) 6.79 (bs, 3H) 6.99 (bs, 1H) 7.30 (d, J=8.30 Hz, 1H) 7.31 (d, J=2.44 Hz, 1H) 7.37 (dd, J=8.30, 2.32 Hz, 1H) 7.83 (d, J=2.69 Hz, 1H) 8.45 (s, 1H) 11.66 (bs, 1H).

HRMS (ESI) calcd for C$_{24}$H$_{18}$ClN$_5$O+H$^+$ 428.1273. found 428.1278.

Example 7

5-(2-Amino-5-ethynylpyrimidin-4-yl)-2-(5-chloro-2-methylphenyl)-1H-pyrrole-3-carboxamide [(I), R1=ethynyl, R2=R3=R4=H, R5=5-chloro-2-methylphenyl, R6=NH$_2$] (compd. 68)

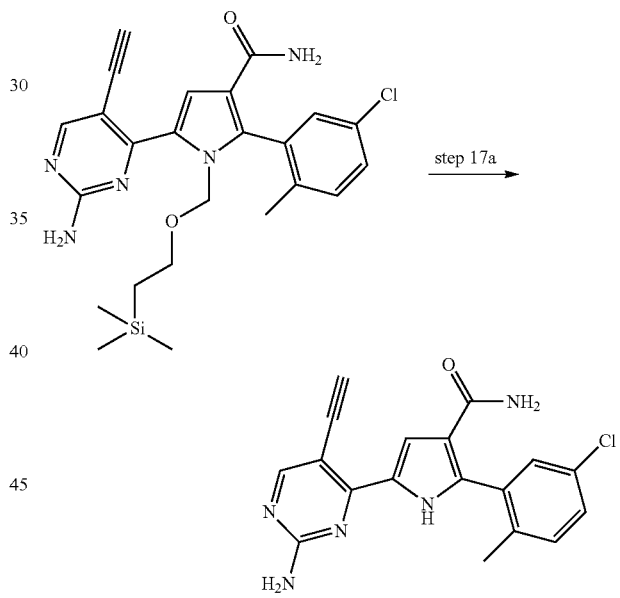

Scheme C, Step 17a

Trifluoroacetic acid (1.4 mL) was added to a solution of 5-(2-amino-5-ethynylpyrimidin-4-yl)-2-(5-chloro-2-methylphenyl)-1-{[2-(trimethylsilyl)ethoxy]methyl}-1H-pyrrole-3-carboxamide (67 mg, 0.14 mmol) in dry DCM (2.8 mL) and stirred for 4 h at room temperature. After solvent removal, the residue was treated with EtOH (3 mL), 33% NH$_4$OH (0.4 mL) and stirred for 0.5 h. The solvent was evaporated to dryness and the residue was purified by flash-chromatography on silica gel (DCM/MeOH/7N NH$_3$ in MeOH 94/5/1) to afford the title compound as white solid (42 mg, 85%).

ESI (+) MS: m/z 352 (MH$^+$).

Example 8

5-(2-Amino-5-{[4-(4-methylpiperazin-1-yl)phenyl]ethynyl}pyrimidin-4-yl)-2-(5-chloro-2-methylphenyl)-1H-pyrrole-3-carboxamide [(I), R1=[4-(4-methylpiperazin-1-yl)phenyl]ethynyl, R2=R3=R4=H, R5=5-chloro-2-methylphenyl, R6=NH₂] (compd. 11)

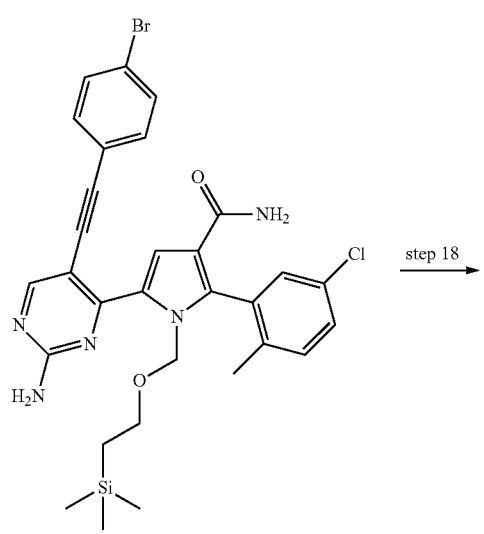

step 18 →

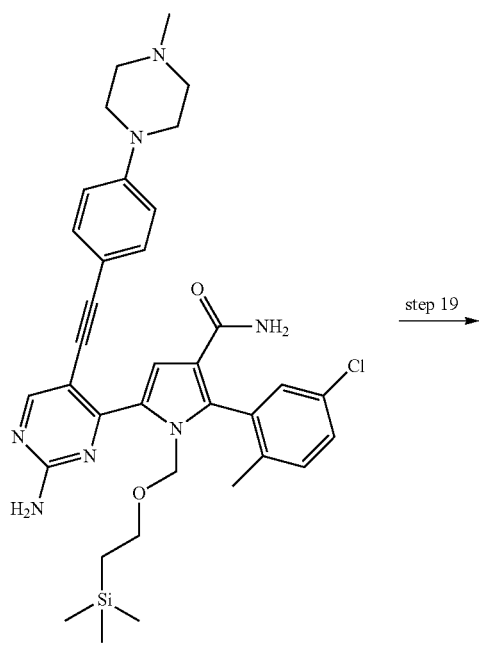

step 19 →

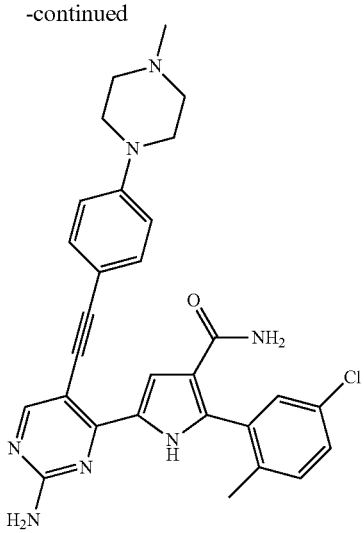

Scheme D, Steps 18, 19

Step 18: 5-(2-Amino-5-{[4-(4-methylpiperazin-1-yl)phenyl]ethynyl}pyrimidin-4-yl)-2-(5-chloro-2-methylphenyl)-1-{[2-(trimethylsilyl)ethoxy]methyl}-1H-pyrrole-3-carboxamide (XXIII)

A suspension of 5-{2-amino-5-[(4-bromophenyl)ethynyl]pyrimidin-4-yl}-2-(5-chloro-2-methylphenyl)-1-{[2-(trimethylsilyl)ethoxy]methyl}-1H-pyrrole-3-carboxamide (prepared according to Example 2 step 9, 554 mg, 0.87 mmol), Pd₂(dba)₃ (40 mg, 0.043 mmol), 2-dicyclohexylphosphino-2-(N,N'-dimethylamino)biphenyl (17 mg, 0.043 mmol) in anhydrous THF (6 mL) was degassed and backfilled with Argon for three times. 1-Methyl-4-piperazine (0.242 mL, 2.18 mmol) was added and the mixture was degassed and backfilled with Argon for three times again. Finally LiHMDS 1 M in THF (1.74 mL) was added by a syringe and the mixture was heated to reflux for 2 h. After cooling to room temperature the reaction mixture was filtered on a pad of celite washing with THF (30 mL). The filtrate was evaporated under vacuum and the black oil so obtained was purified by flash chromatography on silica gel (DCM/MeOH 90/10) to afford the title compound (428 mg, 75%).

ESI (+) MS: m/z 656 (MH⁺).

Step 19: 5-(2-Amino-5-{[4-(4-methylpiperazin-1-yl)phenyl]ethynyl}pyrimidin-4-yl)-2-(5-chloro-2-methylphenyl)-1H-pyrrole-3-carboxamide R1=[4-(4-methylpiperazin-1-yl)phenyl]ethynyl, R2=R3=R4=H, R5=5-chloro-2-methylphenyl, R6=NH₂] (compd. 11)

Trifluoroacetic acid (1.4 mL) was added to a solution of 5-(2-amino-5-{[4-(4-methylpiperazin-1-yl)phenyl]ethynyl}pyrimidin-4-yl)-2-(5-chloro-2-methylphenyl)-1-{[2-(trimethylsilyl)ethoxy]methyl}-1H-pyrrole-3-carboxamide (92 mg, 0.14 mmol) in dry DCM (2.8 mL) and stirred for 4 h at room temperature. After solvent removal, the residue was treated with EtOH (3 mL), 33% NH₄OH (0.4 mL) and stirred for 0.5 h. The solvent was evaporated to dryness and the residue was purified by flash-chromatography on silica gel (DCM/MeOH/7N NH₃ in MeOH 94/5/1) to afford the title compound as white solid (52 mg, 71%).

¹H NMR (400 MHz, DMSO-d₆) δ ppm 2.14 (s, 3H) 2.22 (s, 3H) 2.42-2.47 (m, 4H) 3.19-3.25 (m, 4H) 6.68 (bs, 2H) 6.78 (bs, 1H) 6.91-6.99 (m, 3H) 7.26-7.35 (m, 2H) 7.35-7.38 (m, 1H) 7.40-7.48 (m, 2H) 7.81 (d, J=2.56 Hz, 1H) 8.40 (s, 1H) 11.60 (s, 1H).

HRMS (ESI) calcd for $C_{26}H_{28}ClN_7O+H^+$ 526.2117. found 526.2121.

Example 9

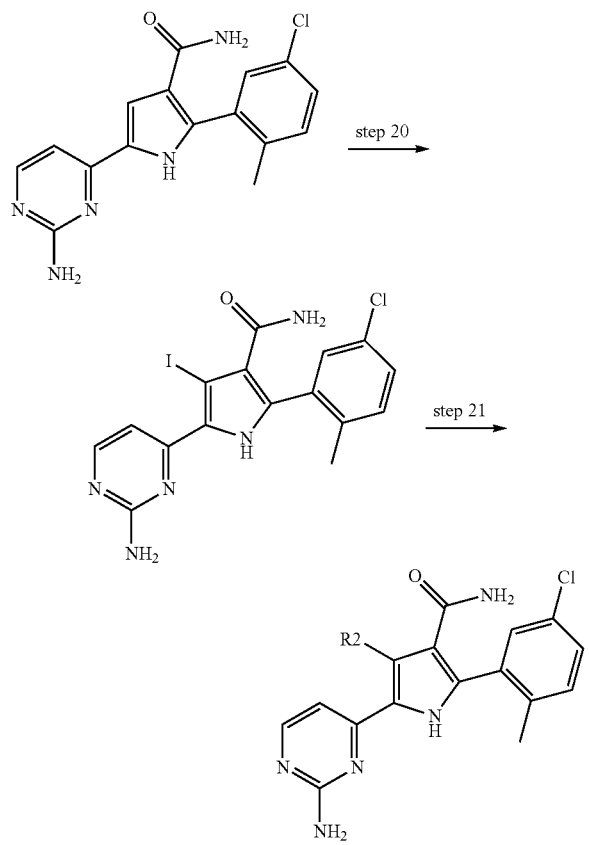

Scheme E, Steps 20, 21

Step 20: 5-(2-Amino-pyrimidin-4-yl)-2-(5-chloro-2-methyl-phenyl)-4-iodo-1H-pyrrole-3-carboxamide (XXIV)

5-(2-Amino-pyrimidin-4-yl)-2-(5-chloro-2-methyl-phenyl)-1H-pyrrole-3-carboxamide (1.1 g, 3.36 mmol) in dry DMF (6 mL) was treated with solid N-iodosuccinimide (830 mg, 3.69 mmol), stirred at room temperature for 4.5 h and poured into iced water (150 mL). The solid was then filtered with suction, washed thoroughly with water, dried in an oven under vacuum at 50° C. and purified by flash chromatography over silica gel (DCM/MeOH/7 N NH₃ in MeOH 95/5/0.5) to afford the title compound (654 mg, 43%).

¹H NMR (400 MHz, DMSO-d₆) δ ppm 2.20 (s, 3H) 6.41 (bs, 2H) 7.00 (bs, 1H) 7.13 (bs, 1H) 7.30 (d, J=8.30 Hz, 1H) 7.31 (d, J=5.25 Hz, 1H) 7.34 (d, J=2.30 Hz, 1H) 7.36 (dd, J=8.30, 2.30 Hz, 1H) 8.29 (d, J=5.25 Hz, 1H) 11.90 (s, 1H).

The above procedure was employed to synthesize the following compound:

5-(2-Amino-pyrimidin-4-yl)-2-(5-chloro-2-ethyl-phenyl)-4-iodo-1H-pyrrole-3-carboxamide (XXIV)

¹H NMR (400 MHz, DMSO-d₆) δ ppm 1.01 (t, J=7.57 Hz, 3H) 6.59 (bs, 2H) 6.96 (bs, 1H) 7.13 (bs, 1H) 7.30-7.37 (m, 3H) 7.38-7.45 (m, 1H) 8.29 (d, J=5.37 Hz, 1H) 11.99 (s, 1H).

Step 2: General Procedure 5-(2-Amino-pyrimidin-4-yl)-2-(5-chloro-2-methyl-phenyl)-4-iodo-1H-pyrrole-3-carboxamide (45 mg, 0.1 mmol, 1 eq.) in dry ACN (1 mL) was treated with the alkyne (0.2 mmol, 2 eq.) and TEA (0.14 mL, 1 mmol, 10 eq.). The flask was stirred, purged with nitrogen and then solid CuI (0.005 mmol, 0.05 eq) and Pd (Ph₃P)₂Cl₂ (0.005 mmol, 0.05 eq) were added. The reaction was then either refluxed or heated under microwave irradiation at 80° C. until full conversion of the starting material was observed (typically from 1 to several hours were required). If precipitation of the product occurred upon cooling, the solid was filtered, washed in sequence with ACN (3×1 mL), H₂O/MeOH 9/1 (2×1 mL) and finally dried under vacuum at 50° C. Conversely, the reaction was diluted with DCM (20 mL), washed with water (5 mL), dried over sodium sulfate and evaporated. The residue was then purified by flash chromatography. Typically, DCM/MeOH 95/5 under gradient conditions or reverse phase purification (Phase A: 0.05 NH₄OH/ACN 95/5; Phase B: ACN/H₂O 95/5 Gradient: 10-70 in 10 CV).

The above procedure was employed to synthesize the following compounds:

5-(2-Amino-pyrimidin-4-yl)-2-(5-chloro-2-methyl-phenyl)-4-phenylethynyl-1H-pyrrole-3-carboxamide [(I), R1=H, R2=phenylethynyl, R3=R4=H, R5=5-chloro-2-methylphenyl, R6=NH₂] (compd. 69)

¹H NMR (400 MHz, DMSO-d₆) δ ppm 2.16 (s, 3H) 6.37 (bs, 2H) 7.05 (bs, 1H) 7.22 (bs, 1H) 7.29 (d, J=8.40 Hz, 1H) 7.30 (d, J=2.20 Hz, 1H) 7.36 (dd, J=8.40, 2.20 Hz, 1H) 7.42-7.47 (m, 3H) 7.48 (d, J=5.25 Hz, 1H) 7.55-7.60 (m, 2H) 8.36 (d, J=5.25 Hz, 1H) 12.06 (bs, 1H).

HRMS (ESI) calcd for $C_{24}H_{18}ClN_5O+H^+$ 428.1273. found 428.1274.

5-(2-Aminopyrimidin-4-yl)-2-(5-chloro-2-methylphenyl)-4-[(3-hydroxyphenyl)ethynyl]-1H-pyrrole-3-carboxamide [(I), R1=H, R2=(3-hydroxyphenyl)ethynyl, R3=R4=H, R5=5-chloro-2-methylphenyl, R6=NH₂] (compd. 70)

¹H NMR (400 MHz, DMSO-d₆) δ ppm 2.15 (s, 3H) 6.32 (bs, 2H) 6.82 (ddd, J=8.18, 2.44, 0.73 Hz, 1H) 6.93 (dd, J=2.14, 1.65 Hz, 2H) 6.98 (dt, J=7.60, 1.14 Hz, 1H) 7.02 (bs, 1H) 7.17 (bs, 1H) 7.24 (t, J=7.87 Hz, 1H) 7.27 (d, J=7.90 Hz, 1H) 7.28 (d, J=2.00 Hz, 1H) 7.34 (dd, J=7.93, 2.00 Hz, 1H) 7.45 (d, J=5.25 Hz, 1H) 8.32 (d, J=4.88 Hz, 1H) 9.77 (bs, 1H) 12.03 (bs, 1H).

HRMS (ESI) calcd for $C_{24}H_{18}ClN_5O_2+H^+$ 444.1222. found 444.1219.

5-(2-Aminopyrimidin-4-yl)-2-(5-chloro-2-methylphenyl)-4-[(4-methoxyphenyl)ethynyl]-1H-pyrrole-3-carboxamide [(I), R1=H, R2=(4-methoxyphenyl)ethynyl, R3=R4=H, R5=5-chloro-2-methylphenyl, R6=NH₂] (compd. 71

¹H NMR (400 MHz, DMSO-d₆) δ ppm 2.15 (s, 3H) 3.81 (s, 3H) 6.35 (bs, 2H) 7.02 (d, J=8.91 Hz, 2H) 7.04 (bs, 1H) 7.21

(bs, 1H) 7.28 (d, J=8.30 Hz, 1H) 7.29 (d, J=2.32 Hz, 1H) 7.36 (dd, J=8.20, 2.20 Hz, 1H) 7.48 (d, J=5.25 Hz, 1H) 7.52 (d, J=8.91 Hz, 2H) 8.34 (d, J=5.25 Hz, 1H) 12.00 (s, 1H).

HRMS (ESI) calcd for $C_{25}H_{20}ClN_5O_2+H^+$ 458.1379. found 458.1378.

4-[(3-Aminophenyl)ethynyl]-5-(2-aminopyrimidin-4-yl)-2-(5-chloro-2-methylphenyl)-1H-pyrrole-3-carboxamide [(I), R1=H, R2=(3-aminophenyl)ethynyl, R3=R4=H, R5=5-chloro-2-methylphenyl, R6=NH₂] (compd. 72)

$^1$H NMR (400 MHz, DMSO-d$_6$) δ ppm 2.15 (s, 3H) 5.27 (br. s., 2H) 6.36 (bs, 2H) 6.62 (ddd, J=8.09, 2.29, 0.98 Hz, 1H) 6.70 (dt, J=7.63, 1.13 Hz, 1H) 6.75 (t, J=1.77 Hz, 1H) 7.01 (bs, 1H) 7.08 (t, J=7.87 Hz, 1H) 7.22 (bs, 1H) 7.27-7.31 (m, 2H) 7.33-7.39 (m, 1H) 7.48-7.50 (m, 1H) 8.35 (d, J=5.25 Hz, 1H) 12.02 (s, 1H).

HRMS (ESI) calcd for $C_{24}H_{19}ClN_6O+H^+$ 443.1382. found 443.1379.

5-(2-Aminopyrimidin-4-yl)-2-(5-chloro-2-methylphenyl)-4-[(2-methoxyphenyl)ethynyl]-1H-pyrrole-3-carboxamide [(I), R1=H, R2=(2-methoxyphenyl)ethynyl, R3=R4=H, R5=5-chloro-2-methylphenyl, R6=NH₂] (compd. 73)

$^1$H NMR (400 MHz, DMSO-d$_6$) δ ppm 2.12 (s, 3H) 3.92 (s, 3H) 6.35 (bs, 2H) 7.03 (td, J=7.48, 0.92 Hz, 1H) 7.13 (d, J=8.06 Hz, 1H) 7.26-7.29 (m, 2H) 7.34-7.37 (m, 1H) 7.38 (bs, 2H) 7.39-7.45 (m, 1H) 7.51-7.54 (m, 1H) 7.66 (d, J=5.25 Hz, 1H) 8.39 (d, J=5.25 Hz, 1H) 12.08 (bs, 1H).

HRMS (ESI) calcd for $C_{25}H_{20}ClN_5O_2+H^+$ 458.1379. found 458.1373.

[(2-Aminophenyl)ethynyl]-4-(2-Amino-phenylethynyl)-5-(2-amino-pyrimidin-4-yl)-2-(5-chloro-2-methyl-phenyl)-1H-pyrrole-3-carboxamide [(I), R1=H, R2=(2-aminophenyl)ethynyl, R3=R4=H, R5=5-chloro-2-methylphenyl, R6=NH₂] (compd. 74)

$^1$H NMR (400 MHz, DMSO-d$_6$) δ ppm 2.18 (s, 3H) 5.74 (s, 2H) 6.34 (bs, 2H) 6.55 (td, J=7.45, 0.98 Hz, 1H) 6.61 (bs, 1H) 6.73 (dd, J=8.30, 0.61 Hz, 1H) 7.08 (ddd, J=8.27, 7.17, 1.53 Hz, 1H) 7.18 (bs, 1H) 7.26 (dd, J=7.63, 1.40 Hz, 1H) 7.33 (d, J=8.30 Hz, 1H) 7.37 (d, J=2.32 Hz, 1H) 7.40 (dd, J=8.30, 2.32 Hz, 1H) 7.54 (d, J=5.25 Hz, 1H) 8.34 (d, J=5.13 Hz, 1H) 11.99 (s, 1H).

HRMS (ESI) calcd for $C_{24}H_{19}ClN_6O+H^+$ 443.1382. found 443.1379.

4-[(4-amino-2-methoxyphenyl)ethynyl]-5-(2-aminopyrimidin-4-yl)-2-(5-chloro-2-methylphenyl)-1H-pyrrole-3-carboxamide [(I), R1=H, R2=(4-amino-2-methoxyphenyl)ethynyl, R3=R4=H, R5=5-chloro-2-methylphenyl, R6=NH₂] (compd. 75)

$^1$H NMR (400 MHz, DMSO-d$_6$) δ ppm 2.17 (s, 3H) 3.71 (s, 3H) 5.78 (s, 2H) 6.17 (dd, J=8.48, 2.50 Hz, 1H) 6.30 (d, J=2.44 Hz, 1H) 6.32 (bs, 2H) 6.60 (bs, 1H) 7.16 (bs, 1H) 7.18 (d, J=8.54 Hz, 1H) 7.32 (d, J=8.30 Hz, 1H) 7.36 (d, J=2.32 Hz, 1H) 7.39 (dd, J=8.30, 2.32 Hz, 1H) 7.54 (d, J=5.25 Hz, 1H) 8.33 (d, J=5.25 Hz, 1H) 11.93 (s, 1H).

HRMS (ESI) calcd for $C_{25}H_{21}ClN_6O_2+H^+$ 473.1488. found 473.1492.

4-[(4-Aminophenyl)ethynyl]-5-(2-amino-pyrimidin-4-yl)-2-(5-chloro-2-methyl-phenyl)-1H-pyrrole-3-carboxamide [(I), R1=H, R2=(4-aminophenyl)ethynyl, R3=R4=H, R5=5-chloro-2-methylphenyl, R6=NH₂] (compd. 76)

$^1$H NMR (400 MHz, DMSO-d$_6$) δ ppm 2.14 (s, 3H) 5.60 (bs, 2H) 6.31 (bs, 2H) 6.60 (d, J=8.54 Hz, 2H) 7.05 (bs, 1H) 7.19 (bs, 1H) 7.24 (d, J=8.67 Hz, 2H) 7.27 (d, J=2.32 Hz, 1H) 7.28 (d, J=8.30 Hz, 1H) 7.35 (dd, J=8.30, 2.32 Hz, 1H) 7.50 (d, J=5.25 Hz, 1H) 8.33 (d, J=5.25 Hz, 1H) 11.91 (s, 1H).

HRMS (ESI) calcd for $C_{24}H_{19}ClN_6O+H^+$ 443.1382. found 443.1385.

5-(2-Aminopyrimidin-4-yl)-2-(5-chloro-2-methylphenyl)-4-[(2-methylphenyl)ethynyl]-1H-pyrrole-3-carboxamide [(I), R1=H, R2=(2-methylphenyl)ethynyl, R3=R4=H, R5=5-chloro-2-methylphenyl, R6=NH₂] (compd. 77)

$^1$H NMR (400 MHz, DMSO-d$_6$) δ ppm 2.17 (s, 3H) 6.37 (bs, 2H) 7.05 (bs, 1H) 7.23-7.34 (m, 5H) 7.37 (dd, J=8.30, 2.32 Hz, 1H) 7.52 (d, J=5.13 Hz, 1H) 7.53 (d, J=7.32 Hz, 1H) 8.35 (d, J=5.25 Hz, 1H) 12.06 (s, 1H).

HRMS (ESI) calcd for $C_{25}H_{20}ClN_5O+H^+$ 442.1429. found 442.1427.

5-(2-Aminopyrimidin-4-yl)-2-(5-chloro-2-methylphenyl)-4-[(4-fluorophenyl)ethynyl]-1H-pyrrole-3-carboxamide [(I), R1=H, R2=(4-fluorophenyl)ethynyl, R3=R4=H, R5=5-chloro-2-methylphenyl, R6=NH₂] (compd. 78)

$^1$H NMR (401 MHz, DMSO-d6) δ ppm 2.13 (s, 3H) 6.34 (bs, 2H) 7.01 (bs, 1H) 7.17 (bs, 1H) 7.24-7.31 (m, 4H) 7.33 (dd, J=8.60, 2.55 Hz, 1H) 7.42 (d, J=5.13 Hz, 1H) 7.59-7.63 (m, 2H) 8.32 (d, J=5.25 Hz, 1H) 12.03 (s, 1H).

HRMS (ESI) calcd for $C_{24}H_{17}ClFN_5O+H^+$ 446.1179. found 446.1184.

4-[(5-Amino-2-methoxyphenyl)ethynyl]-5-(2-aminopyrimidin-4-yl)-2-(5-chloro-2-methylphenyl)-1H-pyrrole-3-carboxamide [(I), R1=H, R2=(5-amino-2-methoxyphenyl)ethynyl, R3=R4=H, R5=5-chloro-2-methylphenyl, R6=NH₂] (compd. 79)

$^1$H NMR (400 MHz, DMSO-d$_6$) δ ppm 2.12 (s, 3H) 3.78 (s, 3H) 4.81 (bs, 2H) 6.34 (bs, 2H) 6.64 (dd, J=8.79, 2.81 Hz, 1H) 6.75 (d, J=2.81 Hz, 1H) 6.84 (d, J=8.79 Hz, 1H) 7.26 (d, J=2.20 Hz, 1H) 7.27 (d, J=8.12 Hz, 1H) 7.35 (dd, J=8.12, 2.26 Hz, 2H) 7.65 (d, J=5.25 Hz, 1H) 8.36 (d, J=5.37 Hz, 1H) 12.04 (bs, 1H).

HRMS (ESI) calcd for $C_{25}H_{21}ClN_6O_2+H^+$ 473.1488. found 473.1485.

5-(2-Aminopyrimidin-4-yl)-2-(5-chloro-2-methylphenyl)-4-({3-[(1-methylpiperidin-4-yl)amino]phenyl}ethynyl)-1H-pyrrole-3-carboxamide [(I), R1=H, R2={3-[(1-methylpiperidin-4-yl)amino]phenyl}ethynyl, R3=R4=H, R5=5-chloro-2-methylphenyl, R6=NH₂] (compd. 80)

$^1$H NMR (400 MHz, DMSO-d$_6$) δ ppm 1.34-1.46 (m, 2H) 1.89 (d, J=11.72 Hz, 2H) 1.97-2.09 (m, 2H) 2.15 (s, 3H) 2.18 (s, 3H) 2.68-2.81 (m, 2H) 3.20 (d, J=7.08 Hz, 2H) 5.67 (d, J=8.06 Hz, 1H) 6.36 (bs, 2H) 6.58-6.67 (m, 1H) 6.67-6.72 (m, 1H) 6.72-6.75 (m, 1H) 7.02 (bs, 1H) 7.12 (t, J=7.87 Hz, 1H)

7.22 (bs, 1H) 7.26-7.31 (m, 3H) 7.33-7.38 (m, 1H) 7.45-7.51 (m, 1H) 8.33 (d, J=5.25 Hz, 1H) 12.03 (bs, 1H).

HRMS (ESI) calcd for $C_{30}H_{30}ClN_7O+H^+$ 540.2273. found 540.2271.

5-(2-Aminopyrimidin-4-yl)-2-(5-chloro-2-methylphenyl)-4-({3-[(4-methylpiperazin-1-yl)methyl]phenyl}ethynyl)-1H-pyrrole-3-carboxamide [(I), R1=H, R2={3-[(4-methylpiperazin-1-yl)methyl]phenyl}ethynyl, R3=R4=H, R5=5-chloro-2-methylphenyl, R6=NH₂] (compd. 81)

$^1$H NMR (400 MHz, DMSO-d$_6$) δ ppm 2.16 (s, 3H) 2.19 (s, 3H) 2.32-2.47 (m, 10H) 6.38 (bs, 2H) 7.04 (bs, 1H) 7.22 (bs, 1H) 7.27-7.51 (m, 8H) 8.35 (d, J=5.13 Hz, 1H) 12.06 (bs, 1H).

HRMS (ESI) calcd for $C_{30}H_{30}ClN_7O+H^+$ 540.2273. found 540.2266.

4-({3-[(2-Aminoethyl)amino]phenyl}ethynyl)-5-(2-aminopyrimidin-4-yl)-2-(5-chloro-2-methylphenyl)-1H-pyrrole-3-carboxamide [(I), R1=H, R2={3-[(2-aminoethyl)amino]phenyl}ethynyl, R3=R4=H, R5=5-chloro-2-methylphenyl, R6=NH₂] (compd. 82)

Obtained from tert-butyl {2-[(3-{[2-(2-aminopyrimidin-4-yl)-4-carbamoyl-5-(5-chloro-2-methylphenyl)-1H-pyrrol-3-yl]ethynyl}phenyl)amino]ethyl}carbamate after treatment with TFA in DCM (69% yield).

$^1$H NMR (400 MHz, DMSO-d$_6$) δ ppm 2.15 (s, 3H) 2.80 (t, J=6.29 Hz, 2H) 3.11 (q, J=6.10 Hz, 2H) 5.83 (t, J=5.55 Hz, 1H) 6.36 (bs, 2H) 6.63-6.68 (m, 1H) 6.71-6.79 (m, 2H) 7.02 (bs, 1H) 7.15 (t, J=7.93 Hz, 2H) 7.22 (bs, 1H) 7.26-7.31 (m, 3H) 7.33-7.38 (m, 2H) 7.46-7.53 (m, 2H) 8.34 (d, J=5.25 Hz, 1H).

HRMS (ESI) calcd for $C_{26}H_{24}ClN_7O+H^+$ 486.1804. found 486.1799.

5-(2-Aminopyrimidin-4-yl)-2-(5-chloro-2-methylphenyl)-4-{[4-(4-methylpiperazin-1-yl)phenyl]ethynyl}-1H-pyrrole-3-carboxamide [(I), R1=H, R2=[4-(4-methylpiperazin-1-yl)phenyl]ethynyl, R3=R4=H, R5=5-chloro-2-methylphenyl, R6=NH₂] (compd. 83)

$^1$H NMR (400 MHz, DMSO-d$_6$) δ ppm 2.14 (s, 3H) 2.23 (s, 3H) 2.41-2.47 (m, 4H) 3.20-3.27 (m, 4H) 6.33 (bs, 2H) 6.98 (d, J=9.03 Hz, 2H) 7.05 (bs, 1H) 7.21 (bs, 1H) 7.25-7.30 (m, 2H) 7.33-7.37 (m, 1H) 7.38-7.44 (m, 2H) 7.47-7.56 (m, 1H) 8.33 (d, J=5.25 Hz, 1H) 11.96 (s, 1H).

HRMS (ESI) calcd for $C_{26}H_{28}ClN_7O+H^+$ 526.2117. found 526.2116.

5-(2-Aminopyrimidin-4-yl)-2-(5-chloro-2-methylphenyl)-4-({2-[(2-hydroxyethyl)amino]phenyl}ethynyl)-1H-pyrrole-3-carboxamide [(I), R1=H, R2={2-[(2-hydroxyethyl)amino]phenyl}ethynyl, R3=R4=H, R5=5-chloro-2-methylphenyl, R6=NH₂] (compd. 84)

$^1$H NMR (400 MHz, DMSO-d$_6$) δ ppm 2.19 (s, 3H) 3.22-3.27 (m, 2H) 3.65 (q, J=5.94 Hz, 2H) 4.86 (t, J=5.74 Hz, 1H) 5.89 (t, J=5.55 Hz, 1H) 6.35 (bs, 2H) 6.59 (td, J=7.42, 0.92 Hz, 1H) 6.64 (bs, 1H) 6.68 (d, J=8.30 Hz, 1H) 7.10-7.24 (m, 2H) 7.30-7.36 (m, 2H) 7.36-7.44 (m, 2H) 7.55 (d, J=5.25 Hz, 1H) 8.36 (d, J=5.25 Hz, 1H) 12.03 (s, 1H).

HRMS (ESI) calcd for $C_{26}H_{23}ClN_6O_2+H^+$ 487.1644. found 487.1648.

5-(2-Aminopyrimidin-4-yl)-2-(5-chloro-2-methylphenyl)-4-{[2-fluoro-4-(4-methylpiperazin-1-yl)phenyl]ethynyl}-1H-pyrrole-3-carboxamide [(I), R1=H, R2=[2-fluoro-4-(4-methylpiperazin-1-yl)phenyl]ethynyl, R3=R4=H, R5=5-chloro-2-methylphenyl, R6=NH₂] (compd. 85)

$^1$H NMR (400 MHz, DMSO-d$_6$) δ ppm 2.14 (s, 3H) 2.22 (s, 3H) 2.40-2.46 (m, 4H) 3.24-3.28 (m, 4H) 6.34 (bs, 2H) 6.82 (dd, J=8.79, 2.44 Hz, 1H) 6.88 (dd, J=13.79, 2.32 Hz, 1H) 7.04 (bs, 1H) 7.26 (bs, 1H) 7.26-7.30 (m, 2H) 7.33-7.37 (m, 1H) 7.41 (t, J=8.73 Hz, 1H) 7.53 (d, J=5.25 Hz, 1H) 8.31 (d, J=5.25 Hz, 1H) 12.02 (s, 1H).

HRMS (ESI) calcd for $C_{26}H_{27}ClFN_7O+H^+$ 544.2023. found 544.2028.

5-(2-Aminopyrimidin-4-yl)-2-(5-chloro-2-methylphenyl)-4-{[2-methoxy-5-(4-methylpiperazin-1-yl)phenyl]ethynyl}-1H-pyrrole-3-carboxamide [(I), R1=H, R2=[2-methoxy-5-(4-methylpiperazin-1-yl)phenyl]ethynyl, R3=R4=H, R5=5-chloro-2-methylphenyl, R6=NH₂] (compd. 86)

$^1$H NMR (400 MHz, DMSO-d$_6$) δ ppm 2.12 (s, 3H) 2.24 (s, 3H) 2.46-2.49 (m, 4H) 3.07-3.11 (m, 4H) 3.85 (s, 3H) 6.35 (bs, 2H) 6.89-7.09 (m, 3H) 7.26-7.30 (m, 2H) 7.32-7.40 (m, 2H) 7.66 (d, J=5.25 Hz, 1H) 8.38 (d, J=5.25 Hz, 1H) 12.06 (s, 1H).

HRMS (ESI) calcd for $C_{30}H_{30}ClN_7O_2+H^+$ 556.2223. found 556.2217.

5-(2-Aminopyrimidin-4-yl)-2-(5-chloro-2-methylphenyl)-4-[(2-{[2-(dimethylamino)ethyl]amino}phenyl)ethynyl]-1H-pyrrole-3-carboxamide [(I), R1=H, R2=(2-{[2-(dimethylamino)ethyl]amino}phenyl)ethynyl, R3=R4=H, R5=5-chloro-2-methylphenyl, R6=NH₂] (compd. 87)

$^1$H NMR (400 MHz, DMSO-d$_6$) δ ppm 2.16 (s, 6H) 2.18 (s, 3H) 5.83 (t, J=5.19 Hz, 1H) 6.35 (bs, 2H) 6.60 (t, J=7.38 Hz, 1H) 6.66 (d, J=8.18 Hz, 1H) 7.16-7.24 (m, 2H) 7.29-7.37 (m, 3H) 7.37-7.42 (m, 1H) 7.54 (d, J=5.37 Hz, 1H) 8.34 (d, J=5.25 Hz, 1H) 12.02 (s, 1H).

HRMS (ESI) calcd for $C_{28}H_{28}ClN_7O+H^+$ 514.2117. found 514.2110.

5-(2-Aminopyrimidin-4-yl)-2-(5-chloro-2-methylphenyl)-4-[3-(dimethylamino)prop-1-yn-1-yl]-1H-pyrrole-3-carboxamide carboxamide [(I), R1=H, R2=3-(dimethylamino)prop-1-yn-1-yl, R3=R4=H, R5=5-chloro-2-methylphenyl, R6=NH₂] (compd. 88)

$^1$H NMR (400 MHz, DMSO-d$_6$) δ ppm 2.14 (s, 3H) 2.53-2.62 (m, 6H) 3.94 (bs, 2H) 6.37 (bs, 2H) 6.90 (bs, 1H) 7.20 (bs, 1H) 7.26-7.32 (m, 2H) 7.33-7.40 (m, 2H) 8.28 (d, J=5.25 Hz, 1H) 12.01 (bs, 1H).

HRMS (ESI) calcd for $C_{21}H_{21}ClN_6O+H^+$ 409.1538. found 409.1543.

5-(2-Aminopyrimidin-4-yl)-2-(5-chloro-2-methylphenyl)-4-{[2-methoxy-4-(4-methylpiperazin-1-yl)phenyl]ethynyl}-1H-pyrrole-3-carboxamide [(I), R1=H, R2=[2-methoxy-4-(4-methylpiperazin-1-yl)phenyl]ethynyl, R3=R4=H, R5=5-chloro-2-methylphenyl, R6=NH₂] (compd. 89)

$^1$H NMR (400 MHz, DMSO-d$_6$) δ ppm 2.11 (s, 3H) 2.28 (bs, 3H) 2.50-2.55 (m, 4H) 3.90 (s, 3H) 6.31 (bs, 2H) 6.55-

6.60 (m, 2H) 7.24-7.30 (m, 2H) 7.30-7.37 (m, 3H) 7.39 (bs, 1H) 7.66 (d, J=5.25 Hz, 1H) 8.36 (d, J=5.13 Hz, 1H) 11.95 (s, 1H).

HRMS (ESI) calcd for $C_{30}H_{30}ClN_7O_2+H^+$ 556.2223. found 556.2220.

5-(2-Aminopyrimidin-4-yl)-2-(5-chloro-2-methylphenyl)-4-{[3-(4-methylpiperazin-1-yl)phenyl]ethynyl}-1H-pyrrole-3-carboxamide carboxamide [(I), R1=H, R2=[3-(4-methylpiperazin-1-yl)phenyl]ethynyl, R3=R4=H, R5=5-chloro-2-methylphenyl, R6=NH₂] (compd. 90)

$^1$H NMR (400 MHz, DMSO-$d_6$) δ ppm 2.15 (s, 3H) 2.24 (s, 3H) 2.44-2.49 (m, 4H) 3.10-3.23 (m, 4H) 6.36 (bs, 2H) 6.90-7.09 (m, 4H) 7.23 (bs, 0H) 7.25-7.31 (m, 3H) 7.33-7.39 (m, 1H) 7.46-7.50 (m, 1H) 8.35 (d, J=5.25 Hz, 1H) 12.04 (s, 1H).

HRMS (ESI) calcd for $C_{26}H_{28}ClN_7O+H^+$ 526.2117. found 526.2120.

5-(2-Aminopyrimidin-4-yl)-2-(5-chloro-2-methylphenyl)-4-({3-[(1-methylpiperidin-4-yl)oxy]phenyl}ethynyl)-1H-pyrrole-3-carboxamide [(I), R1=H, R2={3-[(1-methylpiperidin-4-yl)oxy]phenyl}ethynyl, R3=R4=H, R5=5-chloro-2-methylphenyl, R6=NH₂] (compd. 91)

$^1$H NMR (400 MHz, DMSO-$d_6$) δ ppm 1.58-1.72 (m, 2H) 1.88-1.99 (m, 2H) 2.16 (s, 3H) 2.19 (s, 3H) 2.15-2.24 (m, 2H) 2.57-2.66 (m, 2H) 4.30-4.52 (m, 1H) 6.37 (bs, 2H) 7.04 (d, J=2.44 Hz, 1H) 7.08-7.11 (m, 1H) 7.13 (d, J=7.69 Hz, 1H) 7.22 (bs, 1H) 7.26-7.39 (m, 4H) 7.46 (d, J=5.25 Hz, 1H) 8.35 (d, J=5.25 Hz, 1H) 12.06 (bs, 1H).

HRMS (ESI) calcd for $C_{30}H_{29}ClN_6O_2+H^+$ 541.2114. found 541.2109.

5-(2-Aminopyrimidin-4-yl)-2-(5-chloro-2-methylphenyl)-4-({4-[(1-methylpiperidin-4-yl)oxy]phenyl}ethynyl)-1H-pyrrole-3-carboxamide [(I), R1=H, R2={4-[(1-methylpiperidin-4-yl)oxy]phenyl}ethynyl, R3=R4=H, R5=5-chloro-2-methylphenyl, R6=NH₂] (compd. 92)

$^1$H NMR (400 MHz, DMSO-$d_6$) δ ppm 1.53-1.73 (m, 2H) 1.90-1.99 (m, 2H) 2.15 (s, 3H) 2.19 (s, 3H) 2.18-2.25 (m, 2H) 2.58-2.66 (m, 2H) 4.35-4.52 (m, 1H) 6.35 (bs, 2H) 6.91-7.08 (m, 3H) 7.20 (bs, 1H) 7.25-7.32 (m, 2H) 7.33-7.38 (m, 1H) 7.42-7.54 (m, 3H) 8.26-8.43 (m, 1H) 12.01 (bs, 1H).

HRMS (ESI) calcd for $C_{30}H_{29}ClN_6O_2+H^+$ 541.2114. found 541.2110.

5-(2-Aminopyrimidin-4-yl)-2-(5-chloro-2-methylphenyl)-4-{[2-fluoro-5-(4-methylpiperazin-1-yl)phenyl]ethynyl}-1H-pyrrole-3-carboxamide [(I), R1=H, R2=[2-fluoro-5-(4-methylpiperazin-1-yl)phenyl]ethynyl, R3=R4=H, R5=5-chloro-2-methylphenyl, R6=NH₂] (compd. 93)

$^1$H NMR (400 MHz, DMSO-$d_6$) δ ppm 2.15 (s, 3H) 2.25 (s, 5H) 2.47-2.51 (m, 4H) 3.03-3.18 (m, 4H) 6.37 (bs, 2H) 7-00-7.09 (m, 3H) 7.20 (t, J=9.03 Hz, 1H) 7.23-7.34 (m, 3H) 7.34-7.39 (m, 1H) 7.51 (d, J=5.25 Hz, 1H) 8.32 (d, J=5.13 Hz, 1H) 12.12 (s, 1H).

HRMS (ESI) calcd for $C_{26}H_{27}ClFN_7O+H^+$ 544.2023. found 544.2017.

5-(2-Aminopyrimidin-4-yl)-2-(5-chloro-2-methylphenyl)-4-({2-[(1-methylpiperidin-4-yl)amino]phenyl}ethynyl)-1H-pyrrole-3-carboxamide [(I), R1=H, R2={2-[(1-methylpiperidin-4-yl)amino]phenyl}ethynyl, R3=R4=H, R5=5-chloro-2-methylphenyl, R6=NH₂] (compd. 94)

$^1$H NMR (400 MHz, DMSO-$d_6$) δ ppm 1.68-1.83 (m, 2H) 1.94-2.05 (m, 2H) 2.20 (s, 3H) 2.97-3.18 (m, 4H) 4.42-4.51 (m, 1H) 5.66 (d, J=7.81 Hz, 1H) 6.35 (bs, 2H) 6.52 (bs, 1H) 6.60 (t, J=7.69 Hz, 1H) 6.73 (d, J=8.42 Hz, 1H) 7.10 (bs, 1H) 7.14-7.23 (m, 1H) 7.30-7.45 (m, 4H) 7.56 (d, J=5.25 Hz, 1H) 8.36 (d, J=5.25 Hz, 1H) 12.02 (bs, 1H).

HRMS (ESI) calcd for $C_{30}H_{30}ClN_7O+H^+$ 540.2273. found 544.2069.

5-(2-Aminopyrimidin-4-yl)-2-(5-chloro-2-methylphenyl)-4-({4-[4-(4-methylpiperazin-1-yl)piperidin-1-yl]phenyl}ethynyl)-1H-pyrrole-3-carboxamide [(I), R1=H, R2={4-[4-(4-methylpiperazin-1-yl)piperidin-1-yl]phenyl}ethynyl, R3=R4=H, R5=5-chloro-2-methylphenyl, R6=NH₂] (compd. 95)

$^1$H NMR (400 MHz, DMSO-$d_6$) δ ppm 1.40-1.55 (m, 2H) 1.83 (d, J=11.47 Hz, 2H) 2.14 (s, 3H) 2.18 (s, 3H) 2.25-2.44 (m, 5H) 2.71-2.84 (m, 2H) 3.84 (d, J=12.69 Hz, 2H) 6.33 (bs, 2H) 6.95-7.00 (m, 2H) 7.05 (bs, 1H) 7.21 (bs, 1H) 7.26-7.30 (m, 2H) 7.34-7.36 (m, 1H) 7.37-7.41 (m, 2H) 7.47-7.51 (m, 1H) 8.33 (d, J=5.27 Hz, 1H) 11.97 (bs, 1H).

HRMS (ESI) calcd for $C_{34}H_{37}ClN_8O+H^+$ 609.2852. found 609.2858.

5-(2-Aminopyrimidin-4-yl)-2-(5-chloro-2-methylphenyl)-4-({4-[4-(dimethylamino)piperidin-1-yl]phenyl}ethynyl)-1H-pyrrole-3-carboxamide [(I), R1=H, R2={4-[4-(dimethylamino)piperidin-1-yl]phenyl}ethynyl, R3=R4=H, R5=5-chloro-2-methylphenyl, R6=NH₂] (compd. 96)

$^1$H NMR (400 MHz, DMSO-$d_6$) δ ppm 1.43-1.62 (m, 2H) 1.85-2.02 (m, 2H) 2.12-2.16 (m, 3H) 2.47 (bs, 6H) 2.72-2.83 (m, 2H) 3.91 (d, J=12.45 Hz, 2H) 6.33 (bs, 2H) 7.00 (d, J=9.03 Hz, 2H) 7.04 (bs, 1H) 7.21 (bs, 1H) 7.26-7.31 (m, 2H) 7.32-7.38 (m, 1H) 7.40 (d, J=8.79 Hz, 2H) 7.46-7.51 (m, 1H) 8.33 (d, J=5.25 Hz, 1H) 11.97 (s, 1H).

HRMS (ESI) calcd for $C_{31}H_{32}ClN_7O+H^+$ 554.2430. found 554.2437.

5-(2-Aminopyrimidin-4-yl)-4-{[4-(1,4'-bipiperidin-1'-yl)phenyl]ethynyl}-2-(5-chloro-2-methylphenyl)-1H-pyrrole-3-carboxamide [(I), R1=H, R2=[4-(1,4'-bipiperidin-1'-yl)phenyl]ethynyl, R3=R4=H, R5=5-chloro-2-methylphenyl, R6=NH₂] (compd. 97)

$^1$H NMR (400 MHz, DMSO-$d_6$) δ ppm 1.32-1.62 (m, 8H) 1.82 (bs, 2H) 2.14 (s, 3H) 2.75 (t, J=11.41 Hz, 2H) 3.87 (d, J=11.60 Hz, 2H) 6.33 (bs, 2H) 6.98 (d, J=9.03 Hz, 2H) 7.04 (bs, 1H) 7.21 (bs, 1H) 7.26-7.30 (m, 2H) 7.34-7.37 (m, 1H) 7.39 (d, J=8.91 Hz, 2H) 7.46-7.51 (m, 1H) 8.33 (d, J=5.25 Hz, 1H) 11.96 (bs, 1H).

HRMS (ESI) calcd for $C_{34}H_{36}ClN_7O+H^+$ 594.2743. found 594.2739.

5-(2-Aminopyrimidin-4-yl)-2-(5-chloro-2-methylphenyl)-4-({4-[4-(pyrrolidin-1-yl)piperidin-1-yl]phenyl}ethynyl)-1H-pyrrole-3-carboxamide [(I), R1=H, R2={4-[4-(pyrrolidin-1-yl)piperidin-1-yl]phenyl}ethynyl, R3=R4=H, R5=5-chloro-2-methylphenyl, R6=NH₂] (compd. 98)

$^1$H NMR (400 MHz, DMSO-$d_6$) δ ppm 1.42-1.62 (m, 6H) 1.82 (bs, 2H) 2.14 (s, 3H) 2.82 (t, J=11.41 Hz, 2H) 3.84-3.92

(m, 2H) 6.33 (bs, 2H) 6.93-7.03 (m, 2H) 7.04 (bs, 1H) 7.21 (bs, 1H) 7.26-7.30 (m, 2H) 7.34-7.43 (m, 3H) 7.46-7.51 (m, 1H) 8.33 (d, J=5.25 Hz, 1H) 11.98 (bs, 1H).

HRMS (ESI) calcd for $C_{33}H_{34}ClN_7O+H^+$ 580.2586. found 580.2578.

5-(2-Aminopyrimidin-4-yl)-2-(5-chloro-2-methylphenyl)-4-{[4-(piperazin-1-yl)phenyl]ethynyl}-1H-pyrrole-3-carboxamide [(I), R1=H, R2=[4-(piperazin-1-yl)phenyl]ethynyl, R3=R4=H, R5=5-chloro-2-methylphenyl, R6=NH₂] (compd. 99)

¹H NMR (400 MHz, DMSO-d₆) δ ppm 2.12 (s, 3H) 3.07-3.13 (m, 4H) 6.31 (bs, 2H) 7.00 (d, J=9.03 Hz, 3H) 7.18 (bs, 1H) 7.23-7.28 (m, 2H) 7.29-7.36 (m, 1H) 7.42 (d, J=8.79 Hz, 2H) 7.44-7.50 (m, 1H) 8.30 (d, J=5.26 Hz, 1H) 11.96 (bs, 1H).

HRMS (ESI) calcd for $C_{28}H_{26}ClN_7O+H^+$ 512.1960. found 512.1964.

5-(2-Aminopyrimidin-4-yl)-2-(5-chloro-2-methylphenyl)-4-({4-[(4-methylpiperazin-1-yl)carbonyl]phenyl}ethynyl)-1H-pyrrole-3-carboxamide [(I), R1=H, R2={4-[(4-methylpiperazin-1-yl)carbonyl]phenyl}ethynyl, R3=R4=H, R5=5-chloro-2-methylphenyl, R6=NH₂] (compd. 100)

¹H NMR (400 MHz, DMSO-d₆) δ ppm 2.16 (s, 3H) 2.21 (s, 3H) 2.25-2.42 (m, 4H) 3.46-3.69 (m, 2H) 6.39 (bs, 2H) 7.05 (bs, 1H) 7.22 (bs, 1H) 7.27-7.33 (m, 2H) 7.33-7.39 (m, 1H) 7.43-7.48 (m, 3H) 7.61-7.65 (m, 2H) 8.36 (d, J=5.25 Hz, 1H) 12.11 (bs, 1H).

HRMS (ESI) calcd for $C_{30}H_{28}ClN_7O_2+H^+$ 554.2066. found 554.2064.

According to this procedure, but starting from 5-(2-aminopyrimidin-4-yl)-2-(5-chloro-2-ethyl-phenyl)-4-iodo-1H-pyrrole-3-carboxamide, the following compounds were prepared:

5-(2-Aminopyrimidin-4-yl)-2-(5-chloro-2-ethylphenyl)-4-[(2-{[2-(dimethylamino)ethyl]amino}phenyl)ethynyl]-1H-pyrrole-3-carboxamide [(I), R1=H, R2=(2-{[2-(dimethylamino)ethyl]amino}phenyl)ethynyl, R3=R4=H, R5=5-chloro-2-ethylphenyl, R6=NH₂] (compd. 101)

¹H NMR (400 MHz, DMSO-d₆) δ ppm 1.02 (t, J=7.57 Hz, 3H) 2.17 (s, 6H) 3.20-3.30 (m, 4H) 5.83-5.89 (m, 1H) 6.34 (bs, 2H) 6.60 (td, J=7.45, 0.98 Hz, 1H) 6.64-6.68 (m., 1H) 6.65 (s, 1H) 7.16 (bs, 2H) 7.18-7.23 (m, 1H) 7.31-7.39 (m, 3H) 7.43-7.47 (m, 1H) 7.54 (d, J=5.25 Hz, 1H) 8.34 (d, J=5.25 Hz, 1H) 12.06 (bs, 1H).

HRMS (ESI) calcd for $C_{29}H_{30}ClN_7O+H^+$ 528.2273. found 528.2280.

5-(2-Aminopyrimidin-4-yl)-2-(5-chloro-2-ethylphenyl)-4-({3-[(1-methylpiperidin-4-yl)oxy]phenyl}ethynyl)-1H-pyrrole-3-carboxamide [(I), R1=H, R2={3-[(1-methylpiperidin-4-yl)oxy]phenyl}ethynyl, R3=R4=H, R5=5-chloro-2-ethylphenyl, R6=NH₂] (compd. 102)

¹H NMR (400 MHz, DMSO-d₆) δ ppm 1.00 (t, J=7.57 Hz, 3H) 1.58-1.70 (m, 2H) 1.89-1.98 (m, 2H) 2.19 (s, 3H) 2.20-2.24 (m, 2H) 2.58-2.65 (m, 2H) 4.40-4.47 (m, 1H) 6.36 (bs, 2H) 6.99 (bs, 1H) 7.03 (dd, J=8.12, 2.26 Hz, 1H) 7.11 (d, J=2.44 Hz, 1H) 7.13 (d, J=7.69 Hz, 1H) 7.20 (bs, 1H) 7.27 (d, J=2.32 Hz, 1H) 7.31-7.38 (m, 1H) 7.39-7.43 (m, 1H) 7.46 (d, J=5.25 Hz, 1H) 8.34 (d, J=5.25 Hz, 1H) 12.10 (s, 1H).

HRMS (ESI) calcd for $C_{31}H_{31}ClN_6O_2+H^+$ 555.2270. found 555.2272.

5-(2-Aminopyrimidin-4-yl)-2-(5-chloro-2-ethylphenyl)-4-{[4-(4-methylpiperazin-1-yl)phenyl]ethynyl}-1H-pyrrole-3-carboxamide [(I), R1=H, R2=[4-(4-methylpiperazin-1-yl)phenyl]ethynyl, R3=R4=H, R5=5-chloro-2-ethylphenyl, R6=NH₂] (compd. 103)

¹H NMR (400 MHz, DMSO-d₆) δ ppm 1.00 (t, J=7.57 Hz, 3H) 2.23 (s, 3H) 2.43-2.47 (m, 4H) 3.21-3.25 (m, 4H) 6.32 (bs, 2H) 6.99 (d, J=9.03 Hz, 2H) 7.01 (bs, 1H) 7.18 (bs, 1H) 7.25 (d, J=2.32 Hz, 1H) 7.28-7.34 (m, 1H) 7.38-7.43 (m, 3H) 7.48-7.52 (m, 1H) 8.33 (d, J=5.13 Hz, 1H) 12.00 (s, 1H).

HRMS (ESI) calcd for $C_{30}H_{30}ClN_7O+H^+$ 540.2273. found 540.2275.

Example 10

2-(5-Chloro-2-methylphenyl)-5-[2-(methylamino)-5-{[4-(4-methylpiperazin-1-yl)phenyl]ethynyl}pyrimidin-4-yl]-1H-pyrrole-3-carboxamide [(I), R1=[4-(4-methylpiperazin-1-yl)phenyl]ethynyl, R2=H, R3=R4=H, R5=5-chloro-2-methylphenyl, R6=CH₃NH] (compd. 104)

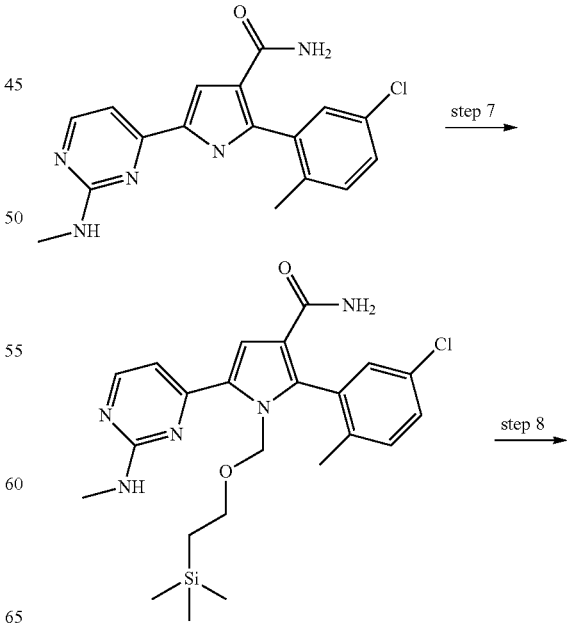

-continued

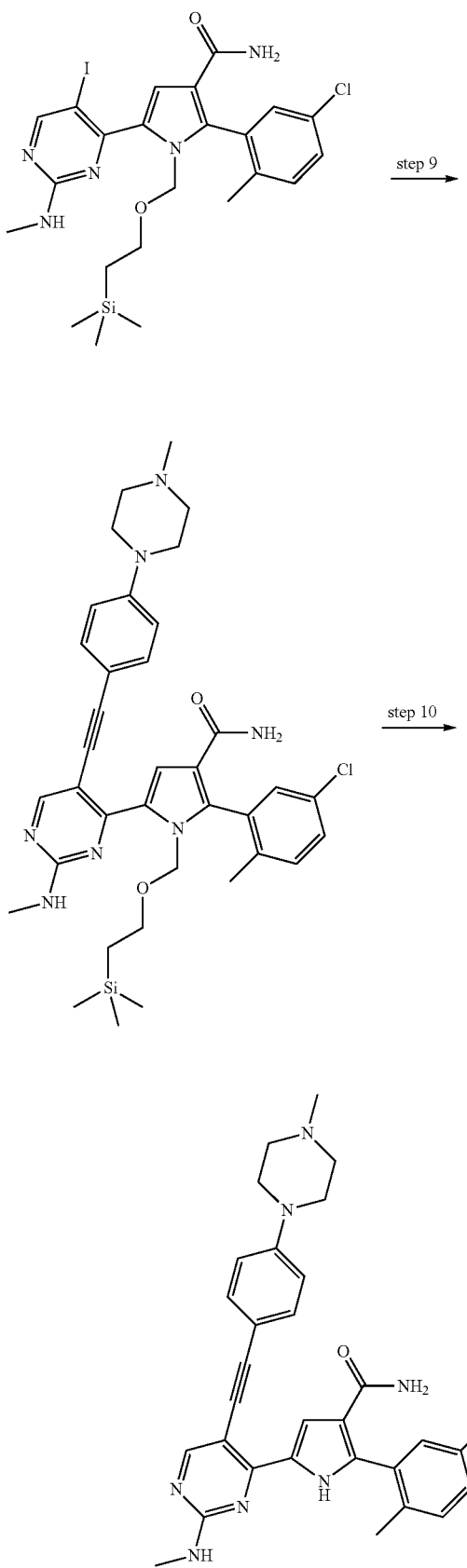

Scheme B, Steps 7, 8, 9, 10

Step 7: 2-(5-Chloro-2-methylphenyl)-5-[2-(methylamino)pyrimidin-4-yl]-1-{[2-(trimethylsilyl)ethoxy]methyl}-1H-pyrrole-3-carboxamide (XI)

NaH (60% dispersion in mineral oil, 160 mg, 4.0 mmol) was added to a suspension of 2-(5-chloro-2-methyl-phenyl)-5-(2-methylamino-pyrimidin-4-yl)-1H-pyrrole-3-carboxamide (1.0 g, 2.92 mmol) in dry THF (15 mL) at 0° C. The reaction was kept at the same temperature for 20 min then 2-(chloromethoxy)ethyl](trimethyl)silane (0.714 mL, 4.0 mmol) was added and the mixture was stirred at room temperature for 2 h. Saturated aqueous NaCl (20 mL) was added at 0° C. and the mixture was extracted with EtOAc (2×30 mL). The separated organic phase was dried over sodium sulfate and the solvent evaporated. The crude was purified by flash chromatography on silica gel (DCM/EtOH 94/6) to afford the title compound (620 mg, 45%).
ESI (+) MS: m/z 472 (MH⁺).

Step 8: 2-(5-Chloro-2-methyl-phenyl)-5-[5-iodo-2-(methylamino)pyrimidin-4-yl]-1-(2-trimethylsilanyl-ethoxymethyl)-1H-pyrrole-3-carboxamide (XII)

N-iodosuccinimide (301 mg, 1.34 mmol) was added to a solution of 2-(5-chloro-2-methyl-phenyl)-5-(2-methylamino-pyrimidin-4-yl)-1H-pyrrole-3-carboxamide (600 mg, 1.27 mmol) in dry DMF (5 mL). The reaction mixture was heated at 65° C. for 7 h, allowed to cool to room temperature and then diluted with EtOAc (10 mL), washed with water (2×5 mL) brine, dried over sodium sulphate, and evaporated. The crude was purified by flash chromatography on silica gel (DCM/MeOH 97/3) to afford the title compound as yellow solid (520 mg, 65%).
ESI (+) MS: m/z 598 (MH⁺).

Step 9: 2-(5-Chloro-2-methylphenyl)-5-[2-(methylamino)-5-{[4-(4-methylpiperazin-1-yl)phenyl]ethynyl}pyrimidin-4-yl]-1-{[3-(trimethylsilyl)propoxy]methyl}-1H-pyrrole-3-carboxamide (XIII)

To a degassed solution of 2-(5-chloro-2-methylphenyl)-5-[5-iodo-2-(methylamino)pyrimidin-4-yl]-1-{[2-(trimethylsilyl)ethoxy]methyl}-1H-pyrrole-3-carboxamide 5 (0.143 g, 0.24 mmol), 1-(4-ethynylphenyl)-4-methylpiperazine (86 mg, 0.43 mmol) and TEA (0.335 mL, 2.4 mmol) in dry ACN (2.5 mL) were added copper iodide (2.5 mg, 0.012 mmol) and Pd(PPh₃)₂Cl₂ (8.4 mg, 0.012 mmol). The mixture was heated at 80° C. for 2 h, then the solvent was evaporated. The crude was purified by flash chromatography on silica gel (DCM/MeOH/7N NH₃ in MeOH 95/4/1) to afford the title compound (139 mg, 85%).
ESI (+) MS: m/z 670 (MH⁺).

Step 10: 2-(5-Chloro-2-methylphenyl)-5-[2-(methylamino)-5-{[4-(4-methylpiperazin-1-yl)phenyl]ethynyl}pyrimidin-4-yl]-1H-pyrrole-3-carboxamide
[(I), R1=[4-(4-methylpiperazin-1-yl)phenyl]ethynyl, R2=H, R3=R4=H, R5=5-chloro-2-methylphenyl, R6=R6=CH₃NH] (compd. 104)

Trifluoroacetic acid (1.4 mL) was added to a solution of 2-(5-chloro-2-methylphenyl)-5-[2-(methylamino)-5-{[4-(4-methylpiperazin-1-yl)phenyl]ethynyl}pyrimidin-4-yl]-1-{[3-(trimethylsilyl)propoxy]methyl}-1H-pyrrole-3-carboxamide (96 mg, 0.14 mmol) in dry DCM (2.8 mL) and stirred for 4 h at room temperature. After solvent removal, the residue was treated with EtOH (3 mL), 33% NH$_4$OH (0.4 mL) and stirred for 0.5 h. The solvent was evaporated to dryness and the residue was purified by flash-chromatography on silica gel (DCM/MeOH/7N NH$_3$ in MeOH 94/5/1) to afford the title compound as white solid (63 mg, 85%).

ESI (+) MS: m/z 540 (MH$^+$).

According to this procedure, but starting from 2-(5-chloro-2-methyl-phenyl)-5-(pyrimidin-4-yl)-1H-pyrrole-3-carboxamide, the following compound was prepared:

2-(5-Chloro-2-methylphenyl)-5-(5-{[4-(4-methylpiperazin-1-yl)phenyl]ethynyl}pyrimidin-4-yl)-1H-pyrrole-3-carboxamide [(I), R1=[4-(4-methylpiperazin-1-yl)phenyl]ethynyl, R2=H, R3=R4=H, R5=5-chloro-2-methylphenyl, R6=H] (compd. 105)

ESI (+) MS: m/z 511 (MH$^+$).

According to this procedure, but starting from 2-(5-chloro-2-methylphenyl)-5-(2-methylpyrimidin-4-yl)-1H-pyrrole-3-carboxamide, the following compound was prepared:

2-(5-Chloro-2-methylphenyl)-5-(2-methyl-5-{[4-(4-methylpiperazin-1-yl)phenyl]ethynyl}pyrimidin-4-yl)-1H-pyrrole-3-carboxamide [(I), R1=[4-(4-methylpiperazin-1-yl)phenyl]ethynyl, R2=H, R3=R4=H, R5=5-chloro-2-methylphenyl, R6=CH$_3$] (compd. 106)

ESI (+) MS: m/z 525 (MH$^+$).

Example 11

2-(5-Chloro-2-methylphenyl)-5-[2-(methylamino)pyrimidin-4-yl]-4-{[4-(4-methylpiperazin-1-yl)phenyl]ethynyl}-1H-pyrrole-3-carboxamide [(I), R1=H, R=[4-(4-methylpiperazin-1-yl)phenyl]ethynyl, R3=R4=H, R5=5-chloro-2-methylphenyl, R6=NHCH$_3$] (compd. 107)

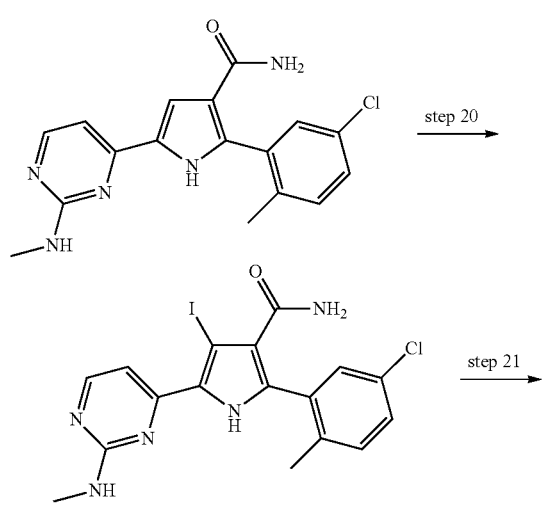

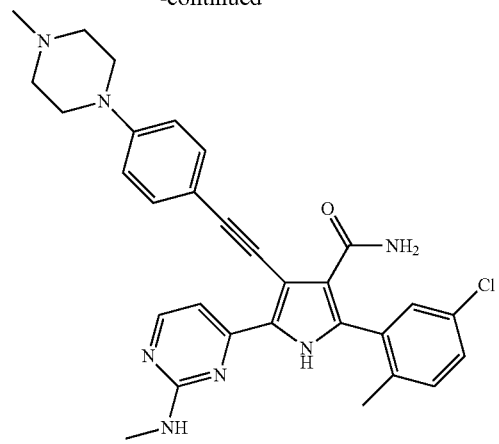

Scheme E, Steps 20, 21

Step 20: 2-(5-Chloro-2-methylphenyl)-4-iodo-5-[2-(methylamino)pyrimidin-4-yl]-1H-pyrrole-3-carboxamide (XXIV)

N-iodosuccinimide (301 mg, 1.34 mmol) was added to a solution of 2-(5-chloro-2-methylphenyl)-5-[2-(methylamino)pyrimidin-4-yl]-1H-pyrrole-3-carboxamide (433 mg, 1.27 mmol) in dry DMF (5 mL). The reaction mixture was stirred at room temperature for 5 h and poured into iced water (50 mL). The solid was then filtered with suction, washed thoroughly with water, dried in an oven under vacuum at 50° C. and purified by flash chromatography over silica gel (DCM/MeOH/7 N NH$_3$ in MeOH 95/5/0.5) to afford the title compound (344 mg, 58%).

ESI (+) MS: m/z 468 (MH$^+$).

The above procedure was employed to synthesize the following compounds:

2-(5-Chloro-2-methylphenyl)-4-iodo-5-(pyrimidin-4-yl)-1H-pyrrole-3-carboxamide (XXIV)

ESI (+) MS: m/z 439 (MH$^+$).

2-(5-Chloro-2-methylphenyl)-4-iodo-5-(2-methylpyrimidin-4-yl)-1H-pyrrole-3-carboxamide (XXIV)

ESI (+) MS: m/z 453 (MH$^+$).

Step 21: 2-(5-Chloro-2-methylphenyl)-5-[2-(methylamino)pyrimidin-4-yl]-4-{[4-(4-methylpiperazin-1-yl)phenyl]ethynyl}-1H-pyrrole-3-carboxamide [(I), R1=H, R=[4-(4-methylpiperazin-1-yl)phenyl]ethynyl, R3=R4=H, R5=5-chloro-2-methylphenyl, R6=CH$_3$NH] (compd. 107)

2-(5-Chloro-2-methylphenyl)-4-iodo-5-[2-(methylamino)pyrimidin-4-yl]-1H-pyrrole-3-carboxamide (47 mg, 0.1 mmol) in dry ACN (1 mL) was treated with 1-(4-ethynylphenyl)-4-methylpiperazine (40 mg, 0.2 mmol) and TEA (0.14 mL, 1 mmol). The flask was stirred and purged with nitrogen and then solid CuI (1.0 mg, 0.005 mmol) and Pd(Ph$_3$P)$_2$Cl$_2$ (3.5 mg, 0.005 mmol) were added. The reaction was refluxed for 2 h, then the solvent was evaporated. The crude was purified by flash chromatography on silica gel (DCM/MeOH/7N NH$_3$ in MeOH 95/4/1) to afford the title compound (41 mg, 76%).

ESI (+) MS: m/z 540 (MH$^+$).

According to this step, but starting from 2-(5-chloro-2-methylphenyl)-4-iodo-5-(pyrimidin-4-yl)-1H-pyrrole-3-carboxamide, the following compound was prepared:

2-(5-Chloro-2-methylphenyl)-4-{[4-(4-methylpiperazin-1-yl)phenyl]ethynyl}-5-(pyrimidin-4-yl)-1H-pyrrole-3-carboxamide [(I), R1=H, R=[4-(4-methylpiperazin-1-yl)phenyl]ethynyl, R3=R4=H, R5=5-chloro-2-methylphenyl, R6=H] (compd. 108)

ESI (+) MS: m/z 511 (MH+).

According to this step, but starting from 2-(5-chloro-2-methylphenyl)-4-iodo-5-(2-methylpyrimidin-4-yl)-1H-pyrrole-3-carboxamide, the following compound was prepared:

2-(5-Chloro-2-methylphenyl)-4-{[4-(4-methylpiperazin-1-yl)phenyl]ethynyl}-5-(2-methylpyrimidin-4-yl)-1H-pyrrole-3-carboxamide [(I), R1=H, R=[4-(4-methylpiperazin-1-yl)phenyl]ethynyl, R3=R4=H, R5=5-chloro-2-methylphenyl, R6=CH3] (compd. 109)

ESI (+) MS: m/z 525 (MH+).

Example 12

5-(2-Amino-5-{[4-(4-methylpiperazin-1-yl)phenyl]ethynyl}pyrimidin-4-yl)-2-(5-chloro-2-ethylphenyl)-1H-pyrrole-3-carboxamide [(I), R1=[4-(4-methylpiperazin-1-yl)phenyl]ethynyl, R2=R3=R4=H, R5=5-chloro-2-ethylphenyl, R6=NH2] (compd. 110)

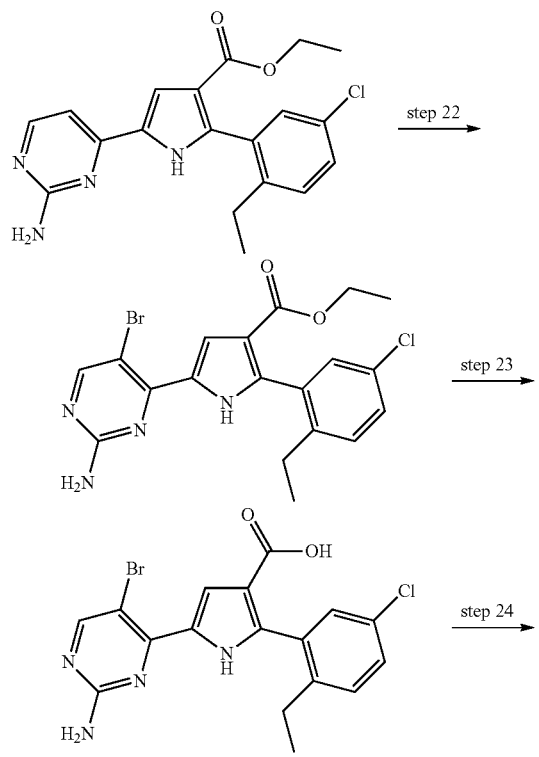

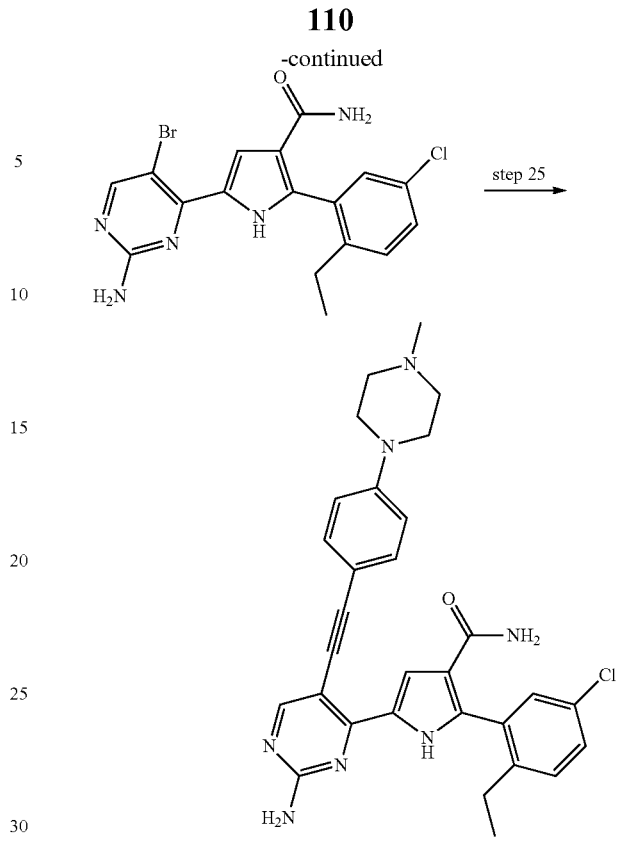

Scheme F, Steps 22, 23, 24, 25

Step 22: Ethyl 5-(2-amino-5-bromopyrimidin-4-yl)-2-(5-chloro-2-ethylphenyl)-1H-pyrrole-3-carboxylate (XXV)

Ethyl 5-(2-aminopyrimidin-4-yl)-2-(5-chloro-2-ethylphenyl)-1H-pyrrole-3-carboxylate (450 mg, 1.21 mmol) in DMF (7.5 mL) was treated with N-bromosuccinimide (216 mg, 1.21 mmol). The mixture was stirred overnight at room temperature, then poured into water, extracted with EtOAc (2×30 mL). The separated organic phase was dried over sodium sulfate and the solvent evaporated. Crystallization from diethyl ether afforded the title compound (420 mg, 77%).
$^1$H NMR (400 MHz, DMSO-$d_6$) δ ppm 0.98 (t, J=7.57 Hz, 3H), 1.04 (t, J=7.08 Hz, 3H), 2.43 (q, J=7.57 Hz, 2H), 4.03 (q, J=7.08 Hz, 2H), 6.56 (bs, 2H), 7.27 (d, J=2.20 Hz, 1H), 7.35 (d, J=8.30 Hz, 1H), 7.44 (dd, J=8.30, 2.32 Hz, 1H), 7.67 (d, J=2.69 Hz, 1H), 8.38 (s, 1H), 12.02 (bs, 1H).

According to this step, but starting from ethyl 5-(2-aminopyrimidin-4-yl)-2-(5-chloro-2-methylphenyl)-1H-pyrrole-3-carboxylate, the following compound was prepared:

Ethyl 5-(2-amino-5-bromopyrimidin-4-yl)-2-(5-chloro-2-methylphenyl)-1H-pyrrole-3-carboxylate (XXV)

$^1$H NMR (400 MHz, DMSO-$d_6$) δ ppm 1.07 (t, J=7.08 Hz, 3H), 2.10 (s, 3H), 4.01-4.09 (m, 2H), 6.57 (bs, 2H), 7.30-7.34 (m, 2H), 7.38-7.42 (m, 1H), 7.67 (d, J=2.69 Hz, 1H), 8.38 (s, 1H), 12.00 (bs, 1H).

According to this step, but starting from ethyl 5-(2-aminopyrimidin-4-yl)-2-[2-methyl-5-(trifluoromethyl)phenyl]-1H-pyrrole-3-carboxylate, the following compound was prepared:

Ethyl 5-(2-amino-5-bromopyrimidin-4-yl)-2-[2-methyl-5-(trifluoromethyl)phenyl]-1H-pyrrole-3-carboxylate (XXV)

ESI (+) MS: m/z 470 (MH$^+$).

According to this step, but starting from ethyl 5-(2-aminopyrimidin-4-yl)-2-[2-ethyl-5-(trifluoromethyl)phenyl]-1H-pyrrole-3-carboxylate, the following compound was prepared:

Ethyl 5-(2-amino-5-bromopyrimidin-4-yl)-2-[2-ethyl-5-(trifluoromethyl)phenyl]-1H-pyrrole-3-carboxylate (XXV)

ESI (+) MS: m/z 484 (MH$^+$).

According to this step, but starting from ethyl 5-(2-aminopyrimidin-4-yl)-2-(5-chloro-2-methylphenyl)-1H-pyrrole-3-carboxylate and using N-chlorosuccimide instead of N-bromosuccinimide, the following compound was prepared:

Ethyl 5-(2-amino-5-chloropyrimidin-4-yl)-2-(5-chloro-2-methylphenyl)-1H-pyrrole-3-carboxylate (XXV)

$^1$H NMR (400 MHz, DMSO-d$_6$) δ ppm 1.07 (t, J=7.14 Hz, 3H), 2.10 (s, 3H), 4.05 (q, J=7.08 Hz, 2H), 6.55 (bs, 2H), 7.32 (d, J=8.30 Hz, 1H), 7.31 (d, J=1.95 Hz, 1H), 7.40 (dd, J=8.30, 2.56 Hz, 1H), 7.55 (d, J=2.56 Hz, 1H), 8.30 (s, 1H), 12.04 (bs, 1H).

According to this step, but starting from ethyl 5-(2-aminopyrimidin-4-yl)-2-(5-chloro-2-ethylphenyl)-1H-pyrrole-3-carboxylate and using N-chlorosuccimide instead of N-bromosuccinimide, the following compound was prepared:

Ethyl 5-(2-amino-5-chloropyrimidin-4-yl)-2-(5-chloro-2-ethylphenyl)-1H-pyrrole-3-carboxylate (XXV)

$^1$H NMR (400 MHz, DMSO-d$_6$) δ ppm 0.97 (t, J=7.57 Hz, 3H), 1.04 (t, J=7.08 Hz, 3H), 2.43 (q, J=7.65 Hz, 2H), 4.03 (q, J=7.12 Hz, 2H), 6.54 (bs, 2H), 7.27 (d, J=2.32 Hz, 1H), 7.35 (d, J=8.30 Hz, 1H), 7.44 (dd, J=8.30, 2.32 Hz, 1H), 7.55 (d, J=2.69 Hz, 1H), 8.30 (s, 1H), 12.07 (bs, 1H).

According to this step, but starting from ethyl 5-(2-aminopyrimidin-4-yl)-2-[2-methyl-5-(trifluoromethyl)phenyl]-1H-pyrrole-3-carboxylate and using N-chlorosuccimide instead of N-bromosuccinimide, the following compound was prepared:

Ethyl 5-(2-amino-5-chloropyrimidin-4-yl)-2-[2-methyl-5-(trifluoromethyl)phenyl]-1H-pyrrole-3-carboxylate (XXV)

$^1$H NMR (400 MHz, DMSO-d$_6$) δ ppm 1.03 (t, J=7.08 Hz, 3H), 2.20 (s, 3H), 4.03 (q, J=7.04 Hz, 2H), 6.56 (bs, 2H), 7.53 (d, J=8.06 Hz, 1H), 7.56-7.59 (m, 1H), 7.58 (d, J=2.69 Hz, 1H), 7.70 (dd, J=7.99, 1.77 Hz, 1H), 8.31 (s, 1H), 12.16 (bs, 1H).

According to this step, but starting from ethyl 5-(2-aminopyrimidin-4-yl)-2-[2-ethyl-5-(trifluoromethyl)phenyl]-1H-pyrrole-3-carboxylate and using N-chlorosuccimide instead of N-bromosuccinimide, the following compound was prepared:

Ethyl 5-(2-amino-5-chloropyrimidin-4-yl)-2-[2-ethyl-5-(trifluoromethyl)phenyl]-1H-pyrrole-3-carboxylate (XXV)

ESI (+) MS: m/z 439 (MH$^+$).

Step 23: 5-(2-Amino-5-bromopyrimidin-4-yl)-2-(5-chloro-2-ethylphenyl)-1H-pyrrole-3-carboxylic acid (VI)

Ethyl 5-(2-amino-5-bromopyrimidin-4-yl)-2-(5-chloro-2-ethylphenyl)-1H-pyrrole-3-carboxylate (400 mg, 0.89 mmol) was treated with a 1.5 M solution of potassium hydroxide in 95% EtOH (11.86 mL, 20 eq) under reflux overnight. After cooling, the residue was concentrated, dissolved in water and washed with DCM. To the aqueous phase cooled to 5° C., a solution of 2 N HCl was added, under agitation. The resultant precipitate was collected by filtration to give the title compound (356 mg, 95%).

$^1$H NMR (400 MHz, DMSO-d$_6$) δ ppm 0.99 (t, J=7.57 Hz, 3H), 2.45 (q, J=7.61 Hz, 2H), 6.54 (bs, 2H), 7.27 (d, J=2.32 Hz, 1H), 7.34 (d, J=8.30 Hz, 1H), 7.42 (dd, J=8.30, 2.30 Hz, 1H), 7.68 (d, J=2.81 Hz, 1H), 8.36 (s, 1H), 11.88 (bs, 1H).

The above procedure was employed to synthesize the following compounds:

5-(2-Amino-5-chloropyrimidin-4-yl)-2-(5-chloro-2-methylphenyl)-1H-pyrrole-3-carboxylic acid (VI)

$^1$H NMR (400 MHz, DMSO-d$_6$) δ ppm 2.12 (s, 3H), 6.54 (bs, 2H), 7.31 (d, J=8.30 Hz, 1H), 7.30 (d, J=2.20 Hz, 1H), 7.38 (dd, J=8.30, 2.32 Hz, 1H), 7.55 (s, 1H), 8.29 (s, 1H), 11.90 (bs, 1H).

5-(2-Amino-5-chloropyrimidin-4-yl)-2-(5-chloro-2-ethylphenyl)-1H-pyrrole-3-carboxylic acid (VI)

$^1$H NMR (400 MHz, DMSO-d$_6$) δ ppm 0.98 (t, J=7.63 Hz, 3H), 2.45 (q, J=7.57 Hz, 2H), 6.54 (bs, 2H), 7.27 (d, J=2.32 Hz, 1H), 7.34 (d, J=8.30 Hz, 1H), 7.42 (dd, J=8.30, 2.32 Hz, 1H), 7.55 (d, J=2.69 Hz, 1H), 8.29 (s, 1H), 11.85 (bs, 1H), 11.93 (bs, 1H).

5-(2-Amino-5-chloropyrimidin-4-yl)-2-[2-methyl-5-(trifluoromethyl)phenyl]-1H-pyrrole-3-carboxylic acid (VI)

$^1$H NMR (400 MHz, DMSO-d$_6$) δ ppm 2.23 (s, 3H), 6.51 (bs, 2H), 7.50 (d, J=8.18 Hz, 1H), 7.55 (bs, 2H), 7.65 (dd, J=8.18, 1.71 Hz, 1H), 8.27 (s, 1H), 11.80 (bs, 1H).

Step 24: 5-(2-Amino-5-bromopyrimidin-4-yl)-2-(5-chloro-2-ethylphenyl)-1H-pyrrole-3-carboxamide (VIII)

Crude 5-(2-amino-5-bromopyrimidin-4-yl)-2-(5-chloro-2-ethylphenyl)-1H-pyrrole-3-carboxylic acid (200 mg, 0.47 mmol) in DMF (2 mL) and DIPEA (0.332 mL, 1.89 mmol) was stirred at 0° C. EDCl (180 mg, 0.94 mmol) and HOBT.NH$_3$ (143 mg, 0.94 mmol) were added and the reaction mixture was stirred for 2 h at room temperature. The reaction mixture was poured into saturated solution of sodium hydrogen carbonate. The solid was filtered with suction and the panel washed thoroughly with water and dried under vacuum in an oven at 50° C. The crude compound may be purified by flash chromatography (DCM/MeOH 95/5) to give the title compound (336 mg, 85%).

¹H NMR (400 MHz, DMSO-d$_6$) δ ppm 0.98 (t, J=7.57 Hz, 3H), 2.45 (q, J=7.61 Hz, 2H), 6.52 (bs, 2H), 6.76 (bs, 1H), 7.17 (bs, 1H), 7.24 (d, J=2.20 Hz, 1H), 7.32 (d, J=8.30 Hz, 1H), 7.41 (dd, J=8.30, 2.32 Hz, 1H), 7.76 (d, J=2.56 Hz, 1H), 8.35 (s, 1H), 11.60 (bs, 1H).

According to the above procedure, but starting from ethyl 5-(2-amino-5-bromopyrimidin-4-yl)-2-(5-chloro-2-methylphenyl)-1H-pyrrole-3-carboxylate, the following compound was synthesized:

5-(2-Amino-5-bromopyrimidin-4-yl)-2-(5-chloro-2-methylphenyl)-1H-pyrrole-3-carboxamide (VIII)

¹H NMR (400 MHz, DMSO-d$_6$) δ ppm 2.12 (s, 3H), 6.53 (bs, 2H), 6.78 (bs, 1H), 7.23 (bs, 1H), 7.27 (d, J=2.32 Hz, 1H), 7.28 (d, J=8.20 Hz, 1H), 7.36 (dd, J=8.20, 2.32 Hz, 1H), 7.75 (d, J=2.56 Hz, 1H), 8.35 (s, 1H), 11.57 (bs, 1H).

According to the above procedure, but starting from ethyl 5-(2-amino-5-bromopyrimidin-4-yl)-2-[2-methyl-5-(trifluoromethyl)phenyl]-1H-pyrrole-3-carboxylate, the following compound was synthesized:

5-(2-Amino-5-bromopyrimidin-4-yl)-2-[2-methyl-5-(trifluoromethyl)phenyl]-1H-pyrrole-3-carboxamide (VIII)

ESI (+) MS: m/z 441 (MH⁺).

According to the above procedure, but starting from ethyl 5-(2-amino-5-bromopyrimidin-4-yl)-2-[2-ethyl-5-(trifluoromethyl)phenyl]-1H-pyrrole-3-carboxylate, the following compound was synthesized:

5-(2-Amino-5-bromopyrimidin-4-yl)-[2-ethyl-5-(trifluoromethyl)phenyl]-1H-pyrrole-3-carboxamide (VIII)

ESI (+) MS: m/z 455 (MH⁺).

According to the above procedure, but starting from ethyl 5-(2-amino-5-chloropyrimidin-4-yl)-2-(5-chloro-2-methylphenyl)-1H-pyrrole-3-carboxylate, the following compound was synthesized:

5-(2-Amino-5-chloropyrimidin-4-yl)-2-(5-chloro-2-methylphenyl)-1H-pyrrole-3-carboxamide (VIII)

¹H NMR (400 MHz, DMSO-d$_6$) δ ppm 2.11 (s, 3H), 6.50 (bs, 2H), 6.77 (bs, 1H), 7.28 (bs, 1H), 7.27 (d, J=2.32 Hz, 1H), 7.28 (d, J=8.30 Hz, 1H), 7.35 (dd, J=8.30, 2.32 Hz, 1H), 7.69 (d, J=2.69 Hz, 1H), 8.26 (s, 1H), 11.60 (bs, 1H).

According to the above procedure, but starting from ethyl 5-(2-amino-5-chloropyrimidin-4-yl)-2-(5-chloro-2-ethylphenyl)-1H-pyrrole-3-carboxylate, the following compound was synthesized:

5-(2-Amino-5-chloropyrimidin-4-yl)-2-(5-chloro-2-ethylphenyl)-1H-pyrrole-3-carboxamide (VIII)

¹H NMR (400 MHz, DMSO-d$_6$) δ ppm 0.97 (t, J=7.57 Hz, 3H), 2.45 (q, J=7.57 Hz, 2H), 6.50 (bs, 5H), 6.75 (bs, 1H), 7.23 (bs, 1H), 7.24 (d, J=2.32 Hz, 1H), 7.32 (d, J=8.30 Hz, 1H), 7.40 (dd, J=8.30, 2.32 Hz, 1H), 7.70 (d, J=2.69 Hz, 1H), 8.26 (s, 1H), 11.63 (bs, 1H).

According to the above procedure, but starting from ethyl 5-(2-amino-5-chloropyrimidin-4-yl)-2-[2-methyl-5-(trifluoromethyl)phenyl]-1H-pyrrole-3-carboxylate, the following compound was synthesized:

5-(2-Amino-5-chloropyrimidin-4-yl)-2-[2-methyl-5-(trifluoromethyl)phenyl]-1H-pyrrole-3-carboxamide (VIII)

¹H NMR (400 MHz, DMSO-d$_6$) δ ppm 2.21 (s, 3H), 6.50 (bs, 2H), 6.77 (bs, 1H), 7.41 (bs, 1H), 7.49 (d, J=7.69 Hz, 1H), 7.52 (d, J=1.34 Hz, 1H), 7.64 (dd, J=7.99, 1.53 Hz, 1H), 7.73 (d, J=2.56 Hz, 1H), 8.27 (s, 1H), 11.74 (bs, 1H).

According to the above procedure, but starting from ethyl 5-(2-amino-5-chloropyrimidin-4-yl)-2-[2-ethyl-5-(trifluoromethyl)phenyl]-1H-pyrrole-3-carboxylate, the following compound was synthesized:

5-(2-Amino-5-chloropyrimidin-4-yl)-[2-ethyl-5-(trifluoromethyl)phenyl]-1H-pyrrole-3-carboxamide (VIII)

ESI (+) MS: m/z 410 (MH⁺).

According to the above procedure, but employing the suitable amine in the step 24, the following compounds were synthesized:

5-(2-Amino-5-bromopyrimidin-4-yl)-2-(5-chloro-2-methylphenyl)-N-methyl-1H-pyrrole-3-carboxamide (VIII)

ESI (+) MS: m/z 421 (MH⁺).

5-(2-Amino-5-bromopyrimidin-4-yl)-2-(5-chloro-2-ethylphenyl)-N-methyl-1H-pyrrole-3-carboxamide (VIII)

¹H NMR (400 MHz, DMSO-d$_6$) δ ppm 0.96 (t, J=7.57 Hz, 3H), 2.43 (q, J=7.57 Hz, 2H), 2.62 (d, J=4.52 Hz, 3H), 6.52 (bs, 2H), 7.22 (d, J=2.32 Hz, 1H), 7.31 (d, J=8.30 Hz, 1H), 7.40 (dd, J=8.30, 2.30 Hz, 1H), 7.74 (d, J=2.56 Hz, 1H), 7.81 (q, J=4.60 Hz, 1H), 8.35 (s, 1H), 11.58 (bs, 1H).

5-(2-Amino-5-bromopyrimidin-4-yl)-2-(5-chloro-2-ethylphenyl)-N-ethyl-1H-pyrrole-3-carboxamide (VIII)

¹H NMR (400 MHz, DMSO-d$_6$) δ ppm 0.96 (t, J=7.57 Hz, 3H), 1.01 (t, J=7.14 Hz, 3H), 2.43 (q, J=7.57 Hz, 2H), 3.12 (qd, J=7.14, 5.68 Hz, 2H), 6.53 (bs, 2H), 7.24 (d, J=2.32 Hz, 1H), 7.31 (d, J=8.30 Hz, 1H), 7.40 (dd, J=8.30, 2.30 Hz, 1H), 7.74 (d, J=2.56 Hz, 1H), 7.79 (t, J=5.61 Hz, 1H), 8.35 (s, 1H), 11.58 (bs, 1H).

5-(2-Amino-5-bromopyrimidin-4-yl)-2-(5-chloro-2-ethylphenyl)-N-(2-hydroxyethyl)-1H-pyrrole-3-carboxamide (VIII)

¹H NMR (400 MHz, DMSO-d$_6$) δ ppm 0.97 (t, J=7.63 Hz, 3H), 2.43 (q, J=7.61 Hz, 2H), 3.17 (q, J=6.06 Hz, 2H), 3.39 (q, J=6.27 Hz, 2H), 4.60 (t, J=5.49 Hz, 1H), 6.53 (bs, 2H), 7.23 (d, J=0.32 Hz, 1H), 7.31 (d, J=0.32 Hz, 1H), 7.40 (dd, J=8.32, 2.32 Hz, 1H), 7.73 (t, J=5.61 Hz, 1H), 7.76 (d, J=2.56 Hz, 1H), 8.35 (s, 1H), 11.60 (bs, 1H).

5-(2-Amino-5-bromopyrimidin-4-yl)-[2-ethyl-5-(trifluoromethyl)phenyl]-N-methyl-1H-pyrrole-3-carboxamide (VIII)

ESI (+) MS: m/z 469 (MH⁺).

5-(2-Amino-5-bromopyrimidin-4-yl)-[2-ethyl-5-(trifluoromethyl)phenyl]-N-ethyl-1H-pyrrole-3-carboxamide (VIII)

ESI (+) MS: m/z 483 (MH+).

5-(2-Amino-5-bromopyrimidin-4-yl)-[2-ethyl-5-(trifluoromethyl)phenyl]-N-(2-hydroxyethyl)-1H-pyrrole-3-carboxamide (VIII)

ESI (+) MS: m/z 499 (MH+).

5-(2-Amino-5-chloropyrimidin-4-yl)-2-(5-chloro-2-methylphenyl)-N-methyl-1H-pyrrole-3-carboxamide (VIII)

$^1$H NMR (400 MHz, DMSO-d$_6$) δ ppm 2.09 (s, 3H), 2.63 (d, J=4.52 Hz, 3H), 6.50 (bs, 2H), 7.25 (d, J=2.44 Hz, 1H), 7.27 (d, J=8.40 Hz, 1H), 7.35 (dd, J=8.30, 2.32 Hz, 1H), 7.67 (d, J=2.56 Hz, 1H), 7.87 (q, J=4.35 Hz, 1H), 8.27 (s, 1H), 11.61 (d, J=0.73 Hz, 1H).

5-(2-Amino-5-chloropyrimidin-4-yl)-2-(5-chloro-2-methylphenyl)-N-(2-hydroxyethyl)-1H-pyrrole-3-carboxamide (VIII)

$^1$H NMR (400 MHz, DMSO-d$_6$) δ ppm 2.09 (s, 3H), 3.18 (q, J=6.14 Hz, 2H), 3.41 (q, J=5.94 Hz, 2H), 4.62 (t, J=5.49 Hz, 1H), 6.51 (bs, 2H), 7.26 (d, J=2.07 Hz, 1H), 7.27 (d, J=7.57 Hz, 1H), 7.35 (dd, J=8.18, 2.20 Hz, 1H), 7.70 (d, J=2.56 Hz, 1H), 7.83 (t, J=5.74 Hz, 1H), 8.27 (s, 1H), 11.62 (bs, 1H).

5-(2-Amino-5-chloropyrimidin-4-yl)-2-(5-chloro-2-ethylphenyl)-N-methyl-1H-pyrrole-3-carboxamide (VIII)

$^1$H NMR (400 MHz, DMSO-d$_6$) δ ppm 0.96 (t, J=7.63 Hz, 3H), 2.43 (q, J=7.57 Hz, 2H), 2.62 (d, J=4.52 Hz, 3H), 6.49 (bs, 2H), 7.22 (d, J=2.20 Hz, 1H), 7.30 (d, J=8.30 Hz, 1H), 7.39 (dd, J=8.30, 2.30 Hz, 1H), 7.67 (d, J=2.44 Hz, 1H), 7.84 (q, J=4.19 Hz, 1H), 8.26 (s, 1H), 11.62 (bs, 1H).

5-(2-Amino-5-chloropyrimidin-4-yl)-2-(5-chloro-2-ethylphenyl)-N-ethyl-1H-pyrrole-3-carboxamide (VIII)

$^1$H NMR (400 MHz, DMSO-d$_6$) δ ppm 0.96 (t, J=7.57 Hz, 3H), 1.02 (t, J=7.14 Hz, 3H), 2.43 (q, J=7.53 Hz, 2H), 3.12 (qd, J=7.16, 5.61 Hz, 2H), 6.49 (bs, 2H), 7.23 (d, J=2.32 Hz, 1H), 7.31 (d, J=8.30 Hz, 1H), 7.40 (dd, J=8.30, 2.30 Hz, 1H), 7.68 (d, J=2.56 Hz, 1H), 7.83 (t, J=5.61 Hz, 1H), 8.27 (s, 1H), 11.61 (bs, 1H).

5-(2-Amino-5-chloropyrimidin-4-yl)-2-(5-chloro-2-ethylphenyl)-N-(2-hydroxyethyl)-1H-pyrrole-3-carboxamide (VIII)

$^1$H NMR (400 MHz, DMSO-d$_6$) δ ppm 0.96 (t, J=7.57 Hz, 3H), 2.43 (q, J=7.61 Hz, 2H), 3.17 (q, J=6.10 Hz, 2H), 3.40 (q, J=6.06 Hz, 2H), 4.61 (t, J=5.49 Hz, 1H), 6.50 (bs, 2H), 7.23 (d, J=2.32 Hz, 1H), 7.31 (d, J=8.30 Hz, 1H), 7.40 (dd, J=8.30, 2.30 Hz, 1H), 7.70 (d, J=2.56 Hz, 1H), 7.79 (t, J=5.55 Hz, 1H), 8.27 (s, 1H), 11.63 (bs, 1H).

5-(2-Amino-5-chloropyrimidin-4-yl)-N-methyl-2-[2-methyl-5-(trifluoromethyl)phenyl]-1H-pyrrole-3-carboxamide (VIII)

$^1$H NMR (400 MHz, DMSO-d$_6$) δ ppm 2.19 (s, 3H), 2.63 (d, J=4.52 Hz, 3H), 6.50 (bs, 2H), 7.48 (d, J=7.81 Hz, 1H), 7.51 (d, J=1.46 Hz, 1H), 7.64 (dd, J=7.99, 1.65 Hz, 1H), 7.70 (d, J=2.56 Hz, 1H), 7.94 (q, J=4.64 Hz, 1H), 8.27 (s, 1H), 11.74 (bs, 1H).

5-(2-Amino-5-chloropyrimidin-4-yl)-N-ethyl-2-[2-methyl-5-(trifluoromethyl)phenyl]-1H-pyrrole-3-carboxamide (VIII)

$^1$H NMR (400 MHz, DMSO-d$_6$) δ ppm 1.03 (t, J=7.20 Hz, 3H), 2.20 (s, 3H), 3.13 (qd, J=7.18, 5.43 Hz, 2H), 6.50 (bs, 2H), 7.48 (d, J=7.93 Hz, 1H), 7.52 (d, J=1.46 Hz, 1H), 7.64 (dd, J=7.93, 1.59 Hz, 1H), 7.70 (d, J=2.56 Hz, 1H), 7.95 (t, J=5.61 Hz, 1H), 8.28 (s, 1H), 11.73 (bs, 1H).

5-(2-Amino-5-chloropyrimidin-4-yl)-[2-ethyl-5-(trifluoromethyl)phenyl]-N-methyl-1H-pyrrole-3-carboxamide (VIII)

ESI (+) MS: m/z 424 (MH+).

5-(2-Amino-5-chloropyrimidin-4-yl)-[2-ethyl-5-(trifluoromethyl)phenyl]-N-ethyl-1H-pyrrole-3-carboxamide (VIII)

ESI (+) MS: m/z 438 (MH+).

5-(2-Amino-5-chloropyrimidin-4-yl)-[2-ethyl-5-(trifluoromethyl)phenyl]-N-(2-hydroxyethyl)-1H-pyrrole-3-carboxamide (VIII)

ESI (+) MS: m/z 454 (MH+).

Step 25: 5-(2-Amino-5-{[4-(4-methylpiperazin-1-yl)phenyl]ethynyl}pyrimidin-4-yl)-2-(5-chloro-2-ethylphenyl)-1H-pyrrole-3-carboxamide [(I), R1=[4-(4-methylpiperazin-1-yl)phenyl]ethynyl, R2=R3=R4=H, R5=5-chloro-2-ethylphenyl, R6=NH$_2$] (compd. 110)

5-(2-Amino-5-bromopyrimidin-4-yl)-2-(5-chloro-2-ethylphenyl)-1H-pyrrole-3-carboxamide (252 mg, 0.599 mmol) in dry ACN (5 mL) was treated with 1-(4-ethynylphenyl)-4-methylpiperazine (180 mg, 0.89 mmol) and TEA (0.83 mL, 5.99 mmol). The flask was stirred and purged with nitrogen and then solid CuI (5.7 mg, 0.029 mmol) and Pd(Ph$_3$R)$_2$Cl$_2$ (21.0 mg, 0.029 mmol) were added. The reaction was then refluxed for 2 h. The reaction mixture was diluted with DCM, washed with water, dried over sodium sulfate and evaporated. The crude was purified by flash chromatography on silica gel (DCM/MeOH/7N NH$_3$ in MeOH 95/4/1) to afford the title compound (155 mg, 48%).

ESI (+) MS: m/z 540 (MH+).

Pharmacology

Biochemical Assay for Inhibitors of JAK Kinase Activity

General Principle

Specific JAK2, JAK1 or JAK3 peptide substrates are trans-phosphorylated by JAK kinases in the presence of ATP traced with 33P-γ-ATP. At the end of the phosphorylation reaction, the unreacted ATP, cold and radioactive, is captured by an excess of dowex ion exchange resin that eventually settles by gravity to the bottom of the reaction plate. The supernatant is subsequently withdrawn and transferred into a counting plate that is then evaluated by β-counting.

Dowex Resin Preparation 500 g of wet resin (SIGMA, custom prepared resin DOWEX 1×8 200-400 mesh, 2.5 Kg) are weighed out and diluted 2 to 1 in 150 mM sodium formate, pH 3.00. The resin is allowed to settle down overnight and then the supernatant is discarded. After three washes as above over a couple of days, the resin is allowed to settle and two volumes (with respect to the resin volume) of 150 mM sodium formate buffer are added.

Kinase Buffer (KB)

Kinase buffer was composed of 50 mM HEPES pH 7.5 containing 10 mM $MgCl_2$, 2.5 mM DTT, 10 μM $Na_3VO_4$ and 0.2 mg/mL BSA.

JAK2 Specific Assay Conditions

Enzyme

Assays were performed with the commercially available JAK2 kinase domain (Invitrogen, Eugene, Oreg.) that showed a linear kinetic without prephosphorylation.

Assay Conditions

The JAK2 kinase assay was run with a final enzyme concentration of 1 nM, in the presence of 60 μM ATP, 3 nM 33P-γ-ATP and 64 μM of substrate BioDBn*306 (Aminoacid sequence: LPLDKDYYVVREPGQ—SEQ ID NO: 1). The peptidic substrate was purchased from American Peptide Company (Sunnyvale, Calif.).

JAK1 Specific Assay Conditions

Enzyme

Assays were performed with the JAK1 kinase domain (residues 861-1152 of the 1154 amino acid long full-length sequence, accession number P23458 of UniProtKB/Swiss-Prot database).

The JAK1 kinase domain was preactivated with ATP for 1 h at 28° C. in order to obtain a linear kinetic.

Assay Conditions

The JAK1 kinase assay was run with a final pre activated enzyme concentration of 2.5 nM, in the presence of 100 μM ATP, 2 nM 33P-γ-ATP and 154 μM of substrate BioDBn*333 (Aminoacid sequence: KKHTDDGYMPMSPGVA—SEQ ID NO: 2). The peptidic substrate was purchased from American Peptide Company (Sunnyvale, Calif.).

JAK3 Specific Assay Conditions

Enzyme

Assays were performed with the JAK3 kinase domain (residues 781-1124 of the 1124 amino acid long full-length sequence, accession number P52333 of UniProtKB/Swiss-Prot database) that showed a linear kinetic without prephosphorylation.

Assay Conditions

The JAK3 kinase assay was run with a final enzyme concentration of 1 nM, in the presence of 22 μM ATP, 1 nM 33P-γ-ATP and 40 μM of substrate BioDBn*306 (Aminoacid sequence: LPLDKDYYVVREPGQ—SEQ ID NO: 1). The peptidic substrate was purchased from American Peptide Company (Sunnyvale, Calif.).

Biochemical Assay for Inhibitors of Lck and Lyn (Src Family) Kinases Activity

General Principle

Specific Lck and Lyn substrates are trans-phosphorylated by Lck and Lyn kinases in the presence of ATP traced with 33P-γ-ATP. At the end of the phosphorylation reaction, the unreacted ATP, cold and radioactive, is captured by an excess of dowex ion exchange resin that eventually settles by gravity to the bottom of the reaction plate. The supernatant is subsequently withdrawn and transferred into a counting plate that is then evaluated by β-counting.

Lck Specific Assay Conditions

Enzyme

The assay has been performed using Lck full length (accession number P06239 of UniProtKB/Swiss-Prot database). The Lck full-length protein showed a linear kinetic without prephosphorylation.

Lck Kinase Buffer (KB)

Kinase buffer was composed of 50 mM HEPES pH 7.5 containing 3 mM $MgCl_2$, 3 mM $MnCl_2$, 1 mM DTT, 3 μM $Na_3VO_4$, and 0.2 mg/mL BSA.

Assay Conditions

The Lck kinase assay was run with a final enzyme concentration of 1.4 nM, in the presence of 6 μM ATP, 3 nM 33P-γ-ATP and 5 μM of substrate Myelin Basic Protein (MBP). The MBP was purchased from Sigma (Sigma-Aldrich St. Louis, Mo.; cod. M-1891)

Lyn Specific Assay Conditions

Enzyme

The assay has been performed using Lyn full length (accession number P07948 of UniProtKB/Swiss-Prot database). The Lyn full-length protein showed a linear kinetic without prephosphorylation.

Lyn Kinase Buffer (KB)

Kinase buffer was composed of 50 mM HEPES pH 7.5 containing 3 mM $MgCl_2$, 1 mM DTT, 3 μM $Na_3VO_4$, and 0.2 mg/mL BSA.

Assay Conditions

The Lyn kinase assay was run with a final enzyme concentration of 1 nM, in the presence of 25 μM ATP, 1.5 nM 33P-γ-ATP and 250 μM of substrate ABI 1 (Aminoacid sequence: EAIYAAPFAKKK—SEQ ID NO: 3). The peptidic substrate was purchased from American Peptide Company (Sunnyvale, Calif.).

$IC_{50}$ Determination

Compound Dilution

For $IC_{50}$ determination, test compounds are received as a 1 mM solution in 100% DMSO, distributed into 96 well plates: compounds are then plated into the first column of a microtiter plate (A1 to G1), 100 μL/well.

An automated station for serial dilutions (Biomek FX, Beckman) is used for producing 1:3 dilutions in 100% DMSO, from line A1 to A10, and for all the compounds in the column. Moreover, 4-5 copies of daughter plates are prepared by reformatting 5 μL of this first set of 100% DMSO dilution plates into 384 deep well-plates: one of these plates with the serial dilutions of test compounds will be thawed the day of the experiments, reconstituted at a 3× concentration with water and used in the $IC_{50}$ determination assays. In a standard experiment, the highest concentration (3×) of all compounds is 30 μM, while the lowest one is 1.5 nM. Each 384 well-plate will contain at least one curve of the standard inhibitor staurosporine and reference wells (total enzyme activity vs. no enzymatic activity) for the Z' and signal to background evaluation.

Assay Scheme 384-well plates, V bottom (test plates) are prepared with 5 μL of the compound dilution (3×) and then placed onto a PlateTrak 12 robotized station (Perkin Elmer; the robot has one 384-tip pipetting head for starting the assay plus one 96-tip head for dispensing the resin) together with one reservoir for the Enzyme mix (3×) and one for the ATP mix (3×). At the start of the run, the robot aspirates 5 μL of ATP mix, makes an air gap inside the tips (3 μl) and aspirates 5 μL of JAK2 mix. The following dispensation into the plates plus 3 cycles of mixing, done by the robot itself, starts the kinase reaction. At this point, the correct concentrations are restored for all the reagents. The robot incubates the plates for 60 minutes at room temperature, and then stops the reaction by pipetting 60 μL of dowex resin suspension into the reaction mix. In order to avoid tip clogging, wide bore tips are used to dispense the resin suspension. Three cycles of mixing are done immediately after the addition of the resin. Another mixing cycle is performed after all the plates are stopped, this time using normal tips: the plates are then allowed to rest for about one hour in order to allow resin sedimentation. At this point, 27 μL of the supernatant are transferred into 384-Optiplates (Perkin-Elmer), with 50 μL of Microscint 40 (Perkin-Elmer); after 5 min of orbital shaking the plates are read on a Perkin-Elmer Top Count radioactivity counter.

Data Fitting

Data are analyzed by an internally customized version of the SW package "Assay Explorer" that provides sigmoidal fitting of the ten-dilutions curves for $IC_{50}$ determination in the secondary assays/hit confirmation routines.

Cell Proliferation

Cell Lines:

The JAK2 dependent human megakaryoblastic leukemia cell line SET-2 (DSMZ, Braunschweig GERMANY) and the JAK2 independent human chronic myelogenous leukaemia cell line K562 (ECACC, Wiltshire, UK) were cultured in RPMI-1640 medium-Glutamax (Gibco BRL, Gaithesburg, Md., USA), supplemented with 10% fetal bovine serum (FBS) at 37° C. and 5% $CO_2$.

Cell Proliferation Assay:

Approximately $5 \times 10^3$ cells were plated into 384 microtiter plate wells in 50 μL of growth media with different concentrations of inhibitors. The cells were incubated at 37° C. and 5% $CO_2$ for 72 hours, then the plates were processed using CellTiter-Glo assay (Promega, Madison, Wis., USA) following the manufacturer's instruction. Briefly 25 μL/well reagent solution is added to each well and after 5 minutes shaking the micro-plates are read by Envision luminometer (PerkinElmer, Waltham, Mass., USA).

Data Fitting

Data are analyzed by Symix Assay Explorer software (Symix Technologies Inc.) that provides sigmoidal fitting algorithm of the 8 points dilutions curves for $IC_{50}$ determination.

In biochemical assays, the compounds of formula (I) tested as described above demonstrate a remarkably potent JAK and SFK inhibitory activity, typically lower than 0.1 μM. See, as an example, the following Table A wherein are reported experimental data ($IC_{50}$) of the compounds of the invention obtained for representative enzymes of JAK (i.e. JAK2) and Src (i.e. Lyn) family Kinases.

In cellular assays, the compounds of formula (I) tested as described above show a remarkably high activity in JAK2 dependent SET-2 cell line (see Table A).

TABLE A

| Compd. | JAK2 $IC_{50}$ μM | Lyn $IC_{50}$ μM | SET-2 $IC_{50}$ μM |
| --- | --- | --- | --- |
| 1 | 0.002 | | 0.30 |
| 2 | 0.002 | 0.006 | 0.52 |
| 4 | 0.001 | 0.001 | 0.15 |
| 5 | 0.005 | | 0.75 |
| 6 | 0.001 | 0.003 | 0.24 |
| 8 | 0.001 | 0.002 | 0.14 |
| 9 | 0.001 | 0.010 | 0.34 |
| 11 | 0.004 | 0.008 | 0.09 |
| 12 | 0.001 | | 0.50 |

TABLE A-continued

| Compd. | JAK2 $IC_{50}$ μM | Lyn $IC_{50}$ μM | SET-2 $IC_{50}$ μM |
| --- | --- | --- | --- |
| 13 | 0.004 | 0.008 | |
| 15 | 0.002 | 0.005 | 0.24 |
| 22 | 0.002 | 0.009 | 0.43 |
| 24 | 0.002 | 0.005 | 0.33 |
| 25 | 0.002 | 0.010 | 0.17 |
| 26 | 0.001 | | 0.29 |
| 27 | 0.001 | 0.001 | 0.58 |
| 28 | 0.001 | 0.001 | 0.33 |
| 31 | 0.001 | | 0.31 |
| 32 | 0.004 | 0.006 | 0.16 |
| 34 | 0.005 | 0.020 | 0.67 |
| 38 | 0.002 | | 0.57 |
| 40 | 0.085 | | 2.48 |
| 42 | 0.011 | 0.009 | 0.24 |
| 43 | 0.013 | | 0.96 |
| 44 | 0.011 | | 0.46 |
| 45 | 0.010 | | 0.56 |
| 46 | 0.006 | 0.018 | 0.29 |
| 47 | 0.003 | 0.006 | 0.22 |
| 48 | 0.006 | 0.008 | 0.16 |
| 49 | 0.005 | 0.020 | 0.14 |
| 50 | 0.007 | 0.026 | 1.38 |
| 53 | 0.002 | | 0.11 |
| 54 | 0.016 | | 0.78 |
| 63 | 0.003 | 0.005 | 0.10 |
| 65 | 0.001 | | 0.08 |
| 66 | 0.001 | 0.001 | 0.19 |
| 67 | 0.001 | 0.001 | 0.19 |
| 69 | 0.008 | 0.020 | 1.45 |
| 72 | 0.002 | 0.010 | 0.42 |
| 74 | 0.004 | 0.013 | 0.12 |
| 76 | 0.003 | 0.008 | 0.50 |
| 80 | 0.006 | | 0.78 |
| 81 | 0.006 | 0.003 | 0.54 |
| 82 | 0.007 | 0.011 | 0.29 |
| 83 | 0.008 | 0.009 | 0.51 |
| 86 | 0.001 | 0.001 | 0.21 |
| 87 | 0.013 | 0.024 | 0.29 |
| 89 | 0.006 | 0.004 | 0.26 |
| 90 | 0.003 | 0.005 | 0.30 |
| 91 | 0.005 | 0.114 | 0.26 |
| 92 | 0.005 | 0.039 | 0.22 |
| 93 | 0.005 | 0.093 | 0.23 |
| 94 | 0.032 | 0.661 | 0.29 |
| 95 | 0.008 | 0.281 | 0.40 |
| 96 | 0.004 | 0.093 | 0.21 |
| 97 | 0.012 | 0.293 | 0.74 |
| 98 | 0.036 | 0.208 | 1.64 |
| 99 | 0.002 | 0.026 | 0.41 |
| 101 | 0.005 | 0.025 | 0.20 |
| 102 | 0.001 | 0.006 | 0.24 |
| 103 | 0.004 | 0.023 | 0.18 |

So far, the novel compounds of the invention are endowed with a potent JAK and Src family kinases inhibitory activity and are thus particularly advantageous, in therapy, against cancer and metastasis, cell proliferative disorders, viral infections, immune disorders, neurodegenerative disorders, cardiovascular diseases and bone related diseases.

The invention claimed is:

1. A compound of formula (I):

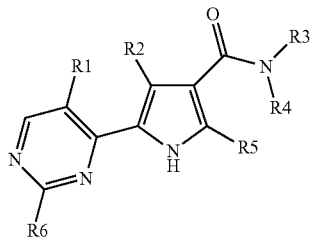

(I)

wherein:

one selected from R1 and R2 is hydrogen and the other is ethynyl-R7, wherein:

R7 is hydrogen, trialkylsylyl or an optionally substituted group selected from straight or branched $C_1$-$C_6$ alkyl, $C_3$-$C_7$ cycloalkyl, cycloalkyl-alkyl, aryl, aryl-alkyl, heterocyclyl and heterocyclyl-alkyl;

R3 and R4 are independently hydrogen or an optionally substituted group selected from straight or branched $C_1$-$C_6$ alkyl, straight or branched $C_2$-$C_6$ alkenyl, straight or branched $C_2$-$C_6$ alkynyl, $C_3$-$C_7$ cycloalkyl, cycloalkyl-alkyl, aryl, arylalkyl, heterocyclyl and heterocyclyl-alkyl, or R3 and R4, taken together with the nitrogen atom to which they are bonded, may form an optionally substituted 5 to 7 membered heterocyclyl group optionally containing one additional heteroatom selected from N, O and S;

R5 is an optionally substituted aryl;

R6 is hydrogen, an optionally substituted straight or branched $C_1$-$C_6$ alkyl or NR8R9, wherein:

R8 and R9 are independently hydrogen or an optionally substituted group selected from straight or branched $C_1$-$C_6$ alkyl, $C_3$-$C_7$ cycloalkyl, cycloalkyl-alkyl, heterocyclyl and heterocyclyl-alkyl, or R8 and R9, taken together with the nitrogen atom to which they are bonded, may form an optionally substituted 5 to 7 membered heterocyclyl group optionally containing one additional heteroatom selected from N, O and S;

or a pharmaceutically acceptable salt thereof.

2. A compound of formula (I) as defined in claim 1 wherein:

R1 is ethynyl-R7 and R2 is hydrogen.

3. A compound of formula (I) as defined in claim 2 wherein:

R3 and R4 are independently hydrogen or an optionally substituted group selected from straight or branched $C_1$-$C_6$ alkyl, $C_3$-$C_7$ cycloalkyl, cycloalkyl-alkyl, aryl, aryl-alkyl, heterocyclyl and heterocyclyl-alkyl.

4. A compound of formula (I) as defined in claims 2 wherein:

R7 is an optionally substituted aryl.

5. A compound of formula (I) as defined in claim 1 wherein:

R1 is hydrogen and R2 is ethynyl-R7.

6. A compound of formula (I) as defined in claim 5 wherein:
R3 and R4 are independently hydrogen or an optionally substituted group selected from straight or branched $C_1$-$C_6$ alkyl, $C_3$-$C_7$ cycloalkyl, cycloalkyl-alkyl, aryl, aryl-alkyl, heterocyclyl and heterocyclyl-alkyl.

7. A compound or a pharmaceutically acceptable salt thereof which is selected from the group consisting of:
5-[2-Amino-5-(phenylethynyl)pyrimidin-4-yl]-2-(5-chloro-2-methylphenyl)-1H-pyrrole-3-carboxamide (compd. 1),
5-{2-Amino-5-[(3-hydroxyphenyl)ethynyl]pyrimidin-4-yl}-2-(5-chloro-2-methylphenyl)-1H-pyrrole-3-carboxamide (compd. 2),
5-{2-Amino-5-[(4-methoxyphenyl)ethynyl]pyrimidin-4-yl}-2-(5-chloro-2-methylphenyl)-1H-pyrrole-3-carboxamide (compd. 3),
5-{2-amino-5-[(3-aminophenyl)ethynyl]pyrimidin-4-yl}-2-(5-chloro-2-methylphenyl)-1H-pyrrole-3-carboxamide (compd. 4),
5-{2-Amino-5-[(2-methoxyphenyl)ethynyl]pyrimidin-4-yl}-2-(5-chloro-2-methylphenyl)-1H-pyrrole-3-carboxamide (compd. 5),
5-{2-Amino-5-[(2-aminophenyl)ethynyl]pyrimidin-4-yl}-2-(5-chloro-2-methylphenyl)-1H-pyrrole-3-carboxamide (compd. 6),
5-{2-Amino-5-[(2,4-difluorophenyl)ethynyl]pyrimidin-4-yl}-2-(5-chloro-2-methylphenyl)-1H-pyrrole-3-carboxamide (compd. 7),
5-{2-Amino-5-[(4-aminophenyl)ethynyl]pyrimidin-4-yl}-2-(5-chloro-2-methylphenyl)-1H-pyrrole-3-carboxamide (compd. 8),
5-{2-Amino-5-[(5-amino-2-methoxyphenyl)ethynyl]pyrimidin-4-yl}-2-(5-chloro-2-methylphenyl)-1H-pyrrole-3-carboxamide (compd. 9),
5-{2-Amino-5-[(4-amino-2-methoxyphenyl)ethynyl]pyrimidin-4-yl}-2-(5-chloro-2-methylphenyl)-1H-pyrrole-3-carboxamide (compd. 10),
5-(2-Amino-5-{[4-(4-methylpiperazin-1-yl)phenyl]ethynyl}pyrimidin-4-yl)-2-(5-chloro-2-methylphenyl)-1H-pyrrole-3-carboxamide (compd. 11),
5-[2-Amino-5-({3-[(1-methylpiperidin-4-yl)amino]phenyl}ethynyl)pyrimidin-4-yl]-2-(5-chloro-2-methylphenyl)-1H-pyrrole-3-carboxamide (compd. 12),
5-(2-Amino-5-{[3-(tetrahydro-2H-pyran-4-ylamino)phenyl]ethynyl}pyrimidin-4-yl)-2-(5-chloro-2-methylphenyl)-1H-pyrrole-3-carboxamide (compd. 13),
tert-Butyl (2-{[3-({2-amino-4-[4-carbamoyl-5-(5-chloro-2-methylphenyl)-1H-pyrrol-2-yl]pyrimidin-5-yl}ethynyl)phenyl]amino}ethyl)carbamate (compd. 14),
5-[2-Amino-5-({3-[(2-hydroxyethyl)amino]phenyl}ethynyl)pyrimidin-4-yl]-2-(5-chloro-2-methylphenyl)-1H-pyrrole-3-carboxamide (compd. 15),
5-[2-Amino-5-({4-[(1-methylpiperidin-4-yl)amino]phenyl}ethynyl)pyrimidin-4-yl]-2-(5-chloro-2-methylphenyl)-1H-pyrrole-3-carboxamide (compd. 16),
tert-Butyl 3-({[3-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate (compd. 17),
5-(2-Amino-5-{[4-(tetrahydro-2H-pyran-4-ylamino)phenyl]ethynyl}primidin-4-yl)-2-(5-chloro-2-methylphenyl)-1H-pyrrole-3-carboxamide (compd. 18),
5-[2-Amino-5-({4-[(2-hydroxyethyl)amino]phenyl}ethynyl)pyrimidin-4-yl]-2-(5-chloro-2-methylphenyl)-1H-pyrrole-3-carboxamide (compd. 19),
tert-Butyl 3-({[4-({2-amino-4-[4-carbamoyl-5-(5-chloro-2-methylphenyl)-1H-pyrrol-2-yl]pyrimidin-5-yl}ethynyl)phenyl]amino}methyl)azetidine-1-carboxylate (compd. 20),
tert-Butyl (2-{[4-({2-amino-4-[4-carbamoyl-5-(5-chloro-2-methylphenyl)-1H-pyrrol-2-yl]pyrimidin-5-yl}ethynyl)phenyl]amino}ethyl)carbamate (compd. 21),
5-[2-Amino-5-({2-methoxy-5-[(1-methylpiperidin-4-yl)amino]phenyl}ethynyl)pyrimidin-4-yl]-2-(5-chloro-2-methylphenyl)-1H-pyrrole-3-carboxamide (compd. 22),
5-{2-Amino-5-[(4-formylphenyl)ethynyl]pyrimidin-4-yl}-2-(5-chloro-2-methylphenyl)-1H-pyrrole-3-carboxamide (compd. 23),
5-[2-Amino-5-({3-[(4-methylpiperazin-1-yl)methyl]phenyl}ethynyl)pyrimidin-4-yl]-2-(5-chloro-2-methylphenyl)-1H-pyrrole-3-carboxamide (compd. 24),
5-[2-Amino-5-({4-[4-(4-methylpiperazin-1-yl)piperidin-1-yl]phenyl}ethynyl)pyrimidin-4-yl]-2-(5-chloro-2-methylphenyl)-1H-pyrrole-3-carboxamide (compd. 25),
5-[2-Amino-5-({4-[4-(pyrrolidin-1-yl)piperidin-1-yl]phenyl}ethynyl)pyrimidin-4-yl]-2-(5-chloro-2-methylphenyl)-1H-pyrrole-3-carboxamide (compd. 26),
5-[2-Amino-5-({3-[(4-methylpiperazin-1-yl)carbonyl]phenyl}ethynyl)pyrimidin-4-yl]-2-(5-chloro-2-methylphenyl)-1H-pyrrole-3-carboxamide (compd. 27),
5-(2-Amino-5-{[4-(4-hydroxypiperidin-1-yl)phenyl]ethynyl}pyrimidin-4-yl)-2-(5-chloro-2-methylphenyl)-1H-pyrrole-3-carboxamide (compd. 28),
5-[2-Amino-5-({2-methoxy-4-[(1-methylpiperidin-4-yl)amino]phenyl}ethynyl)pyrimidin-4-yl]-2-(5-chloro-2-methylphenyl)-1H-pyrrole-3-carboxamide (compd. 29),
5-{2-Amino-5-[3-(1,1-dioxidothiomorpholin-4-yl)prop-1-yn-1-yl]pyrimidin-4-yl}-2-(5-chloro-2-methylphenyl)-1H-pyrrole-3-carboxamide (compd. 30),
5-[2-Amino-5-({4-[(2S)-2-(pyrrolidin-1-ylmethyl)pyrrolidin-1-yl]phenyl}ethynyl)pyrimidin-4-yl]-2-(5-chloro-2-methylphenyl)-1H-pyrrole-3-carboxamide (compd. 31),
5-[2-Amino-5-({3-[(1-methylpiperidin-4-yl)oxy]phenyl}ethynyl)pyrimidin-4-yl]-2-(5-chloro-2-methylphenyl)-1H-pyrrole-3-carboxamide (compd. 32),
N-[3-({2-Amino-4-[4-carbamoyl-5-(5-chloro-2-methylphenyl)-1H-pyrrol-2-yl]pyrimidin-5-yl}ethynyl)-4-methoxyphenyl]-1-methylpiperidine-4-carboxamide (compd. 33),
5-(2-Amino-5-{[2-methoxy-5-(4-methylpiperazin-1-yl)phenyl]ethynyl}pyrimidin-4-yl)-2-(5-chloro-2-methylphenyl)-1H-pyrrole-3-carboxamide (compd. 34),
5-{2-Amino-5-[(5-bromo-2-methoxyphenyl)ethynyl]pyrimidin-4-yl}-2-(5-chloro-2-methylphenyl)-1H-pyrrole-3-carboxamide (compd. 35),
5-[2-Amino-5-(cyclohexylethynyl)pyrimidin-4-yl]-2-(5-chloro-2-methylphenyl)-1H-pyrrole-3-carboxamide (compd. 36),
5-[2-Amino-5-({2-methoxy-4-[(4-methylpiperazin-1-yl)carbonyl]phenyl}ethynyl)pyrimidin-4-yl]-2-(5-chloro-2-methylphenyl)-1H-pyrrole-3-carboxamide (compd. 37),
5-[2-Amino-5-(cyclopropylethynyl)pyrimidin-4-yl]-2-(5-chloro-2-methylphenyl)-1H-pyrrole-3-carboxamide (compd. 38), 5-[2-Amino-5-(3,3-dimethylbut-1-yn-1-yl)pyrimidin-4-yl]-2-(5-chloro-2-methylphenyl)-1H-pyrrole-3-carboxamide (compd. 39),
5-{2-Amino-5-[(4-bromophenyl)ethynyl]pyrimidin-4-yl}-2-(5-chloro-2-methylphenyl)-1H-pyrrole-3-carboxamide (compd. 40),
5-{2-Amino-5-[(4-bromo-2-fluorophenyl)ethynyl]pyrimidin-4-yl}-2-(5-chloro-2-methylphenyl)-1H-pyrrole-3-carboxamide (compd. 41),
5-(2-Amino-5-{[2-fluoro-4-(4-methylpiperazin-1-yl)phenyl]ethynyl}pyrimidin-4-yl)-2-(5-chloro-2-methylphenyl)-1H-pyrrole-3-carboxamide (compd. 42),
5-[2-Amino-5-({2-[(2-hydroxyethyl)amino]phenyl}ethynyl)pyrimidin-4-yl]-2-(5-chloro-2-methylphenyl)-1H-pyrrole-3-carboxamide (compd. 43),
5-{2-Amino-5-[3-(dimethylamino)prop-1-yn-1-yl]pyrimidin-4-yl}-2-(5-chloro-2-methylphenyl)-1H-pyrrole-3-carboxamide (compd. 44),
5-{2-Amino-5-[(2-{2-(dimethylamino)ethyl]amino}phenyl)ethynyl]pyrimidin-4-yl}-2-(5-chloro-2-methylphenyl)-1H-pyrrole-3-carboxamide (compd. 45),
5-(2-Amino-5-{[2-methoxy-4-(4-methylpiperazin-1-yl)phenyl]ethynyl}pyrimidin-4-yl)-2-(5-chloro-2-methylphenyl)-1H-pyrrole-3-carboxamide (compd. 46),
5-(2-Amino-5-{[3-(4-methylpiperazin-1-yl)phenyl]ethynyl}pyrimidin-4-yl)-2-(5-chloro-2-methylphenyl)-1H-pyrrole-3-carboxamide (compd. 47),
5-[2-Amino-5-({4-[(1-methylpiperidin-4-yl)oxy]phenyl}ethynyl)pyrimidin-4-yl]-2-(5-chloro-2-methylphenyl)-1H-pyrrole-3-carboxamide (compd. 48),
5-(2-Amino-5-{[2-fluoro-5-(4-methylpiperazin-1-yl)phenyl]ethynyl}pyrimidin-4-yl)-2-(5-chloro-2-methylphenyl)-1H-pyrrole-3-carboxamide (compd. 49),
5-{2-Amino-5-[3-(4-methylpiperazin-1-yl)prop-1-yn-1-yl]pyrimidin-4-yl}-2-(5-chloro-2-methylphenyl)-1H-pyrrole-3-carboxamide (compd. 50),
5-(2-Amino-5-{3-[(1-methylpiperidin-4-yl)oxy]prop-1-yn-1-yl}pyrimidin-4-yl)-2-(5-chloro-2-methylphenyl)-1H-pyrrole-3-carboxamide (compd. 51),
5-[2-Amino-5-({2-[(1-methylpiperidin-4-yl)amino]phenyl}ethynyl)pyrimidin-4-yl]-2-(5-chloro-2-methylphenyl)-1H-pyrrole-3-carboxamide] (compd. 52),
5-[2-Amino-5-(pyridin-3-ylethynyl)pyrimidin-4-yl]-2-(5-chloro-2-methylphenyl)-1H-pyrrole-3-carboxamide (compd. 53),
5-[2-Amino-5-(3-hydroxy-3-methylbut-1-yn-1-yl)pyrimidin-4-yl]-2-(5-chloro-2-methylphenyl)-1H-pyrrole-3-carboxamide (compd. 54),
5-[2-Amino-5-(3-hydroxybut-1-yn-1-yl)pyrimidin-4-yl]-2-(5-chloro-2-methylphenyl)-1H-pyrrole-3-carboxamide (compd. 55),
5-(2-Amino-5-{3-[benzyl(methyl)amino]prop-1-yn-1-yl}pyrimidin-4-yl)-2-(5-chloro-2-methylphenyl)-1H-pyrrole-3-carboxamide (compd. 56),
5-[2-Amino-5-(phenylethynyl)pyrimidin-4-yl]-2-(5-chloro-2-methylphenyl)-N-methyl-1H-pyrrole-3-carboxamide (compd. 57),
5-(2-Amino-5-{[4-(4-methylpiperazin-1-yl)phenyl]ethynyl}pyrimidin-4-yl)-2-(5-chloro-2-methylphenyl)-N-methyl-1H-pyrrole-3-carboxamide (compd. 58),
5-[2-Amino-5-({4-[(4-methylpiperazin-1-yl)carbonyl]phenyl}ethynyl)pyrimidin-4-yl]-2-(5-chloro-2-methylphenyl)-1H-pyrrole-3-carboxamide (compd. 59),
5-[2-Amino-5-({4-[4-(dimethylamino)piperidin-1-yl]phenyl}ethynyl)pyrimidin-4-yl]-2-(5-chloro-2-methylphenyl)-1H-pyrrole-3-carboxamide (compd. 60),
5-[2-Amino-5-({3-[(azetidin-3-ylmethyl)amino]phenyl}ethynyl)pyrimidin-4-yl]-2-(5-chloro-2-methylphenyl)-1H-pyrrole-3-carboxamide (compd. 61),
5-[2-Amino-5-({4-[(azetidin-3-ylmethyl)amino]phenyl}ethynyl)pyrimidin-4-yl]-2-(5-chloro-2-methylphenyl)-1H-pyrrole-3-carboxamide (compd. 62),
5-[2-Amino-5-({3-[(2-aminoethyl)amino]phenyl}ethynyl)pyrimidin-4-yl]-2-(5-chloro-2-methylphenyl)-1H-pyrrole-3-carboxamide (compd. 63),
5-{2-Amino-5-[(3-{[(1-methyl azetidin-3-yl)methyl]amino}phenyl)ethynyl]pyrimidin-4-yl}-2-(5-chloro-2-methylphenyl)-1H-pyrrole-3-carboxamide (compd. 64),
5-[2-Amino-5-({4-[(4-methylpiperazin-1-yl)methyl]phenyl}ethynyl)pyrimidin-4-yl]-2-(5-chloro-2-methylphenyl)-1H-pyrrole-3-carboxamide (compd. 65),
5-(2-Amino-5-{[4-(pyrrolidin-1-ylmethyl)phenyl]ethynyl}pyrimidin-4-yl)-2-(5-chloro-2-methylphenyl)-1H-pyrrole-3-carboxamide (compd. 66),
5-(2-Amino-5-{[4-(piperidin-1-ylmethyl)phenyl]ethynyl}pyrimidin-4-yl)-2-(5-chloro-2-methylphenyl)-1H-pyrrole-3-carboxamide (compd. 67),
5-(2-Amino-5-ethynylpyrimidin-4-yl)-2-(5-chloro-2-methylphenyl)-1H-pyrrole-3-carboxamide (compd. 68),
5-(2-Amino-pyrimidin-4-yl)-2-(5-chloro-2-methyl-phenyl)-4-phenylethynyl-1H-pyrrole-3-carboxamide (compd. 69),
5-(2-Aminopyrimidin-4-yl)-2-(5-chloro-2-methylphenyl)-4-[(3-hydroxyphenyl)ethml]-1H-pyrrole-3-carboxamide (compd. 70),
5-(2-Aminopyrimidin-4-yl)-2-(5-chloro-2-methylphenyl)-4-[(4-methoxyphenyl)ethynyl]-1H-pyrrole-3-carboxamide (compd. 71),
4-[(3-Aminophenyl)ethynyl]-5-(2-aminoprimidin-4-yl)-2-(5-chloro-2-methylphenyl)-1H-pyrrole-3-carboxamide (compd. 72),
5-(2-Aminopyrimidin-4-yl)-2-(5-chloro-2-methylphenyl)-4-[(2-methoxyphenyl)ethynyl]-1H-pyrrole-3-carboxamide (compd. 73),
[(2-Aminophenyl)ethynyl]-4-(2-Amino-phenylethynyl)-5-(2-amino-pyrimidin-4-yl)-2-(5-chloro-2-methyl-phenyl)-1H-pyrrole-3-carboxamide (compd. 74),
4-[(4-amino-2-methoxyphenyl)ethynyl]-5-(2-aminopyrimidin-4-yl)-2-(5-chloro-2-methylphenyl)-1H-pyrrole-3-carboxamide (compd. 75),
4-[(4-Aminophenyl)ethynyl]-5-(2-amino-pyrimidin-4-yl)-2-(5-chloro-2-methyl-phenyl)-1H-pyrrole-3-carboxamide (compd. 76),
5-(2-Aminopyrimidin-4-yl)-2-(5-chloro-2-methylphenyl)-4-[(2-methylphenyl)ethynyl]-1H-pyrrole-3-carboxamide (compd. 77),
5-(2-Aminopyrimidin-4-yl)-2-(5-chloro-2-methylphenyl)-4-[(4-fluorophenyl)ethynyl]-1H-pyrrole-3-carboxamide (compd. 78),
4-[(5-Amino-2-methoxyphenyl)ethynyl]-5-(2-aminopyrimidin-4-yl)-2-(5-chloro-2-methylphenyl)-1H-pyrrole-3-carboxamide (compd. 79),
5-(2-Aminopyrimidin-4-yl)-2-(5-chloro-2-methylphenyl)-4-({3-[(1-methylpiperidin-4-yl)amino]phenyl}ethynyl)-1H-pyrrole-3-carboxamide (compd. 80),
5-(2-Aminopyrimidin-4-yl)-2-(5-chloro-2-methylphenyl)-4-({3-[(4-methylpiperazin-1-yl)methyl]phenyl}ethynyl)-1H-pyrrole-3-carboxamide (compd. 81), 4-({3-[(2-Aminoethyl)amino]phenyl}ethynyl)-5-(2-aminopyrimidin-4-yl)-2-(5-chloro-2-methylphenyl)-1H-pyrrole-3-carboxamide (compd. 82), 5-(2-Aminopyrimidin-4-yl)-2-(5-chloro-2-methylphenyl)-4-{[4-(4-methylpiperazin-1-yl)phenyl]ethynyl}-1H-pyrrole-3-carboxamide (compd. 83), 5-(2-Aminopyrimidin-4-yl)-2-(5-chloro-2-methylphenyl)-4-({2-[2-hydroxyethyl)amino]phenyl}ethynyl)-1H-pyrrole-3-carboxamide (compd. 84), 5-(2-Aminopyrimidin-4-yl)-2-(5-chloro-2-methylphenyl)-4-{[2-fluoro-4-(4-methylpiperazin-1-yl)phenyl]ethynyl}-1H-pyrrole-3-carboxamide (compd. 85), 5-(2-Aminopyrimidin-4-yl)-2-(5-chloro-2-methylphenyl)-4-{[2-methoxy-5-(4-methylpiperazin-1-yl)phenyl]ethynyl}-1H-pyrrole-3-carboxamide (compd. 86), 5-(2-Aminopyrimidin-4-yl)-2-(5-chloro-2-methylphenyl)-4-[(2-{[2-(dimethylamino)ethyl]amino}phenyl)ethynyl]-1H-pyrrole-3-carboxamide (compd. 87), 5-(2-Aminopyrimidin-4-yl)-2-(5-chloro-2-methylphenyl)-4-[3-(dimethylamino)prop-1-yn-1-yl]-1H-pyrrole-3-carboxamide carboxamide (compd. 88), 5-(2-Aminopyrimidin-4-yl)-2-(5-chloro-2-methylphenyl)-4-{[2-methoxy-4-(4-methylpiperazin-1-yl)phenyl]ethynyl}-1H-pyrrole-3-carboxamide (compd. 89), 5-(2-Aminopyrimidin-4-yl)-2-(5-chloro-2-methylphenyl)-4-{[3-(4-methylpiperazin-1-yl)phenyl]ethynyl}-1H-pyrrole-3-carboxamide carboxamide (compd. 90), 5-(2-Aminopyrimidin-4-yl)-2-(5-chloro-2-methylphenyl)-4-({3-[(1-methylpiperidin-4-yl)oxy]phenyl}ethynyl)-1H-pyrrole-3-carboxamide (compd. 91), 5-(2-Aminopyrimidin-4-yl)-2-(5-chloro-2-methylphenyl)-4-({4-[(1-methylpiperidin-4-yl)oxy]phenyl}ethynyl)-1H-pyrrole-3-carboxamide (compd. 92), 5-(2-Aminopyrimidin-4-yl)-2-(5-chloro-2-methylphenyl)-4-{[2-fluoro-5-(4-methylpiperazin-1-yl)phenyl]ethynyl}-1H-pyrrole-3-carboxamide (compd. 93), 5-(2-Aminopyrimidin-4-yl)-2-(5-chloro-2-methylphenyl)-4-({2-[(1-methylpiperidin-4-yl)amino]phenyl}ethynyl)-1H-pyrrole-3-carboxamide (compd. 94), 5-(2-Aminopyrimidin-4-yl)-2-(5-chloro-2-methylphenyl)-4-({4-[4-(4-methylpiperazin-1-yl)piperidin-1-yl]phenyl}ethynyl)-1H-pyrrole-3-carboxamide (compd. 95), 5-(2-Aminopyrimidin-4-yl)-2-(5-chloro-2-methylphenyl)-4-({4-[4-(dimethylamino)piperidin-1-yl]phenyl}ethynyl)-1H-pyrrole-3-carboxamide (compd. 96), 5-(2-Aminopyrimidin-4-yl)-4-{[4-(1,4'-bipiperidin-1'-yl)phenyl]ethynyl}-2-(5-chloro-2-methylphenyl)-1H-pyrrole-3-carboxamide (compd. 97), 5-(2-Aminopyrimidin-4-yl)-2-(5-chloro-2-methylphenyl)-4-({4-[4-(pyrrolidin-1-yl)piperidin-1-yl]phenyl}ethynyl)-1H-pyrrole-3-carboxamide (compd. 98), 5-(2-Aminopyrimidin-4-yl)-2-(5-chloro-2-methylphenyl)-4-{[4-(piperazin-1-yl)phenyl]ethynyl}-1H-pyrrole-3-carboxamide (compd. 99), 5-(2-Aminopyrimidin-4-yl)-2-(5-chloro-2-methylphenyl)-4-({4-[(4-methylpiperazin-1-yl)carbonyl]phenyl}ethynyl)-1H-pyrrole-3-carboxamide (compd. 100), 5-(2-Aminopyrimidin-4-yl)-2-(5-chloro-2-ethylphenyl)-4-[(2-{[2-(dimethylamino)ethyl]amino}phenyl)ethynyl]-1H-pyrrole-3-carboxamide (compd. 101), 5-(2-Aminopyrimidin-4-yl)-2-(5-chloro-2-ethylphenyl)-4-({3-[(1-methylpiperidin-4-yl)oxy]phenyl}ethynyl)-1H-pyrrole-3-carboxamide (compd. 102), 5-(2-Aminopyrimidin-4-yl)-2-(5-chloro-2-ethylphenyl)-4-{[4-(4-methylpiperazin-1-yl)phenyl]ethynyl}-1H-pyrrole-3-carboxamide (compd. 103), 2-(5-Chloro-2-methylphenyl)-5-[2-(methylamino)-5-{[4-(4-methylpiperazin-1-yl)phenyl]ethynyl}pyrimidin-4-yl]-1H-pyrrole-3-carboxamide (compd. 104), 2-(5-Chloro-2-methylphenyl)-5-(5-{[4-(4-methylpiperazin-1-yl)phenyl]ethynyl}pyrimidin-4-yl)-1H-pyrrole-3-carboxamide (compd. 105), 2-(5-Chloro-2-methylphenyl)-5-(2-methyl-5-{[4-(4-methylpiperazin-1-yl)phenyl]ethynyl}pyrimidin-4-yl)-1H-pyrrole-3-carboxamide (compd. 106), 2-(5-Chloro-2-methylphenyl)-5-[2-(methylamino)pyrimidin-4-yl]-4-{[4-(4-methylpiperazin-1-yl)phenyl]ethynyl}-1H-pyrrole-3-carboxamide (compd. 107), 2-(5-Chloro-2-methylphenyl)-4-{[4-(4-methylpiperazin-1-yl)phenyl]ethynyl}-5-(pyrimidin-4-yl)-1H-pyrrole-3-carboxamide (compd. 108), 2-(5-Chloro-2-methylphenyl)-4-{[4-(4-methylpiperazin-1-yl)phenyl]ethynyl}-5-(2-methylpyrimidin-4-yl)-1H-pyrrole-3-carboxamide (compd. 109), 5-(2-Amino-5-{[4-(4-methylpiperazin-1-yl)phenyl]ethynyl}pyrimidin-4-yl)-2-(5-chloro-2-ethylphenyl)-1H-pyrrole-3-carboxamide (compd. 110), 5-[2-Amino-5-(phenylethynyl)pyrimidin-4-yl]-2-(5-chloro-2-ethylphenyl)-N-methyl-1H-pyrrole-3-carboxamide (compd. 111) and 5-(2-Amino-5-{[4-(4-methylpiperazin-1-yl)phenyl]ethynyl}pyrimidin-4-yl)-2-(5-chloro-2-ethylphenyl)-N-methyl-1H-pyrrole-3-carboxamide (compd. 112).

8. A process for preparing a compound of formula (I) as defined in claim 1 or the pharmaceutically acceptable salts thereof, characterized in that the process comprises the following steps:

Step 1: metal-catalyzed coupling reactions of a halo derivative of formula (II)

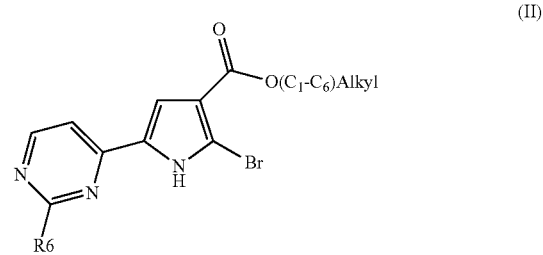

wherein R6 is as defined in claim 1, with an optionally substituted aryl boronic acid of formula (IIIa) or an optionally substituted aryl boronic-ester of formula (IIIb):

-continued

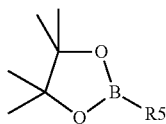
(IIIb)

wherein R5 is as defined in claim 1;

Step 2: hydrolysis under basic conditions of the resultant compound of formula (IV)

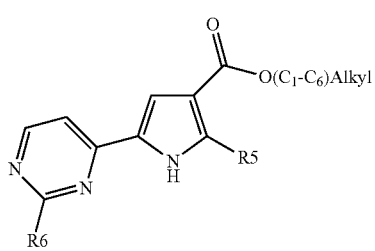
(IV)

wherein R5 and R6 are as defined above;

Step 3: regioselective mono-halogenation of the resultant carboxylic acid of formula (V)

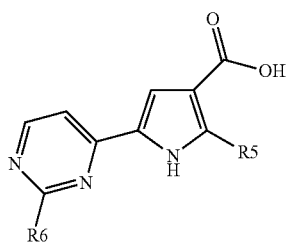
(V)

wherein R5 and R6 are as defined above;

Step 4: amidation of the resultant mono-halogenated carboxylic acid of formula (VI)

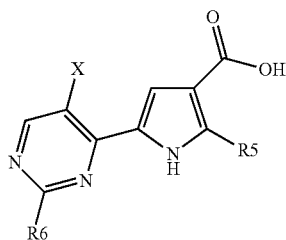
(VI)

wherein R5 and R6 are as defined above and X is a halogen, through reaction with a derivative of formula (VII)

NHR3R4        (VII)

wherein R3 and R4 are as defined in claim 1;

Step 5: metal-catalyzed coupling reactions of the resultant mono-halogenated carboxamide of formula (VIII)

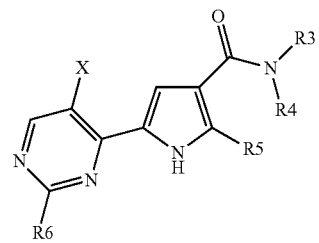
(VIII)

wherein R3, R4, R5 and R6 are as defined above and X is a halogen, through reaction with a derivative of formula (IX):

≡-R7        (IX)

wherein R7 is as defined in claim 1, to give a compound of formula (I)

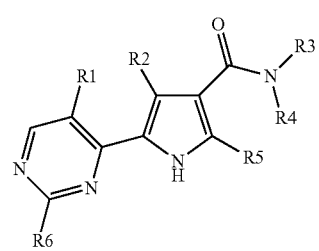
(I)

wherein R1 is ethynyl-R7, R2 is hydrogen, R3, R4, R5, R6 and R7 are as defined above; alternatively Step 6: amidation of the carboxylic acid of formula (V) as defined above, through reaction with an amine of formula (VII) as defined above;

Step 7: regioselective introduction of a 2-(trimethylsilyl)ethoxy]methyl acetal or t-butyloxycarbonyl group on the pyrrole nitrogen of the resultant carboxamide of formula (X)

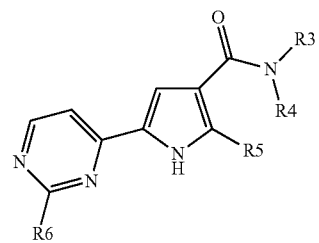
(X)

wherein R3, R4, R5 and R6 are as defined above;

Step 8: regioselective mono-halogenation of the resultant compound of formula (XI)

(XI)

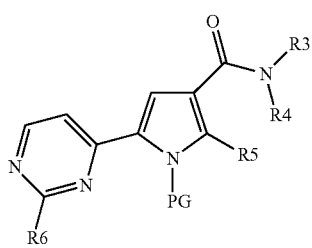

wherein R3, R4, R5 and R6 are as defined above, and PG is 2-(trimethylsilyl)ethoxy]methyl acetal or t-butyloxycarbonyl group Step 9: metal-catalyzed coupling reaction of the resultant mono-halogenated carboxamide of formula (XII)

(XII)

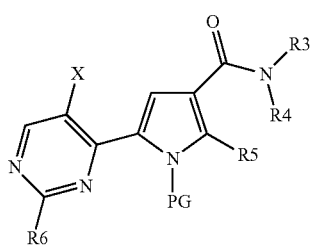

wherein R3, R4, R5, R6 and PG are as defined above, and X is a halogen, through reaction with a derivative of formula (IX) as defined above;

Step 10: deprotection of the resultant compound of formula (XIII)

(XIII)

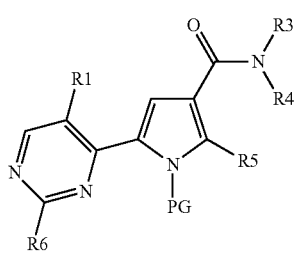

wherein R1 is ethynyl-R7, R3, R4, R5, R7 and PG are as defined above, to give a compound of formula (I)

(I)

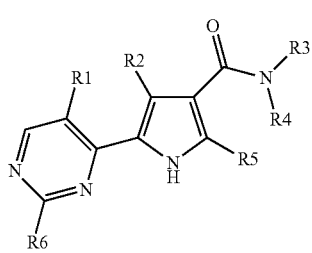

wherein R1 is ethynyl-R7, R2 is hydrogen, R3, R4, R5, R6 and R7 are as defined above; alternatively, Step 11: regioselective introduction of a 2-(trimethylsilyl) ethoxy]methyl acetal or t-butyloxycarbonyl group on the pyrrole nitrogen of the carboxylic ester of formula (IV) as defined above;

Step 12: regioselective mono-halogenation of the resultant carboxylic ester of formula (XIV)

(XIV)

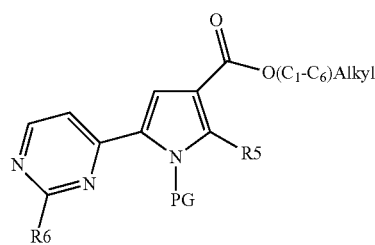

wherein R5, R6 and PG are as defined above;

Step 13: metal-catalyzed coupling reaction of the resultant mono-halogenated carboxylic ester of formula (XV)

(XV)

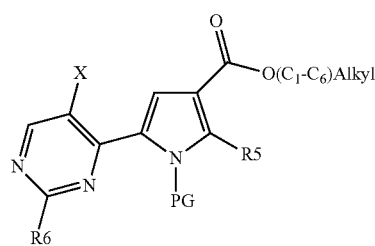

wherein R5, R6, X and PG are as defined above, through reaction with a derivative of formula (IX)'

$$\equiv\text{-R7'} \quad (IX)'$$

wherein R7' is trialkylsylyl;

Step 14: hydrolysis under basic conditions of the resultant trialkylsilyl-protected alkyne of formula (XVI)

(XVI)

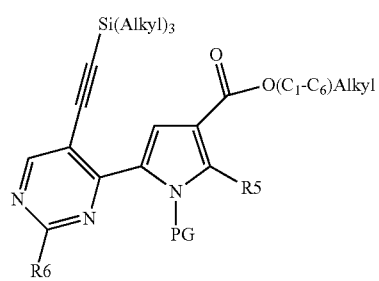

wherein R5, R6 and PG are as defined above;

Step 15: amidation of the resultant carboxylic acid of formula (XVII)

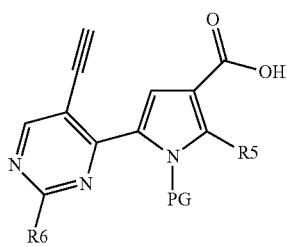

(XVII)

wherein R5, R6 and PG are as defined above, through reaction with an amine derivative of formula (VII) as defined above;

either

Step 16: metal-catalyzed coupling reaction of the terminal alkyne of the resultant carboxamide of formula (XVIII)

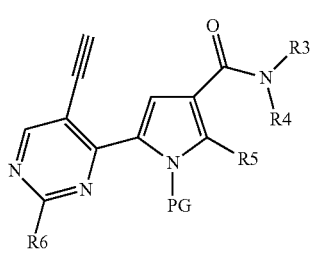

(XVIII)

wherein R3, R4, R5, R6 and PG are as defined above, through reaction with a halo derivative of formula (XIX):

X'—R7''  (XIX)

wherein R7'' is an optionally substituted aryl group and X' is bromine or iodine;

Step 17: then deprotection of the resultant compound of formula (XX)

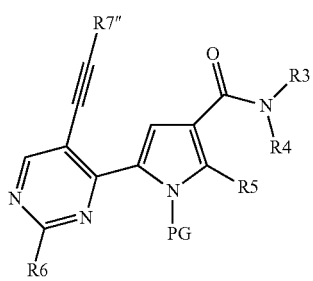

(XX)

wherein R7'', R3, R4, R5, R6 and PG are as defined above, to give a compound of general formula (I)

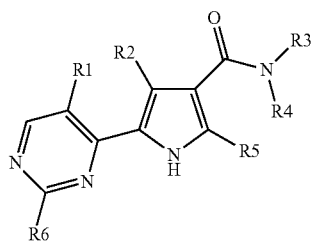

(I)

wherein R1 is optionally substituted arylethynyl, R2 is hydrogen, R3, R4, R5 and R6 are as defined above;

or

Step 17a: direct deprotection the terminal alkyne compound formula (XVIII) as defined above, to give a compound of general formula (I)

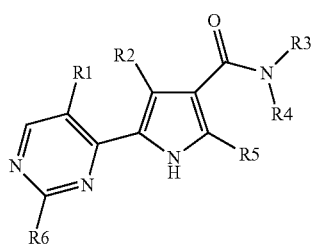

(I)

wherein R1 is ethynyl, R2 is hydrogen, R3, R4, R5 and R6 are as defined above;

alternatively

Step 18: metal-catalyzed coupling reaction of a halo derivative of formula (XXI)

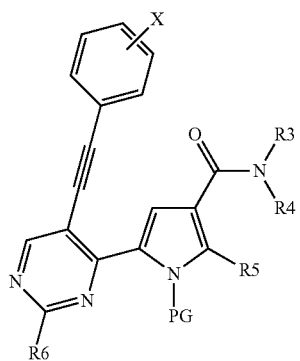

(XXI)

wherein R3, R4, R5, R6, X and PG are as defined above, through reaction with a derivative of formula (XXII)

NHR10R11  (XXII)

wherein R10 and R11 are independently hydrogen or an optionally substituted group selected from straight or branched $C_1$-$C_6$ alkyl, $C_3$-$C_7$ cycloalkyl, cycloalkyl-alkyl, heterocyclyl and heterocyclyl-alkyl, or R10 and R11, taken together with the nitrogen atom to which they are bonded, may form an optionally substituted 5 to 7 membered heterocyclyl group optionally containing one additional heteroatom selected from N, O and S;

Step 19: deprotection of the resultant compound of formula (XXIII)

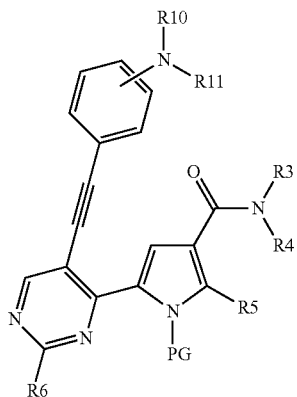

(XXIII)

wherein R3, R4, R5, R6, R10, R11 and PG are as defined above, to give a compound of general formula (I)

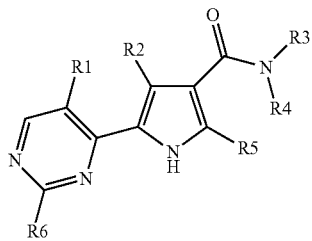

(I)

wherein R1 is amino-aryl-ethynyl, R2 is hydrogen, R3, R4, R5 and R6 are as defined above;

alternatively,

Step 20: regioselective mono-halogenation of a compound of formula (X) as defined above;

Step 21: metal-catalyzed coupling reaction of the resultant halo derivative of formula (XXIV)

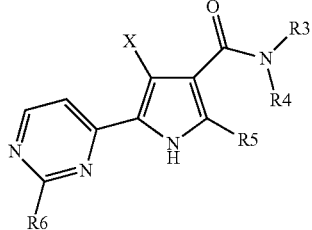

(XXIV)

wherein R3, R4, R5, R6 and X are as defined above, through reaction with a derivative of formula (IX) as defined above, to give a compound of formula (I)

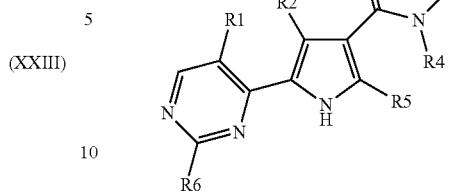

(I)

wherein R1 is hydrogen, R2 is ethynyl-R7, R3, R4, R5, R6 and R7 are as defined above;

alternatively,

Step 22: regioselective mono-halogenation of the carboxylic ester of formula (IV) as defined above;

Step 23: hydrolysis under basic conditions of the resultant compound of formula (XXV)

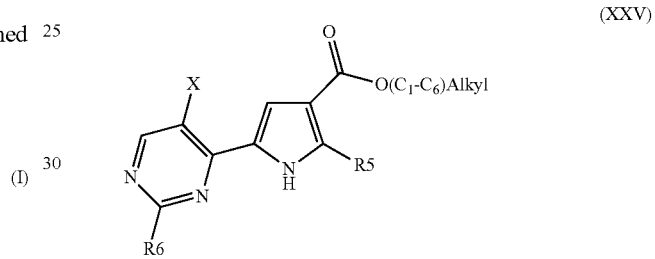

(XXV)

wherein R5 and R6 are as defined above and X is a halogen;

Step 24: amidation of the resultant mono-halogenated carboxylic acid of formula (VI) as defined above through reaction with a derivative of formula (VII) as defined above;

Step 25: metal-catalyzed coupling reactions of the resultant mono-halogenated carboxamide of formula (VIII) as defined above through reaction with a derivative of formula (IX) as defined above to give a compound of formula (I)

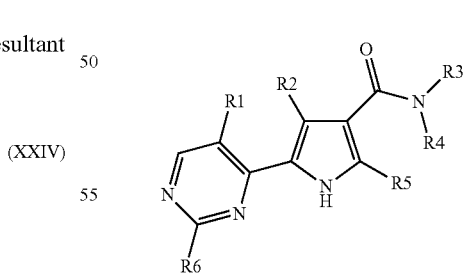

(I)

wherein R1 is ethynyl-R7, R2 is hydrogen, R3, R4, R5, R6 and R7 are as defined above;

optionally converting a compound of formula (I) into another different compound of formula (I), and, if desired, converting a compound of formula (I) into a pharmaceutically acceptable salt thereof or converting a salt into the free compound of formula (I).

9. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

\* \* \* \* \*